United States Patent
Blake et al.

(10) Patent No.: US 8,841,304 B2
(45) Date of Patent: *Sep. 23, 2014

(54) PYRROLOPYRIDINES AS KINASE INHIBITORS

(75) Inventors: James F. Blake, Boulder, CO (US); Indrani W. Gunawardana, Boulder, CO (US); Yvan Le Huerou, Boulder, CO (US); Peter J. Mohr, Boulder, CO (US); Eli M. Wallace, Boulder, CO (US); Bin Wang, Boulder, CO (US)

(73) Assignees: Array Biopharma, Inc., Boulder, CO (US); Genentech, Inc., South San Francisco, CA (US)

( * ) Notice: Subject to any disclaimer, the term of this patent is extended or adjusted under 35 U.S.C. 154(b) by 7 days.

This patent is subject to a terminal disclaimer.

(21) Appl. No.: 12/812,447

(22) PCT Filed: Jan. 8, 2009

(86) PCT No.: PCT/US2009/030443
§ 371 (c)(1),
(2), (4) Date: Jul. 9, 2010

(87) PCT Pub. No.: WO2009/089352
PCT Pub. Date: Jul. 16, 2009

(65) Prior Publication Data
US 2010/0324041 A1 Dec. 23, 2010

Related U.S. Application Data

(60) Provisional application No. 61/019,786, filed on Jan. 8, 2008.

(51) Int. Cl.
C07D 471/04 (2006.01)
A61K 31/496 (2006.01)

(52) U.S. Cl.
USPC ..................... 514/253.04; 544/362

(58) Field of Classification Search
None
See application file for complete search history.

(56) References Cited

U.S. PATENT DOCUMENTS

| | | |
|---|---|---|
| 6,423,716 B1 | 7/2002 | Matsuno et al. |
| 6,627,628 B1 | 9/2003 | Schindler et al. |
| 7,115,741 B2 | 10/2006 | Levy et al. |
| 7,968,545 B2 | 6/2011 | Wilson et al. |
| 7,994,172 B2 | 8/2011 | Rice et al. |
| 8,003,651 B2 | 8/2011 | Mitchell et al. |
| 8,063,050 B2 | 11/2011 | Mitchell et al. |
| 8,076,338 B2 | 12/2011 | Anand et al. |
| 8,178,131 B2 | 5/2012 | Le Huerou et al. |
| 8,372,842 B2 * | 2/2013 | Blake et al. .............. 514/253.04 |
| 2003/0162785 A1 | 8/2003 | Lin et al. |
| 2004/0053933 A1 | 3/2004 | Pontillo et al. |
| 2005/0130954 A1 | 6/2005 | Mitchell et al. |
| 2005/0256157 A1 | 11/2005 | Gesner et al. |
| 2007/0027156 A1 | 2/2007 | Nakai et al. |
| 2007/0082900 A1 | 4/2007 | Guzi et al. |
| 2007/0135466 A1 | 6/2007 | Ledeboer et al. |
| 2009/0099213 A1 | 4/2009 | Berdini et al. |
| 2009/0111850 A1 | 4/2009 | Linsell et al. |
| 2009/0124610 A1 | 5/2009 | Saxty et al. |
| 2010/0210639 A1 | 8/2010 | Collins et al. |
| 2010/0260868 A1 | 10/2010 | Humphries et al. |
| 2010/0280043 A1 | 11/2010 | Blake et al. |
| 2010/0292244 A1 | 11/2010 | Bencsik et al. |
| 2011/0015204 A1 | 1/2011 | Bencsik et al. |
| 2011/0065716 A1 | 3/2011 | Bencsik et al. |
| 2011/0160221 A1 | 6/2011 | Bencsik et al. |
| 2011/0183933 A1 | 7/2011 | Guzi et al. |

(Continued)

FOREIGN PATENT DOCUMENTS

| | | |
|---|---|---|
| WO | WO 03/028724 A1 | 4/2003 |
| WO | 2005/051304 * | 6/2005 |

(Continued)

OTHER PUBLICATIONS

Bartek et al. Cancer Cell, vol. 3, p. 421-429 (2003).*

(Continued)

Primary Examiner — Emily Bernhardt
(74) Attorney, Agent, or Firm — Viksnins, Harris & Padys PLLP

(57) ABSTRACT

Compounds of Formula (I) are useful for inhibition of CHK1 and/or CHK2. Methods of using compounds of Formula (I) and stereoisomers and pharmaceutically acceptable salts thereof, for in vitro, in situ, and in vivo diagnosis, prevention or treatment of such disorders in mammalian cells, or associated pathological conditions are disclosed.

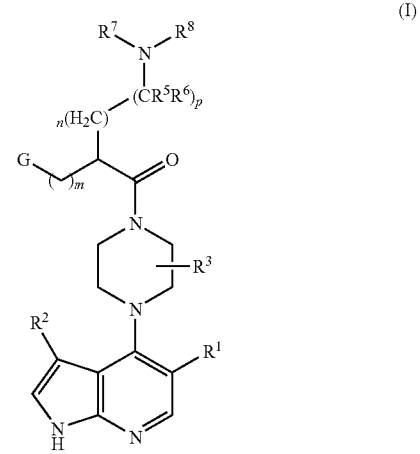

(I)

63 Claims, No Drawings

(56) References Cited

U.S. PATENT DOCUMENTS

| | | |
|---|---|---|
| 2011/0245230 A1 | 10/2011 | Mitchell et al. |
| 2011/0251181 A1 | 10/2011 | Banka et al. |
| 2011/0269773 A1 | 11/2011 | Mitchell et al. |
| 2012/0040935 A1 | 2/2012 | Wilson et al. |

FOREIGN PATENT DOCUMENTS

| | | |
|---|---|---|
| WO | WO 2005/063746 A1 | 7/2005 |
| WO | WO 2005/103036 A1 | 11/2005 |
| WO | WO 2006/077319 A1 | 7/2006 |
| WO | WO 2006/106326 A1 | 10/2006 |
| WO | WO 2006/120573 A2 | 11/2006 |
| WO | WO 2006/130673 A1 | 12/2006 |
| WO | WO 2007/002433 A1 | 1/2007 |
| WO | WO 2007/059219 A1 | 5/2007 |
| WO | WO 2007/090493 A1 | 8/2007 |
| WO | WO 2007/090494 A1 | 8/2007 |
| WO | WO 2007/103308 A2 | 9/2007 |
| WO | WO 2007/125321 A2 | 11/2007 |
| WO | WO 2008/006039 A1 | 1/2008 |
| WO | WO 2008/012635 A2 | 1/2008 |
| WO | WO 2008/075007 A1 | 6/2008 |
| WO | WO 2010/118390 A1 | 10/2010 |
| WO | WO 2012/074754 A1 | 6/2012 |

OTHER PUBLICATIONS

Antoni et al. Nature Reviews/Cancer vol. 7, p. 925-936 (2007).*
Ahn, et al., "The Chk2 protein kinase", *DNA Repair 3*, 1039-1047 (2004).
Arrington et al. "Novel Inhibitors of Checkpoint Kinase 1", *Chemedchem*, vol. 2, 1571-1585 (2007).
Bartek, et al., "CHK2 Kinase—A Busy Messenger", *Nature Reviews Molecular Cell Biology*, vol. 2 (12), 877-886 (2001).
Foloppe et al., "Identification of a buried pocket for potent and selective inhibition of Chk1: Prediction and verification", *Bioorganic & Medicinal Chemistry 14*, 1792-1804 (2006).
Foloppe et al., "Structure-Based Design of Novel Chk1 Inhibitors: Insights into Hydrogen Bonding and Protein—Ligand Affinity", *J. Med. Chem.* 48, 4332-4345 (2005).
Janetka, et al., "Inhibitors of checkpoint kinases: From discovery to the clinic", *Drug Discovery & Development*, vol. 10, No. 4, 473-486 (2007).
Li et al., "Targeting Serine/Threonine Protein Kinase B/Akt and Cell-cycle Checkpoint Kinases for Treating Cancer", *Current Topics in Medicinal Chemistry*, 2, 939-971 (2002).
Patent Cooperation Treaty, International Search Report and Written Opinion for PCT/US2009/030443, 14 pages, Mar. 17, 2009.
Pommier et al., "Targeting Chk2 Kinase: Molecular Interaction Maps and Therapeutic Rationale", *Current Pharmaceutical Design* vol. 11, No. 22, 2855-2872 (2005).
Reader et al., "Identification and Structure-guided Optimisation of Novel Inhibitors of Checkpoint Kinase 1 (Chk1) through Combined Biochemical and Crystallographic Screening", *AACR, Poster, Abstract 757, Sareum Ltd, UK, Cancer Research UK Centre for Cancer Therapeutics, and The Institute of Cancer Research, UK*, 1 page.
Tao et al., "Chk1 Inhibitors for Novel Cancer Treatment", *Anti-Cancer Agents in Medicinal Chemistry*, 6, 377-388 (2006).
Tse et al., "Targeting Checkpoint Kinase 1 in Cancer Therapeutics", *Clin. Cancer Res.* 13 (7), 1955-1960 (2007).
Wang et al., "1-(5-Chloro-2-alkoxyphenyl)-3-(5-cyanopyrazin-2-1)ureas as potent and selective inhibitors of Chk1 kinase: synthesis, preliminary SAR, and biological activities", *Journal of Medicinal Chemistry, American Chemical Society*, vol. 48, No. 9, 3118-3121, XP002456672 (2005).

* cited by examiner

PYRROLOPYRIDINES AS KINASE INHIBITORS

RELATED APPLICATIONS

This application claims priority to U.S. Provisional Application No. 61/019,786 that was filed on Jan. 8, 2008.

BACKGROUND OF THE INVENTION

1. Field of the Invention

The present invention relates to novel compounds, to pharmaceutical compositions comprising the compounds, to a process for making the compounds and to the use of the compounds in therapy. More particularly it relates to certain 4-substituted pyrrolo[2,3-b]pyridines useful in the treatment and prevention of hyperproliferative diseases.

2. Description of the State of the Art

Protein kinases are kinase enzymes that phosphorylate other proteins. The phosphorylation of these proteins usually produces a functional change in the protein. Most kinases act on serine and threonine or tyrosine, and some kinases act on all three. Through these functional changes, kinases can regulate many cellular pathways. Protein kinase inhibitors are compounds that inhibit these protein kinases, and thus can be used to affect cellular pathways.

Checkpoint kinase 1 ("CHK1") is a serine/threonine kinase. CHK1 regulates cell-cycle progression and is a main factor in DNA-damage response within a cell. CHK1 inhibitors have been shown to sensitize tumor cells to a variety of genotoxic agents, such as chemotherapy and radiation. (Tse, Archie N., et al., "Targeting Checkpoint Kinase 1 in Cancer Therapeutics." *Clin. Cancer Res.* 13(7) (2007) 1955-1960). It has been observed that many tumors are deficient in the $G_1$ DNA damage checkpoint pathway, resulting in the reliance on S and $G_2$ checkpoints to repair DNA damage and survive. (Janetka, James W., et al., "Inhibitors of checkpoint kinases: From discovery to the clinic." *Drug Discovery & Development* Vol. 10, No. 4 (2007) 473-486). The S and $G_2$ checkpoints are regulated by CHK1 Inhibition of CHK1 has been shown to cancel the S and $G_2$ checkpoints, thereby impairing DNA repair and resulting in increased tumor cell death. However, non-cancerous cells have a functioning $G_1$ checkpoint, allowing for DNA repair and survival.

Checkpoint kinase 2 ("CHK2") is also a serine/threonine kinase. CHK2's functions are central to the induction of cell cycle arrest and apoptosis by DNA damage. (Ahn, Jinwoo, et al., "The Chk2 protein kinase." *DNA Repair* 3 (2004) 1039-1047). CHK2 is activated in response to genotoxic insults and propagates the checkpoint signal along several pathways, which eventually causes cell-cycle arrest in the $G_1$, S and $G_2$/M phases, activation of DNA repair, and apoptotic cell death. (Bartek, Jiri, et al., "CHK2 Kinase—A Busy Messenger." *Nature Reviews Molecular Cell Biology* Vol. 2(12) (2001) 877-886). Cancer cells often lack one or more genome-integrity checkpoints, so inhibition of CHK2 could make tumor cells selectively more sensitive to anti-cancer therapies, such as γ-radiation or DNA-damaging drugs. Normal cells would still activate other checkpoints and recover, while cancer cells deprived of checkpoints would be more likely to die. It has been demonstrated that a peptide-based inhibitor of CHK2 abrogated the G2 checkpoint and sensitized p53-defective cancer cells to DNA damaging agents. (Pommier, Yves, et al., "Targeting Chk2 Kinase: Molecular Interaction Maps and Therapeutic Rationale." Current Pharmaceutical Design Vol. 11, No. 22 (2005) 2855-2872).

CHK1 and/or CHK2 inhibitors are known, see for example, International Publication Number WO 2007/090493, International Publication Number WO 2007/090494, International Publication WO 2006/106326, International Publication WO 2006/120573, International Publication WO 2005/103036 and International Publication WO 03/028724.

Certain pyrrolopyridines are known, but not as CHK1/2 inhibitors, see for example, United States Patent Application Publication 2005/0130954, United States Patent Application Publication 2007/0135466, U.S. Pat. No. 7,115,741, and International Publication Number WO 2007/002433.

SUMMARY OF THE INVENTION

In one aspect, the present invention relates to compounds that are inhibitors of CHK1 and/or CHK2. Accordingly, the compounds of the present invention are useful in the treatment of diseases and conditions that can be treated by the inhibition of CHK1 and/or CHK2 protein kinases.

More specifically, one aspect of the present invention provides compounds of Formula I:

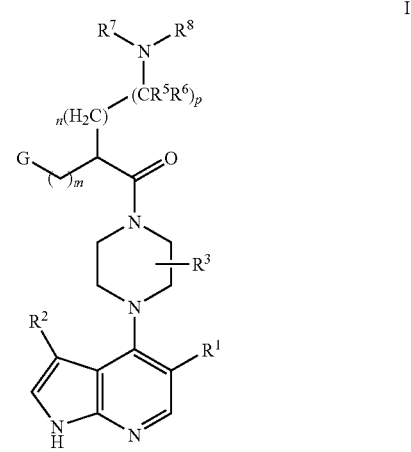

and stereoisomers and pharmaceutically acceptable salts thereof, wherein G, $R^1$, $R^2$, $R^3$, $R^5$, $R^6$, $R^7$, $R^8$, m, n, and p are as defined herein.

Another aspect of the present invention provides methods of preventing or treating a disease or disorder modulated by CHK1 and/or CHK2, comprising administering to a mammal in need of such treatment an effective amount of a compound of this invention or a stereoisomer or pharmaceutically acceptable salt thereof. Examples of such diseases and disorders include, but are not limited to, hyperproliferative disorders (such as cancer), neurodegeneration, cardiac hypertrophy, pain, migraine and neurotraumatic disease.

Another aspect of the present invention provides methods of preventing or treating cancer, comprising administering to a mammal in need of such treatment an effective amount of a compound of this invention, or a stereoisomer or pharmaceutically acceptable salt thereof, alone or in combination with one or more additional compounds having anti-cancer properties.

Another aspect of the present invention provides a method of treating a hyperproliferative disease in a mammal comprising administering a therapeutically effective amount of a compound of this invention to the mammal.

Another aspect of the present invention provides the compounds of this invention for use in therapy.

Another aspect of the present invention provides the compounds of this invention for the use in the treatment of a hyperproliferative disease.

Another aspect of the present invention provides the use of a compound of this invention in the manufacture of a medicament for the treatment of a hyperproliferative disease. In a further embodiment, the hyperproliferative disease is cancer.

Another aspect of the present invention provides the use of a compound of the present invention in the manufacture of a medicament, for use as a CHK1 and/or CHK2 inhibitor in the treatment of a patient undergoing cancer therapy.

Another aspect of the present invention provides the use of a compound of the present invention in the treatment of a hyperproliferative disease. In a further aspect, the hyperproliferative disease is cancer.

Another aspect of the present invention provides a pharmaceutical composition comprising a compound of the present invention for use in the treatment of a hyperproliferative disease.

Another aspect of the present invention provides a pharmaceutical composition comprising a compound of the present invention for use in the treatment of cancer.

Another aspect of the present invention provides a pharmaceutical composition comprising a compound of this invention or a pharmaceutically acceptable salt thereof, and a pharmaceutically acceptable carrier or excipient.

Another aspect of the present invention includes methods of preparing, methods of separation, and methods of purification of the compounds of this invention.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

Definitions

The term "alkyl" includes linear or branched-chain radicals of carbon atoms. Some alkyl moieties have been abbreviated, for example, methyl ("Me"), ethyl ("Et"), propyl ("Pr") and butyl ("Bu"), and further abbreviations are used to designate specific isomers of compounds, for example, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu") and the like. The abbreviations are sometimes used in conjunction with elemental abbreviations and chemical structures, for example, methanol ("MeOH") or ethanol ("EtOH").

Additional abbreviations used throughout the application include benzyl ("Bn") and phenyl ("Ph").

The term "heterocycle" or "heterocyclic" means a four to six membered ring containing one, two or three heteroatoms selected from the group consisting of oxygen, nitrogen and sulfur.

The term "heteroaryl" means a five to six membered aromatic ring containing one, two or three heteroatoms selected from the group consisting of oxygen, nitrogen and sulfur.

The terms "treat" or "treatment" refer to therapeutic, prophylactic, palliative or preventative measures. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder or those in which the condition or disorder is to be prevented.

The phrases "therapeutically effective amount" or "effective amount" mean an amount of a compound of the present invention that, when administered to a mammal in need of such treatment, sufficient to (i) treat or prevent the particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein. The amount of a compound that will correspond to such an amount will vary depending upon factors such as the particular compound, disease condition and its severity, the identity (e.g., weight) of the mammal in need of treatment, but can nevertheless be routinely determined by one skilled in the art.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, skin cancers, including melanoma, as well as head and neck cancer.

The phrase "pharmaceutically acceptable" indicates that the substance or composition must be compatible chemically and/or toxicologically, with the other ingredients comprising a formulation, and/or the mammal being treated therewith.

The phrase "pharmaceutically acceptable salt," as used herein, refers to pharmaceutically acceptable organic or inorganic salts of a compound of the invention.

The compounds of this invention also include other salts of such compounds which are not necessarily pharmaceutically acceptable salts, and which may be useful as intermediates for preparing and/or purifying compounds of this invention and/or for separating enantiomers of compounds of this invention.

The term "mammal" means a warm-blooded animal that has or is at risk of developing a disease described herein and includes, but is not limited to, guinea pigs, dogs, cats, rats, mice, hamsters, and primates, including humans.

CHK1/2 Inhibitor Compounds

The present invention provides certain 4-substituted 1H-pyrrolo[2,3-b]pyridines that are CHK1 and/or CHK2 inhibitors useful in the treatment of diseases, conditions and/or disorders modulated by CHK1 and/or CHK2.

It has surprisingly been found that 4-substituted 1H-pyrrolo[2,3-b]pyridines having particular substituents at the 3 and/or 5 positions are inhibitors of CHK1 and/or CHK2. Furthermore, some of these compounds have been found to be selective for CHK1 over certain other protein kinases.

Accordingly, the present invention provides compounds of Formula I:

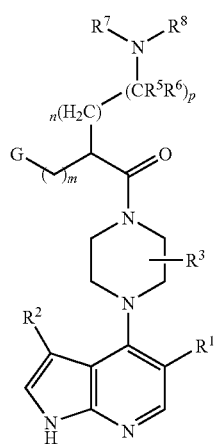

and stereoisomers and pharmaceutically acceptable salts thereof, wherein:

G is cyclohexyl or phenyl optionally substituted by 1-3 independent $R^4$ groups, or when m is 0, G may additionally be absent or $C_1$-$C_4$ alkyl;

$R^1$ is selected from hydrogen, halogen, CN, $C_1$-$C_4$ alkyl optionally substituted with halogen, —C(=O)$OR^a$, —$OR^e$, $C_3$-$C_6$ cycloalkyl, 5 or 6 membered heteroaryl, phenyl or —O-phenyl, wherein the heteroaryl, phenyl or —O-phenyl may be optionally substituted with one or two $R^b$ groups;

$R^2$ is selected from hydrogen, $CH_3$, or —NHC(=O)$R^f$, provided that when $R^1$ is hydrogen, $R^2$ is —NHC(=O)$R^f$;

$R^3$ is selected from H or $C_1$-$C_3$ alkyl;

each $R^4$ is independently selected from halogen, $CF_3$, $OCF_3$ and CN;

$R^5$ and $R^6$ are independently selected from hydrogen or $CH_3$;

$R^7$ and $R^8$ are independently selected from hydrogen or $C_1$-$C_6$ alkyl;

$R^a$ is $C_1$-$C_4$ alkyl;

each $R^b$ group is independently selected from halogen, CN, $OCH_3$ or $C_1$-$C_4$ alkyl optionally substituted with halogen, OH, oxo, 5 or 6 membered heteroaryl or $NR^gR^h$;

$R^e$ is $C_1$-$C_4$ alkyl optionally substituted with OH or a 5 or 6 membered heterocycle;

$R^f$ is $C_1$-$C_4$ alkyl optionally substituted with OH, a 5 or 6 membered heterocycle optionally substituted with one or two groups selected from oxo, halogen, CN, $CF_3$ or $C_1$-$C_3$ alkyl, or a 5 or 6 membered heteroaryl optionally substituted with one or two groups selected from halogen, CN, $CF_3$ or $C_1$-$C_3$ alkyl;

$R^g$ and $R^h$ are independently hydrogen or $C_1$-$C_4$ alkyl;

m, n and p are independently 0 or 1;

or $R^5$ is hydrogen, $R^6$ and $R^7$ together with the atoms to which they are attached form an optionally substituted 5-6 membered heterocyclic ring having one ring nitrogen atom, and $R^8$ is selected from the group consisting of hydrogen or $C_1$-$C_4$ alkyl optionally substituted with OH or O($C_1$-$C_3$ alkyl) such that the compound of Formula I has the structure of Formula II:

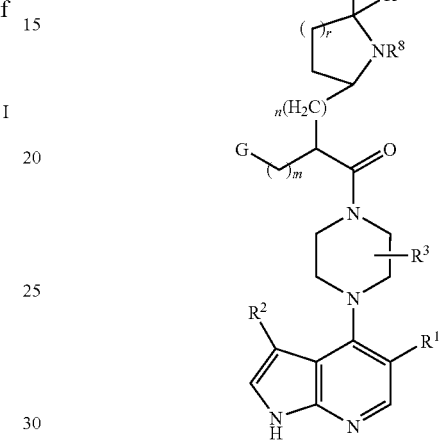

wherein $R^c$ and $R^d$ are independently selected from hydrogen or $C_1$-$C_4$ alkyl; and r is 1 or 2.

In certain embodiments, G is cyclohexyl.

In certain embodiments, G is phenyl optionally substituted by one to three $R^4$ groups. In certain embodiments, $R^4$ is halogen. In particular embodiments, G is 4-fluorophenyl, 4-chlorophenyl, 4-bromophenyl, 3-fluoro-4-chlorophenyl or 3-chloro-4-fluorophenyl.

Referring to the G group of Formula I, examples include phenyl optionally substituted with one or more $R^4$ groups independently selected from halogen, $CF_3$, $OCF_3$ and CN.

In certain embodiments, m is 0 and G is cyclohexyl, phenyl optionally substituted by 1-3 independent $R^4$ groups, absent or $C_1$-$C_4$ alkyl.

In certain embodiments, m is 0 and G is absent.

In certain embodiments, m is 0 and G is $C_1$-$C_4$ alkyl.

In certain embodiments, m is 0 and G is isopropyl.

In certain embodiments, $R^1$ is selected from halogen, CN, $C_1$-$C_4$ alkyl optionally substituted with halogen, —C(=O)$OR^a$, —$OR^e$, $C_3$-$C_6$ cycloalkyl, 5 or 6 membered heteroaryl, phenyl or —O-phenyl, wherein the heteroaryl, phenyl or —O-phenyl may be optionally substituted with one or two $R^b$ groups.

In certain embodiments, $R^1$ is selected from Br, CN, $C_1$-$C_4$ alkyl optionally substituted with halogen, —C(=O)$OR^a$, —$OR^e$, $C_3$-$C_6$ cycloalkyl, 5 or 6 membered heteroaryl, phenyl or —O-phenyl, wherein the heteroaryl, phenyl or —O-phenyl may be optionally substituted with one or two $R^b$ groups.

In certain embodiments, $R^1$ is selected from halogen, CN, $C_1$-$C_4$ alkyl optionally substituted with halogen, —C(=O)$OR^a$, —$OR^e$, $C_3$-$C_6$ cycloalkyl, phenyl or —O-phenyl, wherein the phenyl or —O-phenyl may be optionally substituted with one or two $R^b$ groups.

In certain embodiments, $R^1$ is selected from Br, CN, $C_1$-$C_4$ alkyl optionally substituted with halogen, —C(=O)OR$^a$, —OR$^e$, $C_3$-$C_6$ cycloalkyl, phenyl or —O-phenyl, wherein the phenyl or —O-phenyl may be optionally substituted with one or two R$^b$ groups.

In certain embodiments, $R^1$ is selected from CN, $C_1$-$C_4$ alkyl optionally substituted with halogen, —C(O)OR$^a$, —OR$^e$, $C_3$-$C_6$ cycloalkyl, phenyl or —O-phenyl, wherein the phenyl or —O-phenyl may be optionally substituted with one or two R$^b$ groups.

In certain embodiments, $R^1$ is selected from CN, $C_1$-$C_4$ alkyl optionally substituted with halogen, —C(O)OR$^a$, —OR$^e$, phenyl or —O-phenyl, wherein the phenyl or —O-phenyl may be optionally substituted with one or two R$^b$ groups.

In certain embodiments, $R^1$ is Br.

In certain embodiments, $R^1$ is CN.

In certain embodiments, $R^1$ is $C_1$-$C_4$ alkyl.

In certain embodiments, $R^1$ is $C_1$-$C_4$ alkyl optionally substituted with halogen. In certain embodiments, $R^1$ is $CF_3$.

In certain embodiments, $R^1$ is C(=O)OR$^a$. In certain embodiments, R$^a$ is $C_1$-$C_4$ alkyl. In a further embodiment, R$^a$ is $CH_3$. In certain embodiments, $R^1$ is C(=O)OCH$_3$.

In certain embodiments, $R^1$ is —OR$^e$. In certain embodiments, R$^e$ is $C_1$-$C_4$ alkyl optionally substituted with OH or 5 or 6 membered heterocycle.

In certain embodiments, R$^e$ is 5 or 6 membered heterocycle. In certain embodiments, R$^e$ is morpholinyl.

In certain embodiments, R$^e$ is $C_1$-$C_4$ alkyl. In certain embodiments, R$^e$ is isopropyl. In certain embodiments, $R^1$ is —OCH(CH$_3$)$_2$.

In certain embodiments, R$^e$ is $C_1$-$C_4$ alkyl substituted with OH. In certain embodiments, R$^e$ is 2-hydroxybutane. In certain embodiments, $R^1$ is —OCH$_2$CH(OH)CH$_2$CH$_3$.

In certain embodiments, R$^e$ is $C_1$-$C_4$ alkyl optionally substituted with a 5 or 6 membered heterocycle. In certain embodiments, R$^e$ is $C_1$-$C_4$ alkyl optionally substituted with morpholinyl. In certain embodiments, R$^e$ is CH$_2$CH$_2$-morpholin-4-yl or CH$_2$CH$_2$CH$_2$-morpholin-4-yl. In certain embodiments, $R^1$ is —OCH$_2$CH$_2$-morpholin-4-yl or —OCH$_2$CH$_2$CH$_2$-morpholin-4-yl.

In certain embodiments, $R^1$ is $C_3$-$C_6$ cycloalkyl.

In certain embodiments, $R^1$ is cyclopropyl.

In certain embodiments, $R^1$ is a 5 or 6 membered heteroaryl optionally substituted with one or two R$^b$ groups. In certain embodiments, the 5 or 6 membered heteroaryl is pyrazolyl, 1-oxa-3,4-diazolyl, thiophenyl or pyridinyl.

In certain embodiments, each R$^b$ is independently selected from halogen, CN, OCH$_3$ or $C_1$-$C_4$ alkyl optionally substituted with halogen, OH, oxo, 5 or 6 membered heteroaryl or NR$^g$R$^h$.

In certain embodiments, R$^b$ is 5 or 6 membered heteroaryl. In particular embodiments, R$^b$ is pyrazolyl.

In certain embodiments, each R$^b$ is independently selected from halogen, CN, OCH$_3$ or $C_1$-$C_4$ alkyl optionally substituted with halogen, OH, oxo, pyrazolyl or NR$^g$R$^h$.

In certain embodiments, $R^1$ is a pyrazolyl optionally substituted with one or two R$^b$ groups. In certain embodiments, $R^1$ is a pyrazolyl substituted with one R$^b$ group. In certain embodiments, R$^b$ is methyl. In certain embodiments, $R^1$ is a 1-methyl-1H-pyrazol-yl.

In certain embodiments, $R^1$ is 1-oxa-3,4-diazolyl optionally substituted with one or two R$^b$ groups. In certain embodiments, $R^1$ is 1-oxa-3,4-diazolyl substituted with one R$^b$ group. In certain embodiments, R$^b$ is $C_1$-$C_4$ alkyl. In certain embodiments, $R^1$ is 2-isopropyl-1-oxa-3,4-diazol-5-yl. In certain embodiments, $R^1$ is 2-methyl-1-oxa-3,4-diazol-5-yl.

In certain embodiments, $R^1$ is pyridinyl optionally substituted with one or two R$^b$ groups. In certain embodiments, $R^1$ is pyridinyl. In certain embodiments, $R^1$ is pyridin-3-yl.

In certain embodiments, $R^1$ is thiophenyl optionally substituted with one or two R$^b$ groups. In certain embodiments, $R^1$ is thiophen-2-yl.

In certain embodiments, $R^1$ is phenyl optionally substituted with one or two R$^b$ groups. In certain embodiments, each R$^b$ is independently selected from halogen, OCH$_3$, —C(=O)NR$^g$R$^h$ or $C_1$-$C_4$ alkyl optionally substituted with halogen, OH, oxo, 5 or 6 membered heteroaryl or NR$^g$R$^h$.

In certain embodiments, $R^1$ is phenyl optionally substituted with one or two R$^b$ groups. In certain embodiments, each R$^b$ is independently selected from halogen, OCH$_3$, —C(=O)NR$^g$R$^h$ or $C_1$-$C_4$ alkyl optionally substituted with halogen, OH, oxo, pyrazolyl or NR$^g$R$^h$.

In certain embodiments, $R^1$ is phenyl.

In certain embodiments, $R^1$ is phenyl substituted with one or two R$^b$ groups. In certain embodiments, R$^b$ is selected from halogen, CN, OCH$_3$ or $C_1$-$C_4$ alkyl optionally substituted with halogen, OH, oxo, 5 or 6 membered heteroaryl or NR$^g$R$^h$.

In certain embodiments, $R^1$ is phenyl substituted with one or two R$^b$ groups. In certain embodiments, R$^b$ is selected from halogen, CN, OCH$_3$ or $C_1$-$C_4$ alkyl optionally substituted with halogen, OH, oxo, pyrazolyl or NR$^g$R$^h$.

In certain embodiments, $R^1$ is phenyl substituted with one R$^b$ group. In certain embodiments, R$^b$ is halogen. In certain embodiments, $R^1$ is phenyl substituted with F or Cl. In certain embodiments, $R^1$ is 2-fluorophenyl, 3-fluorophenyl, 3-chlorophenyl or 4-fluorophenyl.

In certain embodiments, $R^1$ is phenyl substituted with one R$^b$ group. In certain embodiments, R$^b$ is CN. In certain embodiments, $R^1$ is phenyl substituted with CN. In certain embodiments, $R^1$ is 3-cyanophenyl.

In certain embodiments, $R^1$ is phenyl substituted with one R$^b$ group. In certain embodiments, R$^b$ is OCH$_3$. In certain embodiments, $R^1$ is phenyl substituted with OCH$_3$. In certain embodiments, $R^1$ is 3-methoxyphenyl or 4-methoxyphenyl.

In certain embodiments, $R^1$ is phenyl substituted with one R$^b$ group. In certain embodiments, R$^b$ is $C_1$-$C_4$ alkyl. In certain embodiments, R$^b$ is isopropyl. In certain embodiments, $R^1$ is 3-isopropylphenyl.

In certain embodiments, $R^1$ is phenyl substituted with one R$^b$ group. In certain embodiments, R$^b$ is $C_1$-$C_4$ alkyl substituted with halogen. In certain embodiments, R$^b$ is $CF_3$. In certain embodiments, $R^1$ is 3-trifluoromethylphenyl.

In certain embodiments, $R^1$ is phenyl substituted with one R$^b$ group. In certain embodiments, R$^b$ is $C_1$-$C_4$ alkyl substituted with OH. In certain embodiments, R$^b$ is —CH$_2$OH. In certain embodiments, $R^1$ is 3-hydroxymethylphenyl or 4-hydroxymethylphenyl.

In certain embodiments, $R^1$ is phenyl substituted with one R$^b$ group. In certain embodiments, R$^b$ is $C_1$-$C_4$ alkyl substituted with a 5 or 6 membered heteroaryl. In certain embodiments, R$^b$ is $C_1$-$C_4$ alkyl substituted with pyrazolyl. In certain embodiments, R$^b$ is (1H-pyrazol-1-yl)methyl. In certain embodiments, $R^1$ is 4-((1H-pyrazol-1-yl)methyl)phenyl.

In certain embodiments, $R^1$ is phenyl substituted with one R$^b$ group. In certain embodiments, R$^b$ is $C_1$-$C_4$ alkyl substituted with NR$^g$R$^h$. In certain embodiments, R$^g$ and R$^h$ are methyl. In certain embodiments, R$^b$ is —CH$_2$N(CH$_3$)$_2$. In certain embodiments, $R^1$ is 3-(CH$_2$N(CH$_3$)$_2$)phenyl.

In certain embodiments, $R^1$ is phenyl substituted with one R$^b$ group. In certain embodiments, R$^b$ is $C_1$-$C_4$ alkyl substituted with oxo and NR$^g$R$^h$. In certain embodiments, R$^b$ is —C(=O)NR$^g$R$^h$. In certain embodiments, R$^g$ is methyl and $R^h$ is hydrogen. In certain embodiments, $R^h$ is —C(=O)NHCH$_3$ (N-methylformamide). In certain embodiments, $R^1$ is 4-(C(=O)NHCH$_3$)phenyl.

In certain embodiments, $R^1$ is phenyl substituted with one $R^h$ group. In certain embodiments, $R^h$ is $C_1$-$C_4$ alkyl substituted with oxo and NR$^g$R$^h$. In certain embodiments, $R^b$ is —CH$_2$C(=O)NR$^g$R$^h$. In certain embodiments, R$^g$ and R$^h$ are hydrogen. In certain embodiments, $R^b$ is —CH$_2$C(=O)NH$_2$. In certain embodiments, $R^1$ is 3-phenylacetamide (phenyl-CH$_2$C(=O)NH$_2$).

In certain embodiments, $R^1$ is phenyl substituted with one $R^h$ group. In certain embodiments, $R^h$ is $C_1$-$C_4$ alkyl substituted with oxo and NR$^g$R$^h$. In certain embodiments, R$^g$ and R$^h$ are hydrogen. In certain embodiments, $R^h$ is —C(=O)NH$_2$. In certain embodiments, $R^1$ is 3-(C(=O)NH$_2$)phenyl or 4-(C(=O)NH$_2$)phenyl.

In certain embodiments, $R^1$ is phenyl substituted with two $R^h$ group. In certain embodiments, $R^h$ is OCH$_3$. In certain embodiments, $R^1$ is phenyl disubstituted with OCH$_3$. In certain embodiments, $R^1$ is 3,4-dimethoxyphenyl.

In certain embodiments, $R^1$ is phenyl substituted with two $R^h$ group. In certain embodiments, $R^h$ is halogen. In certain embodiments, $R^1$ is phenyl disubstituted with F. In certain embodiments, $R^1$ is 3,5-difluorophenyl.

In certain embodiments, $R^1$ is phenyl substituted with two $R^h$ group. In certain embodiments, each $R^h$ is independently selected from halogen and OCH$_3$. In certain embodiments, $R^1$ is phenyl substituted with F and OCH$_3$. In certain embodiments, $R^1$ is 3-fluoro-5-methoxyphenyl.

In certain embodiments, $R^1$ is phenyl substituted by at least one $R^h$ group at the 3-phenyl position. In certain embodiments, each $R^h$ group is independently selected from halogen, CN, OCH$_3$ or $C_1$-$C_4$ alkyl optionally substituted with halogen, OH, oxo or NR$^g$R$^h$. In certain embodiments, $R^1$ is 3-fluorophenyl, 3-chlorophenyl, 3-isopropylphenyl, 3-methoxyphenyl, 3-cyanophenyl, 3-hydroxymethylphenyl, 3-trifluoromethylphenyl, 3-(CH$_2$N(CH$_3$)$_2$)phenyl, 3-(CH$_2$C(=O)NH$_2$)phenyl, or 3-(C(=O)NH$_2$)Phenyl.

In certain embodiments, $R^1$ is phenyl substituted by at least one $R^b$ group at the 4-phenyl position. In certain embodiments, each $R^b$ group is independently selected from halogen, OCH$_3$ or $C_1$-$C_4$ alkyl optionally substituted with OH, oxo, 5 or 6 membered heteroaryl or NR$^g$R$^h$.

In certain embodiments, each $R^b$ group is independently selected from halogen, OCH$_3$ or $C_1$-$C_4$ alkyl optionally substituted with OH, oxo, pyrazolyl or NR$^g$R$^h$. In certain embodiments, $R^1$ is 4-fluorophenyl, 4-methoxyphenyl, 4-hydroxymethylphenyl, 4-((1H-pyrazol-1-yl)methyl)phenyl or 4-(C(=O)NHCH$_3$)phenyl or 4-(C(=O)NH$_2$)phenyl.

In certain embodiments, $R^1$ is phenyl substituted by at least one $R^b$ group at the 2-phenyl position. In certain embodiments, $R^b$ is halogen. In certain embodiments, $R^1$ is 2-fluorophenyl.

In certain embodiments, $R^1$ is phenyl substituted with two $R^b$ groups. In certain embodiments, each $R^b$ is independently selected from halogen, CN, OCH$_3$ or $C_1$-$C_4$ alkyl optionally substituted with halogen, OH, oxo, 5 or 6 membered heteroaryl or NR$^g$R$^h$. In certain embodiments, each $R^b$ is independently selected from halogen, CN, OCH$_3$ or $C_1$-$C_4$ alkyl optionally substituted with halogen, OH, oxo, pyrazolyl or NR$^g$R$^h$.

In certain embodiments, $R^1$ is phenyl substituted with two $R^b$ groups at the 3 and 4 positions. In certain embodiments, each $R^b$ is OCH$_3$. In certain embodiments, $R^1$ is 3,4-dimethoxyphenyl.

In certain embodiments, $R^1$ is phenyl substituted with two $R^b$ groups at the 3 and 5 positions. In certain embodiments, each $R^b$ is independently selected from halogen or OCH$_3$. In certain embodiments, $R^1$ is 3,5-difluorophenyl or 3-fluoro-5-methoxyphenyl.

In certain embodiments, $R^1$ is hydrogen, provided that when $R^1$ is hydrogen, then $R^2$ is —NHC(=O)R$^f$.

In certain embodiments, $R^2$ is hydrogen.

In certain embodiments, $R^2$ is CH$_3$.

In certain embodiments, $R^2$ is —NHC(=O)R$^f$. In certain embodiments, $R^f$ is $C_1$-$C_4$ alkyl optionally substituted with OH, a 5 or 6 membered heterocycle optionally substituted with one or two groups selected from oxo, halogen, CN, CF$_3$ or $C_1$-$C_3$ alkyl, or a 5 or 6 membered heteroaryl optionally substituted with one or two groups selected from halogen, CN, CF$_3$ or $C_1$-$C_3$ alkyl.

In certain embodiments, $R^f$ is $C_1$-$C_4$ alkyl. In certain embodiments, $R^f$ is methyl or propyl. In certain embodiments, $R^2$ is —NHC(=O)CH$_3$ or —NHC(=O)CH$_2$CH$_2$CH$_3$.

In certain embodiments, $R^f$ is $C_1$-$C_4$ alkyl substituted with OH. In certain embodiments, $R^f$ is hydroxymethyl. In certain embodiments, $R^2$ is —NHC(=O)CH$_2$OH.

In certain embodiments, $R^f$ is a 5 or 6 membered heterocycle optionally substituted with one or two groups selected from oxo, halogen, CN, CF$_3$ or $C_1$-$C_3$ alkyl.

In certain embodiments, $R^f$ is a 5 or 6 membered heteroaryl. In certain embodiments, $R^f$ is pyridinyl. In certain embodiments, $R^2$ is nicotinamide (—NHC(=O)-pyridin-3-yl).

In certain embodiments, $R^f$ is a 5 or 6 membered heteroaryl. In certain embodiments, $R^f$ is pyridinyl. In certain embodiments, $R^2$ is selected from nicotinamide and 1H-pyrazole-4-carboxamide.

In certain embodiments, $R^f$ is a 5 or 6 membered heteroaryl optionally substituted with one or two groups selected from halogen, CN, CF$_3$ or $C_1$-$C_3$ alkyl.

In certain embodiments, $R^f$ is a 5 or 6 membered heteroaryl optionally substituted with one or two groups selected from halogen, CN, CF$_3$ or $C_1$-$C_3$ alkyl. In certain embodiments, $R^2$ is selected from 5-chloronicotinamide and 5-methylnicotinamide.

In certain embodiments, $R^3$ is hydrogen.

In certain embodiments, m is 0 or 1. In certain embodiments, m is 0. In certain embodiments, m is 1.

In certain embodiments, $R^4$ is a halogen. In a further embodiment, $R^4$ is Cl.

In certain embodiments, n is 0 or 1. In certain embodiments, n is 0. In certain embodiments, n is 1.

In certain embodiments, p is 0 or 1. In certain embodiments, p is 0. In certain embodiments, p is 1.

In certain embodiments, $R^5$ and $R^6$ are independently selected from hydrogen or CH$_3$. In certain embodiments, $R^5$ and $R^6$ are hydrogen. In certain embodiments, $R^5$ and $R^6$ are CH$_3$.

In certain embodiments, $R^7$ and $R^8$ are independently selected from hydrogen or $C_1$-$C_6$ alkyl.

In certain embodiments, $R^7$ is hydrogen.

In certain embodiments, $R^8$ is hydrogen.

In certain embodiments, $R^7$ and $R^8$ are hydrogen.

In certain embodiments, $R^7$ is $C_1$-$C_6$ alkyl. In a further embodiment, $R^7$ is a $C_3$ alkyl. In a further embodiment, $R^7$ is an isopropyl group. In certain embodiments, $R^8$ is hydrogen or methyl.

In certain embodiments, $R^8$ is methyl.

In certain embodiments, $R^2$ is isopropyl and $R^8$ is methyl.

In certain embodiments, $R^5$ is hydrogen, $R^6$ and $R^2$ together with the atoms to which they are attached form an optionally substituted 5-6 membered heterocyclic ring having one ring nitrogen atom, and $R^8$ is selected from the group consisting of hydrogen or $C_1$-$C_4$ alkyl optionally substituted with OH or $O(C_1$-$C_3$ alkyl) such that the compound of Formula I has the structure of Formula II:

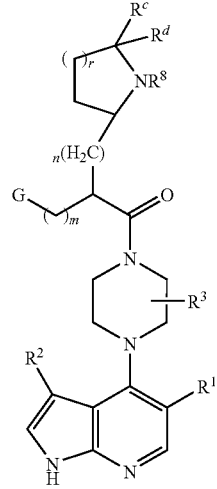

II wherein $R^1$, $R^2$, $R^3$, $R^c$, $R^d$, G, m, n and r are as defined herein.

In certain embodiments, r is 1 (having the structure of Formula IIa):

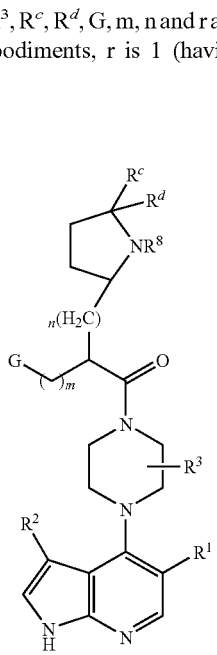

IIa wherein $R^1$, $R^2$, $R^3$, $R^c$, $R^d$, G, m and n are as defined herein.

In certain embodiments of Formula IIa, n is 0.
In certain embodiments of Formula IIa, $R^c$ is hydrogen.
In certain embodiments of Formula IIa, $R^d$ is hydrogen.
In certain embodiments of Formula IIa, $R^c$ and $R^d$ are both hydrogen.
In certain embodiments of Formula IIa, $R^c$ is methyl.
In certain embodiments of Formula IIa, $R^d$ is methyl.
In certain embodiments of Formula IIa, $R^c$ and $R^d$ are both methyl.
In certain embodiments of Formula IIa, $R^8$ is H.
In certain embodiments of Formula IIa, $R^8$ is methyl.
In certain embodiments, n is 0 and r is 1 (having the structure of Formula IIa1):

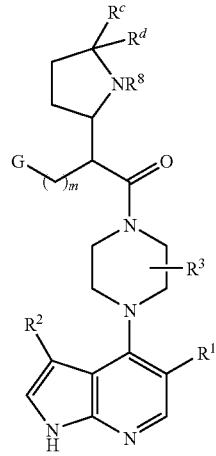

IIa1 wherein $R^1$, $R^2$, $R^3$, $R^c$, $R^d$, G and m are as defined herein.

In certain embodiments, r is 2 (having the structure of Formula IIb):

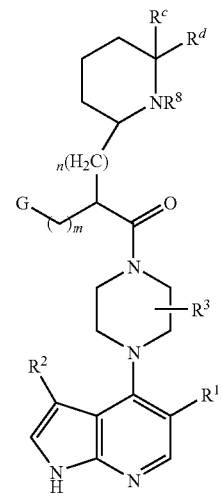

IIb wherein $R^1$, $R^2$, $R^3$, $R^c$, $R^d$, G, m and n are as defined herein.

In certain embodiments, n is 0 and r is 2 (having the structure of Formula IIb1):

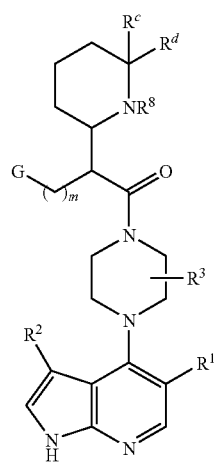

IIb1 wherein $R^1$, $R^2$, $R^3$, $R^c$, $R^d$, G and m are as defined herein.

In certain embodiments, Formula I has the structure of Formula III:

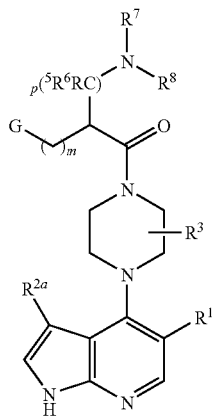

III wherein $R^{2a}$ is H or methyl, and $R^1$, $R^3$, $R^5$, $R^6$, $R^7$, $R^8$, G, m and p are as defined herein.

In certain embodiments, Formula I has the structure of Formula IV:

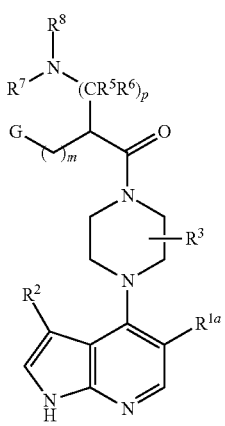

IV wherein $R^{1a}$ is halogen or $C_1$-$C_4$ alkyl optionally substituted with halogen (for example $CF_3$), and $R^2$, $R^3$, $R^5$, $R^6$, $R^7$, $R^8$, G, m and p are as defined herein.

In certain embodiments, m is 0 and G is $G^1$, such that the compounds of Formula I have the structure of Formula V:

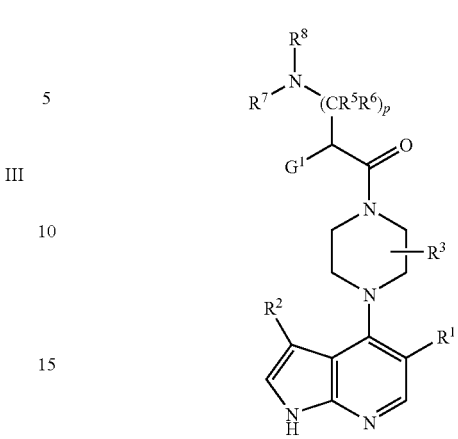

V wherein $G^1$ is absent or $C_1$-$C_4$ alkyl, and $R^1$, $R^2$, $R^3$, $R^5$, $R^6$, $R^7$, $R^8$ and p are as defined herein.

In certain embodiments of Formula V, $G^1$ is absent.
In certain embodiments of Formula V, $G^1$ is $C_1$-$C_4$ alkyl.
In certain embodiments of Formula V, $G^1$ is isopropyl.
In certain embodiments, m and n are 0, $R^5$ is hydrogen, $R^6$ and $R^7$ together with the atoms to which they are attached form an optionally substituted 5-6 membered heterocyclic ring having one ring nitrogen atom, $R^8$ is selected from the group consisting of hydrogen or $C_1$-$C_4$ alkyl optionally substituted with OH or O($C_1$-$C_3$ alkyl) and G is $G^1$, such that the compounds of Formula I have the structure of Formula VI:

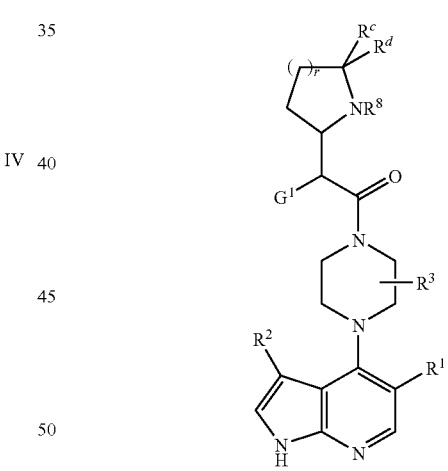

VI wherein $G^1$ is absent or $C_1$-$C_4$ alkyl, and $R^1$, $R^2$, $R^3$, $R^c$, $R^d$ and r are as defined herein.

In certain embodiments of Formula VI, $G^1$ is absent.
In certain embodiments of Formula VI, $G^1$ is $C_1$-$C_4$ alkyl.
In certain embodiments of Formula VI, $G^1$ is isopropyl.
In certain embodiments of Formula VI, r is 1.
In certain embodiments of Formula VI, r is 2.
In certain embodiments of Formula VI, $R^8$ is selected from the group consisting of hydrogen or $C_1$-$C_4$ alkyl optionally substituted with OH or O($C_1$-$C_3$ alkyl).
In certain embodiments of Formula VI, $R^c$ is hydrogen or $C_1$-$C_4$ alkyl.
In certain embodiments of Formula VI, $R^d$ is hydrogen or $C_1$-$C_4$ alkyl.

In certain embodiments, m and n are 0, $R^5$ is hydrogen, $R^6$ and $R^7$ together with the atoms to which they are attached form an optionally substituted 5 membered heterocyclic ring having one ring nitrogen atom, $R^8$ is selected from the group consisting of hydrogen or $C_1$-$C_4$ alkyl optionally substituted with OH or O($C_1$-$C_3$ alkyl) and G is $G^1$, such that the compounds of Formula I have the structure of Formula VIa:

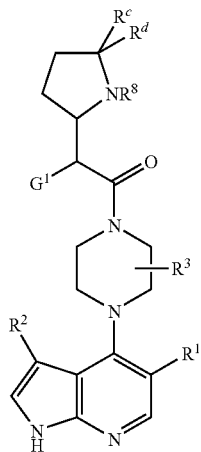

VIa wherein $G^1$ is absent or $C_1$-$C_4$ alkyl, and $R^1$, $R^2$, $R^3$, $R^c$, and $R^d$ are as defined herein.

In certain embodiments, m and n are 0, $R^5$ is hydrogen, $R^6$ and $R^7$ together with the atoms to which they are attached form an optionally substituted 6 membered heterocyclic ring having one ring nitrogen atom, $R^8$ is selected from the group consisting of hydrogen or $C_1$-$C_4$ alkyl optionally substituted with OH or O($C_1$-$C_3$ alkyl) and G is $G^1$, such that the compounds of Formula I have the structure of Formula VIb:

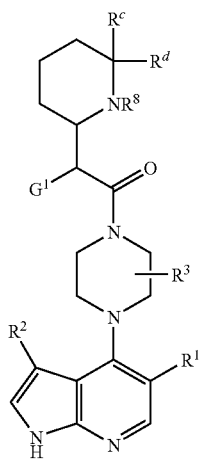

VIb wherein $G^1$ is absent or $C_1$-$C_4$ alkyl, and $R^1$, $R^2$, $R^3$, $R^8$, $R^c$, and $R^d$ are as defined herein.

It will be appreciated that certain compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

It will be further appreciated that the compounds of the present invention may exist in unsolvated as well as solvated forms with pharmaceutically acceptable solvents such as water, ethanol, and the like, and it is intended that the invention embrace both solvated and unsolvated forms.

Synthesis of Compounds

Compounds of the present invention may be synthesized by synthetic routes that include processes analogous to those well-known in the chemical arts, particularly in light of the description contained herein. The starting materials are generally available from commercial sources such as Sigma-Aldrich (St. Louis, Mo.), Alfa Aesar (Ward Hill, Mass.), or TCI (Portland, Oreg.), or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the Beilstein online database)).

For illustrative purposes, Schemes 1-6 and Schemes A-H shows a general method for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme 1

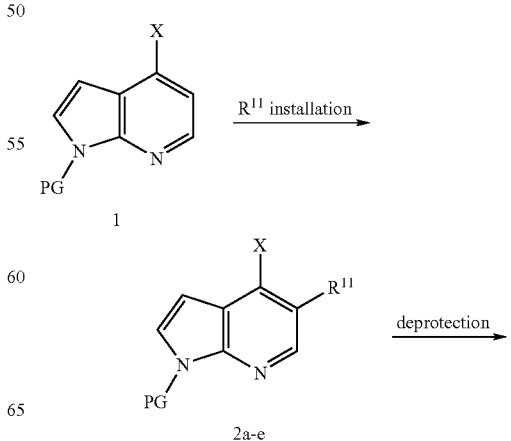

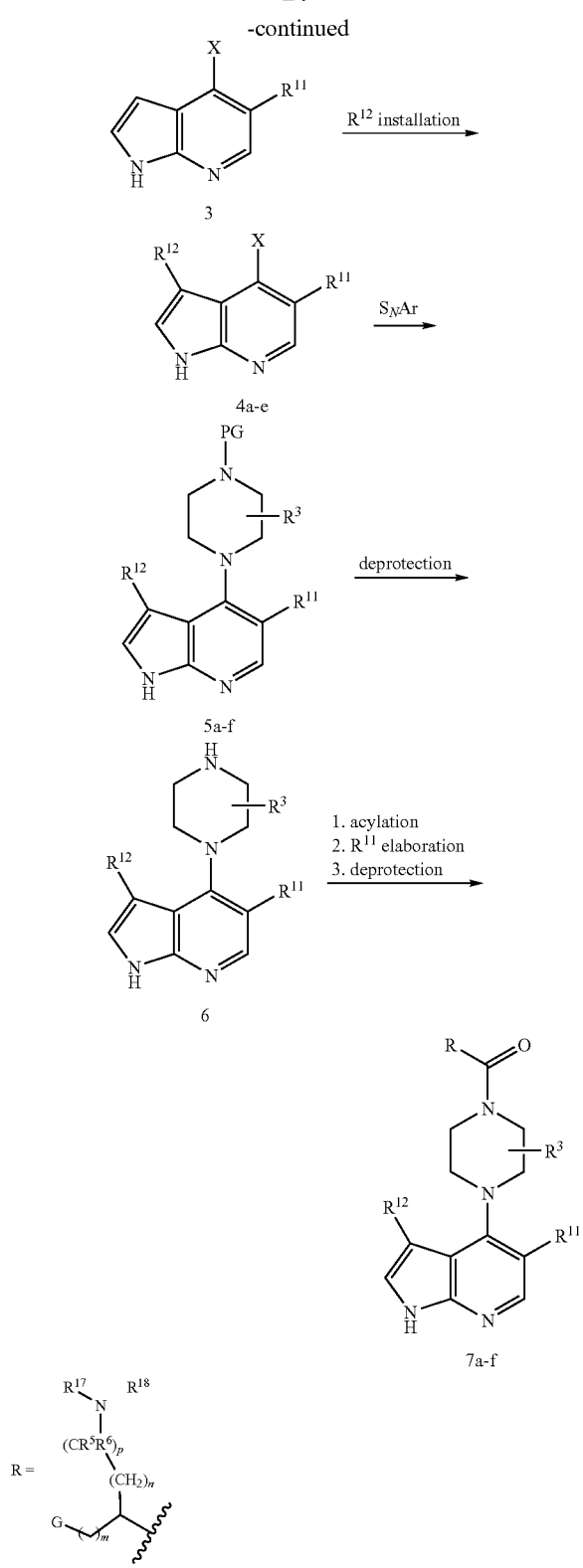

stituted with one or two $R^b$ groups, —OR% or —C(=O)OR$^j$, R$^r$ is aryl optionally substituted with one or two R$^b$ groups, heteroaryl, C$_3$-C$_8$ cycloalkyl, a 5-7 membered heterocycle or C$_1$-C$_6$ alkyl optionally substituted with OH or a 5 or 6 membered heterocycle, IV is H, NH$_2$ or C$_1$-C$_6$ alkyl; R$^{12}$ is W—Y or —NHC(=O)R$^u$ (both defined in Scheme 3) and R$^3$ and R$^b$ are as defined herein. Preparation of compound 1, wherein PG is a protecting group and X is a halogen, can be carried out as described in the literature (L'Heureux, Alexandre, et al., "Synthesis of functionalized 7-azaindoles via directed orthomatalations." Tetrahedron Lett. 45 (2004) 2317-2319 and Thibault, Carl, et al., "Concise and efficient synthesis of 4-fluoro-1H-pyrrolo[2,3-b]pyridine." Organic Letters 5, (2003), 5023-5025). Functionalization of compound 1 to install R$^{11}$ can be carried out via lithiation under standard conditions (e.g., s-BuLi in an appropriate solvent such as tetrahydrofuran, "THF") and trapping with a suitable electrophile (CBr$_4$, (1R)-(−)-(10-camphorsulfonyl)oxaziridine, methylchloroformate, etc., as detailed in Scheme 2) to give compound 2. Removal of the protecting group under standard conditions (for example, tetra-N-butylammonium fluoride, ("TBAF") to remove a silyl group) provides compound 3. Installation of the R$^{12}$ group can be carried out on compound 3 as described in Scheme 3 to give 4. Compound 5 is obtained by reacting compound 4 with an appropriately substituted piperazine under standard S$_N$Ar reaction conditions. Further elaboration of 5 can be carried out as necessary as shown in Scheme 4. Compound 5 is then deprotected to yield compound 6. Acylation of 6 with an appropriate acid in the presence of a coupling reagent (such as 2-(1H-benzotriazole-1-yl)-1,1,3,3-tetramethyluronium hexafluorophosphate, "HBTU"), followed by elaboration of R$^1$ (as detailed in Scheme 5) and deprotection (if necessary), gives compound 7 of Formula I, wherein R$^{17}$ and R$^{18}$ are independently selected from hydrogen; C$_1$-C$_6$ alkyl optionally substituted with halogen, oxo, OH, OCH$_3$, CF$_3$, NH$_2$, NH(C$_1$-C$_6$ alkyl), N(C$_1$-C$_6$ alkyl)$_2$, C$_3$-C$_6$ cycloalkyl, a 4-6 membered heterocycle, C$_4$-C$_6$ aryl, a 5-6 membered heteroaryl and the cycloalkyl, heterocycle, aryl and heteroaryl are further optionally substituted with one to three substituents selected from halogen, C$_1$-C$_3$ alkyl, OH, O(C$_1$-C$_3$ alkyl), CF$_3$, CN, cyclopropylmethyl or oxo (only on the cycloalkyl or heterocycle); —O—(C$_1$-C$_6$ alkyl) wherein the alkyl is optionally substituted with halogen, oxo, OH, O(C$_1$-C$_3$ alkyl), CF$_3$, NH$_2$, NH(C$_1$-C$_6$ alkyl), N(C$_1$-C$_6$ alkyl)$_2$, C$_3$-C$_6$ cycloalkyl, a 4-6 membered heterocycle, C$_4$-C$_6$ aryl, a 5-6 membered heteroaryl and the cycloalkyl, heterocycle, aryl and heteroaryl are further optionally substituted with one to three substituents selected from halogen, C$_1$-C$_3$ alkyl, OH, O(C$_1$-C$_3$ alkyl), CF$_3$, CN, cyclopropylmethyl or oxo (only on the cycloalkyl or heterocycle); C$_3$-C$_6$ cycloalkyl, a 4-6 membered heterocycle, C$_4$-C$_6$ aryl, a 5-6 membered heteroaryl, wherein the cycloalkyl, heterocycle, aryl and heteroaryl are further optionally substituted with one to three substituents selected from halogen, C$_1$-C$_3$ alkyl, OH, O(C$_1$-C$_3$ alkyl), CF$_3$, CN, NH$_2$, NH(C$_1$-C$_6$ alkyl), N(C$_1$-C$_6$ alkyl)$_2$, cyclopropyl, cyclopropylmethyl or oxo (only on the cycloalkyl or heterocycle); or —CH(CH$_3$)CH(OH)phenyl; and R$^5$, R$^6$, G, m, n and p are as defined above.

Scheme 1 shows a method of preparing compound 7 of Formula I, wherein R$^{11}$ is hydrogen, halogen, CN, alkyl optionally substituted with halogen, aryl optionally substituted with one or two R$^b$ groups, heteroaryl optionally sub- In another embodiment of the present invention, a process for preparing compounds of Formula I is provided, comprising:

(a) acylation of a compound of Formula 6:

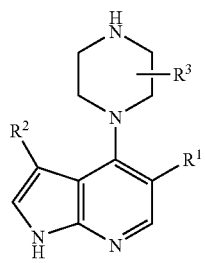

wherein $R^1$ is selected from hydrogen, halogen, CN, $C_1$-$C_4$ alkyl optionally substituted with halogen, —C(=O)O$R^a$, —O$R^e$, $C_3$-$C_6$ cycloalkyl, 5 or 6 membered heteroaryl, phenyl or —O-phenyl, wherein the heteroaryl, phenyl or —O-phenyl may be optionally substituted with one or two $R^b$ groups;

$R^2$ is selected from hydrogen, $CH_3$, or —NHC(=O)$R^f$, provided that when $R^1$ is hydrogen, $R^2$ is —NHC(=O)$R^f$;

$R^3$ is selected from H or $C_1$-$C_3$ alkyl;

$R^a$ is $C_1$-$C_4$ alkyl;

each $R^b$ group is independently selected from halogen, CN, $OCH_3$ or $C_1$-$C_4$ alkyl optionally substituted with halogen, OH, oxo, 5 or 6 membered heteroaryl or $NR^gR^h$;

$R^e$ is $C_1$-$C_4$ alkyl optionally substituted with OH or a 5 or 6 membered heterocycle;

$R^f$ is $C_1$-$C_4$ alkyl optionally substituted with OH, a 5 or 6 membered heterocycle optionally substituted with one or two groups selected from oxo, halogen, CN, $CF_3$ or $C_1$-$C_3$ alkyl or a 5 or 6 membered heteroaryl optionally substituted with one or two groups selected from halogen, CN, $CF_3$ or $C_1$-$C_3$ alkyl; and $R^g$ and $R^h$ are independently hydrogen or $C_1$-$C_4$ alkyl; with a compound of Formula A:

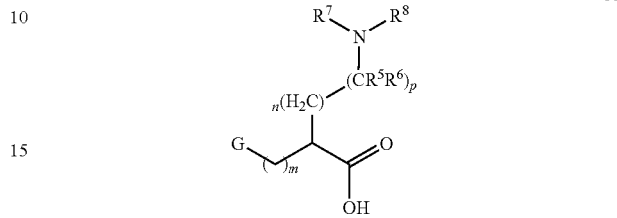

wherein G is cyclohexyl or phenyl optionally substituted by 1-3 independent $R^4$ groups, or when m is 0, G may additionally be absent or $C_1$-$C_4$ alkyl;

each $R^4$ is independently selected from halogen, $CF_3$, $OCF_3$ and CN;

$R^5$ and $R^6$ are independently selected from hydrogen or $CH_3$;

$R^7$ and $R^8$ are independently selected from hydrogen or $C_1$-$C_6$ alkyl;

m, n and p are independently 0 or 1; in the presence of a coupling reagent;

(b) followed by optional elaboration of $R^1$; and (c) followed by optional deprotection provides compounds of Formula I.

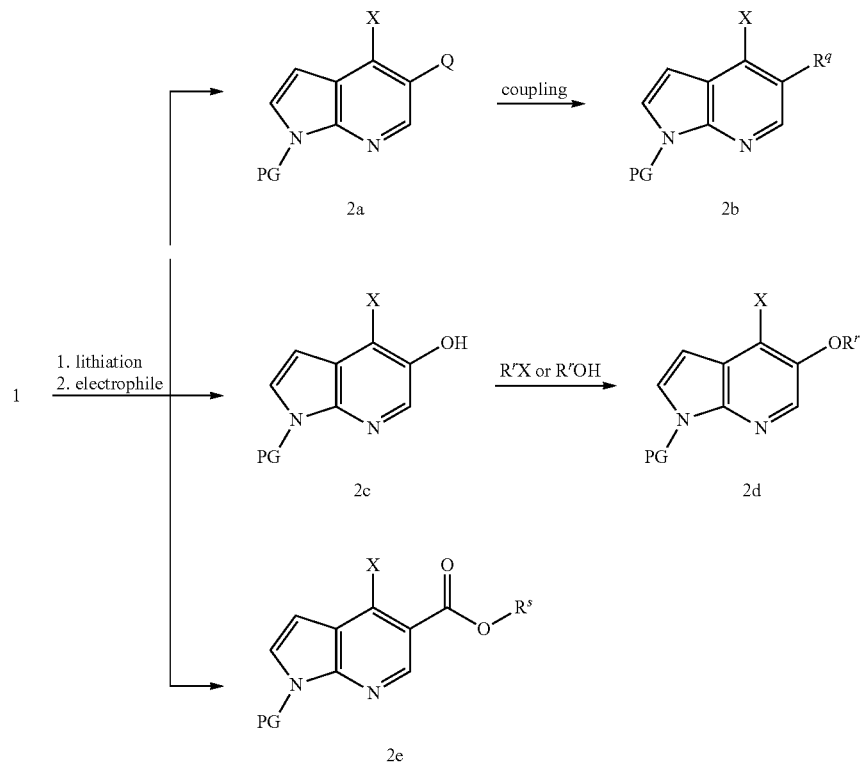

Scheme 2

Scheme 2 shows a method of preparing compounds 2a, 2b, 2c, 2d and 2e, wherein $R^s$ is $C_1$-$C_6$ alkyl, $R^q$ is alkyl, aryl or a 5-7 membered heteroaryl, $R^r$ is $C_1$-$C_6$ alkyl, aryl, heteroaryl, $C_3$-$C_8$ cycloalkyl, 5-7 membered heterocycle, etc., Q is a halogen and X and PG are as described in Scheme 1. As described in Scheme 1, lithiation of compound 1 and reaction with the appropriate electrophile gives compounds 2a, 2c or 2e. Further elaboration of 2a can be carried out using an appropriate coupling reaction (such as, but not limited to, a Suzuki or Negishi coupling) to give compound 2b. Compound 2c can also be transformed to compound 2d using a substitution reaction with an appropriate alkyl halide or a Mitsunobu reaction with an appropriate alcohol.

cycloalkyl, aryl, heterocycle or heteroaryl may be optionally substituted with one to three substituents selected from halogen, OH, $C_1$-$C_3$ alkyl, $CF_3$, CN or oxo (only on the alkyl, alkenyl, cycloalkyl or heterocycle). Alternatively, compound 3 may be converted to a 3-formyl-pyrrolo[2,3-b]pyridine as described in Bioorganic & Medicinal Chemistry, 12(21), 5505-5513 (2004), wherein the formyl substitution can be further elaborated to $R^t$ by a variety of substitution reactions, such as, Wittig, Horner-Emmons or Emmons-Wadsworth. Additionally, compound 4d, appropriately protected on pyrrole nitrogen, could be converted to 4b where $R^t$ is NHY by reductive amination, alkylation or transition metal mediated coupling. Choice of reaction condition will depend on the nature of Y.

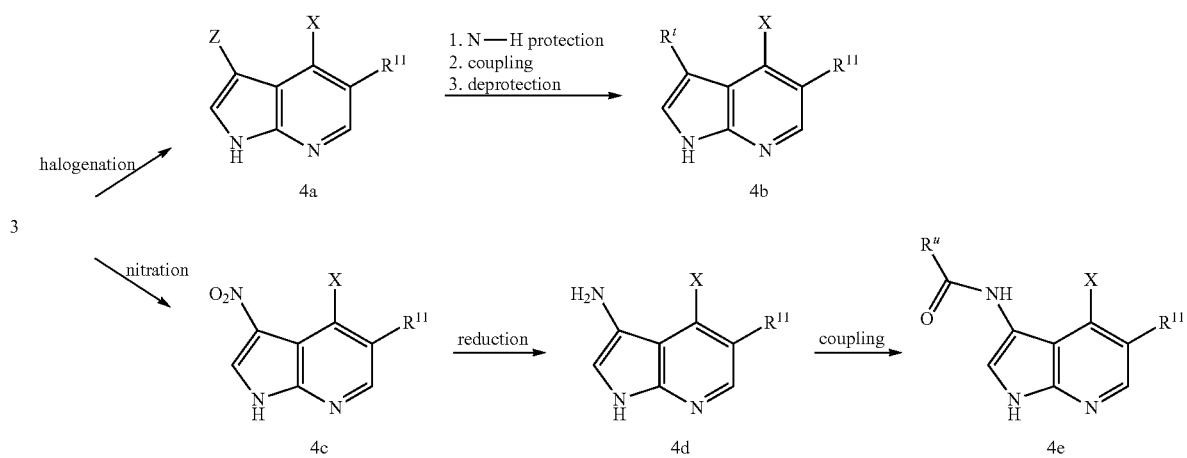

Scheme 3

Scheme 3 shows a method for installation of the $R^{12}$ group to provide compounds 4a-e. Halogenation of compound 3 of Scheme 1 under standard conditions gives compound 4a, wherein Z is a halogen and $R^{11}$ and X are as defined in Scheme 1. Compound 4a can be converted to compound 4b, wherein $R^t$ is W—Y, and W is O, $CH_2$, NH or a direct bond to Y and Y is $C_1$-$C_6$ alkyl, $C_1$-$C_6$ alkenyl (wherein when Y is alkenyl, W is a direct bond to Y), $C_3$-$C_6$ cycloalkyl, aryl, a 5 or 6 membered heterocycle or a 5 or 6 membered heteroaryl, wherein the aryl, heterocycle or heteroaryl may be further optionally substituted with one to three substituents selected from halogen, OH, $CF_3$, CN or oxo (only on the heterocycle), and the alkyl, alkenyl and cycloalkyl may be optionally substituted with one to three substitutents selected from halogen, OH, $CF_3$, CN, oxo, aryl, heterocycle or heteroaryl; by protecting the pyrrole N—H followed by a suitable coupling reaction. These coupling reactions include, but are not limited to, Negishi, Heck, Suzuki or a variety of transition metal mediated coupling methods including Cu, Pd and Ni, which can be used to install a variety of $R^t$ groups. Specific coupling procedures are detailed in the Examples section. Deprotection then gives compound 4b. Nitration of compound 3 can also be carried out to give compound 4c, which can then be reduced to the amine 4d. Coupling of amine 4d with an appropriate acid or acid chloride gives compound 4e, wherein $R^u$ is a $C_1$-$C_6$ alkyl, aryl, heteroaryl, $C_3$-$C_8$ carbocycle, 5-7 membered heterocycle, etc, wherein the alkyl, alkenyl,

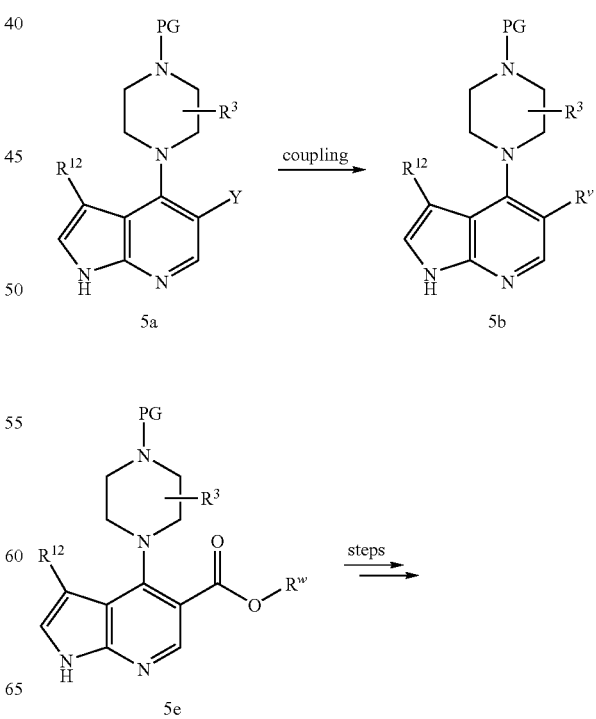

Scheme 4

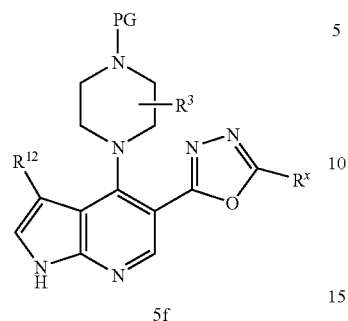

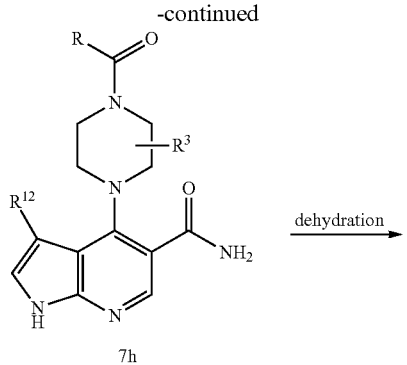

Scheme 4 shows a method for elaboration of compound 5 of Scheme 1. Compound 5a, wherein Y is a halogen and $R^{12}$, $R^3$ and PG are as defined in Scheme 1, can be converted to compound 5b, wherein $R^v$=aryl or heteroaryl, using a procedure similar to that for the conversion of 2a to 2b as described in Scheme 2. Alternatively, compound 5e, wherein $R^w$ is $CH_3$, can be elaborated to compound 5f, wherein $R^x$ is a $C_1$-$C_6$ alkyl, using the procedures detailed in the Examples section.

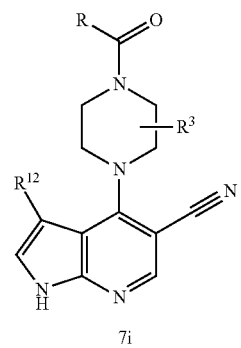

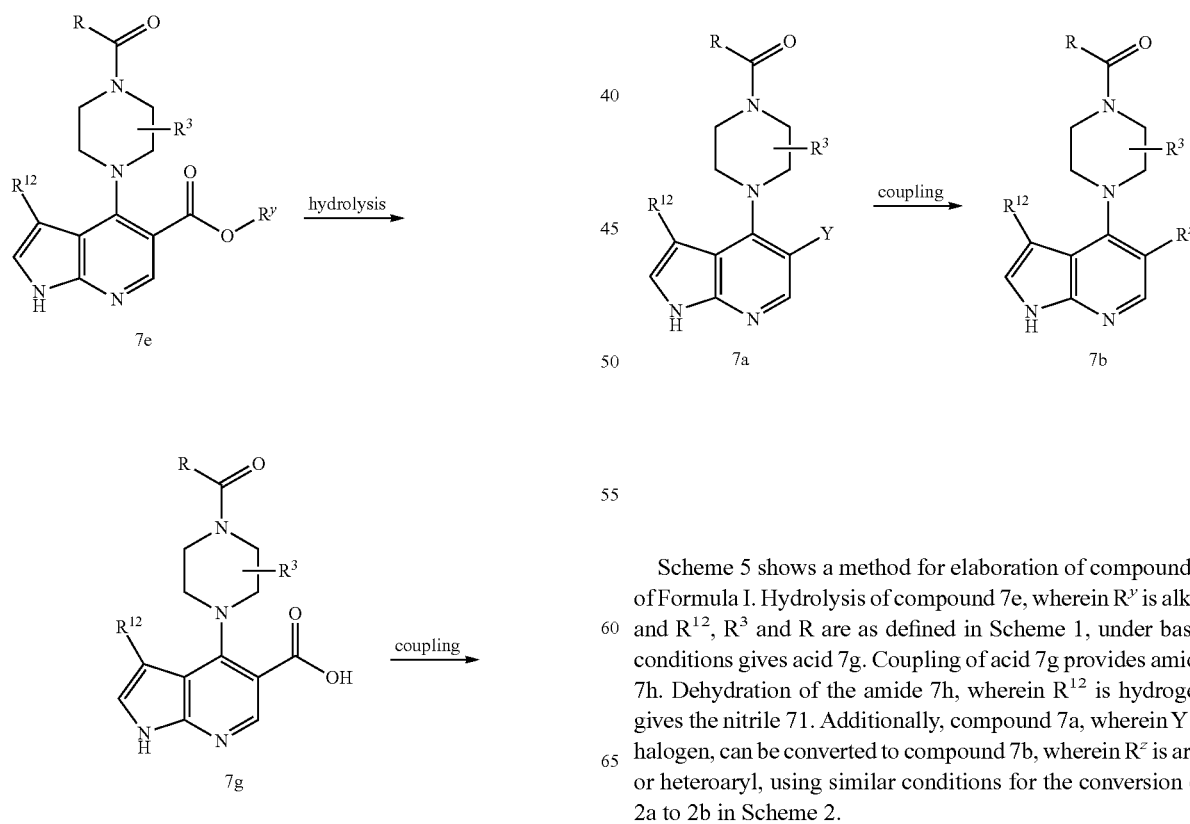

Scheme 5 shows a method for elaboration of compound 7 of Formula I. Hydrolysis of compound 7e, wherein $R^y$ is alkyl and $R^{12}$, $R^3$ and R are as defined in Scheme 1, under basic conditions gives acid 7g. Coupling of acid 7g provides amide 7h. Dehydration of the amide 7h, wherein $R^{12}$ is hydrogen gives the nitrile 7l. Additionally, compound 7a, wherein Y is halogen, can be converted to compound 7b, wherein $R^z$ is aryl or heteroaryl, using similar conditions for the conversion of 2a to 2b in Scheme 2.

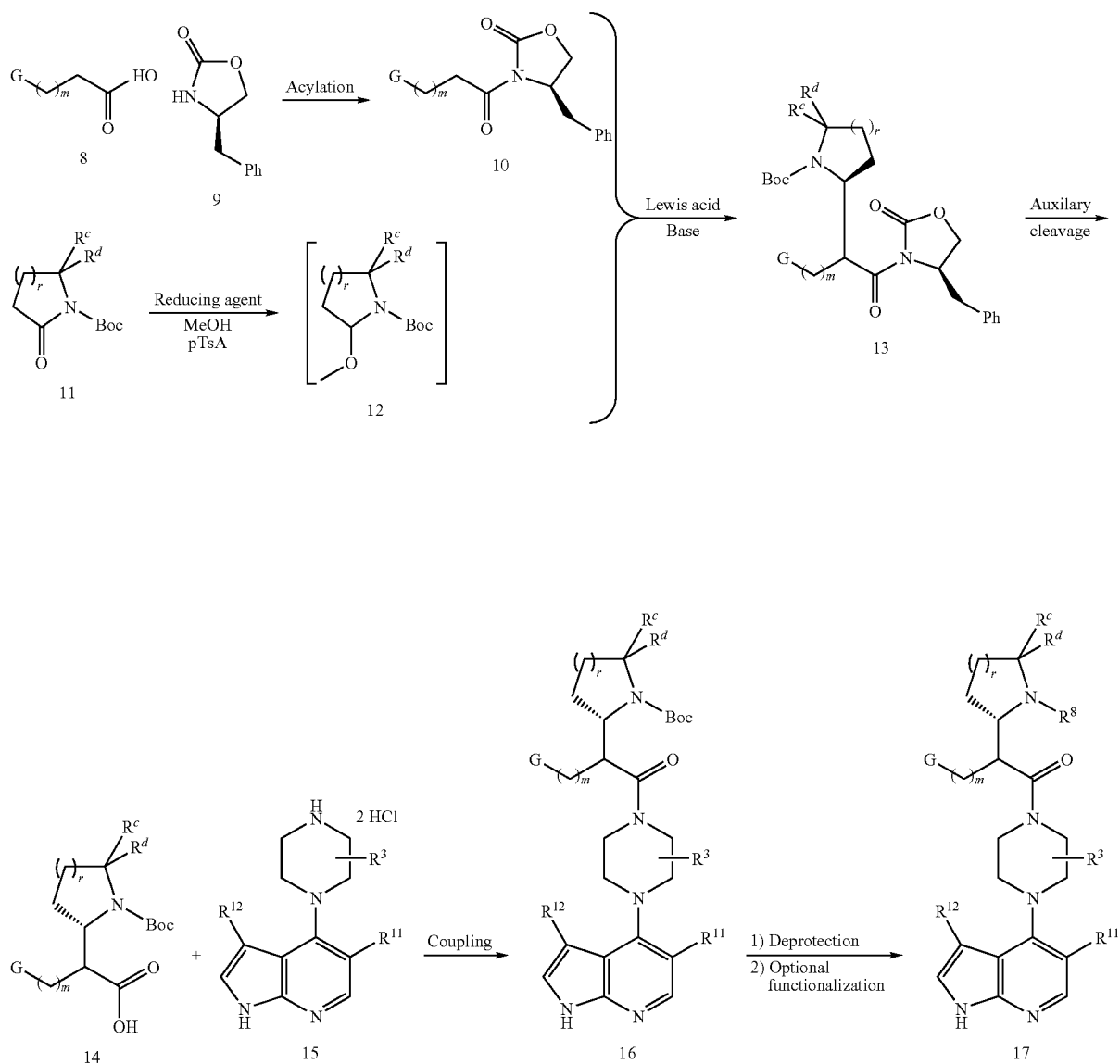

Scheme 6 shows a method of preparing compound 17. Condensation of an appropriately substituted phenyl acetic acid 8, wherein G and m are as defined herein, with a chiral auxiliary (e.g. an Evans' oxazolidinone 9) can be performed using an acid chloride, such as pivaloyl chloride, as activating agent in the presence of a tertiary amine base, such as Hunig's base. Reduction of lactam 11, wherein $R^c$, $R^d$ and r are as defined herein, with a reducing agent (for example, diisobutylaluminium hydride ("DIBAL-H") at −78° C. to 25° C.), and quenching with methanol and in the presence of an acid such as pTsOH produces the intermediate methoxyheterocycle 12. Condensation of 10 and 12 can be accomplished using an appropriate Lewis acid and a mild base (e.g., titanium tetrachloride and diisopropylethylamine) to form a 2-substituted heterocycle 13. This reaction may need to be carried out at low temperature (e.g., −100° C. to 0° C.) to obtain acceptable diastereoselectivity in the reaction. Hydrolysis of the chiral auxiliary using a base (e.g., LiOH, $H_2O_2$) at 0° C. to 50° C. produces the carboxylic acid 14. A fully elaborated analog can be synthesized by coupling an acid 14 to the piperazine intermediate 15, wherein $R^{11}$, $R^{12}$ and $R^3$ are as defined herein, using peptide bond forming conditions (e.g. HBTU and, N,N-diisopropylethylamine ("DIEA") at 0° C. to 50° C.). Deprotection of compound 16 using anhydrous acid (e.g., HCl in dioxane) produces the free amine. If desired, reductive amination of this amine (using an aldehyde and reducing agent (e.g., $NaBH(OAc)_3$), or alkylation under standard conditions allows the preparation of the tertiary amine 17, wherein $R^8$ is as defined herein.

The amino acids used in the synthesis of compounds of the present invention as illustrated in Schemes 1-6 and in the Examples are either commercially available or may be prepared according to the methods disclosed herein. For example, in certain embodiments the amino acids used to prepare compounds of Formula I include β-phenylglycine amino acids having the Formula 1A, γ-phenylglycine amino acids having the Formula 2A, β-phenylalanine amino acids having the Formula 3A, and γ-phenylalanine amino acids having the Formula 4A.
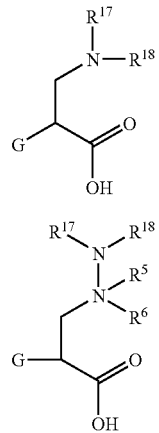
1A
2A
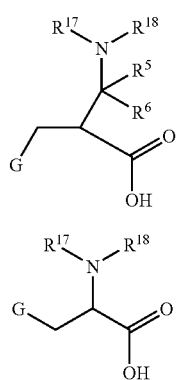
3A
4A
wherein $R^{17}$, $R^{18}$, G, $R^5$ and $R^6$ are as defined above.
Methods of preparing amino acids of Formulas 1A-4A are shown in Schemes A-H.
Scheme A
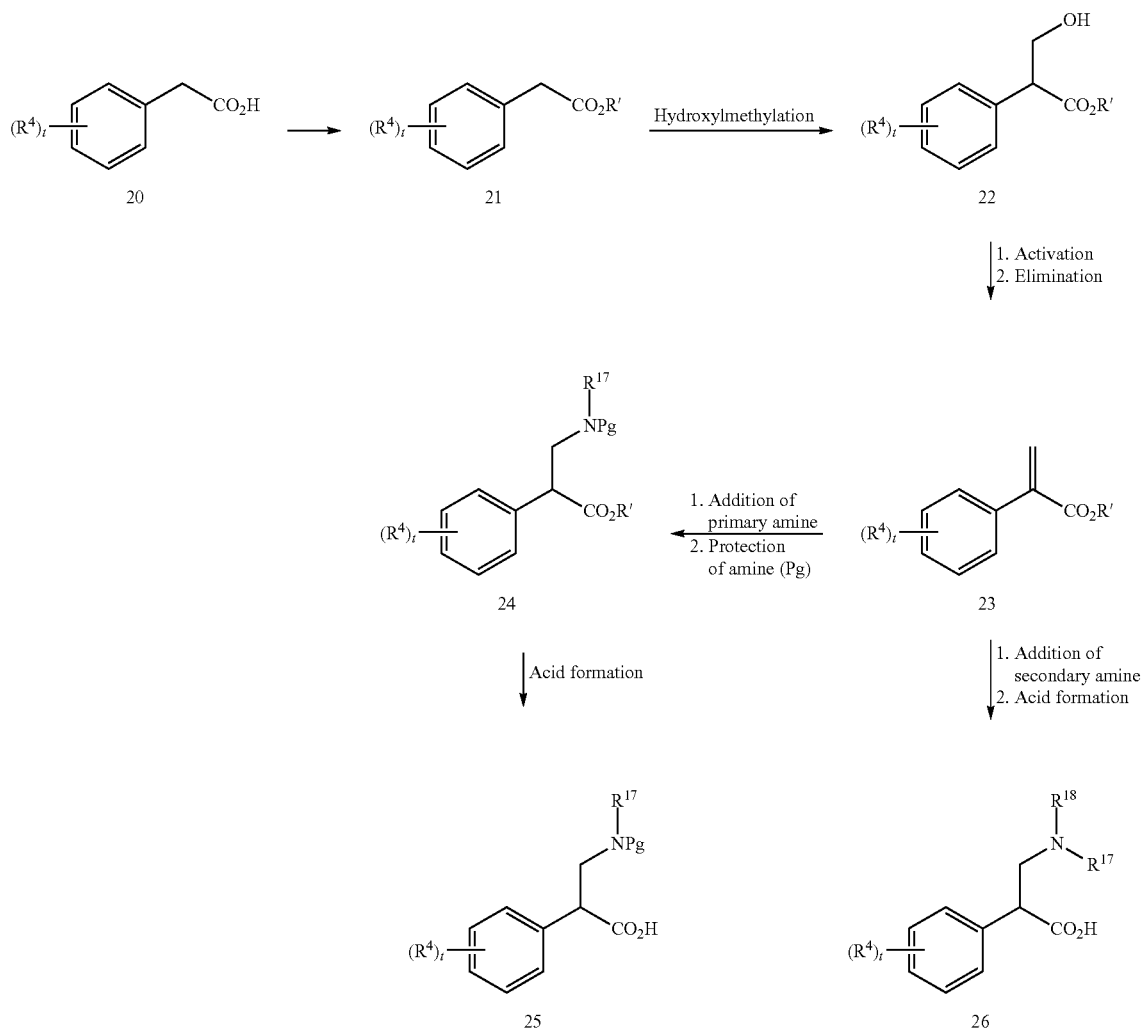

Scheme A illustrates a method of preparing optionally substituted β-phenylglycine amino acids 25 and 26 of the Formula 1A, wherein t is 0 to 3, PG is an amine protecting group, $R^{17}$, $R^{18}$ and $R^4$ are as defined above. According to Scheme A, the acid 20 is converted to an ester 21, wherein R' is $C_1$-$C_6$ alkyl, using standard conditions such as treatment with an appropriate alcohol (e.g., MeOH) in the presence of a catalytic amount of an acid such as concentrated $H_2SO_4$ or a coupling agent such as dicyclohexylcarbodiimide ("DCC")/ 4-dimethylaminopyridine ("DMAP"); or alternatively by treatment with an appropriate electrophile (e.g., MeI, EtBr, BnBr) in the presence of a base such as $NEt_3$/DMAP at an appropriate temperature (e.g., −20° C. to 100° C.). The appropriate choice of ester is determined by the conditions required to reform the acid at the end of the synthesis, with many appropriate examples and conditions being listed in 'Protective Groups in Organic Synthesis' by Greene and Wuts, Wiley-Interscience, third edition, Chapter 5. Introduction of the hydroxymethyl group to provide compound 22 may be performed by treatment with an appropriate aldehyde (e.g., formaldehyde) in the presence of base such as NaOEt at an appropriate temperature (e.g., −20° C. to room temperature). Activation of the alcohol group of compound 22 to form a leaving group (e.g., a mesylate, tosylate, halide) may be accomplished by treatment with, for example, methanesulphonyl chloride in the presence of excess base such as $NEt_3$, DIEA, or 1,8-diazabicycloundec-7-ene ("DBU") at an appropriate temperature (e.g., −20° C. to room temperature). In many cases, the olefin 23 can be isolated directly from this procedure, in other cases warming (30° C. to 100° C.) or additional base (e.g., DBU in the case of halide) may be required to complete the elimination to provide compound 23. The activated olefin 23 may be treated with the desired primary amine (e.g., ethylamine) in a suitable solvent, such as THF, at an appropriate temperature (e.g., −20° C. to reflux) to generate the amino ester intermediate. In the case where compound 23 has an electron rich aromatic ring or electron poor/bulky primary amine, heating (e.g., 30-240° C. in a sealed tube) or microwave chemistry may be required. Protection of the amine group (for example a t-butoxycarbonyl ("Boc") group) may be accomplished using di-tert-butyl dicarbonate ("$Boc_2O$") under standard conditions to provide compound 24, wherein Pg is a protecting group. Alternative protecting groups may be used, and many appropriate examples are listed in 'Protective Groups in Organic Synthesis' by Greene and Wuts, Wiley-Interscience, third edition, Chapter 7. Saponification of the ester 24 to form the protected amino acid 25 may be accomplished using conditions appropriate for the ester (e.g., aqueous LiOH for methyl esters, hydrogenation for benzyl esters, acid for t-butyl esters).

Alternatively, the activated olefin 23 may be treated with a secondary amine (e.g., diethylamine) in a suitable solvent such as THF at an appropriate temperature (e.g., −20° C. to reflux) to generate the aminoester intermediate (not shown). In the case wherein compound 23 has an electron rich aromatic ring or electron poor/bulky secondary amine, heating (e.g., 30-240° C. in a sealed tube) or microwave chemistry may be required. Saponification of the ester to form the amino acid 26 may be accomplished using conditions appropriate for the ester (e.g., aqueous LiOH for methyl esters, hydrogenation for benzyl esters, acid for t-butyl esters, etc.).

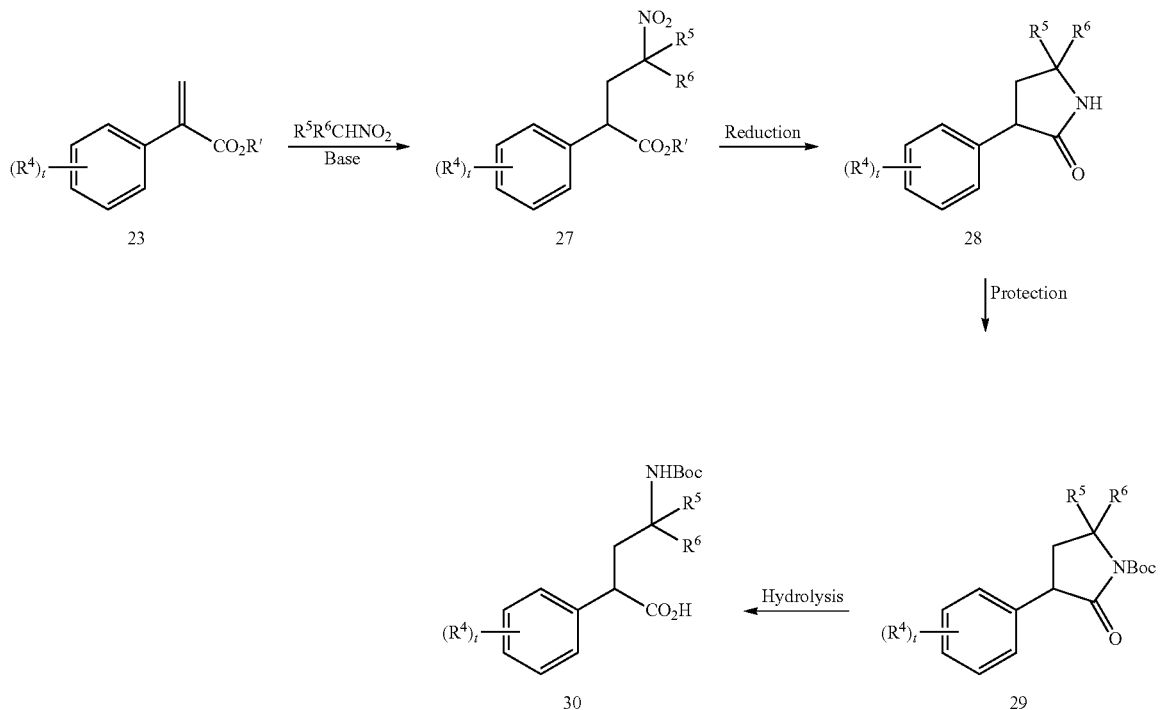

Scheme B shows a method of preparing optionally substituted γ-phenylglycine amino acids 30 of Formula 2A, wherein $R^4$, $R^5$, and $R^6$ are as defined herein, and t is 0 to 4. The starting unsaturated ester 23 (may be prepared according to Scheme A) can be treated with a substituted nitromethane derivative (e.g., nitroethane) in the presence of a base, such as DBU, at an appropriate temperature (e.g., 0° C. to room temperature) to give the homologated adduct 27. The nitro group of compound 27 can be reduced using standard conditions (e.g., hydrogenation, Zn/acid, etc.) at an appropriate temperature (e.g., room temperature to reflux), and the resulting intermediate can be cyclized to give the lactam intermediate 28. Protection of the amine, for example with a Boc-group to provide compound 29, may be accomplished using $Boc_2O$ under standard conditions. Alternative protecting groups may be used, and many appropriate examples are listed in 'Protective Groups in Organic Synthesis' by Greene and Wuts, Wiley-Interscience, third edition, Chapter 7. Treatment of compound 29 with an aqueous base such as LiOH or KOH at an appropriate temperature (e.g., 0° C. to 100° C.) effects ring opening of the lactam to give the appropriately substituted protected amino acid compound 30.

In one alternative of Scheme B, Boc may be replaced with $R^{17}$ in compounds 29 and 30.

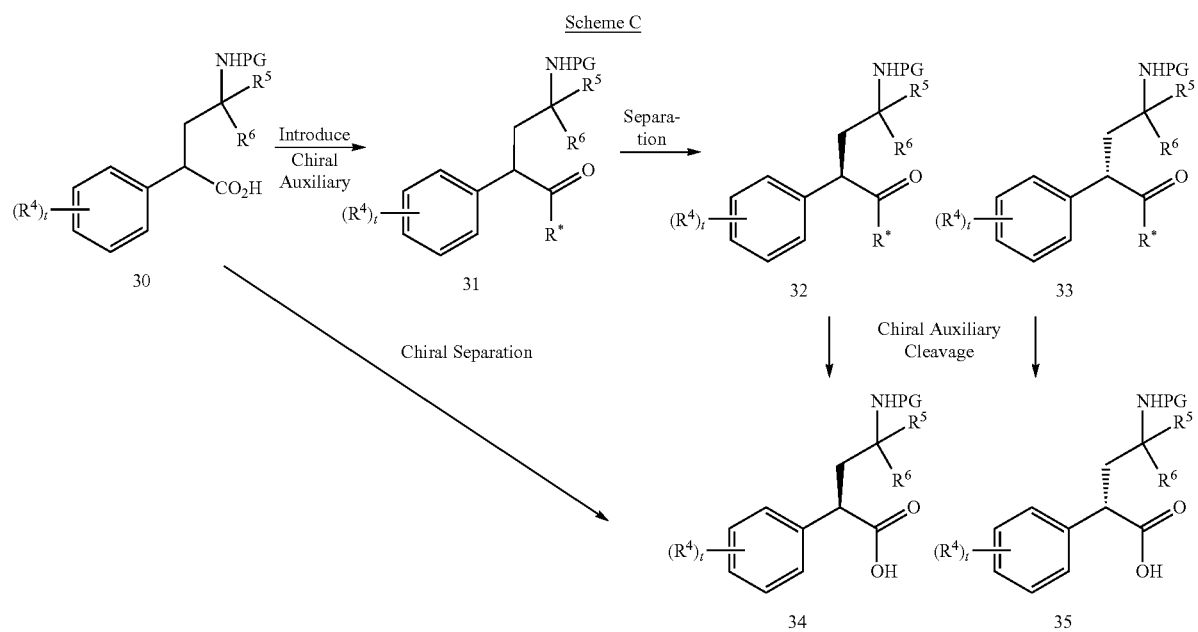

Scheme C

Scheme C shows representative methods of forming the single enantiomers of the gamma amino acids 34 and 35, wherein t is 0 to 3, PG is an amine protecting group such as Boc, R* is a chiral auxiliary (such as Evans' oxazolidinone) and $R^4$, $R^5$, and $R^6$ are as defined herein. In one possible method, the racemic amino acid is subject to chiral chromatographic separation using a chiral stationary phase. Alternatively, a diastereomeric mixture may be prepared which could be separated by conventional chromatographic or crystallization techniques. For example, activation of compound 30 (e.g., $COCl_2$, base) and introduction of a chiral auxiliary (e.g., an Evans' oxazolidinone) in the presence of a basic amine (e.g., Hunig's base) at −20° C. to 50° C. gives the diastereomeric mixture of compounds 32 and 33. This mixture may be separated using standard conditions (e.g., column chromatography, HPLC, SFC, etc.) to give the individual diastereomers. These may be converted to the desired acids by cleavage of the chiral auxiliary (in the case of an Evans' auxiliary, by using (for example) LiOH/HOOH at −15° C. to room temperature) to give the compounds 34 and 35. The temperature may need to be kept low so as to prevent racemization of the newly separated chiral center.

Scheme D

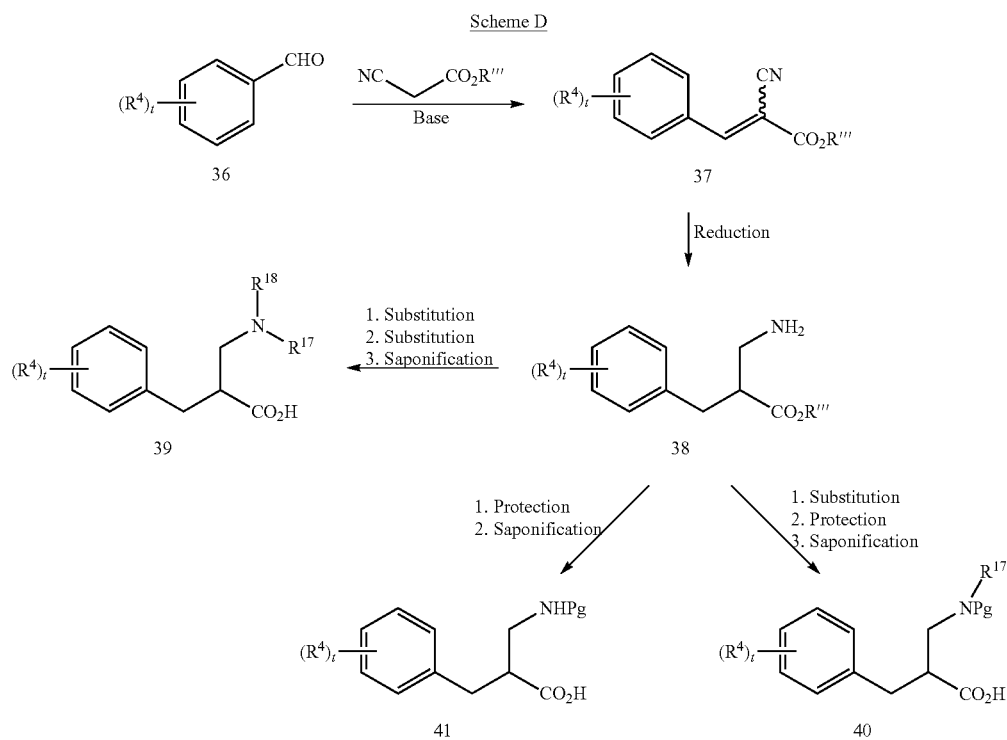

Scheme D shows a method of preparing optionally substituted β-phenylalanine amino acids 39, 40 and 41 of Formula 3A, wherein t is 0 to 3, PG is an amine protecting group, $R^{17}$ and $R^{18}$ are defined above, and $R^4$ is as defined herein. An appropriately substituted aldehyde 36 can be treated with a cyanoacetate of the formula CN—$CH_2CO_2R'''$, wherein R''' is $C_1$-$C_6$ alkyl (e.g., ethyl 2-cyanoacetate), in the presence of a suitable base, such as piperidine, at an appropriate temperature (e.g., room temperature to reflux) to give the unsaturated ester 37. Reduction of the olefin and the nitrile groups of compound 37 to provide compound 38 may be accomplished in a number of ways. For example, the olefin may be reduced with any agent known to effect 1,4-reductions, such as $NaBH_4$. The nitrile may be reduced using agents such as $LiAlH_4$ or $NaBH_4$ in the presence of a Lewis acid such as $BF_3OEt_2$ or trifluoroacetic acid ("TFA"). A number of alternative reducing agents may be used, such as those listed in 'Reductions in Organic Chemistry' by Hudlicky, ACS monograph, $21^{nd}$ edition, Chapter 18. If desired, the primary amine 38 can be monoalkylated or bisalkylated at this stage using standard conditions (e.g., reductive amination using an appropriate aldehyde, Lewis acid and reducing agent) to provide intermediates (not shown) en route to compounds 39 and 40. To prepare primary and secondary amines, protection may be accomplished using any number of protecting groups (e.g., 'Protective Groups in Organic Synthesis' by Greene and Wuts, Wiley-Interscience, third edition, Chapter 7), for example as a Boc-group using Boc anhydride at 0° C. to room temperature. Cleavage of the ester group to form the amino acid 39, 40 or 41 may be accomplished using an aqueous bases such as LiOH or KOH, or any of the alternative reagents listed in the aforementioned 'Protecting Groups' text (e.g., hydrogenation for a benzyl ester).

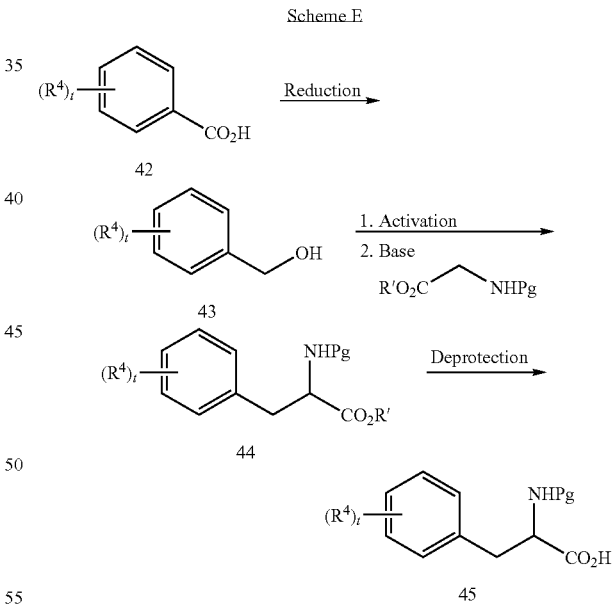

Scheme E shows a method of preparing optionally substituted α-phenylalanine amino acids 45 of Formula 4A, wherein t is 0 to 3, PG is an amine protecting group and $R^4$ is as defined herein. An appropriately substituted acid 42 may be reduced to the benzyl alcohol 43 using, for example, $LiAlH_4$ at a temperature ranging from room temperature to reflux. The alcohol group of compound 43 can be activated as a leaving group (e.g., halide, mesylate, etc.) using, for example, $PBr_3$, $MsCl/NEt_3$, etc. Displacement of this leaving group using a protected glycine derivative such as ethyl 2-(diphenylmethyleneamino)acetate in the presence of strong base, such as lithium diisopropylamide ("LDA") or n-BuLi, provides the amino ester intermediate 44, wherein R' is $C_1$-$C_6$ alkyl. Appropriate protecting groups are listed in 'Protective Groups in Organic Synthesis' by Greene and Wuts, Wiley-Interscience. The amine protecting group may be changed at this stage, for example, to introduce a Boc-group. Subsequent deprotection of the ester 44 (e.g., using 3N HCl, LiOH, hydrogenation for a benzyl ester, etc.) at an appropriate temperature (e.g., 0° C. to reflux) provides the desired N-protected amino acid 45.

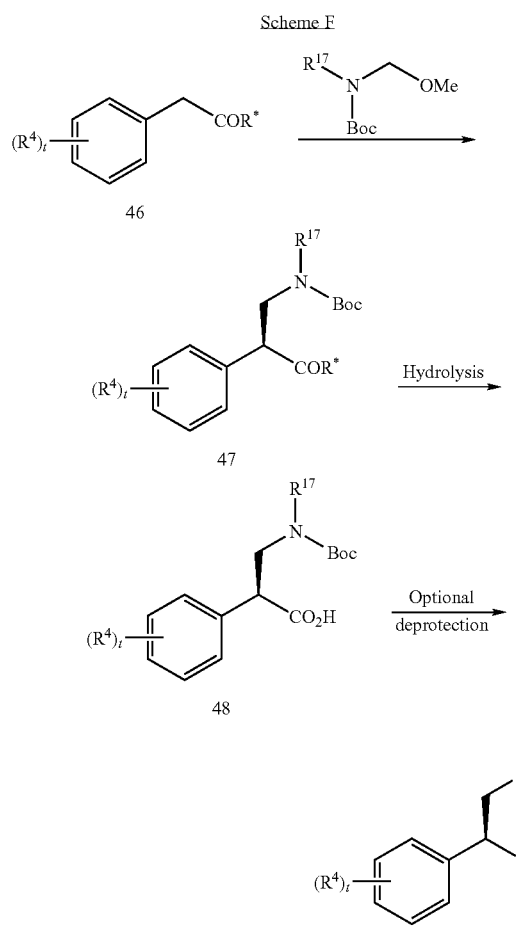

Either enantiomer of the β-amino acids may be prepared using a procedure such as that shown in Scheme F. A 2-phenylacetate 46, wherein t is 0 to 3 and $R^4$ is as defined herein, having an appropriate chiral auxillary (R*) (for example, an Evans' auxiliary or a Sultam) with the appropriate stereochemistry to generate the desired chemistry at the (3-position of the amino acid may be treated with an imine or iminium ion synthon (e.g., prepared in situ by the presence of a Lewis acid (e.g., $TiCl_4$) and an appropriately substituted alkoxymethanamine or N-(alkoxymethyl)amide/carbamate at $-100°$ C. to 50° C.) to prepare compound 47, wherein $R^{17}$ is an amine protecting group or as defined above. The asymmetric addition may require the presence of Lewis acids (e.g., $TiCl_4$), amine bases (e.g., Hunig's base) and lower temperatures (e.g., $-100°$ C. to 0° C.) to generate the best levels of stereochemical induction. If the diastereoselectivity is lower than required, the separate diastereomers may be separated at this stage by, for example, chromatography or crystallization. Cleavage of the chiral auxillary, using methods known to cleave the chosen auxillary (e.g., $LiOH/H_2O_2$ at $-50°$ C. to 50° C. for the Evans auxillary) then leads to the desired N-protected (3-amino acid 48 with the desired stereochemistry at the (3-position. Additionally, if $R^{17}$ is also a protecting group (e.g., 2,4-dimethoxybenzyl), it may be removed in the presence of the Boc-group (e.g., hydrogenation or DDQ, etc.) to give the Boc-amino acid 71, which upon removal of the Boc-group would provide the primary amine (not shown), which may be further functionalized by alkylation, acylation or reductive amination (either prior to or after coupling with the pyrimidine-piperazine unit). Alternatively, the Boc group of compound 48 may be elaborated to $R^{18}$, which is defined above.

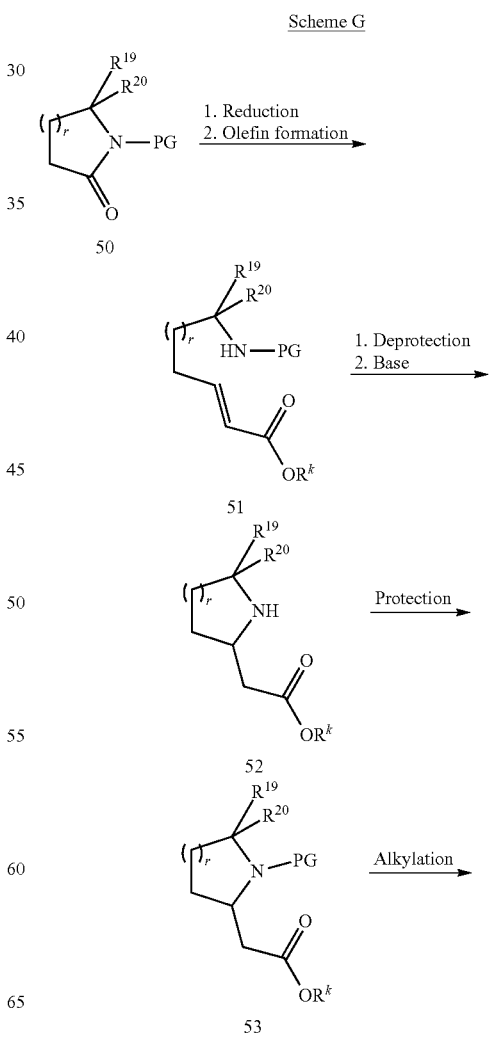

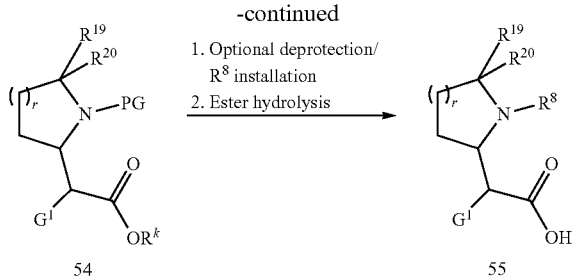

Scheme G shows a method of preparing optionally substituted amino acids 55 used in preparing compounds of Formula VI, wherein $R^k$ is methyl or ethyl, $R^{19}$ and $R^{20}$ are independently selected from hydrogen, halogen, $C_1$-$C_4$ alkyl optionally substituted with one to three substituents selected from halogen, OH, $CF_3$, CN or oxo, PG is an amine protecting group, and $R^8$, $G^1$ and r are as defined above. An appropriately substituted lactam 50 may be reduced to an aminal using, for example, $LiBEt_3H$. The aminal can then be treated with sodium hydride and a reagent such as $(EtO)_2P(O)CH_2CO_2Et$ to provide the unsaturated ester 51. Removal of the protecting group PG, and treatment with base (for example, $Et_3N$), provides the cyclized compound 52. Subsequent protection of the amine gives compound 53. Optional installation of the $G^1$ group can be carried out on compound 53 using an appropriate base (for example, lithium hexamethyldisilazide ("LHMDS")) and an alkyl halide to provide compound 54. Ester hydrolysis can then be carried out directly on 54 to give the corresponding acid directly, or compound 54 can be optionally deprotected, followed by $R^8$ installation and ester hydrolysis to give compound 55.

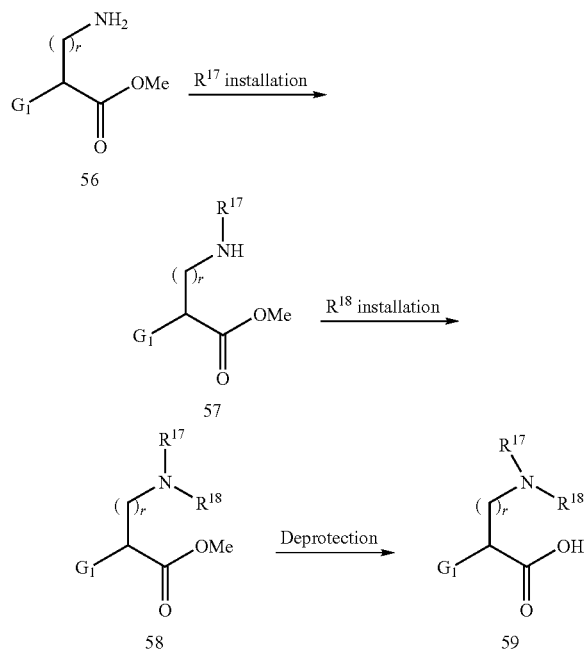

Scheme H shows a method of preparing optionally substituted amino acids 59 used in the preparation of compounds of Formula V, wherein PG1 is the same as PG as defined above, and $R^{17}$, $R^{18}$ and $G^1$ are as defined above. $R^{17}$ can be installed by reductive amination, alkylation or transition metal catalyzed coupling of a commercially available amino acid methyl ester or prepared from corresponding amino acids to give compound 57. $R^{18}$ can be installed in a similar manner, and followed by hydrolysis to give the optional substituted amino acid 59.

In preparing compounds of Formula I, protection of remote functionalities (e.g., primary or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, Boc, benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Methods of Separation

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine(amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. *J. Org. Chem.*, (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111).

By method (3), a racemic mixture of two enantiomers can be separated by chromatography using a chiral stationary phase (W. J. Lough, Ed., Chapman and Hall, New York, "Chiral Liquid Chromatography" (1989); Okamoto, *J. of Chromatogr.*, 513:375-378 (1990)). Enriched or purified enantiomers can be distinguished by methods used to distinguish other chiral molecules with asymmetric carbon atoms, such as optical rotation and circular dichroism.

Administration and Pharmaceutical Formulations

The compounds of the invention may be administered by any convenient route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal.

The compounds may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents. If parenteral administration is desired, the compositions will be sterile and in a solution or suspension form suitable for injection or infusion.

A typical formulation is prepared by mixing a compound of the present invention and a carrier or excipient. Suitable carriers and excipients are well known to those skilled in the art and are described in detail in, e.g., Howard C. Ansel et al., Pharmaceutical Dosage Forms and Drug Delivery Systems, (8$^{th}$ Ed. 2004); Alfonso R. Gennaro et al., Remington: The Science and Practice of Pharmacy, (20$^{th}$ Ed. 2000); and Raymond C. Rowe, Handbook of Pharmaceutical Excipients, (5$^{th}$ Ed. 2005). The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

One embodiment of the present invention includes a pharmaceutical composition comprising a compound of the present invention, or a stereoisomer or pharmaceutically acceptable salt thereof. In a further embodiment, the present invention provides a pharmaceutical composition comprising a compound of the present invention, or a stereoisomer or pharmaceutically acceptable salt thereof, together with a pharmaceutically acceptable carrier or excipient.

Methods of Treatment with Compounds of the Invention

The invention includes methods of treating or preventing disease or condition by administering one or more compounds of this invention, or a stereoisomer or pharmaceutically acceptable salt thereof. In one embodiment, a human patient is treated with a compound of the present invention, or a stereoisomer or pharmaceutically acceptable salt thereof, and a pharmaceutically acceptable carrier, adjuvant, or vehicle in an amount to detectably inhibit CHK1 activity.

In another embodiment of the present invention, a method of preventing or treating a disease or disorder modulated by CHK1 and/or CHK2, comprising administering to a mammal in need of such treatment an effective amount of a compound of the present invention is provided.

In another embodiment of the present invention, a method of treating a hyperproliferative disease in a mammal comprising administering a therapeutically effective amount of the compound of the present invention, or a stereoisomer or pharmaceutically acceptable salt thereof, to the mammal is provided.

In another embodiment, a method of treating or preventing cancer, including the below identified conditions, in a mammal in need of such treatment, wherein the method comprises administering to said mammal a therapeutically effective amount of a compound of the present invention, or a stereoisomer or pharmaceutically acceptable salt thereof.

Because of the ability of a CHK1 inhibitor to potentiate the activity of many anti-cancer agents it is expected that a wide range of tumor types may be treated by the compositions and methods of the invention. These conditions include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone:

osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; Breast: invasive breast carcinomas (invasive ductal carcinoma and invasive lobular carcinoma), etc.; and Adrenal glands: neuroblastoma. The term hyperproliferative disease includes the above identified conditions. The term "cancerous cell" as provided herein, includes a cell afflicted by any one of the above identified conditions.

Another embodiment of the present invention provides the use of a compound of the present invention, or a stereoisomer or pharmaceutically acceptable salt thereof, in the manufacture of a medicament for the treatment of cancer.

In another embodiment, a method of treating or preventing a disease or disorder modulated by CHK1 and/or CHK2, comprising administering to a mammal in need of such treatment an effective amount of a compound of the present invention, or a stereoisomer or pharmaceutically acceptable salt thereof.

In another embodiment, a method of preventing or treating cancer, comprising administering to a mammal in need of such treatment an effective amount of a compound of the present invention, alone or in combination with one or more additional compounds having anti-cancer properties.

CHK1 inhibitors are expected to potentiate the activity of a wide range of anti-cancer agents, when such agent(s) trigger the CHK1 dependent cell cycle checkpoint.

The invention relates to a composition for the treatment of a hyperproliferative disease in a mammal, comprising a therapeutically effective amount of a compound of the present invention, or a stereoisomer or a pharmaceutically acceptable salt thereof, in combination with an anti-tumor agent selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, anti-androgens, targeted antibodies, HMG-CoA reductase inhibitors, and prenyl-protein transferase inhibitors.

The invention also relates to a method for the treatment of a hyperproliferative disorder in a mammal that comprises administering to said mammal a therapeutically effective amount of a compound of the present invention, or a stereoisomer or a pharmaceutically acceptable salt thereof, in combination with an anti-tumor agent selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, anti-androgens, targeted antibodies, HMG-CoA reductase inhibitors, and prenyl-protein transferase inhibitors.

Another embodiment provides the compounds of the present invention for use in therapy.

Another embodiment provides the compounds of the present invention for use in the treatment of a hyperproliferative disease. In a further embodiment, the hyperproliferative disease is cancer, including the above identified conditions.

This invention also relates to a pharmaceutical composition for inhibiting abnormal cell growth in a mammal which comprises an amount of a compound of the present invention, or a stereoisomer or a pharmaceutically acceptable salt thereof, in combination with an amount of a chemotherapeutic, wherein the amounts of the compound, stereoisomer or salt and of the chemotherapeutic are together effective in inhibiting abnormal cell growth. Many chemotherapeutics are known in the art. In certain embodiments, the chemotherapeutic is selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, anti-androgens, targeted antibodies, HMG-CoA reductase inhibitors, and/or prenyl-protein transferase inhibitors.

This invention relates to a method for inhibiting abnormal cell growth in a mammal or treating a hyperproliferative disorder in which the method comprises administering to the mammal an amount of a compound of the present invention, or a stereoisomer or a pharmaceutically acceptable salt thereof, in combination with radiation therapy, wherein the amounts of the compound or salt, in combination with the radiation therapy is effective in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

It is believed that the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation, which comprises administering to the mammal an amount of a compound of the present invention or a stereoisomer or a pharmaceutically acceptable salt thereof, which amount is effective in sensitizing abnormal cells to radiation treatment. The amount of the compound, stereoisomer or salt to be used in this method can be determined according to means for ascertaining effective amounts of such compounds as described herein or by methods know to those skilled in the art.

Another embodiment of the present invention provides the use of a compound of the present invention, or a stereoisomer or pharmaceutically acceptable salt thereof, in the manufacture of a medicament for the treatment of hyperproliferative diseases. In a further embodiment, the hyperproliferative disease may be cancer, including the above identified conditions.

In another embodiment of the present invention, use of a compound of the present invention, in the manufacture of a medicament, for use as a CHK1 and/or CHK2 inhibitor in the treatment of a patient undergoing cancer therapy, including the above identified conditions, is provided.

Another embodiment of the present invention provides the use of a compound of the present invention in the treatment of a hyperproliferative disease. In a further embodiment, the hyperproliferative disease is cancer, including the above identified conditions.

Another embodiment provides the use of a compound of the present invention in the manufacture of a medicament, for use as a CHK1 and/or CHK2 inhibitor in the treatment of a patient undergoing cancer therapy.

In another embodiment, a pharmaceutical composition comprising a compound of the present invention for use in the treatment of a hyperproliferative disease is provided.

In another embodiment, a pharmaceutical composition comprising a compound of the present invention for use in the treatment of cancer is provided.

Combination Therapy

The compounds of this invention and stereoisomers and pharmaceutically acceptable salts thereof may be employed alone or in combination with other therapeutic agents for treatment. The compounds of the present invention can be used in combination with one or more additional drugs, including compounds that work by a different mechanism of action. The second compound of the pharmaceutical combination formulation or dosing regimen preferably has complementary activities to the compound of this invention such that they do not adversely affect each other. Such molecules are suitably present in combination in amounts that are effective for the purpose intended. The compounds may be administered together in a unitary pharmaceutical composition or separately and, when administered separately this may occur simultaneously or sequentially in any order. Such sequential administration may be close in time or remote in time.

EXAMPLES

In order to illustrate the invention, the following Examples are included. However, it is to be understood that these Examples do not limit the invention and are only meant to suggest a method of practicing the invention. Persons skilled in the art will recognize that the chemical reactions described may be readily adapted to prepare a number of other compounds of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the Examples described below, unless otherwise indicated all temperatures are set forth in degrees Celsius. Reagents were purchased from commercial suppliers such as Sigma-Aldrich, Alfa Aesar, or TCI, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters) or on a Biotage SP4 system using C18H columns (unless otherwise stated). $^1$H NMR spectra were recorded on a Varian instrument operating at 400 MHz. $^1$H-NMR spectra were obtained as $CDCl_3$, $d_6$-DMSO, $CH_3OD$ or $d_6$-acetone solutions (reported in ppm), using TMS as the reference standard. When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

Example A

CHK1 Enzymatic Assay

Compounds were diluted in dimethylsulfoxide ("DMSO") in 3 fold serial dilutions and then added to the reaction to give a final concentration of 1% DMSO. Compounds were tested in an enzymatic assay using human CHK1 kinase domain, amino acids 1 to 273, with 10 additional histidine residues on the carboxy terminus, purified from bacculovirus. The substrate was the flourescent Omnia peptide S/T11 from Invitrogen. The assay contained 25 mM HEPES pH 7.4, 10 mM $MgCl_2$, 1 mM DTT, 0.01% Triton-X100, 0.5 nM CHK1 enzyme, 2 µM S/T 11 peptide substrate, 60M ATP, test compound, 1% DMSO, in a 25 µL reaction volume. The assay was run at room temperature in white 384 well polypropylene plates (available from Nunc, Inc of Naperville, Ill.) collecting data every 50 seconds for 45 minutes in an Envision plate reader (PerkinElmer, Inc. of Waltham, Mass.), excitation 340 nM, emission 495 nM. The collected data from each well was fit to a straight line and the resulting rates were used to calculate a percent of control. $IC_{50}$ values for each test compound were determined from the percent of control vs. compound concentration plots using a four parameter fit.

The compounds of Examples 1-74 were tested in the above assay and found to have an $IC_{50}$ of less than 10.5 µM.

Example B

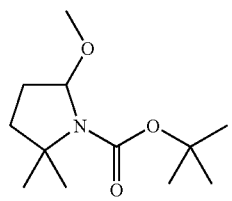 [SMILES: COC1CCC(C)(C)N1C(=O)OC(C)(C)C]

tert-butyl
5-methoxy-2,2-dimethylpyrrolidine-1-carboxylate 5,5-Dimethylpyrrolidin-2-one (0.108 g, 0.953 mmol, prepared as described in Ganem, B., et al., Tet Lett 26:6413

(1985)) was dissolved in THF (3 mL) and cooled to −20° C. The solution was treated with LHMDS (1.05 mL, 1.05 mmol) and stirred at −20° C. for 30 minutes. di-tert-Butyl dicarbonate (0.250 g, 1.14 mmol) was added, and the reaction mixture was allowed to warm to ambient temperature. The reaction was stirred at ambient temperature for two hours and then quenched with saturated $NH_4Cl$, diluted with ethyl acetate and separated. The organic layer was washed with saturated $NH_4Cl$, saturated $NaHCO_3$, saturated NaCl, dried over $Na_2SO_4$ and concentrated in vacuo to an oil. The crude product was subjected to chromatography on $SiO_2$ and eluted with 4:1 hexanes/ethyl acetate. tert-Butyl 2,2-dimethyl-5-oxopyrrolidine-1-carboxylate (Rf of 0.11 in 4:1 hexanes/ethyl acetate) was recovered as a solid (0.87 g, 43%). $^1$H NMR ($CDCl_3$, 400 MHz) δ 2.48 (t, J=7.8, 2H), 1.85 (t, 2H), 1.54 (s, 9H), 1.47 (s, 6H).

DIBAL-H (73.65 mL, 110.5 mmol, 1.5M in toluene) was added portionwise to a solution of tert-butyl 2,2-dimethyl-5-oxopyrrolidine-1-carboxylate (23.10 g, 108.3 mmol) in dry $Et_2O$ (200 mL) cooled to −78° C. The reaction was stirred for 1 hour at −78° C. and then allowed to warm to room temperature and stirred overnight. The reaction was quenched with $NH_4OH$ (50 mL) and stirred for 20 minutes. The reaction was then diluted with EtOAc (200 mL), 0.5M Rochelle's Salt (100 mL) was added, and the layers were separated. The organic fraction was washed with 0.5M Rochelle's Salt (2×100 mL), brine (100 mL), dried ($MgSO_4$) and concentrated to an oil. The oil was taken up in a solution of p-TsOH monohydrate (2.06 g, 10.8 mmol) in MeOH (200 mL) and stirred overnight at room temperature. The reaction was then concentrated, taken up in EtOAc (200 mL), washed with saturated $Na_2CO_3$ (2×100 mL), brine (50 mL), dried ($MgSO_4$) and concentrated to give tert-butyl 5-methoxy-2,2-dimethylpyrrolidine-1-carboxylate (24.07 g, 96.9% yield) as an oil.

Example C 1.0M $TiCl_4$ in toluene (3.52 mL, 3.52 mmol) was added to a solution of (R)-4-benzyl-3-(2-(4-bromophenyl)acetyl)oxazolidin-2-one (1.26 g, 3.35 mmol) in dichloromethane ("DCM"; 30 mL) at −78° C. DIEA (0.64 mL, 3.69 mmol) was then added to the cold stirring solution. The reaction was stirred at −78° C. for 15 minutes, followed by the addition of a solution of tert-butyl 5-methoxy-2,2-dimethylpyrrolidine-1-carboxylate (1.00 g, 4.36 mmol, see Example B) in DCM (10 mL). The reaction was then warmed to −10° C. and stirred for 2 hours. The reaction was quenched with a saturated $NH_4Cl$ solution (20 mL), and the organic fraction was isolated, dried over sodium sulfate, filtered and concentrated. The resulting residue was purified by column chromatography to give (S)-tert-butyl 54(R)-2-((R)-4-benzyl-2-oxooxazolidin-3-yl)-1-(4-bromophenyl)-2-oxoethyl)-2,2-dimethylpyrrolidine-1-carboxylate (1.63 g, 85%) as a solid.

30% $H_2O_2$ (0.67 mL, 7.0 mmol) was added to a solution of LiOH—$H_2O$ (0.24 g, 5.60 mmol) in THF/water (2:1, 93 mL), and the solution was stirred at room temperature for 10 minutes. The solution was then cooled to 0° C. and treated with a solution of (S)-tert-butyl 5-((S)-2-((R)-4-benzyl-2-oxooxazolidin-3-yl)-1-(4-bromophenyl)-2-oxo ethyl)-2,2-dimethylpyrrolidine-1-carboxylate (1.60 g, 2.80 mmol) in THF (10 mL). The reaction was stirred at 0° C. for 2 hours and allowed to warm to room temperature and stirred overnight. The reaction was then cooled to 0° C. and treated with 1M $Na_2SO_3$ (10 mL) and stirred for 10 minutes. The reaction was then warmed to room temperature and stirred for 10 minutes. The reaction was next concentrated and extracted with EtOAc (2×20 mL). The aqueous layer was then acidified with 1N HCl to a pH of about 1 to about 2 and extracted with DCM (2×20 mL). The combined DCM fractions were dried over sodium sulfate, filtered, and concentrated to give (S)-2-(4-bromophenyl)-2-((S)-1-(tert-butoxycarbonyl)-5,5-dimethylpyrrolidin-2-yl)acetic acid (1.01 g, 87% yield) as a solid. MS ESI (+) m/z 412 detected.

Example D

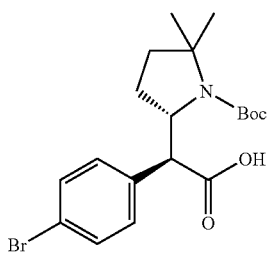 [SMILES: CC(C)(C)OC(=O)N1[C@H]([C@@H](C(=O)O)c2ccc(Br)cc2)CCC1(C)C]

(S)-2-(4-bromophenyl)-2-((S)-1-(tert-butoxycarbonyl)-5,5-dimethylpyrrolidin-2-yl)acetic Acid 2-(4-Bromophenyl)acetic acid (7.85 g, 36.5 mmol) and (R)-4-benzyloxazolidin-2-one (3.23 g, 18.3 mmol) were combined in toluene (30 mL) and triethylamine (10.2 mL, 73.0 mmol). The solution was then heated to 80° C., and a solution of pivaloyl chloride (4.49 mL, 36.5 mmol) in toluene (7.5 mL) was added slowly. The reaction was heated to 110° C. and stirred overnight. The reaction was then cooled, and the toluene solution was washed with 2N HCl, water, 5% $Na_2CO_3$, brine and then dried over $Na_2SO_4$. After removal of the solvent, the residue was purified by column chromatography to give (R)-4-benzyl-3-(2-(4-bromophenypacetypoxazolidin-2-one (5.65 g, 83%) as a solid.

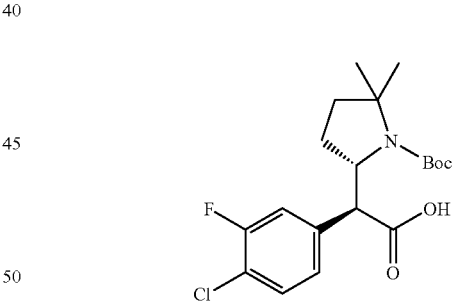

(S)-2-((S)-1-(tert-butoxycarbonyl)-5,5-dimethylpyrrolidin-2-yl)-2-(4-chloro-3-fluorophenyl)acetic Acid 2-(4-Chloro-3-fluorophenyl)acetic acid (1.00 g, 5.30 mmol) was dissolved in THF (14 mL) at 0° C. and treated with triethylamine (0.81 mL, 5.8 mmol). Pivaloyl chloride (0.69 mL, 5.6 mmol) was then added to the solution, and the mixture was allowed to stir for one hour at 0° C. In a separate flask, (R)-4-benzyloxazolidin-2-one (0.987 g, 5.57 mmol) was dissolved in THF (14 mL) at −78° C. and treated with n-BuLi (2.54 mL, 5.83 mmol). The above anion solution was stirred for 20 minutes and then cannulated into the anhydride at −78° C. The reaction was then allowed to stir for one hour at −78° C., and then warmed to 0° C. for two hours. The mixture was quenched with the addition of saturated NH₄Cl solution (20 mL) and concentrated in vacuo. The resulting residue was then partitioned between ethyl acetate and water. The aqueous layer was extracted once with ethyl acetate, and the organic fractions were combined, washed with brine, separated, dried over MgSO₄, filtered, and concentrated in vacuo. The resulting residue was purified by column chromatography (3:1 hexanes:ethyl acetate) to give (R)-4-benzyl-3-(2-(4-chloro-3-fluorophenyl)acetyl)oxazolidin-2-one (0.95 g, 51%) as an oil, which solidified upon standing.

TiCl₄ in toluene (7.79 mL, 7.79 mmol) was added to a solution of (R)-4-benzyl-3-(2-(4-chloro-3-fluorophenyl)acetyl)oxazolidin-2-one (2.58 g, 7.42 mmol) in DCM (60 mL). DIEA (1.42 mL, 8.16 mmol) was added to this stirring cold solution, followed by a solution of tert-butyl 5-methoxy-2,2-dimethylpyrrolidine-1-carboxylate (2.21 g, 9.65 mmol) in DCM (20 mL). The reaction was stirred for 15 minutes at −78° C. and then warmed to −10° C. and stirred for 3 hours. The reaction was quenched with a saturated NH₄Cl solution (20 mL), and the organic layer was separated and dried over sodium sulfate. After removal of the solvent, the resulting residue was purified by column chromatography to give (S)-tert-butyl 5-((R)-2-((R)-4-benzyl-2-oxooxazolidin-3-yl)-1-(4-bromophenyl)-2-oxo ethyl)-2,2-dimethylpyrrolidine-1-carboxylate (2.62 g, 65%) as a solid.

30% H₂O₂ (0.159 mL, 1.65 mmol) was added to a solution of LiOH—H₂O (0.055 g, 1.32 mmol) in 2:1 THF:H₂O (40 mL). The mixture was stirred for 20 minutes and then cooled to 0° C. A solution of (S)-tert-butyl 5-((S)-2-((R)-4-benzyl-2-oxooxazolidin-3-yl)-1-(4-chloro-3-fluorophenyl)-2-oxo-ethyl)-2,2-dimethylpyrrolidine-1-carboxylate (0.360 g, 0.660 mmol) in THF (3 mL) was next added slowly. Upon completion of the addition, the reaction was allowed to warm to room temperature and stirred overnight. The reaction mixture was then recooled to 0° C., and 1M Na₂SO₃ (4 mL) was added. The reaction was stirred for 10 minutes at 0° C. and then warmed to room temperature and stirred for an additional 10 minutes. The reaction was then concentrated in vacuo to remove THF, and the resulting mixture was washed with EtOAc. The organic fraction was then dried over sodium sulfate, filtered and concentrated to give (S)-2-((S)-1-(tert-butoxycarbonyl)-5,5-dimethylpyrrolidin-2-yl)-2-(4-chloro-3-fluorophenyl)acetic acid sodium salt (0.24 g, 94%) as a powder. MS ESI (+) m/z 386 detected.

Example E addition, 3-(4-chlorophenyl)propanoic acid (10.0 g, 54.1 mmol) was added in several portions. Upon completion of the addition, the cooling bath was removed, and the reaction mixture was slowly warmed to room temperature and stirred overnight. The reaction was then concentrated to dryness, and the resulting residue was dissolved in DCM (100 mL), washed with saturated NaHCO₃, dried (MgSO₄), filtered, and concentrated to give methyl 3-(4-chlorophenyl)propanoate as an oil (10.48 g, 97%).

BuLi (5.2 mL, 1.6M in hexanes) was added to a 0° C. solution of diisopropylamine (0.91 g, 9.0 mmol) in THF (40 mL). The reaction mixture was then stirred at 0° C. for 30 minutes, and then cooled to −78° C. A solution of methyl 3-(4-chlorophenyl)propanoate (1.5 g, 7.5 mmol) in THF (8 mL) was added slowly, and the reaction mixture was stirred at −78° C. for 40 minutes. A solution tert-butyl 2-bromoacetate (4.4 g, 22.7 mmol) in THF (5 mL) was then added. The reaction was then stirred for 30 minutes at −78° C. and then warmed to room temperature and stirred overnight. The reaction was then quenched with saturated NH₄Cl and concentrated to remove THF. The reaction was then extracted with EtOAc, and the combined extracts were dried (Na₂SO₄), filtered, concentrated, and dried in vacuo to give 4-tert-butyl 1-methyl 2-(4-chlorobenzyl)succinate (1.91 g, 81%) as an oil.

TFA (15 mL) was added dropwise to a solution of 4-tert-butyl 1-methyl 2-(4-chlorobenzyl)succinate (1.91 g, 6.1 mmol) in DCM (30 mL) at 0° C. The reaction mixture was then warmed to room temperature and stirred for 5 hours. The reaction was then concentrated to dryness to give 3-(4-chlorobenzyl)-4-methoxy-4-oxobutanoic acid as a syrup (1.55 g, 95%), which was used without further purification.

Diphenylphosphoryl azide (2.1 g, 76 mmol) was added to a solution of 3-(4-chlorobenzyl)-4-methoxy-4-oxobutanoic acid (1.6 g, 6.4 mmol) and triethylamine ("TEA"; 0.97 g, 9.58 mmol) in t-BuOH (40 mL). The reaction mixture was then heated to reflux and stirred for 6 hours. The reaction was then cooled to room temperature and concentrated to an oil. Purification by column chromatography (9:1 to 5:1 hexane:EtOAc) gave methyl 3-(tert-butoxycarbonylamino)-2-(4-chlorobenzyl)propanoate (0.64 g, 31%).

LiOH—H₂O (0.09 g, 2.1 mmol) was added to a solution of methyl 3-(tert-butoxycarbonylamino)-2-(4-chlorobenzyl)propanoate (0.64 g, 1.9 mmol) in 2:1 THF:H₂O (20 mL). The reaction was then stirred for 3 hours at room temperature and then diluted with H₂O (50 mL) and washed with ether (50 mL). The aqueous layer was next acidified with solid KHSO₄, saturated with solid NaCl, and extracted with DCM. The combined organic extracts were dried (Na₂SO₄), filtered, concentrated, and dried in vacuo to give 3-(tert-butoxycarbonylamino)-2-(4-chlorobenzyl)propanoic acid (0.523 g, 85%) as a solid. MS ESI (−) m/z 312 detected.

Example F

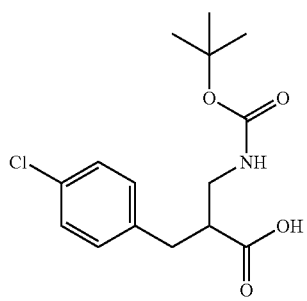 [SMILES: CC(C)(C)OC(=O)NCC(Cc1ccc(Cl)cc1)C(=O)O]

3-(tert-butoxycarbonylamino)-2-(4-chlorobenzyl) propanoic Acid

Neat SOCl₂ (25.7 g, 216.7 mmol) was added dropwise to a −60° C. solution of MeOH (100 mL). Upon completion of the

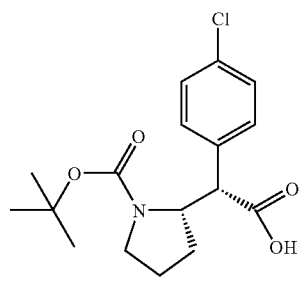 [SMILES: CC(C)(C)OC(=O)N1CCC[C@H]1[C@@H](C(=O)O)c1ccc(Cl)cc1]

(S)-2-4S)-1-(tert-butoxycarbonyl)pyrrolidin-2-yl)-2-(4-chlorophenyl)acetic Acid 2-(4-Chlorophenyl)acetic acid (20.00 g, 117.2 mmol) and (R)-4-benzyloxazolidin-2-one (10.39 g, 58.62 mmol) were combined in toluene (100 mL). Triethylamine (32.68 mL, 234.5 mmol) was added, and the solution was heated to 80° C. A solution of pivaloyl chloride (14.42 mL, 117.2 mmol) in toluene (25 mL) was added dropwise. After addition, the mixture was heated to reflux for 16 hours. The reaction was cooled and washed with 2N HCl (2×), water, 5% $Na_2CO_3$ (2×), saturated NaCl, dried over $Na_2SO_4$ and concentrated in vacuo to a solid. The crude solid was subjected to chromatography on $SiO_2$ eluting with 4:1 hexane/ethyl acetate. (R)-4-Benzyl-3-(2-(4-chlorophenyl)acetyl)oxazolidin-2-one was recovered as a solid (30.7 g, 80%). $^1$H NMR ($CDCl_3$, 400 MHz) □7.34-7.26 (m, 7H), 7.16-7.11 (m, 2H), 4.71-4.64 (m, 1H), 4.35-4.16 (m, 4H), 3.26 (dd, $J_1$=2.9, $J_2$=13.2, 1H), 2.76 (dd, $J_1$=9.3, $J_2$=13.2, 1H).

tert-Butyl 2-oxopyrrolidine-1-carboxylate (12.33 g, 66.57 mmol) was dissolved in $Et_2O$ (60 mL) and cooled to −78° C. The suspension was treated dropwise with DIBAL-H (45.27 mL, 67.90 mmol; 1.5M in toluene), and the mixture was stirred at −78° C. for 2 hours. The mixture was allowed to warm to ambient temperature with a bath and stirred overnight. The reaction was quenched by addition of a solution of p-toluenesulfonic acid hydrate (0.075 g) in MeOH (75 mL). The mixture was stirred at ambient temperature for 16 hours. The suspension was concentrated in vacuo to a solid. This was resuspended in a mixture of Rochelle's salt (0.5N) and ethyl acetate. The layers were separated, and the aqueous layer was washed with methylene chloride (2×). The combined organic layers were washed with saturated NaCl, dried over $Na_2SO_4$ and concentrated in vacuo to provide an oil. A solution of titanium (IV) chloride (10.0 mL, 10.0 mmol; 1 M in toluene) was cooled to 0° C. and treated with a solution of (R)-4-benzyl-3-(2-(4-chlorophenyl)acetyl)oxazolidin-2-one (3.00 g, 9.10 mmol) dissolved in dichloromethane (20 mL). After 5 minutes, diisopropylethylamine (1.74 mL, 10.0 mmol) was added. The resultant solution was stirred for 1 hour at 0° C. then cooled to −20° C. A solution of tert-butyl 2-methoxypyrrolidine-1-carboxylate (2.55 g, 13.65 mmol) dissolved in dichloromethane (20 mL) was added, and the mixture was stirred at −20° C. for 75 minutes. The mixture was quenched with saturated $NH_4Cl$ (about 100 mL) and diluted with water to dissolve the solids. After separation, the aqueous layer was washed with methylene chloride (3×). The combined organics were washed with water (2×), dried over $Na_2SO_4$ and concentrated in vacuo. The recovered oil was subjected to chromatography on $SiO_2$ eluting with 8:1 hexanes/ethyl acetate. (S)-tert-Butyl 2-((S)-2-((R)-4-benzyl-2-oxo oxazolidin-3-yl)-1-(4-chlorophenyl)-2-oxoethyl)pyrrolidine-1-carboxylate was recovered as a sticky foam (1.55 g, 40%). MS (APCI+) [M+Na] 521.1.

Lithium hydroxide hydrate (0.0471 g, 1.12 mmol) was added to a solution of THF/water (3:1, 19 mL) and stirred until dissolved. The mixture was cooled to 0° C. and treated with 30% hydrogen peroxide (0.231 mL, 2.24 mmol) and stirred for 10 minutes. A solution of (S)-tert-butyl 2-((S)-2-((R)-4-benzyl-2-oxooxazolidin-3-yl)-1-(4-chlorophenyl)-2-oxoethyl)pyrrolidine-1-carboxylate (0.280 g, 0.561 mmol) in THF (2 mL) was added. The reaction was stirred for 30 minutes at 0° C. Thin layer chromatography ("TLC") did not show much progress, therefore the reaction was allowed to warm to ambient temperature and stirred overnight. The reaction was quenched by addition of 1.5 M $Na_2SO_3$ (1 mL) and stirred for 15 minutes. The reaction mixture was diluted with $Et_2O$ and separated. The aqueous portion was washed (2×) with $Et_2O$ then adjusted to a pH of 1 with 3N HCl. The aqueous portion was extracted (3×) with ethyl acetate. The combined organic layers were washed with water (2×), saturated NaCl, dried over $Na_2SO_4$ and concentrated in vacuo to a thick oil which slowly solidified to give (S)-2-((S)-1-(tert-butoxycarbonyl)-pyrrolidin-2-yl)-2-(4-chlorophenyl)acetic acid as a foam (0.55 g, 72%). $^1$H NMR ($CDCl_3$, 400 MHz) □7.30 (d, 2H), 7.21 (d, 2H), 4.53-4.40 (m, 1H), 4.37-4.27 (m, 1H), 3.34-3.22 (m, 1H), 2.98-2.90 (m, 1H), 2.02-1.90 (m, 1H), 1.83-1.74 (m, 1H), 1.64-1.53 (m, 2H), 1.50 (s, 9H).

Example G

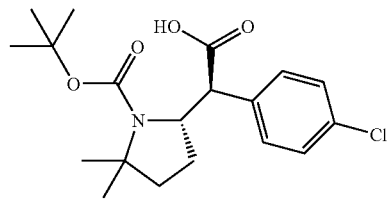 [SMILES: CC(C)(C)OC(=O)N1[C@H]([C@@H](C(=O)O)c2ccc(Cl)cc2)CCC1(C)C]

(S)-2-((S)-1-(tert-butoxycarbonyl)-5,5-dimethylpyrrolidin-2-yl)-2-(4-chlorophenyl)acetic Acid 5,5-Dimethylpyrrolidin-2-one (0.108 g, 0.953 mmol, may be prepared as described in Ganem, B. and Osby, J O; Tet Lett 26:6413 (1985)) was dissolved in THF (3 mL) and cooled to −20° C. The solution was treated with LHMDS (1.05 mL, 1.05 mmol) and stirred at −20° C. for 30 minutes. di-tert-Butyl dicarbonate (0.250 g, 1.14 mmol) was added, and the reaction mixture was allowed to warm to ambient temperature. The reaction was stirred at ambient temperature for two hours, and then quenched with saturated $NH_4Cl$, diluted with ethyl acetate and separated. The organic layer was washed with saturated $NH_4Cl$, saturated $NaHCO_3$, saturated NaCl, dried over $Na_2SO_4$ and concentrated in vacuo to an oil. The crude product was subjected to chromatography on $SiO_2$ and eluted with 4:1 hexanes/ethyl acetate. tert-Butyl 2,2-dimethyl-5-oxopyrrolidine-1-carboxylate (Rf of 0.11 in 4:1 hexanes/ethyl acetate) was recovered as a solid (0.087 g, 43%). $^1$H NMR ($CDCl_3$, 400 MHz) □2.48 (t, J=7.8, 2H), 1.85 (t, 2H), 1.54 (s, 9H), 1.47 (s, 6H).

tert-Butyl 2,2-dimethyl-5-oxopyrrolidine-1-carboxylate (1.17 g, 5.49 mmol) was dissolved in $Et_2O$ (15 mL) and cooled to −78° C. The solution was treated with DIBAL-H (3.73 mL, 5.60 mmol). The mixture was stirred at −78° C. for 2 hours and then warmed to ambient temperature overnight. The reaction was quenched by addition of an aliquot (7 mL) of a solution of p-toluenesulfonic acid hydrate (0.012 g) in MeOH (12 mL). The mixture was stirred at ambient temperature for 60 hours. The suspension was concentrated in vacuo and re-suspended in a mixture of Rochelle's salt (0.5N) and ethyl acetate. After separation, the aqueous portion was washed with ethyl acetate (2×). The combined organics were then washed with saturated NaCl, dried over $Na_2SO_4$ and concentrated in vacuo to an oil (92%). A solution of titanium (IV) chloride (3.71 mL, 3.71 mmol) in toluene was cooled to 0° C. and treated with a solution of (R)-4-benzyl-3-(2-(4-chlorophenyl)acetyl)oxazolidin-2-one (1.11 g, 3.38 mmol) dissolved in dichloromethane (7 mL). After 5 minutes, diisopropylethylamine (0.647 mL, 3.71 mmol) was added. The resultant solution was stirred for 1 hour at 0° C. and then cooled to −20° C. A solution of tert-butyl 5-hydroxy-2,2-dimethylpyrrolidine-1-carboxylate (1.09 g, 5.06 mmol) in dichloromethane (7 mL) was added, and the mixture was stirred at −20° C. for 75 minutes. The reaction was quenched with saturated NH₄Cl (about 4 mL) and diluted with water to dissolve the solids. After separation, the aqueous portion was washed with methylene chloride (3×). The combined organics were washed with water (2×), dried over Na₂SO₄ and concentrated in vacuo. The crude product was subjected to chromatography on SiO₂ and eluted with 9:1 hexanes/ethyl acetate to produce (S)-tert-butyl 5-((S)-2-((R)-4-benzyl-2-oxooxazolidin-3-yl)-1-(4-chlorophenyl)-2-oxoethyl)-2,2-dimethylpyrrolidine-1-carboxylate (1.62 g, 61%). MS (ESI+) [M+1-1] 526.7/528.8.

(S)-2-((S)-1-(tert-Butoxycarbonyl)-5,5-dimethylpyrrolidin-2-yl)-2-(4-chlorophenyl)acetic acid was prepared according to the procedure described in Example D using (S)-tert-butyl 5-((S)-2-((R)-4-benzyl-2-oxo oxazolidin-3-yl)-1-(4-chlorophenyl)-2-oxo ethyl)-2,2-dimethylpyrrolidine-1-carboxylate. $^{1}$H NMR (CDCl₃, 400 MHz) □7.33-7.21 (m, 4H), 4.60-4.51 (m, 1H), 4.39-4.32 (m, 1H), 2.04-1.92 (m, 2H), 1.78-1.68 (m, 2H), 1.51 (s, 9H), 1.22 (s, 6H).

Example H

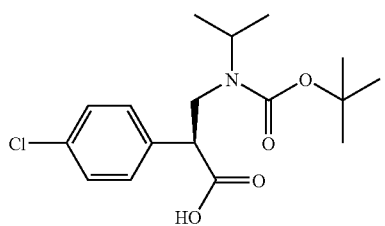 [SMILES: CC(C)N(C[C@@H](C(=O)O)c1ccc(Cl)cc1)C(=O)OC(C)(C)C]

(S)-3-(tert-butoxycarbonyl(isopropyl)amino)-2-(4-chlorophenyl)propanoic Acid

Methyl 2-(4-chlorophenyl)acetate (36.7 g, 199 mmol) and paraformaldehyde (6.27 g, 209 mmol) were dissolved/suspended in DMSO (400 mL) and treated with NaOMe (537 mg, 9.94 mmol). The mixture was allowed to stir at room temperature for 2 hours to completion by TLC analysis of the crude. The reaction was poured into ice-cold water (700 mL; emulsion) and neutralized with the addition of 1M HCl solution. The aqueous layer was extracted with ethyl acetate (3×), and the organics were combined. The organic layer was washed with water (2×), brine (1×), separated, dried over MgSO₄, filtered, and concentrated in vacuo to afford the crude product as an oil. The residue was loaded onto a large fritted filtered with silica gel and eluted with 9:1 hexanes:ethyl acetate until the starting material/olefin were collected. The plug was then eluted with 1:1 hexanes:ethyl acetate until the pure desired product was eluted completely. The concentrated pure fractions yielded methyl 2-(4-chlorophenyl)-3-hydroxypropanoate as an oil (39.4 g, 92%).

Methyl 2-(4-chlorophenyl)-3-hydroxypropanoate (39.4 g, 184 mmol) was dissolved in DCM (500 mL) and treated with TEA (64.0 mL, 459 mmol). The solution was cooled to 0° C. and slowly treated with MsCl (15.6 mL, 202 mmol), then allowed to stir for 30 minutes to completion by TLC analysis. The solution was partitioned with 1N HCl solution, and the aqueous layer was extracted once with DCM. The combined organic layer was washed once more with 1N HCl solution, separated, washed with diluted NaHCO₃ solution, and separated. The organic layer was dried over MgSO₄, filtered, and concentrated in vacuo to afford an oil. The residue was loaded onto a large fritted filter with a plug of silica gel and eluted with 9:1 hexanes:ethyl acetate affording the pure desired product by TLC analysis. The concentrated pure fractions yielded the methyl 2-(4-chlorophenyl)acrylate as an oil (30.8 g, 85%). This methyl 2-(4-chlorophenyl)acrylate (500 mg, 2.54 mmol) was added as a solution in THF (1.35 mL) to a stirring solution of i-PrNH₂ (217 μL, 2.54 mmol) in THF (5.0 mL) at 0° C. The reaction was allowed to stir at room temperature overnight to completion by LCMS analysis. The Boc₂O (584 μL, 2.54 mmol) was added to the stirring amine via pipet. The reaction was allowed to stir overnight to completion by LCMS and TLC analysis of the mixture. The solution was concentrated in vacuo to afford methyl 3-(tert-butoxycarbonyl(isopropyl)amino)-2-(4-chlorophenyl)propanoate as an oil (854 mg, 94%). LC/MS (APCI+) m/z 256.1 [M-Boc]+.

Methyl 3-(tert-butoxycarbonyl(isopropyl)amino)-2-(4-chlorophenyl)propanoate (133 g, 374 mmol) was dissolved in THF (1.0 L) and treated with potassium trimethylsilanolate ("KOTMS"; 56.0 g, 392 mmol) at room temperature. The mixture was allowed to stir overnight to completion by LCMS analysis of the crude. The mixture was concentrated in vacuo to afford a wet foam, which was allowed to dry under vacuum overnight to afford potassium 3-(tert-butoxycarbonyl(isopropyl)amino)-2-(4-chlorophenyl)propanoate as a solid (148.7 g, 105%). LC/MS (APCI+) m/z 242.1 [M-Boc-K]+.

Potassium 3-(tert-butoxycarbonyl(isopropyl)amino)-2-(4-chlorophenyl) propanoate (77.2 g, 203 mmol) was dissolved in THF (515 mL) and treated with pivaloyl chloride (26.3 mL, 213 mmol) at room temperature. The mixture was allowed to stir for 3 hours to form the mixed anhydride. (S)-4-Benzyloxazolidin-2-one (46.1 g, 260 mmol) was dissolved in THF (600 mL) and cooled to −78° C. in a separate flask. The solution was treated with n-BuLi (102 mL of a 2.50M solution in hexanes, 254 mmol) and allowed to stir for one hour. The prepared anhydride solution was added to the stirring Li-oxazolidinone via cannula, and the mixture was allowed to warm to room temperature overnight. The mixture was quenched with the addition of saturated ammonium chloride solution, and then partitioned between more water and ethyl acetate. The aqueous layer was extracted several times, and the organics were combined. The organic layer was washed with water, then brine, separated, dried over MgSO₄, filtered, and concentrated in vacuo. The residue was purified/separated (diastereomers) via chromatography (silica gel eluted with 4:1 hexanes:ethyl acetate) to afford the completely separated diastereomers as viscous oils: tert-butyl (R)-34(S)-4-benzyl-2-oxooxazolidin-3-yl)-2-(4-chlorophenyl)-3-oxopropyl(isopropyl)carbamate (12.16 g, 24% based on ½ of acid racemate) and tert-butyl (S)-3-((S)-4-benzyl-2-oxooxazolidin-3-yl)-2-(4-chlorophenyl)-3-oxopropyl(isopropyl) carbamate (39.14 g, 77% based on ½ of acid racemate). LC/MS (APCI+) m/z 401.2 [M-Boc]+.

LiOH—H₂O (168 mg, 4.00 mmol) was added to a stirring solution of THF (30 mL) and water (15 mL) at room temperature until it was dissolved. The mixture was treated with hydrogen peroxide (658 μL of a 35% wt. solution in water, 8.00 mmol) and allowed to stir at room temperature for 10 minutes. The reaction was cooled to 0° C. in an ice bath, and the tert-butyl (S)-3-((S)-4-benzyl-2-oxooxazolidin-3-yl)-2-(4-chlorophenyl)-3-oxopropyl(isopropyl) carbamate (1.00 g, 2.00 mmol) was added dropwise via addition funnel as a solution in THF (15 mL) over 10 minutes. The mixture was allowed to stir overnight at room temperature to completion by LCMS analysis of the crude. The reaction was cooled to 0° C., and then treated with 1M Na$_2$SO$_3$ (9.00 mL) solution via addition funnel over a 10 minute period. After the addition was complete, the mixture was allowed to warm to room temperature for 10 minutes. The mixture was concentrated to remove the THF, and then diluted with water. The aqueous layer was washed twice with ethyl acetate (discarded). The aqueous layer was partitioned with ethyl acetate, and then 1M HCl was added dropwise while stirring until a pH of about 2 to about 3 was attained. The aqueous layer was extracted twice with ethyl acetate, and the organics were combined. The organic was washed with brine, separated, dried over MgSO$_4$, filtered, and concentrated in vacuo. The oil product was dried under high vacuum for one hour to afford (S)-3-(tert-butoxycarbonyl(isopropyl)amino)-2-(4-chlorophenyl) propanoic acid as a viscous oil/foam (685 mg, 100%). LC/MS (APCI+) m/z 242.1 [M-Boc]+.

Example 1

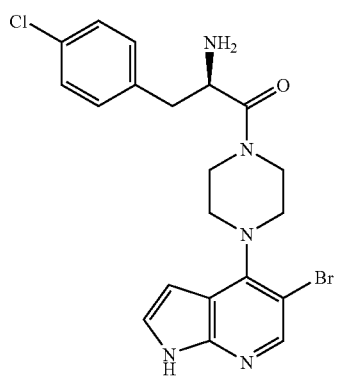 [SMILES: N[C@H](Cc1ccc(Cl)cc1)C(=O)N1CCN(c2c(Br)cnc3[nH]ccc23)CC1]

(R)-2-amino-1-(4-(5-bromo-1H-pyrrolo[2,3-b]pyridin-4-yl)piperazin-1-yl)-3-(4-chlorophenyl)propan-1-one meta-Chloroperbenzoic acid ("m-CPBA"; 25.4 g, 147 mmol) was added portionwise to 1H-pyrrolo[2,3-b]pyridine (15.0 g, 127 mmol) in 1:2 dimethoxyethane ("DME"):heptane (80:160 mL) at 10° C. The reaction was then stirred at room temperature for 1 hour. The precipitate was filtered and washed with 1:2 DME:heptane. The precipitate was then dried to give 7-hydroxy-1H-pyrrolo[2,3-b]pyridin-7-ium 3-chlorobenzoate (33.0 g, 89.4% yield).

POCl$_3$ (10 mL) was added to 7-hydroxy-1H-pyrrolo[2,3-b]pyridin-7-ium 3-chlorobenzoate (1.0 g, 3.4 mmol). The resulting mixture was heated to 90° C. for 18 hours. The mixture was then cooled to room temperature and concentrated. The resulting residue was diluted with acetonitrile ("ACN"; 3 mL) and water (3 mL). The pH was adjusted with 50% NaOH to a pH of 9. The resulting solid was filtered and washed with water. The solid was then washed with DCM to give 4-chloro-1H-pyrrolo[2,3-b]pyridine (0.30 g, 57% yield).

NaH (0.177 g, 4.42 mmol) was added to 4-chloro-1H-pyrrolo[2,3-b]pyridine (0.450 g, 2.95 mmol) in dimethylformamide ("DMF"; 5 mL) at 0° C. The reaction was then warmed to room temperature and stirred for 1 hour. The reaction was then cooled to 0° C. Chlorotriisopropylsilane (0.945 mL, 4.42 mmol) was added to the mixture. The reaction mixture was warmed to 70° C. and stirred for 2 hours. Next, the reaction was poured into water (50 mL) and extracted with DCM (3×50 mL). The combined organic fractions were dried (MgSO$_4$), filtered and concentrated. The resulting residue was purified by column chromatography (10:1 hexanes:DCM) to give 4-chloro-1-(triisopropylsilyl)-1H-pyrrolo[2,3-b]pyridine (0.55 g, 60.4% yield).

4-Chloro-1-(triisopropylsilyl)-1H-pyrrolo[2,3-b]pyridine (0.55 g, 1.78 mmol) was dissolved in THF (15 mL) and cooled to −78° C. s-BuLi (2.80 mL, 3.92 mmol) was then added dropwise. The solution was then stirred at −78° C. for 30 minutes. CBr$_4$ (1.48 g, 4.45 mmol) was then added as a THF (2 mL) solution. The reaction was stirred for an additional 30 minutes as it was allowed to warm to 0° C. The reaction was then quenched with saturated NH$_4$Cl and allowed to warm to room temperature. The reaction was then extracted with DCM (3×50 mL), dried, and filtered to give a crude residue. The crude residue was purified by chromatography with hexane to give 5-bromo-4-chloro-1-(triisopropylsilyl)-1H-pyrrolo[2,3-b]pyridine (0.502 g, 72.7% yield).

5-Bromo-4-chloro-1-(triisopropylsilyl)-1H-pyrrolo[2,3-b]pyridine (0.375 g, 0.96 mmol) and piperazine (0.666 g, 7.73 mmol) were placed in N-methylpyrrolidone ("NMP"; 3 mL) and heated to 130° C. in a microwave for 3 hours. The reaction was then diluted with DCM (15 mL). Triethylamine (0.20 mL, 1.45 mmol) and Boc$_2$O (3.17 g, 14.5 mmol) were then added. The reaction was stirred for 1 hour at room temperature. The reaction was then quenched with saturated NaHCO$_3$, and extracted with DCM. The organic fractions were dried, filtered, and concentrated to give a crude residue that was dissolved in 2:1 THF:MeOH (18 mL total). LiOH (4.83 mL, 14.5 mmol) was then added, and the reaction was stirred for 1 hour. The reaction was then diluted with water (20 mL) and extracted with methyl tert-butyl ether ("MTBE"). The organic fraction was dried, filtered, and concentrated to give a crude residue. The crude residue was purified by column chromatography (500:7 DCM:MeOH) to give tert-butyl 4-(5-bromo-1H-pyrrolo[2,3-b]pyridin-4-yl)piperazine-1-carboxylate (0.2 g, 54% yield).

tert-Butyl 4-(5-bromo-1H-pyrrolo[2,3-b]pyridin-4-yl)piperazine-1-carboxylate (0.40 g, 1.05 mmol) was placed in DCM (3 mL) at room temperature. TFA (0.3 mL) was then added. The reaction was stirred at room temperature for 1 hour and concentrated to dryness. The resulting residue was dissolved in minimal DCM and added to a stirring solution of 1M HCl in ether. The resulting solid was collected by filtration, washed with ether, and dried to give 5-bromo-4-(piperazin-1-yl)-1H-pyrrolo[2,3-b]pyridine (0.28 g, 94.9% yield) as the dihydrochloride salt.

5-Bromo-4-(piperazin-1-yl)-1H-pyrrolo[2,3-b]pyridine dihydrochloride (0.20 g, 0.56 mmol) and (R)-2-(tert-butoxycarbonylamino)-3-(4-chlorophenyl)propanoic acid (0.677 g, 2.25 mmol) were placed in DCM (5 mL) at room temperature. 1-Hydroxybenzotriazole ("HOBT")—H$_2$O (0.121 g, 0.79 mmol), 1-ethyl-3-(3-dimethylaminopropyl)carbodiimide ("EDCI"; 0.14 g, 0.73 mmol), and triethylamine (0.39 mL, 2.82 mmol) were then added, and the reaction was stirred at room temperature for 18 hours. The reaction was then quenched with saturated Na$_2$CO$_3$ and extracted with DCM. The combined organic fractions were dried, filtered, and concentrated to give a crude residue. The crude residue was purified by column chromatography (500:7 DCM:MeOH) to give (R)-tert-butyl 1-(4-(5-bromo-1H-pyrrolo[2,3-b]pyridin-4-yl)piperazin-1-yl)-3-(4-chlorophenyl)-1-oxopropan-2-yl-carbamate (0.20 g, 62.9% yield).

(R)-tert-Butyl 1-(4-(5-bromo-1H-pyrrolo[2,3-b]pyridin-4-yl)piperazin-1-yl)-3-(4-chlorophenyl)-1-oxopropan-2-ylcarbamate (0.022 g, 0.039 mmol) was placed in DCM (3 mL) at room temperature. TFA (0.3 mL) was then added. The reaction was stirred at room temperature for 1 hour and then concentrated. The resulting residue was dissolved in minimal DCM and added to a stirring solution of 1M HCl in ether. The resulting solid (R)-2-amino-1-(4-(5-bromo-1H-pyrrolo[2,3-b]pyridin-4-yl)piperazin-1-yl)-3-(4-chlorophenyl)propan-1-one (0.016 g, 88% yield) was collected and dried as the dihydrochloride salt. MS ESI (+) m/z 463 detected.

Example 2

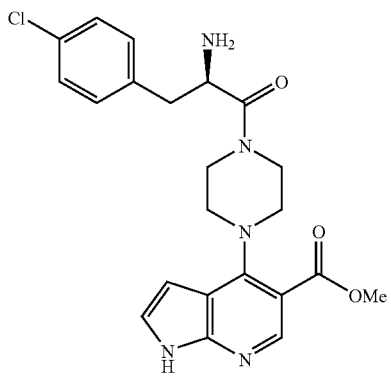 [SMILES: COC(=O)c1cnc2[nH]ccc2c1N1CCN(C(=O)[C@H](N)Cc2ccc(Cl)cc2)CC1]

(R)-methyl 4-(4-(2-amino-3-(4-chlorophenyl)propanoyl)piperazin-1-yl)-1H-pyrrolo[2,3-b]pyridine-5-carboxylate 4-Chloro-1-(triisopropylsilyl)-1H-pyrrolo[2,3-b]pyridine (0.50 g, 1.612 mmol, see Example 1) was dissolved in THF (15 mL) and cooled to −78° C. s-BuLi (2.54 mL, 3.56 mmol) was then added dropwise, and the solution was stirred at −78° C. for 30 minutes. Methyl chloroformate (0.38 mL, 4.98 mmol) was then added as a THF (2 mL) solution, and the reaction was stirred for an additional 30 minutes. The reaction was then quenched with saturated NH$_4$Cl and allowed to warm to room temperature. The reaction was then extracted with DCM (3×50 mL), dried, and filtered to give a crude residue. The crude residue was purified by column chromatography with 5:1 hexane:DCM to give methyl 4-chloro-1-(triisopropylsilyl)-1H-pyrrolo[2,3-b]pyridine-5-carboxylate (0.55 g, 91% yield).

Methyl 4-chloro-1-(triisopropylsilyl)-1H-pyrrolo[2,3-b]pyridine-5-carboxylate (0.45 g, 1.23 mmol) and piperazine (0.845 g, 9.81 mmol) were placed in NMP (5 mL) and heated to 100° C. in a microwave for 30 minutes. The reaction was then diluted with DCM (5 mL). Triethylamine (0.259 mL, 1.84 mmol) and Boc$_2$O (4.01 g, 18.4 mmol) were added, and the reaction stirred at room temperature for 1 hour. The crude reaction was washed with saturated NaHCO$_3$ and extracted with DCM. The combined organic fractions were dried, filtered and concentrated to give a crude residue. The residue was purified by column chromatography (2:1 to 1:1 hexanes:ethyl acetate ("EtOAc")) to give 1-tert-butyl 5-methyl 4-(4-(tert-butoxycarbonyl)piperazin-1-yl)-1H-pyrrolo[2,3-b]pyridine-1,5-dicarboxylate (0.40 g, 70.8% yield).

1-tert-Butyl 5-methyl 4-(4-(tert-butoxycarbonyl)piperazin-1-yl)-1H-pyrrolo[2,3-b]pyridine-1,5-dicarboxylate (0.34 g, 0.74 mmol) was placed in DCM (3 mL) at room temperature. TFA (0.5 mL) was then added. The reaction was stirred at room temperature for 4 hours and then concentrated to dryness. The resulting residue was dissolved in minimal DCM and added to a stirring solution of 1M HCl in ether. The resulting solid methyl 4-(piperazin-1-yl)-1H-pyrrolo[2,3-b]pyridine-5-carboxylate (0.19 g, 98.9% yield) was collected and dried as the dihydrochloride salt.

Methyl 4-(piperazin-1-yl)-1H-pyrrolo[2,3-b]pyridine-5-carboxylate (0.23 g, 0.69 mmol) and (R)-2-(tert-butoxycarbonylamino)-3-(4-chlorophenyl)propanoic acid (0.227 g, 0.759 mmol) were placed in DCM (5 mL) at room temperature. HOBT-H$_2$O (0.147 g, 0.966 mmol), EDCI (0.172 g, 0.897 mmol) and triethylamine (0.48 mL, 3.45 mmol) were then added, and the reaction was stirred at room temperature for 18 hours. The reaction was then quenched with saturated Na$_2$CO$_3$ and extracted with DCM. The combined organic fractions were dried, filtered, and concentrated to give a crude residue. The residue was purified by column chromatography (500:7 DCM:MeOH) to give (R)-methyl 4-(4-(2-(tert-butoxycarbonylamino)-3-(4-chlorophenyl)propanoyl)piperazin-1-yl)-1H-pyrrolo[2,3-b]pyridine-5-carboxylate (0.11 g, 29.4% yield).

(R)-Methyl 4-(4-(2-(tert-butoxycarbonylamino)-3-(4-chlorophenyl)propanoyl)piperazin-1-yl)-1H-pyrrolo[2,3-b]pyridine-5-carboxylate (0.025 g, 0.046 mmol) was placed in DCM (3 mL) at room temperature. TFA (0.3 mL) was then added. The reaction was stirred at room temperature for 1 hour and then concentrated. The resulting residue was dissolved in minimal DCM and added to a stirring solution of 1M HCl in ether. The resulting solid (R)-methyl 4-(4-(2-amino-3-(4-chlorophenyl)propanoyl)piperazin-1-yl)-1H-pyrrolo[2,3-b]pyridine-5-carboxylate (0.015 g, 74% yield) was collected and dried as the dihydrochloride salt. MS ESI (+) m/z 442 detected.

Example 3

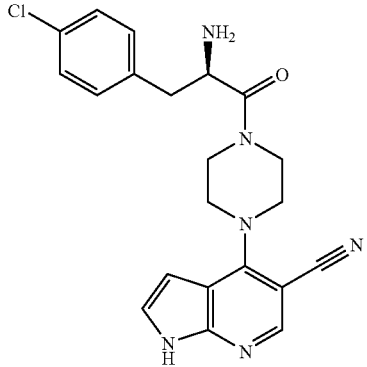 [SMILES: N#Cc1cnc2[nH]ccc2c1N1CCN(C(=O)[C@H](N)Cc2ccc(Cl)cc2)CC1]

(R)-4-(4-(2-amino-3-(4-chlorophenyl)propanoyl)piperazin-1-yl)-1H-pyrrolo[2,3-b]pyridine-5-carbonitrile (R)-Methyl 4-(4-(2-(tert-butoxycarbonylamino)-3-(4-chlorophenyl)propanoyl)piperazin-1-yl)-1H-pyrrolo[2,3-b]pyridine-5-carboxylate (0.210 g, 0.3874 mmol, see Example 2) was placed in 2:1 THF:MeOH (6 mL). 3M LiOH (aq., 1.29 mL, 3.87 mmol) was then added, and the reaction was heated to 65° C. for 2 hours. The reaction was then diluted with water and extracted with DCM. The combined organic fractions were dried, filtered, and concentrated to give a crude residue.

The residue was purified by column:chromatography (20:1 DCM:MeOH) to give (R)-4-(4-(2-(tert-butoxycarbonylamino)-3-(4-chlorophenyl)propanoyl)piperazin-1-yl)-1H-pyrrolo[2,3-b]pyridine-5-carboxylic acid (0.050 g, 24.4% yield).

(R)-4-(4-(2-(tert-Butoxycarbonylamino)-3-(4-chlorophenyl)propanoyl)piperazin-1-yl)-1H-pyrrolo[2, 3-1)]pyridine-5-carboxylic acid (0.050 g, 0.0947 mmol) was placed in DMF (3 mL) at room temperature. $NH_4Cl$ (0.020 g, 0.378 mmol), DIEA (d 0.742; 0.082 mL, 0.473 mmol) and HBTU (0.071 g, 0.189 mmol) were then added to the mixture. The reaction was stirred for 1 hour at room temperature, quenched with water and extracted with EtOAc. The combined organic fractions were dried, filtered, and concentrated. The crude residue was purified (20:1 DCM:MeOH) to give (R)-tert-butyl 1-(4-(5-carbamoyl-1H-pyrrolo[2,3-b]pyridin-4-yl)piperazin-1-yl)-3-(4-chlorophenyl)-1-oxopropan-2-ylcarbamate (0.030 g, 60.1% yield).

(R)-tert-Butyl 1-(4-(5-carbamoyl-1H-pyrrolo[2,3-b]pyridin-4-yl)piperazin-1-yl)-3-(4-chlorophenyl)-1-oxopropan-2-ylcarbamate (0.035 g, 0.066 mmol) was placed in $POCl_3$ (2 mL) and heated to 70° C. for 2 hours. The reaction was then concentrated, diluted with DCM, and washed with saturated $NaHCO_3$. The organic fraction was dried, filtered and concentrated to give a crude residue. The residue was purified (SP4, 12+M, water/CAN 95/5→60/40, 20CV) to give (R)-4-(4-(2-amino-3-(4-chlorophenyl)propanoyl)piperazin-1-yl)-1H-pyrrolo[2,3-b]pyridine-5-carbonitrile (0.002 g, 7.4% yield). MS ESI (+) m/z 409 detected.

Example 4

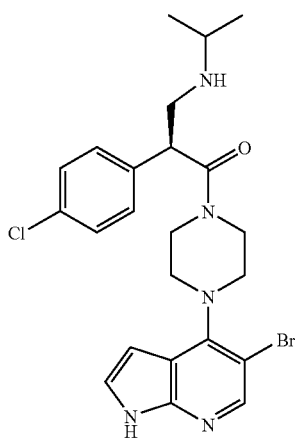 [SMILES: CC(C)NC[C@@H](C(=O)N1CCN(c2c(Br)cnc3[nH]ccc23)CC1)c1ccc(Cl)cc1]

(S)-1-(4-(5-bromo-1H-pyrrolo[2,3-b]pyri din-4-yl)piperazin-1-yl)-2-(4-chlorophenyl)-3-(isopropylamino)propan-1-one 5-Bromo-4-(piperazin-1-yl)-1H-pyrrolo[2,3-b]pyridine dihydrochloride (0.100 g, 0.282 mmol, see Example 1), (S)-3-(tert-butoxycarbonyl(isopropyl)amino)-2-(4-chlorophenyl)propanoic acid (0.145 g, 0.424 mmol, see Example H), HOBT-$H_2O$ (0.0606 g, 0.395 mmol), EDCI (0.0704 g, 0.367 mmol), and triethylamine (0.0394 mL, 0.282 mmol) were stirred in DCM (5 mL) at room temperature for 5 hours. The reaction was quenched with saturated $Na_2CO_3$ and extracted into DCM. The organics were dried, filtered, and concentrated to give the crude product. Purification (500:6 DCM:MeOH) gave (S)-tert-butyl 3-(4-(5-bromo-1H-pyrrolo[2,3-b]pyridin-4-yl)piperazin-1-yl)-2-(4-chlorophenyl)-3-oxopropyl(isopropyl)carbamate (0.103 g, 60.2% yield).

(S)-tert-Butyl 3-(4-(5-bromo-1H-pyrrolo[2,3-b]pyridin-4-yl)piperazin-1-yl)-2-(4-chlorophenyl)-3-oxopropyl(isopropyl)carbamate (0.040 g, 0.066 mmol) was placed in DCM (3 mL). TFA (0.3 mL) was then added. The reaction was stirred at room temperature for 1 hour. The reaction was then concentrated to dryness, dissolved in minimal DCM, and added dropwise to a stirring solution of 1M HCl in ether. The solid product was filtered, washed with ether, and dried to give (S)-1-(4-(5-bromo-1H-pyrrolo[2,3-b]pyri din-4-yl)piperazin-1-yl)-2-(4-chlorophenyl)-3-(isopropylamino)propan-1-one (0.03 g, 90% yield) as the dihydrochloride salt. MS ESI (+) m/z 505 detected.

Example 5

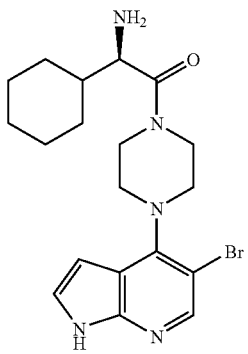 [SMILES: N[C@@H](C(=O)N1CCN(c2c(Br)cnc3[nH]ccc23)CC1)C1CCCCC1]

(R)-2-amino-1-(4-(5-bromo-1H-pyrrolo[2,3-b]pyridin-4-yl)piperazin-1-yl)-2-cyclohexylethanone 5-Bromo-4-(piperazin-1-yl)-1H-pyrrolo[2,3-b]pyridine (0.075 g, 0.26 mmol, see Example 1) and (R)-2-(tert-butoxycarbonylamino)-2-cyclohexylacetic acid (0.205 g, 0.80 mmol) were placed in DCM (3 mL) at room temperature. HOBT-$H_2O$ (0.057 g, 0.37 mmol), EDCI (0.066 g, 0.39 mmol), and triethylamine (0.18 mL, 1.33 mmol) were then added. The reaction was stirred at room temperature overnight. The reaction was then quenched with saturated $Na_2CO_3$ and extracted into DCM. The product was then dried, filtered, and concentrated. The product was purified (500:5 DCM:MeOH) to yield (R)-tert-butyl 2-(4-(5-bromo-1H-pyrrolo[2,3-b]pyridin-4-yl)piperazin-1-yl)-1-cyclohexyl-2-oxo ethylcarbamate (0.025 g, 18.0% yield).

(R)-tert-Butyl 2-(4-(5-bromo-1H-pyrrolo[2,3-b]pyridin-4-yl)piperazin-1-yl)-1-cyclohexyl-2-oxoethylcarbamate (0.010 g, 0.019 mmol) was placed in DCM (3 mL) at room temperature. TFA (0.3 mL) was then added. The reaction was stirred at room temperature for 1 hour. The reaction was then concentrated to dryness, dissolved in minimal DCM, and added dropwise to a stirring solution of 1M HCl in ether. The solid product was filtered, washed with ether, and dried to give (R)-2-amino-1-(4-(5-bromo-1H-pyrrolo[2,3-b]pyri din-4-yl)piperazin-1-yl)-2-cyclohexylethanone (0.005 g, 62% yield) as the dihydrochloride salt. MS ESI (+) m/z 421 detected.

Example 6

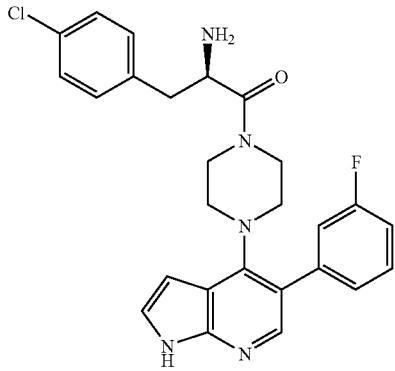 [SMILES: N[C@H](Cc1ccc(Cl)cc1)C(=O)N1CCN(c2c(-c3cccc(F)c3)cnc3[nH]ccc23)CC1]

(R)-2-amino-3-(4-chlorophenyl)-1-(4-(5-(3-fluo-rophenyl)-1H-pyrrolo[2,3-b]pyridin-4-yl)piperazin-1-yl)propan-1-one 5-Bromo-4-chloro-1-(triisopropylsilyl)-1H-pyrrolo[2,3-b]pyridine (4.1 g, 10.57 mmol, see Example 1) was placed in THF (80 mL) at room temperature. TBAF (1.1 equivalents) was then added, and the reaction was stirred at room temperature for 1 hour. The reaction was then poured into water and extracted with DCM. The combined organic fractions were dried, filtered, and concentrated to give a crude solid. The solid was then suspended in 10:1 hexanes:DCM, and filtered to give the solid product 5-bromo-4-chloro-1H-pyrrolo[2,3-b]pyridine (2.20 g, 89.9% yield).

5-Bromo-4-chloro-1H-pyrrolo[2,3-b]pyridine (0.50 g, 2.160 mmol) was placed in DMF (5 mL) at 0° C. NaH (0.10 g, 2.59 mmol) was then added, and the reaction was stirred for 20 minutes. Benzenesulfonyl chloride (0.304 mL, 2.38 mmol) was then added, and the reaction was stirred for 30 minutes at 0° C. Water (50 mL) was then added. The precipitate was filtered, washed with water, washed with ether, and dried to give 5-bromo-4-chloro-1-(phenylsulfonyl)-1H-pyrrolo[2,3-b]pyridine (0.8 g, 99.6% yield).

5-Bromo-4-chloro-1-(phenylsulfonyl)-1H-pyrrolo[2,3-b]pyridine (0.660 g, 1.78 mmol), 3-fluorophenylboronic acid (0.298 g, 2.13 mmol), Pd(PPh$_3$)$_4$ (0.103 g, 0.0888 mmol) and 10% K$_2$CO$_3$ (aq., 3.70 mL, 2.66 mmol) were added to an argon degassed solution of 2:1 toluene:EtOH (6 mL). The reaction was then heated to 80° C. for 18 hours. The reaction was then diluted with water and extracted with DCM. The organic fractions were dried, filtered, concentrated, and purified by column chromatography (1:1 hexanes:DCM) to give 4-chloro-5-(3-fluorophenyl)-1-(phenylsulfonyl)-1H-pyrrolo[2,3-b]pyridine (0.508 g, 73.9% yield).

4-Chloro-5-(3-fluorophenyl)-1-(phenylsulfonyl)-1H-pyrrolo[2,3-b]pyridine (0.100 g, 0.259 mmol) and piperazine (0.356 g, 4.14 mmol) were placed in NMP (1 mL) and heated to 150° C. in a microwave for 1 hour. The reaction was then diluted with DCM (20 mL), and Boc$_2$O (1.92 g, 8.79 mmol) was added. The reaction was then stirred for 1 hour, poured into water, and extracted with DCM. The organic fractions were dried, filtered, and concentrated. The crude residue was purified (5:1-4:1 hexane:EtOAc) to give tert-butyl 4-(5-(3-fluorophenyl)-1-(phenylsulfonyl)-1H-pyrrolo[2,3-b]pyridin-4-yl)piperazine-1-carboxylate (0.080 g, 57.7% yield).

tert-Butyl 4-(5-(3-fluorophenyl)-1-(phenyl sulfonyl)-1H-pyrrolo[2,3-b]pyridin-4-yl)piperazine-1-carboxylate (0.220 g, 0.410 mmol) was placed in 1:1 THF:MeOH (6 mL). 3M LiOH (0.683 mL, 2.05 mmol) was then added, and the reaction was stirred at 50° C. for 1 hour. The reaction was then cooled, added to water and extracted with DCM. The organic fractions were dried, filtered and concentrated to give the crude product tert-butyl 4-(5-(3-fluorophenyl)-1H-pyrrolo[2,3-b]pyridin-4-yl)piperazine-1-carboxylate (0.150 g, 92.29% yield), which was used without further purification.

tert-Butyl 4-(5-(3-fluorophenyl)-1H-pyrrolo[2,3-b]pyridin-4-yl)piperazine-1-carboxylate (0.162 g, 0.409 mmol) was placed in DCM (3 mL) at room temperature. TFA (0.3 mL) was then added, and the reaction was stirred at room temperature for 1 hour. The reaction was then concentrated to dryness, dissolved in minimal DCM, and added dropwise to a stirring solution of 1M HCl in ether. The solid product was filtered, washed with ether, and dried to give 5-(3-fluorophenyl)-4-(piperazin-1-yl)-1H-pyrrolo[2,3-b]pyridine (0.116 g, 95.8% yield) as the dihydrochloride salt.

5-(3-Fluorophenyl)-4-(piperazin-1-yl)-1H-pyrrolo[2,3-b]pyridine (0.062 g, 0.168 mmol) and (R)-2-(tert-butoxycarbonylamino)-3-(4-chlorophenyl)propanoic acid (0.0604 g, 0.201 mmol) were placed in DCM (3 mL) at room temperature. HOBT-H$_2$O (0.0360 g, 0.235 mmol), EDCI (0.0418 g, 0.218 mmol), and DIEA (d 0.742; 0.146 mL, 0.840 mmol) were then added. The reaction was stirred at room temperature for 2 hours. The reaction was then quenched with saturated Na$_2$CO$_3$ and extracted with DCM. The organic fractions were dried, filtered, and concentrated to give a crude oil. The oil was purified by column chromatography (500:5 DCM:MeOH) to give (R)-tert-butyl 3-(4-chlorophenyl)-1-(4-(5-(3-fluorophenyl)-1H-pyrrolo[2,3-b]pyridin-4-yl)piperazin-1-yl)-1-oxopropan-2-ylcarbamate (0.045 g, 46.3% yield).

(R)-tert-Butyl 3-(4-chlorophenyl)-1-(4-(5-(3-fluorophenyl)-1H-pyrrolo[2,3-b]pyridin-4-yl)piperazin-1-yl)-1-oxopropan-2-ylcarbamate (0.045 g, 0.078 mmol) was placed in DCM (3 mL) at room temperature. TFA (0.3 mL) was then added, and the reaction was stirred at room temperature for 1 hour. The reaction was then concentrated to dryness, dissolved in minimal DCM, and added dropwise to a stirring solution of 1M HCl in ether. The solid product was filtered, washed with ether, and dried to give (R)-2-amino-3-(4-chlorophenyl)-1-(4-(5-(3-fluorophenyl)-1H-pyrrolo[2,3-b]pyridin-4-yl)piperazin-1-yl)propan-1-one (0.018 g, 48% yield) as the dihydrochloride salt. MS ESI (+) m/z 478 detected.

Example 7

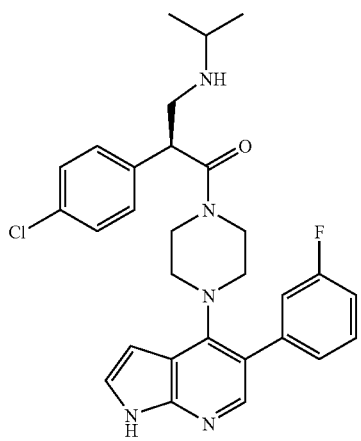 [SMILES: CC(C)NC[C@@H](C(=O)N1CCN(c2c(-c3cccc(F)c3)cnc3[nH]ccc23)CC1)c1ccc(Cl)cc1]

(S)-2-(4-chlorophenyl)-1-(4-(5-(3-fluorophenyl)-1H-pyrrolo[2,3-b]pyri din-4-yl)piperazin-1-yl)-3-(isopropylamino)propan-1-one 5-(3-Fluorophenyl)-4-(piperazin-1-yl)-1H-pyrrolo[2,3-b] pyri dine (0.050 g, 0.135 mmol, see Example 6) and (S)-3-(tert-butoxycarbonyl(isopropyl)amino)-2-(4-chlorophenyl) propanoic acid (0.0555 g, 0.162 mmol, see Example H) were placed in DCM (3 mL) at room temperature. HOBT-H₂O (0.0290 g, 0.190 mmol), EDCI (0.0337 g, 0.176 mmol), and DIEA (d 0.742; 0.118 mL, 0.677 mmol) were then added, and the reaction was stirred at room temperature for 2 hours. The reaction was then quenched with saturated Na₂CO₃ and extracted with DCM. The product was dried, filtered, and concentrated to give the crude product. The crude product was purified (500:5 DCM:MeOH) to yield (S)-tert-butyl 2-(4-chlorophenyl)-3-(4-4(5-(3-fluorophenyl)-1H-pyrrolo [2,3-b]pyridin-4-yl)piperazin-1-yl)-3-oxopropyl(isopropyl) carbamate (0.038 g, 45.2% yield).

(S)-tert-Butyl 2-(4-chlorophenyl)-3-(4-(5-(3-fluorophenyl)-1H-pyrrolo[2,3-b]pyridin-4-yl)piperazin-1-yl)-3-oxopropyl(isopropyl)carbamate (0.040 g, 0.064 mmol) was placed in DCM (3 mL) at room temperature. TFA (0.3 mL) was then added, and the reaction was stirred at room temperature for 1 hour. The reaction was then concentrated to dryness, dissolved in minimal DCM, and added dropwise to a stirring solution of 1M HCl in ether. The solid product was filtered, washed with ether, and dried to give (S)-2-(4-chlorophenyl)-1-(4-(5-(3-fluorophenyl)-1H-pyrrolo[2,3-b]pyri din-4-yl) piperazin-1-yl)-3-(isopropylamino)propan-1-one (0.020 g, 60% yield) as the dihydrochloride salt. MS ESI (+) m/z 521 detected.

Example 8

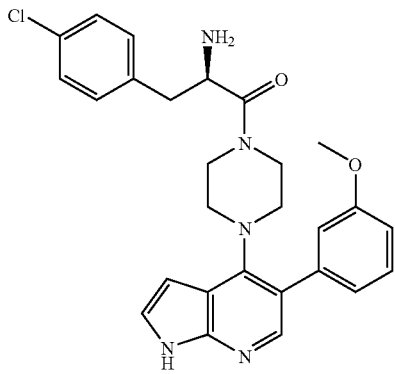 [SMILES: COc1cccc(-c2cnc3[nH]ccc3c2N2CCN(C(=O)[C@H](N)Cc3ccc(Cl)cc3)CC2)c1]

(R)-2-amino-3-(4-chlorophenyl)-1-(4-(5-(3-methoxyphenyl)-1H-pyrrolo[2,3-b]pyridin-4-yl)piperazin-1-yl)propan-1-one 5-Bromo-4-chloro-1-(phenylsulfonyl)-1H-pyrrolo[2,3-b] pyri dine (0.750 g, 2.01 mmol, see Example 6), 3-methoxyphenylboronic acid (0.321 g, 2.11 mmol), Pd(PPh₃)₄ (0.116 g, 0.100 mmol) and K₂CO₃ (4.20 mL, 3.02 mmol) were added to an Ar degassed solution of 2:1 toluene:EtOH (8 mL). The reaction was then heated to 80° C. overnight. The reaction was then poured into water and extracted with DCM. The organic fractions were dried, filtered, and concentrated to give the crude product. The crude product was purified (1:1 to 1:2 hexane:DCM) to give 4-chloro-5-(3-methoxyphenyl)-1-(phenylsulfonyl)-1H-pyrrolo[2,3-b]pyridine (0.610 g, 75.8% yield).

4-Chloro-5-(3-methoxyphenyl)-1-(phenylsulfonyl)-1H-pyrrolo[2,3-b]pyri dine (0.400 g, 1.00 mmol), tert-butyl piperazine-1-carboxylate (0.280 g, 1.50 mmol), Pd(OAc)₂ (0.0225 g, 0.100 mmol), Xantphos (0.0870 g, 0.150 mmol), and Cs₂CO₃ (0.490 g, 1.50 mmol) were placed in degassed toluene (4 mL). The mixture was heated to 100° C. for 24 hours. The reaction was cooled to room temperature, filtered through celite, and concentrated. The product was purified (500:5 to 500:7 DCM:MeOH) to yield tert-butyl 4-(5-(3-methoxyphenyl)-1-(phenylsulfonyl)-1H-pyrrolo[2,3-b]pyri din-4-yl)piperazine-1-carboxylate (0.160 g, 29.0% yield).

tert-Butyl 4-(5-(3-methoxyphenyl)-1-(phenylsulfonyl)-1H-pyrrolo[2,3-b]pyridin-4-yl)piperazine-1-carboxylate (0.150 g, 0.273 mmol) was dissolved in 1:1 THF:MeOH (6 mL). 3M LiOH (0.911 mL, 2.73 mmol) was then added, and the reaction was heated to 50° C. for 1 hour. The reaction was then cooled to room temperature, added to water, and extracted with DCM. The organics were then dried, filtered, and concentrated to give the crude product tert-butyl 4-4(5-(3-methoxyphenyl)-1H-pyrrolo[2,3-b]pyridin-4-yl)piperazine-1-carboxylate (0.111 g, 99.4% yield), which was used without further purification.

tert-Butyl 4-(5-(3-methoxyphenyl)-1H-pyrrolo[2,3-b]pyri din-4-yl)piperazine-1-carboxylate (0.111 g, 0.272 mmol) was placed in DCM (3 mL) at room temperature. TFA (0.3 mL) was then added, and the reaction was stirred at room temperature for 2 hours. The reaction was then concentrated to dryness, dissolved in minimal DCM, and added dropwise to a stirring solution of 1M HCl in ether. The solid product was filtered, washed with ether, and dried to give 5-(3-methoxyphenyl)-4-(piperazin-1-yl)-1H-pyrrolo[2,3-b]pyri dine (0.083 g, 99% yield) as the dihydrochloride salt.

5-(3-Methoxyphenyl)-4-(piperazin-1-yl)-1H-pyrrolo[2,3-b]pyri dine (0.045 g, 0.118 mmol) and (R)-2-(tert-butoxycarbonylamino)-3-(4-chlorophenyl)propanoic acid (0.0425 g, 0.142 mmol) were placed in DCM (3 mL). HOBT-H₂O (0.0253 g, 0.165 mmol), EDCI (0.0294 g, 0.153 mmol), and DIEA (d 0.742; 0.103 mL, 0.591 mmol) were then added, and the reaction was stirred for 2 hours. The reaction was then quenched with saturated Na₂CO₃ and extracted with DCM. The product was dried, filtered, and concentrated to give the crude product. The crude product was purified (500:5 DCM:MeOH) to yield (R)-tert-butyl 3-(4-chlorophenyl)-1-(4-(5-(3-methoxyphenyl)-1H-pyrrolo[2,3-b]pyridin-4-yl)piperazin-1-yl)-1-oxopropan-2-ylcarbamate (0.038 g, 54.6% yield).

(R)-tert-Butyl 3-(4-chlorophenyl)-1-(4-(5-(3-methoxyphenyl)-1H-pyrrolo[2,3-b]pyridin-4-yl)piperazin-1-yl)-1-oxopropan-2-ylcarbamate (0.021 g, 0.036 mmol) was placed in DCM (3 mL) at room temperature. TFA (0.3 mL) was then added, and the reaction was stirred at room temperature for 1 hour. The reaction was then concentrated to dryness, dissolved in minimal DCM, and added dropwise to a stirring solution of 1M HCl in ether. The solid product was filtered, washed with ether, and dried to give (R)-2-amino-3-(4-chlorophenyl)-1-(4-(5-(3-methoxyphenyl)-1H-pyrrolo[2,3-b]pyridin-4-yl)piperazin-1-yl)propan-1-one (0.015 g, 86% yield) as the dihydrochloride salt. MS ESI (+) m/z 491 detected.

Example 9

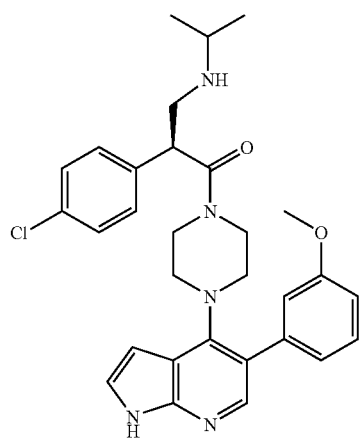 [SMILES: COc1cccc(-c2cnc3[nH]ccc3c2N2CCN(C(=O)[C@H](CNC(C)C)c3ccc(Cl)cc3)CC2)c1]

(S)-2-(4-chlorophenyl)-3-(isopropylamino)-1-(4-(5-(3-methoxyphenyl)-1H-pyrrolo[2,3-b]pyridin-4-yl)piperazin-1-yl)propan-1-one 5-(3-Methoxyphenyl)-4-(piperazin-1-yl)-1H-pyrrolo[2,3-b]pyridine (0.045 g, 0.118 mmol, see Example 8) and (S)-3-(tert-butoxycarbonyl(isopropyl)amino)-2-(4-chlorophenyl)propanoic acid (0.0424 g, 0.124 mmol, see Example H) were placed in DCM (3 mL). HOBT-H₂O (0.0253 g, 0.165 mmol), EDCI (0.0294 g, 0.153 mmol), and DIEA (d 0.742; 0.103 mL, 0.590 mmol) were then added, and the reaction was stirred at room temperature for 2 hours. The reaction was then quenched with saturated Na₂CO₃ and extracted with DCM. The product was dried, filtered, and concentrated to give the crude product. The crude product was purified (500:5 DCM:MeOH) to yield (S)-tert-butyl 2-(4-chlorophenyl)-3-(4-(5-(3-methoxyphenyl)-1H-pyrrolo[2, 3-1)]pyridin-4-yl)piperazin-1-yl)-3-oxopropyl(isopropyl)carbamate (0.040 g, 53.6% yield).

(S)-tert-Butyl 2-(4-chlorophenyl)-3-(4-(5-(3-methoxyphenyl)-1H-pyrrolo[2,3-b]pyridin-4-yl)piperazin-1-yl)-3-oxopropyl(isopropyl)carbamate (0.041 g, 0.065 mmol) was placed in DCM (3 mL) at room temperature. TFA (0.3 mL) was then added, and the reaction was stirred at room temperature for 1 hour. The reaction was then concentrated to dryness, dissolved in minimal DCM, and added dropwise to a stirring solution of 1M HCl in ether. The solid product was filtered, washed with ether, and dried to give (S)-2-(4-chlorophenyl)-3-(isopropylamino)-1-(4-(5-(3-methoxyphenyl)-1H-pyrrolo[2,3-b]pyridin-4-yl)piperazin-1-yl)propan-1-one (0.028 g, 81% yield) as the dihydrochloride salt. MS ESI (+) m/z 533 detected.

Example 10

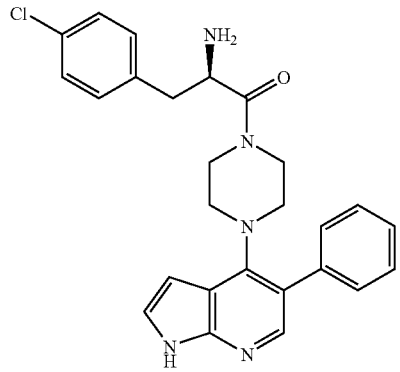 [SMILES: N[C@H](Cc1ccc(Cl)cc1)C(=O)N1CCN(c2c(-c3ccccc3)cnc3[nH]ccc23)CC1]

(R)-2-amino-3-(4-chlorophenyl)-1-(4-(5-phenyl-1H-pyrrolo[2,3-b]pyridin-4-yl)piperazin-1-yl)propan-1-one (R)-tert-Butyl 1-(4-(5-bromo-1H-pyrrolo[2,3-b]pyridin-4-yl)piperazin-1-yl)-3-(4-chlorophenyl)-1-oxopropan-2-ylcarbamate (0.180 g, 0.320 mmol, see Example 1), phenylboronic acid (0.0468 g, 0.384 mmol), Pd(PPh₃)₄ (0.0185 g, 0.0160 mmol) and 10% K₂CO₃ (aq., 0.66 mL, 0.47 mmol) were added to an Ar degassed solution of 2:1 toluene:EtOH (3 mL). The reaction was then heated to 80° C. overnight. The reaction was then cooled to room temperature, diluted with water, and extracted with DCM. The organic fractions were dried, filtered, concentrated, and purified (500:10-500:15) to give (R)-tert-butyl 3-(4-chlorophenyl)-1-oxo-1-(4-(5-phenyl-1H-pyrrolo[2,3-b]pyridin-4-yl)piperazin-1-yl)propan-2-ylcarbamate (0.018 g, 10.0% yield).

(R)-tert-Butyl 3-(4-chlorophenyl)-1-oxo-1-(4-(5-phenyl-1H-pyrrolo[2,3-b]pyridin-4-yl)piperazin-1-yl)propan-2-ylcarbamate (0.020 g, 0.036 mmol) was placed in DCM (3 mL). TFA (0.3 mL) was then added, and the reaction was stirred at room temperature for 1 hour. The reaction was then concentrated to dryness, dissolved in minimal DCM, and added dropwise to a stirring solution of 1M HCl in ether. The solid product was filtered, washed with ether, and dried to give (R)-2-amino-3-(4-chlorophenyl)-1-(4-(5-phenyl-1H-pyrrolo[2,3-b]pyridin-4-yl)piperazin-1-yl)propan-1-one (0.015 g, 79% yield) as the dihydrochloride salt. MS ESI (+) m/z 460 detected.

Example 11

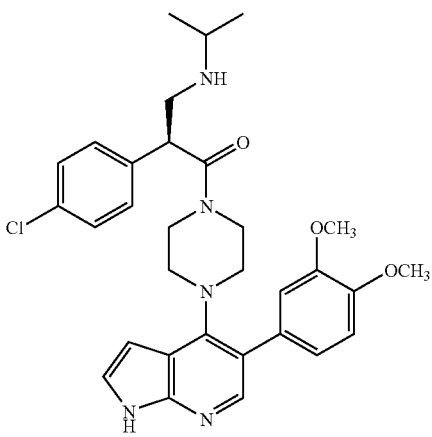 [SMILES: COc1ccc(-c2cnc3[nH]ccc3c2N2CCN(C(=O)[C@H](CNC(C)C)c3ccc(Cl)cc3)CC2)cc1OC]

(S)-2-(4-chlorophenyl)-1-(4-(5-(3,4-dimethoxyphenyl)-1H-pyrrolo[2,3-b]pyridin-4-yl)piperazin-1-yl)-3-(isopropylamino)propan-1-one (S)-tert-Butyl 3-(4-(5-bromo-1H-pyrrolo[2,3-b]pyridin-4-yl)piperazin-1-yl)-2-(4-chlorophenyl)-3-oxopropyl(isopropyl)carbamate (0.100 g, 0.165 mmol, see Example 4), 3,4-dimethoxyphenylboronic acid (0.0361 g, 0.198 mmol), Pd(PPh$_3$)$_4$ (0.009 g, 0.0083 mmol) and 10% K$_2$CO$_3$ (aq., 0.344 mL, 0.248 mmol) were added to an Ar degassed solution of 2:1 toluene:EtOH (3 mL). The reaction was then heated to 80° C. for 24 hours. The reaction was then cooled to room temperature, diluted with water, and extracted with DCM. The organic fractions were dried, filtered, concentrated, and purified (500:10-500:15) to give (S)-tert-butyl 2-(4-chlorophenyl)-3-(4-(5-(3,4-dimethoxyphenyl)-1H-pyrrolo[2,3-b]pyridin-4-yl)piperazin-1-yl)-3-oxopropyl(isopropyl)carbamate (0.020 g, 18.2% yield).

(S)-tert-Butyl 2-(4-chlorophenyl)-3-(4-(5-(3,4-dimethoxyphenyl)-1H-pyrrolo[2,3-b]pyridin-4-yl)piperazin-1-yl)-3-oxopropyl(isopropyl)carbamate (0.013 g, 0.020 mmol) was placed in DCM (3 mL). TFA (0.3 mL) was then added, and the reaction was stirred at room temperature for 1 hour. The reaction was then concentrated to dryness, dissolved in minimal DCM, and added dropwise to a stirring solution of 1M HCl in ether. The solid product was filtered, washed with ether, and dried to give (S)-2-(4-chlorophenyl)-1-(4-(5-(3,4-dimethoxyphenyl)-1H-pyrrolo[2,3-b]pyridin-4-yl)piperazin-1-yl)-3-(isopropylamino)propan-1-one (0.009 g, 72% yield) as the dihydrochloride salt. MS ESI (+) m/z 563 detected.

Example 12

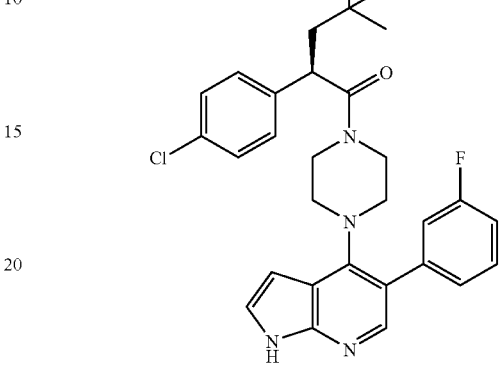

(R)-4-amino-2-(4-chlorophenyl)-1-(4-(5-(3-fluorophenyl)-1H-pyrrolo[2,3-b]pyridin-4-yl)piperazin-1-yl)-4-methylpentan-1-one Methyl 2-(4-chlorophenyl)acetate (15.3 g, 82.7 mmol) was dissolved in DMSO (160 mL) and this solution was added in one portion to paraformaldehyde (2.61 g, 86.9 mmol) and NaOMe (8.27 mL, 4.14 mmol). The mixture was stirred at ambient temperature for 20 hours. The mixture was then poured into ice cold water (550 mL) and neutralized with 1N HCl to a pH of about 8 to about 8.5. The mixture was extracted with EtOAc, and the combined organic fractions were washed with brine, dried over Na$_2$SO$_4$ and concentrated. The crude product methyl 2-(4-chlorophenyl)-3-hydroxypropanoate was recovered as an oil (16.2 g, 91%) and used without further purification.

Methyl 2-(4-chlorophenyl)-3-hydroxypropanoate (16.2 g, 75.5 mmol) was dissolved in DCM (200 mL). Triethylamine (26.3 mL, 188.7 mmol) was then added, and the solution was cooled to 0° C. The solution was then treated with methanesulfonyl chloride (5.84 mL, 75.5 mmol), and the mixture was stirred at 0° C. for 30 minutes. The cold solution was acidified to a pH of 1, and extracted with methylene chloride. The combined organic layers were washed with 1N HCl, water, 6% NaHCO$_3$, dried over Na$_2$SO$_4$ and concentrated. The crude oil was filter chromatographed on SiO$_2$ (with gypsum, Aldrich 28,852-7, 350 g) and eluted with 20:1 hexane:EtOAc to give methyl 2-(4-chlorophenyl)acrylate (10.9 g, 73%).

1,8-Diazabicyclo[5.4.0]undec-7-ene (33.7 mL, 225.2 mmol) was added to a solution of methyl 2-(4-chlorophenyl)acrylate (36.9 g, 187.7 mmol) and 2-nitropropane (20.2 mL, 225.2 mmol) in CH$_3$CN (500 mL) at 0° C. under nitrogen. The mixture was warmed to room temperature and stirred overnight. The solution was concentrated in vacuo and subjected to column chromatography (20% EtOAc/hexanes) to give methyl 2-(4-chlorophenyl)-4-methyl-4-nitropentanoate (52.9 g, 98.7% yield) as an oil. $^1$H NMR (CDCl$_3$, 400 MHz) δ 7.31-7.29 (m, 2H), 7.21-7.19 (m, 2H), 3.66 (s, 3H), 3.60-3.57 (m, 1H), 2.87-2.81 (dd, 1H), 2.39-2.34 (dd, 1H), 1.56 (s, 3H), 1.55 (s, 3H).

Zn dust (128 g, 1.96 mol) was treated with a solution of methyl 2-(4-chlorophenyl)-4-methyl-4-nitropentanoate (28 g, 98.0 mmol) dissolved in ethanol (490 mL). Concentrated HCl (26.9 mL, 323 mmol) was added slowly, and then the reaction was heated to 70° C. for 2 hours. The reaction mixture was filtered through a plug of SiO$_2$ and celite. The filter pad was washed with ethyl acetate, and the filtrate was concentrated in vacuo. The residue was dissolved in minimal ethanol and then treated with water. 3-(4-Chlorophenyl)-5,5-dimethylpyrrolidin-2-one precipitated from the solution and was collected by filtration. The solid was washed with water and air-dried, (11.2 g, 51% yield). $^1$H NMR (CD$_3$OD, 400 MHz) δ 7.35-7.32 (m, 2H), 7.26-7.24 (m, 2H), 3.94-3.90 (m, 1H), 2.50-2.44 (m, 1H), 1.99-1.93 (m, 1H), 1.36 (s, 3H), 1.34 (s, 3H).

Lithium bis(trimethylsilyl)amide (36 mL, 36 mmol) was added to a stirred solution of 3-(4-chlorophenyl)-5,5-dimethylpyrrolidin-2-one (6.7 g, 30 mmol) in THF (200 mL) at −78° C. under nitrogen. The solution was stirred at −78° C. for 30 minutes. Then a solution of di-tert-butyl dicarbonate (7.6 mL, 33 mmol) in THF (30 mL) was added in a single portion. The solution was warmed to room temperature and allowed to stir at room temperature overnight. The reaction was poured into 0.5M HCl solution and extracted with ethyl acetate (2×). The combined organic layer was washed with water, separated, dried over MgSO$_4$, filtered, and concentrated in vacuo to afford the near-pure product (excess Boc$_2$O) as an oil. Column chromatography (20% EtOAc/hexanes) to give pure tert-butyl 4-(4-chlorophenyl)-2,2-dimethyl-5-oxopyrrolidine-1-carboxylate. LCMS (APCI+) [M-Boc+H]+224.1; Rt: 3.68 min. $^1$H NMR (CDCl$_3$, 400 MHz) δ 7.32-7.30 (m, 2H), 7.22-7.20 (m, 2H), 3.80-3.74 (m, 1H), 2.33-2.28 (m, 1H), 2.05-1.97 (m, 1H), 1.58 (s, 3H), 1.55 (s, 9H), 1.53 (s, 3H).

Lithium hydroxide hydrate (6.44 mL, 232 mmol) was added to a stirred solution of tert-butyl 4-(4-chlorophenyl)-2,2-dimethyl-5-oxopyrrolidine-1-carboxylate (7.5 g, 23.2 mmol) in THF/MeOH/H$_2$O (30 mL/30 mL/30 mL) at room temperature. The mixture was stirred at room temperature overnight and concentrated in vacuo. The mixture was taken up into water (200 mL), washed with EtOAc (100 mL), acidified with concentrated HCl and extracted into EtOAc (2×200 mL). The mixture was dried over Na$_2$SO$_4$ and concentrated in vacuo. Residual HCl was removed by evaporating from toluene to give 4-(tert-butoxycarbonylamino)-2-(4-chlorophenyl)-4-methylpentanoic acid (5.0 g, 63.2% yield) as a solid. LCMS (APCI+) [M-Boc+H]+ 242.0; Rt: 2.8 min.

5-(3-Fluorophenyl)-4-(piperazin-1-yl)-1H-pyrrolo[2,3-b]pyridine (0.040 g, 0.108 mmol, see Example 6), (R)-4-(tert-butoxycarbonylamino)-2-(4-chlorophenyl)-4-methylpentanoic acid (0.0407 g, 0.119 mmol, separated using chiral chromatography), HOBT-H$_2$O (0.0232 g, 0.152 mmol), and EDCI (0.0270 g, 0.141 mmol) were placed in DCM (3 mL). DIEA (d 0.742; 0.0943 mL, 0.542 mmol) was then added, and the reaction was stirred overnight at room temperature. The reaction was then poured into Na$_2$CO$_3$, and extracted with DCM. The combined organic fractions were dried, filtered, concentrated. The product was purified (500:5 to 500:10 DCM:MeOH) to give (R)-tert-butyl 4-(4-chlorophenyl)-5-(4-(5-(3-fluorophenyl)-1H-pyrrolo[2,3-b]pyridin-4-yl)piperazin-1-yl)-2-methyl-5-oxopentan-2-yl carbamate (0.022 g, 32.7% yield).

(R)-tert-Butyl 4-(4-chlorophenyl)-5-(4-(5-(3-fluorophenyl)-1H-pyrrolo[2,3-b]pyridin-4-yl)piperazin-1-yl)-2-methyl-5-oxopentan-2-ylcarbamate (0.026 g, 0.042 mmol) was placed in DCM (3 mL) at room temperature. TFA (0.3 mL) was then added, and the reaction was stirred at room temperature for 1 hour. The reaction was then concentrated to dryness. The resulting residue was dissolved in minimal DCM and added to a stirring solution of 1M HCl in ether. The resulting solid product was collected by filtration, washed with ether, and dried to give (R)-4-amino-2-(4-chlorophenyl)-1-(4-(5-(3-fluorophenyl)-1H-pyrrolo[2,3-b]pyridin-4-yl)piperazin-1-yl)-4-methylpentan-1-one (0.019 g, 76% yield) as the dihydrochloride salt. MS ESI (+) m/z 521 detected.

Example 13

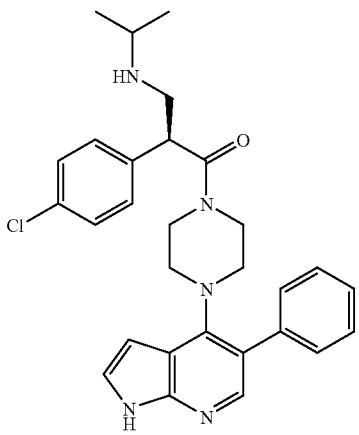 [SMILES: CC(C)NC[C@@H](C(=O)N1CCN(c2c(-c3ccccc3)cnc3[nH]ccc23)CC1)c1ccc(Cl)cc1]

(S)-2-(4-chlorophenyl)-3-(isopropylamino)-1-(4-(5-phenyl-1H-pyrrolo[2,3-b]pyridin-4-yl)piperazin-1-yl)propan-1-one (S)-tert-Butyl 3-(4-(5-bromo-1H-pyrrolo[2,3-b]pyridin-4-yl)piperazin-1-yl)-2-(4-chlorophenyl)-3-oxopropyl(isopropyl)carbamate (0.150 g, 0.248 mmol, see Example 4), phenylboronic acid (0.0363 g, 0.298 mmol), Pd(PPh$_3$)$_4$ (0.0143 g, 0.0124 mmol) and 10% K$_2$CO$_3$ (aq., 0.517 mL, 0.372 mmol) were placed in Ar degassed 2:1 toluene:EtOH and heated to 80° C. overnight. The reaction was cooled to room temperature, diluted with water, and extracted with DCM. The combined organic fractions were dried, filtered, concentrated, and purified (500:7 DCM:MeOH) to give (S)-tert-butyl 2-(4-chlorophenyl)-3-oxo-3-(4-(5-phenyl-1H-pyrrolo[2,3-b]pyridin-4-yl)piperazin-1-yl)propyl(isopropyl)carbamate (0.003 g, 2.0% yield)

(S)-tert-Butyl 2-(4-chlorophenyl)-3-oxo-3-(4-(5-phenyl-1H-pyrrolo[2,3-b]pyridin-4-yl)piperazin-1-yl)propyl(isopropyl)carbamate (0.003 g, 0.0050 mmol) was placed in DCM (2 mL) at room temperature. TFA (0.4 mL) was then added, and the reaction was stirred for 1 hour. The reaction was concentrated to dryness. The crude residue was dissolved in minimal DCM and added dropwise to a stirring solution of 1M HCl in ether (10 mL). The solid product was then filtered, washed with ether, and dried to give (S)-2-(4-chlorophenyl)-3-(isopropylamino)-1-(4-(5-phenyl-1H-pyrrolo[2,3-b]pyridin-4-yl)piperazin-1-yl)propan-1-one (0.001 g, 40% yield) as the dihydrochloride salt. MS ESI (+) m/z 503 detected.

Example 14

(S)-2-(4-chlorophenyl)-3-(isopropylamino)-1-(4-(5-(1-methyl-1H-pyrazol-4-yl)-1H-pyrrolo[2,3-b]pyridin-4-yl)piperazin-1-yl)propan-1-one (S)-tert-Butyl 3-(4-(5-bromo-1H-pyrrolo[2,3-b]pyridin-4-yl)piperazin-1-yl)-2-(4-chlorophenyl)-3-oxopropyl(isopropyl)carbamate (0.05 g, 0.083 mmol, see Example 4) was placed in dioxane (1 mL) and Na$_2$CO$_3$ (aq., 0.087 g, 0.82 mmol) in H$_2$O (0.3 mL). 1-Methyl-4-(4,4,5,5-tetramethyl-1,3,2-dioxaborolan-2-yl)-1H-pyrazole (0.034 g, 0.16 mmol) and PS-Pd(PPh$_3$)$_4$ (0.075 g, 0.1 g/mmol) were then added. The reaction was heated to 150° C. in a microwave for 1 hour. The reaction was then diluted with water and extracted with DCM. The organic fractions were dried, filtered, and concentrated. Purification of the crude residue (500:10 to 500:20 DCM:MeOH) gave (S)-tert-butyl 2-(4-chlorophenyl)-3-(4-(5-(1-methyl-1H-pyrazol-4-yl)-1H-pyrrolo[2,3-b]pyridin-4-yl)piperazin-1-yl)-3-oxopropyl(isopropyl)carbamate (0.005 g, 9.9% yield).

(S)-tert-Butyl 2-(4-chlorophenyl)-3-(4-(5-(1-methyl-1H-pyrazol-4-yl)-1H-pyrrolo[2,3-b]pyridin-4-yl)piperazin-1-yl)-3-oxopropyl(isopropyl)carbamate (0.005 g, 0.008 mmol) was placed in DCM (2 mL) at room temperature. TFA (0.4 mL) was then added, and the reaction was stirred for 1 hour. The reaction was concentrated. The crude residue was dissolved in minimal DCM and added dropwise to a stirring solution of 1M HCl in ether (10 mL). The solid product was then filtered, washed with ether and dried to give (S)-2-(4-chlorophenyl)-3-(isopropylamino)-1-(4-(5-(1-methyl-1H-pyrazol-4-yl)-1H-pyrrolo[2, 3-1)]pyri din-4-yl)piperazin-1-yl)propan-1-one (0.002 g, 48% yield) as the trihydrochloride salt. MS ESI (+) m/z 507 detected.

Example 15

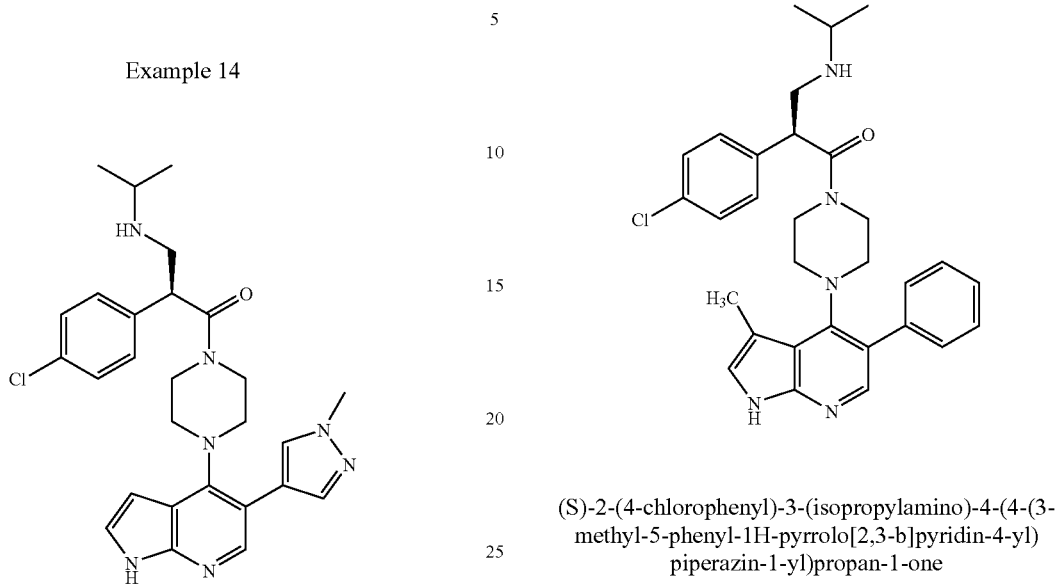

(S)-2-(4-chlorophenyl)-3-(isopropylamino)-4-(4-(3-methyl-5-phenyl-1H-pyrrolo[2,3-b]pyridin-4-yl)piperazin-1-yl)propan-1-one 5-Bromo-4-chloro-1-(phenylsulfonyl)-1H-pyrrolo[2,3-b]pyri dine (3.70 g, 9.96 mmol, see Example 6) and phenylboronic acid (1.27 g, 10.5 mmol) were placed in 2:1 toluene:EtOH (30 mL). The contents were then degassed under Ar and heated to 80° C. for 24 hours. The reaction was cooled to room temperature, diluted with DCM, and poured into water. The organic fraction was filtered, dried, and concentrated. Purification was carried out by column chromatography (1:1 to 1:2 hexane:DCM) to give 4-chloro-5-phenyl-1-(phenylsulfonyl)-1H-pyrrolo[2,3-b]pyridine (3.20 g, 87.1% yield).

4-Chloro-5-phenyl-1-(phenylsulfonyl)-1H-pyrrolo[2,3-b]pyridine (1.70 g, 4.61 mmol) was placed in 1:1 THF:water (30 mL). 3M LiOH (aq., 15.4 mL, 46.1 mmol) was then added, and the reaction was heated to 65° C. for 18 hours. The reaction was cooled to room temperature, diluted with DCM (50 mL) and poured into water. The organic fraction was dried, filtered, and concentrated to give the crude product 4-chloro-5-phenyl-1H-pyrrolo[2,3-b]pyridine (1.01 g, 95.8% yield), which was used without further purification.

4-Chloro-5-phenyl-1H-pyrrolo[2,3-b]pyridine (0.912 g, 3.99 mmol) was placed in CHCl$_3$ (5 mL) at room temperature. N-Bromosuccinimide (0.710 g, 3.99 mmol) was then added, and the reaction was stirred at room temperature for 1 hour. The reaction was diluted with DCM and washed with saturated NaHCO$_3$. The organic fraction was dried, filtered, and concentrated to give the crude product 3-bromo-4-chloro-5-phenyl-1H-pyrrolo[2,3-b]pyridine (1.1 g, 89.7% yield).

3-Bromo-4-chloro-5-phenyl-1H-pyrrolo[2,3-b]pyridine (1.30 g, 4.23 mmol) was placed in DMF (10 mL) at 0° C. NaH (0.203 g, 5.07 mmol) was then added, and the reaction was stirred for 20 minutes. Benzenesulfonyl chloride (0.595 mL, 4.65 mmol) was then added, and the reaction was stirred for 30 minutes at 0° C. The reaction was then poured into water and extracted with EtOAc. The combined organic fractions were dried, concentrated and purified (2:1 D CM:hexanes) to give 3-bromo-4-chloro-5-phenyl-1-(phenylsulfonyl)-1H-pyrrolo[2,3-b]pyri dine (1.80 g, 95.1% yield).

Methyl zinc chloride (3.35 mL, 6.70 mmol) was added to 3-bromo-4-chloro-5-phenyl-1-(phenylsulfonyl)-1H-pyrrolo[2,3-b]pyridine (1.00 g, 2.23 mmol) and Pd(PPh$_3$)$_4$ (0.129 g, 0.111 mmol) in THF (10 mL). The reaction was then heated to 80° C. for 2 hours, cooled to room temperature, and quenched with saturated NH₄Cl. The resulting solids were filtered and discarded. The filtrate was diluted with DCM (500 mL) and was washed with water. The combined organic fractions were dried, filtered, and concentrated to give a crude solid that was purified by column chromatography (2:1 DCM:hexanes) to give 4-chloro-3-methyl-5-phenyl-1-(phenylsulfonyl)-1H-pyrrolo[2,3-b]pyridine (0.75 g, 87.7% yield).

4-Chloro-3-methyl-5-phenyl-1-(phenyl sulfonyl)-1H-pyrrolo[2,3-b]pyridine (0.300 g, 0.784 mmol) and piperazine (0.675 g, 7.84 mmol) were placed in NMP (1 mL) and heated to 200° C. in a microwave for 1 hour. The reaction was then poured into water and extracted with MTBE. The combined organic fractions were dried, filtered, and concentrated to give the crude product 3-methyl-5-phenyl-1-(phenylsulfonyl)-4-(piperazin-1-yl)-1H-pyrrolo[2,3-b]pyridine (0.339 g, 100% yield), which was used without further purification.

3-Methyl-5-phenyl-1-(phenylsulfonyl)-4-(piperazin-1-yl)-1H-pyrrolo[2,3-b]pyridine (0.600 g, 1.39 mmol) was placed in DCM (10 mL). Boc₂O (0.333 g, 1.53 mmol) was then added, and the reaction was stirred at room temperature for 1 hour. The reaction was quenched with NaHCO₃ and extracted into DCM. The combined organic layers were dried, filtered, and concentrated to give the crude product tert-butyl 4-(3-methyl-5-phenyl-1-(phenylsulfonyl)-1H-pyrrolo[2,3-b]pyri din-4-yl)piperazine-1-carboxylate (0.738 g, 100% yield), which was used without further purification.

tert-Butyl 4-(3-methyl-5-phenyl-1-(phenyl sulfonyl)-1H-pyrrolo[2,3-b]pyridin-4-yl)piperazine-1-carboxylate (0.9 g, 1.69 mmol) was placed in 1:1 THF:MeOH (10 mL). 3M LiOH (aq., 5.63 mL, 16.9 mmol) was added, and the reaction was heated to 50° C. for 1 hour. The reaction was then cooled, added to water and extracted with DCM. The organics were dried, filtered and concentrated to give the crude product which was purified (500:3 to 500:8 DCM:MeOH) to give tert-butyl 4-(3-methyl-5-phenyl-1H-pyrrolo[2,3-b]pyridin-4-yl)piperazine-1-carboxylate (0.390 g, 58.8% yield).

tert-Butyl 4-(3-methyl-5-phenyl-1H-pyrrolo[2,3-b]pyri din-4-yl)piperazine-1-carboxylate (0.390 g, 0.994 mmol) was placed in DCM (10 mL) at room temperature. TFA (1 mL) was added, and the reaction was stirred at room temperature for 1 hour. The reaction was then concentrated to dryness, dissolved in minimal DCM, and added dropwise to a stirring solution of 1M HCl in ether. The solid product was filtered, washed with ether, and dried to give 3-methyl-5-phenyl-4-(piperazin-1-yl)-1H-pyrrolo[2,3-b]pyridine (0.350 g, 96.4% yield), which was used without further purification.

3-Methyl-5-phenyl-4-(piperazin-1-yl)-1H-pyrrolo[2,3-b]pyridine (0.050 g, 0.137 mmol) and (S)-3-(tert-butoxycarbonyl(isopropyl)amino)-2-(4-chlorophenyl)propanoic acid (0.0491 g, 0.144 mmol, Example H) were placed in DCM (3 mL) at room temperature. HOBT-H₂O (0.0293 g, 0.192 mmol), EDCI (0.0341 g, 0.178 mmol), and DIEA (d 0.742; 0.0954 mL, 0.548 mmol) were then added, and the reaction was stirred at room temperature for 18 hours. The reaction was then poured into saturated Na₂CO₃ and extracted with DCM. The organic fractions were dried, filtered, concentrated and purified (500:5 DCM:MeOH) to give(S)-tert-butyl 2-(4-chlorophenyl)-3-(4-(3-methyl-5-phenyl-1H-pyrrolo[2,3-b]pyridin-4-yl)piperazin-1-yl)-3-oxopropyl(isopropyl) carbamate (0.047 g, 55.7% yield).

(S)-tert-Butyl 2-(4-chlorophenyl)-3-(4-4(3-methyl-5-phenyl-1H-pyrrolo[2,3-b]pyridin-4-yl)piperazin-1-yl)-3-oxopropyl(isopropyl)carbamate (0.047 g, 0.076 mmol) was placed in DCM (3 mL) at room temperature. TFA (0.3 mL) was then added. The reaction was stirred at room temperature for 1 hour and concentrated to dryness. The resulting residue was dissolved in minimal DCM and added to a stirring solution of 1M HCl in ether. The resulting solid was collected by filtration, washed with ether, and dried to give (S)-2-(4-chlorophenyl)-3-(isopropylamino)-4-(4-(3-methyl-5-phenyl-1H-pyrrolo[2,3-b]pyri din-4-yl)piperazin-1-yl)propan-1-one (0.041 g, 91% yield) as the dihydrochloride salt. MS ESI (+) m/z 517 detected.

Example 16

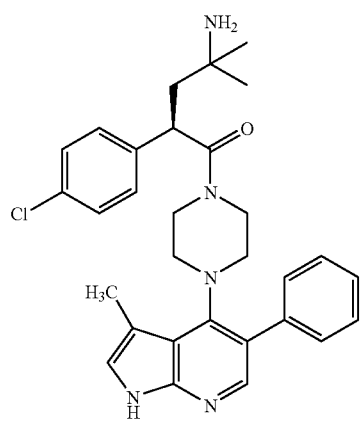 [SMILES: Cc1c[nH]c2ncc(-c3ccccc3)c(N3CCN(C(=O)[C@H](CC(C)(C)N)c4ccc(Cl)cc4)CC3)c12]

(R)-4-amino-2-(4-chlorophenyl)-4-methyl-1-(4-(3-methyl-5-phenyl-1H-pyrrolo[2,3-b]pyridin-4-yl) piperazin-1-yl)pentan-1-one 3-Methyl-5-phenyl-4-(piperazin-1-yl)-1H-pyrrolo[2,3-b] pyridine (0.040 g, 0.110 mmol, see Example 15), (R)-4-(tert-butoxycarbonylamino)-2-(4-chlorophenyl)-4-methylpentanoic acid (0.0412 g, 0.120 mmol, Example 12), HOBT-H₂O (0.0235 g, 0.153 mmol), and EDCI (0.0273 g, 0.142 mmol) were placed in DCM (5 mL) at room temperature. DIEA (d 0.742; 0.0954 mL, 0.548 mmol) was then added, and the reaction was stirred at room temperature for 18 hours. The reaction was then poured into saturated Na₂CO₃ and extracted with DCM. The combined organic fractions were dried, filtered, concentrated and purified (500:5 DCM: MeOH) to give (R)-tert-butyl 4-(4-chlorophenyl)-2-methyl-5-(4-(3-methyl-5-phenyl-1H-pyrrolo[2,3-b]pyridin-4-yl) piperazin-1-yl)-5-oxopentan-2-ylcarbamate (0.040 g, 59.3% yield).

(R)-tert-Butyl 4-(4-chlorophenyl)-2-methyl-5-(4-(3-methyl-5-phenyl-1H-pyrrolo[2,3-b]pyridin-4-yl)piperazin-1-yl)-5-oxopentan-2-ylcarbamate (0.040 g, 0.065 mmol) was placed in DCM (3 mL). TFA (0.3 mL) was then added. The reaction was stirred for 1 hour and then concentrated to dryness. The resulting oil was dissolved in minimal DCM, and added to a stirring solution of 1M HCl in ether. The resulting solid was collected by filtration, washed with ether, and dried to give (R)-4-amino-2-(4-chlorophenyl)-4-methyl-1-(4-(3-methyl-5-phenyl-1H-pyrrolo[2,3-b]pyri din-4-yl)piperazin-1-yl)pentan-1-one (0.034 g, 89% yield) as the dihydrochloride salt. MS ESI (+) m/z 517 detected.

Example 17

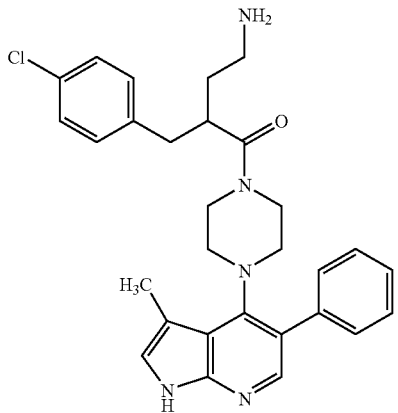 [SMILES: Cc1c[nH]c2ncc(-c3ccccc3)c(N3CCN(C(=O)C(CCN)Cc4ccc(Cl)cc4)CC3)c12]

4-amino-2-(4-chlorobenzyl)-4-(4-(3-methyl-5-phenyl-1H-pyrrolo[2,3-b]pyridin-4-yl)piperazin-1-yl)butan-1-one LHMDS (28.3 mL, 28.3 mmol) was diluted into THF (90 mL) and cooled to −78° C. tert-Butyl 2-oxopyrrolidine-1-carboxylate (5.00 g, 27.0 mmol) was dissolved into THF (35 mL) and added to the LHMDS over a 5 minute period at −78° C. The reaction was allowed to stir for 45 minutes, and then a THF (35 mL) solution of 1-(bromomethyl)-4-chlorobenzene (5.82 g, 28.3 mmol, 1.05 equiv) was added. The reaction was allowed to stir at −78° C. for 1 hour, and then warmed to room temperature over 3 hours. The mixture was quenched with the addition of a 3M LiOH solution (90 mL) and stirred for 48 hours at room temperature. The reaction was then diluted with water and washed with ethyl acetate. The aqueous layer was acidified with 3M HCl and extracted several times with ethyl acetate. The combined organic fractions were washed with water, dried over MgSO$_4$, filtered, and concentrated to give the crude product. The crude product was purified by column chromatography (60:40 hexanes:ethyl acetate) to give 4-(tert-butoxycarbonylamino)-2-(4-chlorobenzyl)butanoic acid (0.84 g, 9.4%).

3-Methyl-5-phenyl-4-(piperazin-1-yl)-1H-pyrrolo[2,3-b]pyridine (0.050 g, 0.137 mmol, see Example 15), 4-(tert-butoxycarbonylamino)-2-(4-chlorobenzyl)butanoic acid (0.0494 g, 0.151 mmol), HOBT-H$_2$O (0.0293 g, 0.192 mmol), and EDCI (0.0341 g, 0.178 mmol) were placed in DCM (3 mL) at room temperature. DIEA (d=0.742; 0.119 mL, 0.684 mmol) was then added, and the reaction was stirred at room temperature for 15 hours. The reaction was then poured into saturated Na$_2$CO$_3$ and extracted with DCM. The combined organic fractions were dried, filtered, concentrated, and purified (500:5 DCM:MeOH) to give tert-butyl 3-(4-chlorobenzyl)-4-(4-(3-methyl-5-phenyl-1H-pyrrolo[2,3-b]pyridin-4-yl)piperazin-1-yl)-4-oxobutylcarbamate (0.010 g, 12.1% yield).

tert-Butyl 3-(4-chlorobenzyl)-4-(4-(3-methyl-5-phenyl-1H-pyrrolo[2,3-b]pyridin-4-yl)piperazin-1-yl)-4-oxobutylcarbamate (0.045 g, 0.075 mmol) was placed in DCM (3 mL). TFA (0.3 mL) was then added. The reaction was stirred for 1 hour and then concentrated to dryness. The resulting oil was dissolved in minimal DCM and added to a stirring solution of 1M HCl in ether. The resulting solid was collected by filtration, washed with ether, and dried to give 4-amino-2-(4-chlorobenzyl)-4-(4-(3-methyl-5-phenyl-1H-pyrrolo[2,3-b]pyridin-4-yl)piperazin-1-yl)butan-1-one (0.032 g, 74% yield) as the dihydrochloride salt. MS ESI (+) m/z 503 detected.

Example 18

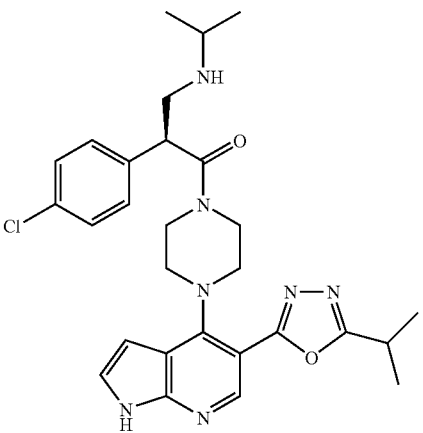 [SMILES: CC(C)NC[C@@H](C(=O)N1CCN(c2c(-c3nnc(C(C)C)o3)cnc3[nH]ccc23)CC1)c1ccc(Cl)cc1]

(S)-2-(4-chlorophenyl)-1-(4-(5-(5-isopropyl-1,3,4-oxadiazol-2-yl)-1H-pyrrolo[2,3-b]pyridin-4-yl)piperazin-1-yl)-3-(isopropylamino)propan-1-one Methyl 4-chloro-1-(triisopropylsilyl)-1H-pyrrolo[2,3-b]pyridine-5-carboxylate (5.0 g, 13.62 mmol) was placed in NMP (40 mL). piperazine (9.39 g, 109 mmol) was then added, and the reaction heated to 100° C. for 45 minutes. The reaction was then cooled to room temperature, and diluted with DCM (100 mL). Boc$_2$O (44.60 g, 204.38 mmol) was then added, followed by the addition of triethylamine (2.85 mL, 20.4 mmol). The reaction was then stirred for 1 hour. The reaction was then poured into water, extracted with DCM and purified by chromatography (100:1 DCM:MeOH) to give methyl 4-(4-(tert-butoxycarbonyl)piperazin-1-yl)-1H-pyrrolo[2,3-b]pyridine-5-carboxylate (8.1 g, 164%), which was contaminated with a significant amount of bis Boc-piperazine.

Hydrazine (1.8 g, 55 mmol) was added to methyl 4-(4-(tert-butoxycarbonyl)piperazin-1-yl)-1H-pyrrolo[2,3-b]pyridine-5-carboxylate (2.0 g, 5.5 mmol) in MeOH (200 mL), and the reaction was heated to reflux for 24 hours. After cooling down, tert-butyl 4-(5-(hydrazinecarbonyl)-1H-pyrrolo[2,3-b]pyridin-4-yl)piperazine-1-carboxylate precipitated as a solid (1.3 g, 65%).

Ethyl 2-ethoxyquinoline-1(2H)-carboxylate (226 mg, 0.916 mmol) was added to acetic acid (50.0 mg, 0.832 mmol) in THF/ACN (5 mL), and the reaction was stirred at room temperature for 1 hour. tert-Butyl 4-(5-(hydrazinecarbonyl)-1H-pyrrolo[2,3-b]pyridin-4-yl)piperazine-1-carboxylate (300 mg, 0.832 mmol) was added, and the reaction was heated to 70° C. for 1 hour. The solution was then concentrated to dryness. The resulting residue was crystallized from DCM to yield tert-butyl 4-(5-(2-acetylhydrazinecarbonyl)-1H-pyrrolo[2,3-b]pyridin-4-yl)piperazine-1-carboxylate (241 mg, 71.9% yield) as a solid.

tert-Butyl 4-(5-(2-acetylhydrazinecarbonyl)-1H-pyrrolo[2,3-b]pyridin-4-yl)piperazine-1-carboxylate (70 mg, 0.16 mmol) in POCl$_3$ (1 mL) was heated to 90° C. for 1 hour. The reaction was then concentrated to dryness to yield 2-methyl- 5-(4-(piperazin-1-yl)-1H-pyrrolo[2,3-b]pyridin-5-yl)-1,3,4-oxadiazole (58 mg, 125% yield) as an oil, which was used without further purification.

(S)-3-(tert-Butoxycarbonyl(isopropyl)amino)-2-(4-chlorophenyl)propanoic acid (180 mg, 0.52 mmol, see Example H), N1-((ethylimino)methylene)-N3,N3-dimethylpropane-1,3-diamine hydrochloride (134 mg, 0.70 mmol), HOBt.H$_2$O (108 mg, 0.70 mmol) and triethylamine (106 mg, 1 mmol) were added to 2-methyl-5-(4-(piperazin-1-yl)-1H-pyrrolo[2,3-b]pyridin-5-yl)-1,3,4-oxadiazole (100 mg, 0.36 mmol) in DCM (10 mL). The reaction was stirred at room temperature for 18 hours. After dilution with DCM, the mixture was washed with 1N HCl, 10% K$_2$CO$_3$ and brine. The organic phase was dried over MgSO$_4$ and purified by chromatography (SP4, 12+M, water/ACN 90/10→10/90, 20CV) to yield (S)-tert-butyl 2-(4-chlorophenyl)-3-(4-(5-(5-methyl-1,3,4-oxadiazol-2-yl)-1H-pyrrolo[2,3-b]pyri din-4-yl)piperazin-1-yl)-3-oxopropyl(isopropyl)carbamate (60 mg) as a solid.

(S)-tert-Butyl 2-(4-chlorophenyl)-3-(4-(5-(5-methyl-1,3,4-oxadiazol-2-yl)-1H-pyrrolo[2,3-b]pyridin-4-yl)piperazin-1-yl)-3-oxopropyl(isopropyl)carbamate (50 mg, 0.082 mmol) in TFA (3 mL) was stirred for 30 minutes and then concentrated to dryness. The resulting residue was dissolved in minimal DCM (0.2 mL) and added to 2N HCl in ether. The resulting solid was filtered and dried under nitrogen to yield (S)-2-(4-chlorophenyl)-3-(isopropylamino)-1-(4-(5-(5-methyl-1,3,4-oxadiazol-2-yl)-1H-pyrrolo[2,3-b]pyridin-4-yl)piperazin-1-yl)propan-1-one (21 mg, 50% yield) hydrochloride as a solid. $^1$H NMR (400 MHz, DMSO-d$_6$) δ 12.10 (s, 1H), 8.84 (s, 1H), 8.35 (s, 2H), 7.52-7.48 (m, 2H), 7.46-4.42 (m, 1H), 7.40-7.36 (m, 2H), 6.64 (s, 1H), 4.58 (m, 1H), 3.70-3.20 (m, 10H), 3.01 (s, 1H), 2.78 (s, 1H), 2.54 (s, 3H), 1.24 (dq, 6H); m/z (ESI pos) 508.4 (100%) [M].

Example 19

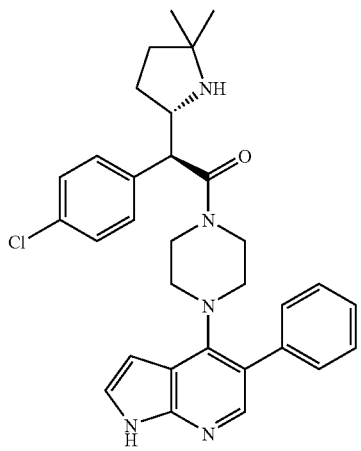 [SMILES: CC1(C)CC[C@@H]([C@@H](C(=O)N2CCN(c3c(-c4ccccc4)cnc4[nH]ccc34)CC2)c2ccc(Cl)cc2)N1]

(S)-2-(4-chlorophenyl)-2-((S)-5,5-dimethylpyrrolidin-2-yl)-1-(4-(5-phenyl-1H-pyrrolo[2,3-b]pyridin-4-yl)piperazin-1-yl)ethanone 4-Chloro-5-phenyl-1-(phenylsulfonyl)-1H-pyrrolo[2,3-b]pyridine (0.30 g, 0.81 mmol) and piperazine (0.701 g, 8.13 mmol) were placed in NMP (0.3 mL) and heated to 150° C. in a microwave for 1 hour. The reaction was then poured into water, and extracted with MTBE. The combined organic fractions were dried, filtered and concentrated to give a crude residue which was placed in DCM (10 mL). Boc$_2$O (0.195 g, 0.895 mmol) was then added, and the reaction was stirred for 1 hour. An aqueous solution of saturated Na$_2$CO$_3$ (30 mL) was added, and the reaction was extracted with DCM (3×50 mL). The combined organic fractions were dried, filtered, and concentrated to give the crude product, tert-butyl 4-(5-phenyl-1-(phenylsulfonyl)-1H-pyrrolo[2,3-b]pyri din-4-yl)piperazine-1-carboxylate (0.40 g, 95.4% yield), which was used in the next step without further purification.

tert-Butyl 4-(5-phenyl-1-(phenylsulfonyl)-1H-pyrrolo[2,3-b]pyridin-4-yl)piperazine-1-carboxylate (1.10 g, 2.12 mmol) was placed in 1:1 THF:MeOH (20 mL). LiOH (3.54 mL, 10.6 mmol) was then added, and the reaction was heated to 50° C. for 1 hour. The reaction was cooled to room temperature, poured into water, and extracted with DCM (3×50 mL). The combined organic fractions were dried, filtered, concentrated, and then purified by column chromatography (500:5 DCM:MeOH) to give tert-butyl 4-(5-phenyl-1H-pyrrolo[2,3-b]pyridin-4-yl)piperazine-1-carboxylate (0.40 g, 49.8% yield).

tert-Butyl 4-(5-phenyl-1H-pyrrolo[2,3-b]pyri din-4-yl)piperazine-1-carboxylate (0.40 g, 1.06 mmol) was placed in DCM (10 mL). TFA (2 mL) was then added, and the reaction was stirred for 1 hour. The reaction was concentrated to dryness, redissolved in minimal DCM, and added to a stirring solution of 1M HCl in ether. The resulting solid was collected by filtration, washed with ether, and dried to give 5-phenyl-4-(piperazin-1-yl)-1H-pyrrolo[2,3-b]pyridine dihydrochloride (0.350 g, 94.3% yield).

DIEA (0.0833 mL, 0.478 mmol) was added to 5-phenyl-4-(piperazin-1-yl)-1H-pyrrolo[2,3-b]pyridine dihydrochloride (0.042 g, 0.120 mmol,), (S)-2-((S)-1-(tert-butoxycarbonyl)-5,5-dimethylpyrrolidin-2-yl)-2-(4-chlorophenyl)acetic acid (0.0440 g, 0.120 mmol, see Example G) and O-(benzotriazol-1-yl)-N,N,N',N'-tetramethyluronium tetrafluoroborate ("TBTU"; 0.0461 g, 0.143 mmol) in DCM (1 mL) and stirred at room temperature for 1 hour. The mixture was directly loaded onto a column and purified by chromatography (1:1 hexane:ethyl acetate) to give (S)-tert-butyl 5-((S)-1-(4-chlorophenyl)-2-oxo-2-(4-(5-phenyl-1H-pyrrolo[2, 3-1)]pyridin-4-yl)piperazin-1-yl)ethyl)-2,2-dimethylpyrrolidine-1-carboxylate as a solid. The product was dissolved in DCM (1 mL), and TFA (0.2 mL) was added. The mixture was stirred at room temperature for 1 hour. The solvent was removed. The residue was dissolved in DCM (0.5 mL), and 2M HCl in ether (1 mL) was added. The resulting solid was collected by filtration to give (S)-2-(4-chlorophenyl)-2-((S)-5,5-dimethylpyrrolidin-2-yl)-1-(4-(5-phenyl-1H-pyrrolo[2,3-b]pyridin-4-yl)piperazin-1-yl)ethanone dihydrochloride (0.042 g, 59%). MS ESI (+) m/z 528 detected.

Example 20

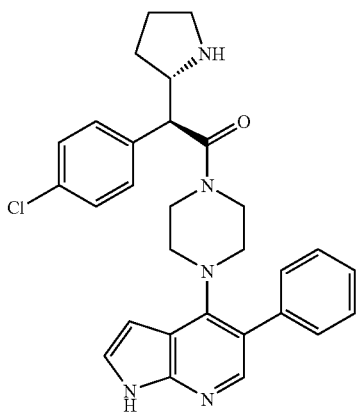 [SMILES: O=C([C@@H](c1ccc(Cl)cc1)[C@@H]1CCCN1)N1CCN(c2c(-c3ccccc3)cnc3[nH]ccc23)CC1]

(S)-2-(4-chlorophenyl)-1-(4-(5-phenyl-1H-pyrrolo[2,3-b]pyridin-4-yl)piperazin-1-yl)-2-((S)-pyrrolidin-2-yl)ethanone DIEA (0.103 mL, 0.592 mmol) was added to 5-phenyl-4-(piperazin-1-yl)-1H-pyrrolo[2,3-b]pyridine dihydrochloride (0.052 g, 0.15 mmol, see Example 19), (S)-2-((S)-1-(tert-butoxycarbonyl)pyrrolidin-2-yl)-2-(4-chlorophenyl)acetic acid (0.0503 g, 0.148 mmol, see Example F) and TBTU (0.0570 g, 0.178 mmol) in DCM (1 mL) and stirred at room temperature for 1 hour. The mixture was directly loaded onto a column and purified by chromatography (1:1 hexane:ethyl acetate) to give (S)-tert-butyl 2-((S)-1-(4-chlorophenyl)-2-oxo-2-(4-(5-phenyl-1H-pyrrolo[2,3-b]pyridin-4-yl)piperazin-1-yl)ethyl)pyrrolidine-1-carboxylate as a solid. The solid was then dissolved in DCM (1 mL), and TFA (0.2 mL) was added. The mixture was stirred at room temperature for 1 hour. The solvent was removed. The residue was dissolved in DCM (0.5 mL), and 2M HCl in ether (1 mL) was added. The resulting solid was collected by filtration to give (S)-2-(4-chlorophenyl)-1-(4-(5-phenyl-1H-pyrrolo[2,3-b]pyridin-4-yl)piperazin-1-yl)-2-((S)-pyrrolidin-2-yl)ethanone dihydrochloride (0.062 g, 63%). MS ESI (+) m/z 500 detected.

Example 21

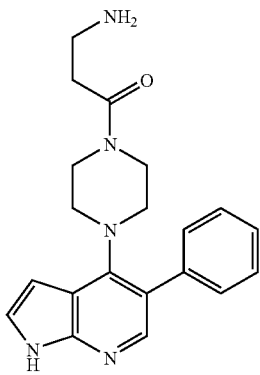 [SMILES: NCCC(=O)N1CCN(c2c(-c3ccccc3)cnc3[nH]ccc23)CC1]

3-amino-1-(4-(5-phenyl-1H-pyrrolo[2,3-b]pyridin-4-yl)piperazin-1-yl)propan-1-one 5-Phenyl-4-(piperazin-1-yl)-1H-pyrrolo[2,3-b]pyridine dihydrochloride (0.10 g, 0.285 mmol, see Example 19), 3-(tert-butoxycarbonylamino)propanoic acid (0.0646 g, 0.342 mmol), HOBT-H$_2$O (0.0610 g, 0.399 mmol), and EDCI (0.0709 g, 0.370 mmol) were placed in DCM (5 mL) at room temperature. DIEA (d 0.742; 0.248 mL, 1.42 mmol) was then added, and the reaction was stirred at room temperature for 18 hours. The reaction was then poured into Na$_2$CO$_3$ and extracted with DCM. The combined organic fractions were dried, filtered, concentrated and purified (500:10 DCM:MeOH) to give tert-butyl 3-oxo-3-(4-(5-phenyl-1H-pyrrolo[2,3-b]pyridin-4-yl)piperazin-1-yl)propylcarbamate (0.055 g, 43.0% yield).

tert-Butyl 3-oxo-3-(4-(5-phenyl-1H-pyrrolo[2,3-b]pyridin-4-yl)piperazin-1-yl)propylcarbamate (0.054 g, 0.12 mmol) was placed in DCM (3 mL) at room temperature. TFA (0.3 mL) was added, and the reaction was stirred at room temperature for 1 hour. The reaction was then concentrated to dryness. The resulting residue was dissolved in minimal DCM and added to a stirring solution of 1M HCl in ether. The resulting solid was collected by filtration, washed with ether, and dried to give 3-amino-1-(4-(5-phenyl-1H-pyrrolo[2,3-b]pyridin-4-yl)piperazin-1-yl)propan-1-one (0.050 g, 99% yield). MS ESI (+) m/z 350 detected.

Example 22

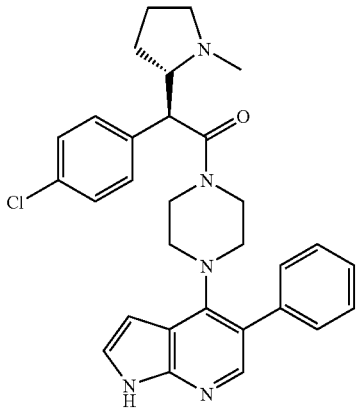 [SMILES: CN1CCC[C@H]1[C@@H](C(=O)N1CCN(c2c(-c3ccccc3)cnc3[nH]ccc23)CC1)c1ccc(Cl)cc1]

(S)-2-(4-chlorophenyl)-2-((S)-1-methylpyrrolidin-2-yl)-1-(4-(5-phenyl-1H-pyrrolo[2,3-b]pyridin-4-yl)piperazin-1-yl)ethanone (S)-2-(4-Chlorophenyl)-1-(4-(5-phenyl-1H-pyrrolo[2,3-b]pyridin-4-yl)piperazin-1-yl)-2-((S)-pyrrolidin-2-yl)ethanone dihydrochloride (0.060 g, 0.105 mmol, see Example 20) in MeOH (0.5 mL) was cooled to a temperature of about 0° C. to about 5° C. Formaldehyde (0.0234 mL, 0.314 mmol) and NaCNBH$_3$ (0.0132 g, 0.210 mmol) were added. The mixture was stirred at a temperature of about 14° C. to about 16° C. for 45 minutes. Methyl amine (2 mL, 2.0M in THF) was added, and the reaction was stirred for 30 minutes. Saturated NaHCO$_3$ (5 mL) was added, and the aqueous phase was extracted with DCM (20 mL). The combined organic phases were washed with brine (10 mL), and dried over sodium sulfate. After removal of the solvent, the resulting residue was dissolved in DCM (0.5 mL), and 2M HCl in ether (1 mL) was added. The resulting solid was collected by filtration to give (S)-2-(4-chlorophenyl)-2-((S)-1-methylpyrrolidin-2-yl)-1-(4-(5-phenyl-1H-pyrrolo[2,3-b]pyridin-4-yl)piperazin-1-yl)ethanone dihydrochloride (0.060 g, 98%). MS ESI (+) m/z 514 detected.

Example 23

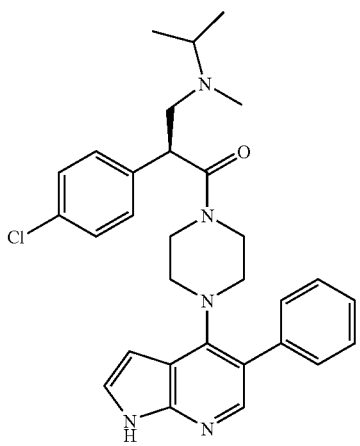 [SMILES: CC(C)N(C)C[C@@H](C(=O)N1CCN(c2c(-c3ccccc3)cnc3[nH]ccc23)CC1)c1ccc(Cl)cc1]

(S)-2-(4-chlorophenyl)-3-(isopropyl(methyl)amino)-1-(4-(5-phenyl-1H-pyrrolo[2,3-b]pyridin-4-yl)piperazin-1-yl)propan-1-one Formaldehyde (0.0712 mL, 0.957 mmol) and NaCNBH₃ (0.0120 g, 0.191 mmol) were added to (S)-2-(4-chlorophenyl)-3-(isopropylamino)-1-(4-(5-phenyl-1H-pyrrolo[2,3-b]pyridin-4-yl)piperazin-1-yl)propan-1-one (0.055 g, 0.096 mmol, see Example 13) in MeOH (0.5 mL). The mixture was stirred at room temperature for 20 minutes. Saturated NaHCO₃ (5 mL) was added, the aqueous layer was extracted with DCM (20 mL), and the combined organic phases were dried over sodium sulfate. After removal of the solvent, the residue was purified by chromatography (20:1:0.1 DCM:ethyl acetate:ammonium hydroxide) to give (S)-2-(4-chlorophenyl)-3-(isopropyl(methyl)amino)-1-(4-(5-phenyl-1H-pyrrolo[2,3-b]pyridin-4-yl)piperazin-1-yl)propan-1-one (0.013 g, 23%) as a solid. MS ESI (+) m/z 516 detected.

Example 24

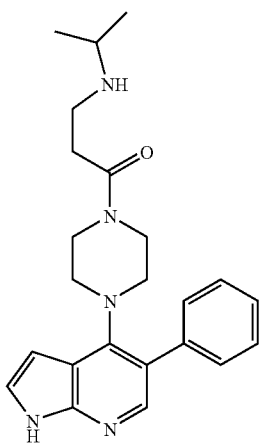 [SMILES: CC(C)NCCC(=O)N1CCN(c2c(-c3ccccc3)cnc3[nH]ccc23)CC1]

3-(isopropylamino)-1-(4-(5-phenyl-1H-pyrrolo[2,3-b]pyridin-4-yl)piperazin-1-yl)propan-1-one 3-Amino-1-(4-(5-phenyl-1H-pyrrolo[2,3-b]pyridin-4-yl)piperazin-1-yl)propan-1-one (0.040 g, 0.095 mmol, see Example 21) and acetone (0.0696 mL, 0.947 mmol) were placed in 1:1 dichloroethylene ("DCE"):DMF (2 mL). DIEA (d 0.742; 0.0495 mL, 0.284 mmol) was then added, followed by the addition of NaBH(OAc)₃ (0.0401 g, 0.189 mmol). The reaction was then stirred for 30 minutes. The reaction was then poured into aqueous Na₂CO₃ and extracted with DCM. The combined organic fractions were dried, filtered, and concentrated to give a crude residue. The residue was purified by chromatography (9:1 DCM:MeOH) to give the pure product. The solid was then dissolved in minimal MeOH, and then 1M HCL in ether was added. The precipitate was collected, washed with ether and dried to give 3-(isopropylamino)-1-(4-(5-phenyl-1H-pyrrolo[2,3-b]pyridin-4-yl)piperazin-1-yl)propan-1-one (0.005 g, 11.4% yield) as the dihydrochloride salt. MS ESI (+) m/z 392 detected.

Example 25

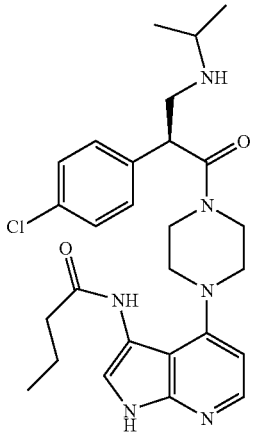 [SMILES: CCCC(=O)Nc1c[nH]c2nccc(N3CCN(C(=O)[C@H](CNC(C)C)c4ccc(Cl)cc4)CC3)c12]

(S)—N-(4-(4-(2-(4-chlorophenyl)-3-(isopropylamino)propanoyl)piperazin-1-yl)-1H-pyrrolo[2,3-b]pyridin-3-yl)butyramide 4-Fluoro-1H-pyrrolo[2,3-b]pyridine (1.80 g, 13.2 mmol, prepared as described in Thibault, et al. as cited in Scheme 1 above) was added slowly to fuming HNO₃ at 0° C. and stirred for 10 minutes. Ice was then added, followed by the addition of water. The reaction was then filtered, and the solid product was washed with water and dried to give 4-fluoro-3-nitro-1H-pyrrolo[2,3-b]pyridine (1.80 g, 75.2% yield).

4-Fluoro-3-nitro-1H-pyrrolo[2,3-b]pyridine (0.300 g, 1.66 mmol) and 1-benzylpiperazine (0.350 g, 1.99 mmol) were placed in NMP (3 mL) and heated to 80° C. in a microwave for 30 minutes. The reaction was then poured into water and extracted with MTBE. The organic fractions were dried, filtered, and concentrated. The crude residue was slurried in minimal DCM, and then triturated with hexane to give 4-(4-benzylpiperazin-1-yl)-3-nitro-1H-pyrrolo[2,3-b]pyridine (0.425 g, 76.1% yield).

4-(4-Benzylpiperazin-1-yl)-3-nitro-1H-pyrrolo[2,3-b]pyridine (0.30 g, 0.889 mmol) was added to a stirring solution of concentrated HCl (5 mL). SnCl₂ (0.843 g, 4.45 mmol) was then added, and the reaction was stirred for 1 hour. The reaction was then cooled to 0° C., and the pH was raised to 8 with saturated aqueous Na₂CO₃. The reaction was then poured into water and extracted into DCM. The organic fractions were combined, dried, filtered and concentrated to give a crude residue that was used immediately without further purification. The crude 4-(4-benzylpiperazin-1-yl)-1H-pyrrolo[2,3-b]pyridin-3-amine (0.125 g, 0.407 mmol) was placed in DCM (2 mL) and pyridine (1 mL). Butyric anhydride (0.0670 mL, 0.407 mmol) was then added, and the reaction was stirred at room temperature for 1 hour. The reaction was then poured into water and extracted into EtOAc. The organic fractions were combined, dried, filtered and concentrated to give a crude residue that was purified by column chromatography (500:5 DCM: MeOH) to give N-(4-(4-benzylpiperazin-1-yl)-1H-pyrrolo[2, 3-1)]pyridin-3-yl) butyramide (0.070 g, 45.6% yield).

N-(4-(4-Benzylpiperazin-1-yl)-1H-pyrrolo[2,3-b]pyridin-3-yl)butyramide (0.070 g, 0.19 mmol) was dissolved in MeOH (1 mL). Pd/C (0.0197 g, 0.0185 mmol) was then added, followed by the addition of 3 drops of concentrated HCl. The reaction was then placed under a H₂ balloon for 18 hours. The reaction was then filtered, washed with MeOH, and concentrated to give the crude product N-(4-(piperazin-1-yl)-1H-pyrrolo[2,3-b]pyridin-3-yl)butyramide (0.050 g, 93.8% yield).

N-(4-(piperazin-1-yl)-1H-pyrrolo[2,3-b]pyridin-3-yl)butyramide (0.050 g, 0.174 mmol), (S)-3-(tert-butoxycarbonyl (isopropyl)amino)-2-(4-chlorophenyl)propanoic acid (0.0625 g, 0.183 mmol, see Example H), HOBT-H₂O (0.0373 g, 0.244 mmol), and EDCI (0.0434 g, 0.226 mmol) were placed in DCM (5 mL) at room temperature. DIEA (d 0.742; 0.152 mL, 0.870 mmol) was then added, and the reaction was stirred at room temperature for 5 hours. The reaction was then poured into saturated Na₂CO₃ and extracted into DCM. The organic fractions were combined, dried, filtered and concentrated to give a crude residue that was purified by column chromatography (500:10-500:20 DCM:MeOH) to give (S)-tert-butyl 3-(4-(3-butyramido-1H-pyrrolo[2,3-b]pyridin-4-yl)piperazin-1-yl)-2-(4-chlorophenyl)-3-oxopropyl(isopropyl)carbamate (0.050 g, 47.0% yield).

(S)-tert-Butyl 3-(4-(3-butyramido-1H-pyrrolo[2, 3-1)]pyridin-4-yl)piperazin-1-yl)-2-(4-chlorophenyl)-3-oxopropyl(isopropyl)carbamate (0.045 g, 0.074 mmol) was placed in DCM (5 mL). TFA (0.5 mL) was then added. The reaction was stirred at room temperature for 1 hour and then concentrated to dryness. The crude residue was then dissolved in minimal DCM and added dropwise to a stirring solution of 1M HCl in ether. The resulting solid was filtered, washed with ether and dried to give (S)—N-(4-(4-(2-(4-chlorophenyl)-3-(isopropylamino)propanoyl)piperazin-1-yl)-1H-pyrrolo[2, 3-b]pyridin-3-yl)butyramide (0.035 g, 81% yield) as the dihydrochloride salt. MS ESI (+) m/z 512 detected.

Example 26

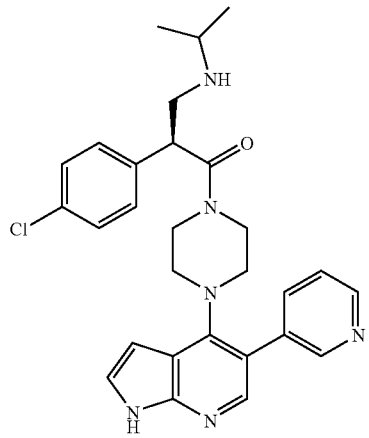 [SMILES: CC(C)NC[C@@H](C(=O)N1CCN(c2c(-c3cccnc3)cnc3[nH]ccc23)CC1)c1ccc(Cl)cc1]

(S)-2-(4-chlorophenyl)-3-(isopropylamino)-1-(4-(5-(pyridin-3-yl)-1H-pyrrolo[2,3-b]pyridin-4-yl)piperazin-1-yl)propan-1-one Pyridin-3-ylboronic acid (20 mg, 0.17 mmol), PS-tetrakis (41 mg, 0.0041 mmol) and sodium carbonate (18 mg, 0.17 mmol, 2N aqueous solution) were added to (S)-tert-butyl 3-(4-(5-bromo-1H-pyrrolo[2,3-b]pyridin-4-yl)piperazin-1-yl)-2-(4-chlorophenyl)-3-oxopropyl(isopropyl)carbamate (50 mg, 0.083 mmol, see Example 4) in degassed (Ar) dioxane (1 mL). The reaction was heated to 160° C. for 1 hour under microwave irradiation. After cooling down, the reaction was diluted with DCM, filtered, dried over MgSO₄ and concentrated to dryness. The resulting residue was purified by reverse phase column chromatography (water:ACN 4:1 to 1:9) to yield (S)-tert-butyl 2-(4-chlorophenyl)-3-oxo-3-(4-(5-(pyridin-3-yl)-1H-pyrrolo[2,3-b]pyridin-4-yl)piperazin-1-yl)propyl(isopropyl)carbamate (32 mg, 64% yield) as a solid.

(S)-tert-Butyl 2-(4-chlorophenyl)-3-oxo-3-(4-(5-(pyridin-3-yl)-1H-pyrrolo[2,3-b]pyridin-4-yl)piperazin-1-yl)propyl (isopropyl)carbamate (25 mg, 0.041 mmol) in TFA (3 mL) was stirred for 30 minutes and then concentrated to dryness. The resulting residue was dissolved in minimal DCM (0.2 mL) and added to 2N HCl in ether. The resulting solid was filtered and dried under nitrogen to yield (S)-2-(4-chlorophenyl)-3-(isopropylamino)-1-(4-(5-(pyridin-3-yl)-1H-pyrrolo[2,3-b]pyridin-4-yl)piperazin-1-yl)propan-1-one (16 mg, 77% yield) trihydro chloride. ¹H NMR (400 MHz, DMSO-d6) δ 12.40 (br s, 1H), 8.96 (s, 1H), 8.77 (d, 1H), 8.45 (m, 1H), 8.13 (s, 1H), 7.89-7.84 (m, 1H), 7.52-7.45 (m, 3H), 7.41-7.32 (m, 3H), 6.74 (s, 1H), 4.66-4.61 (m, 1H), 3.90-3.15 (m, 10H), 3.00-2.96 (m, 1H), 2.82-2.75 (m, 1H), 1.23 (dq, 6H); m/z (APCI pos) 503.3 (100%) [M].

The following compounds were prepared following the above procedure and using the appropriate boronic acid or ester:

TABLE 1

| Ex # | Structure | Name | Data |
|---|---|---|---|
| 27 | 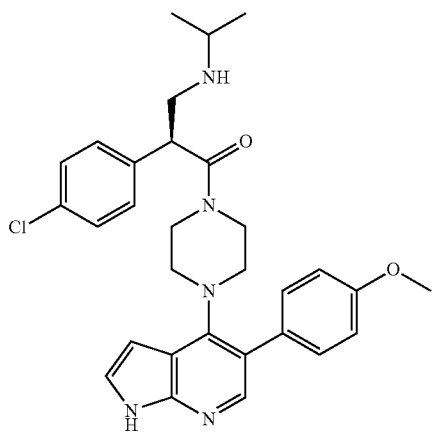 [SMILES: COc1ccc(-c2cnc3[nH]ccc3c2N2CCN(C(=O)[C@H](CNC(C)C)c3ccc(Cl)cc3)CC2)cc1] | (S)-2-(4-chlorophenyl)-3-(isopropylamino)-1-(4-(5-(4-methoxyphenyl)-1H-pyrrolo[2,3-b]pyridin-4-yl)piperazin-1-yl)propan-1-one dihydrochloride | Yield 83%; $^1$H NMR (400 MHz, DMSO-$d_6$) δ 12.40 (br s, 1H), 8.89 (s, 1H), 8.36 (s, 1H), 7.91 (s, 1H), 7.49-7.40 (m, 4H), 7.35-4.31 (m, 2H), 7.04-7.01 (m, 2H), 6.76 (s, 1H), 4.59-4.54 (m, 1H), 3.81 (s, 3H), 3.60-3.15 (m, 10H), 3.00-2.96 (m, 1H), 2.84-2.78 (m, 1H), 1.22 (dq, 6H); m/z (APCI pos) 532.3 (100%) [M + H]. |
| 28 | 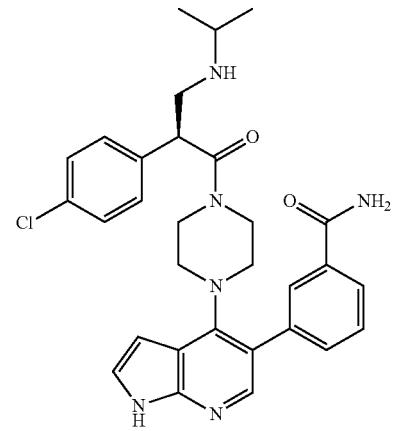 [SMILES: CC(C)NC[C@@H](C(=O)N1CCN(c2c(-c3cccc(C(N)=O)c3)cnc3[nH]ccc23)CC1)c1ccc(Cl)cc1] | (S)-3-(4-(4-(2-(4-chlorophenyl)-3-(isopropylamino)-propanoyl)-piperazin-1-yl)-1H-pyrrolo[2,3-b]pyridin-5-yl)benzamide dihycrochloride | Yield 85%; $^1$H NMR (400 MHz, DMSO-$d_6$) δ 12.40 (s, 1H), 8.86 (s, 1H), 8.32 (s, 1H), 8.08 (s, 1H), 8.05-8.02 (m, 2H), 7.91-7.87 (m, 1H), 7.66-7.62 (m, 1H), 7.56-7.43 (m, 4H), 7.30-7.34 (m, 2H), 6.76 (s, 1H), 4.55-4.50 (m, 1H), 3.70-3.20 (m, 10H), 3.00-2.90 (m, 1H), 2.74-2.68 (m, 1H), 1.22 (dq, 6H); m/z (ESI pos) 545.4 (100%) [M]. |
| 29 | 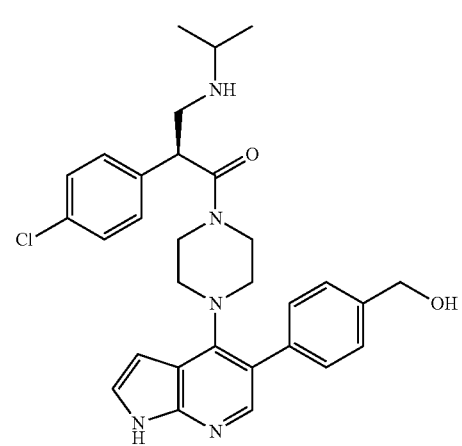 [SMILES: CC(C)NC[C@@H](C(=O)N1CCN(c2c(-c3ccc(CO)cc3)cnc3[nH]ccc23)CC1)c1ccc(Cl)cc1] | (S)-2-(4-chlorophenyl)-1-(4-(5-(4-(hydroxymethyl)phenyl)-1H-pyrrolo[2,3-b]pyridin-4-yl)piperazin-1-yl)-3-(isopropylamino)-propan-1-one dihydrochloride | Yield 30%; $^1$H NMR (400 MHz, DMSO-$d_6$) δ 11.51 (s, 1H), 7.84 (s, 1H), 7.44-7.28 (m, 8H), 6.46 (m, 1H), 5.18 (t, 1H), 4.53 (d, 2H), 4.13-4.08 (m, 1H), 3.50-3.20 (m, 7H), 3.10-3.08 (m, 5H), 2.70-2.63 (m, 2H), 0.91 (dq, 6H); m/z (ESI pos) 532.3 (100%) [M]. |

| Ex # | Structure | Name | Data |
|---|---|---|---|
| 30 | 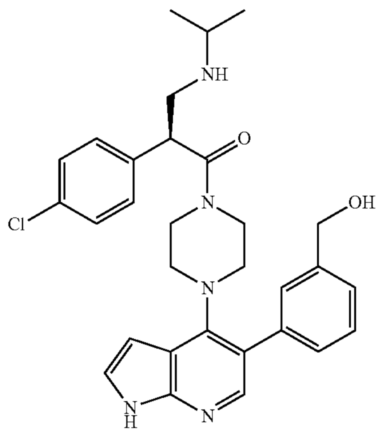 [SMILES: CC(C)NC[C@@H](C(=O)N1CCN(c2c(-c3cccc(CO)c3)cnc3[nH]ccc23)CC1)c1ccc(Cl)cc1] | (S)-2-(4-chlorophenyl)-1-(4-(5-(3-(hydroxymethyl)phenyl)-1H-pyrrolo[2,3-b]pyridin-4-yl)piperazin-1-yl)-3-(isopropylamino)-propan-1-one dihydrochloride | Yield 25%; $^1$H NMR (400 MHz, DMSO-d$_6$) δ 12.20 (s, 1H), 8.70 (s, 1H), 8.30 (s, 1H), 7.98 (s, 1H), 7.49-7.25 (m, 8H), 6.70 (s, 1H), 5.76 (s, 1H), 4.55 (s, 2H), 4.50-4.46 (m, 1H), 3.65-3.20 (m, 10H), 3.00-2.93 (m, 1H), 2.70-2.65 (m, 1H), 1.23 (dq, 6H); m/z (APCI pos) 532.1 (100%) [M]. |
| 31 | 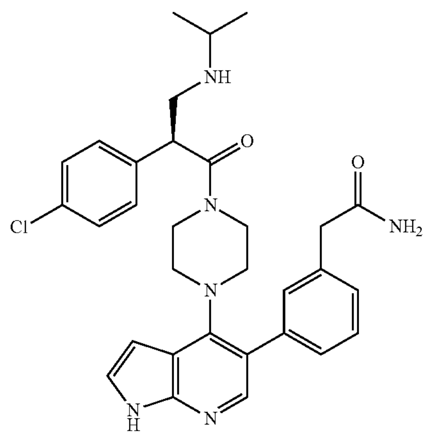 [SMILES: CC(C)NC[C@@H](C(=O)N1CCN(c2c(-c3cccc(CC(N)=O)c3)cnc3[nH]ccc23)CC1)c1ccc(Cl)cc1] | (S)-2-(3-(4-(4-(2-(4-chlorophenyl)-3-(isopropylamino)-propanoyl)-piperazin-1-yl)-1H-pyrrolo[2,3-b]pyridin-5-yl)phenyl)acetamide dihydrochloride | Yield 59%; $^1$H NMR (400 MHz, DMSO-d$_6$) δ 12.55 (s, 1H), 9.00 (s, 1H), 8.44 (s, 1H), 7.95 (s, 1H), 7.60 (s, 1H), 7.52-7.28 (m, 10H), 6.94 (s, 1H), 6.82 (s, 1H), 4.60 (m, 1H), 3.60-3.15 (m, 10H), 3.02-2.95 (m, 1H), 2.88-2.80 (m, 1H), 1.23 (dq, 6H); m/z (APCI pos) 559.1 (100%) [M]. |
| 32 | 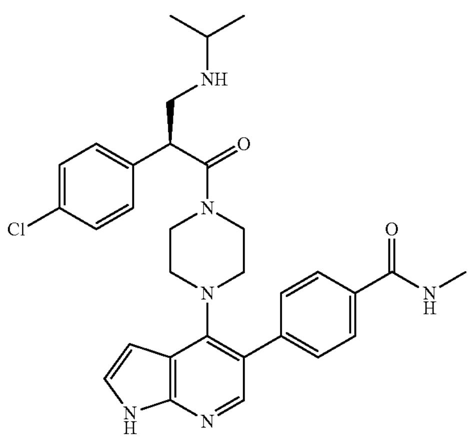 [SMILES: CNC(=O)c1ccc(-c2cnc3[nH]ccc3c2N2CCN(C(=O)[C@H](CNC(C)C)c3ccc(Cl)cc3)CC2)cc1] | (S)-4-(4-(4-(2-(4-chlorophenyl)-3-(isopropylamino)-propanoyl)-piperazin-1-yl)-1H-pyrrolo[2,3-b]pyridin-5-yl)-N-methylbenzamide dihydrochloride | Yield 83%; $^1$H NMR (400 MHz, DMSO-d$_6$) δ 12.30 (s, 1H), 8.80 (s, 1H), 8.54 (s, 1H), 8.32 (s, 1H), 7.99 (s, 1H), 7.91-7.96 (m, 2H), 7.59 (d, 2H), 7.50-7.42 (m, 3H), 7.35-7.30 (m, 2H), 6.74 (s, 1H), 4.52 (m, 1H), 3.70-3.20 (m, 10H), 3.02-2.95 (m, 1H), 2.88-2.80 (m, 1H), 2.82 (d, 3H), 1.22 (dq, 6H); m/z (APCI pos) 559.1 (100%) [M]. |

TABLE 1-continued

| Ex # | Structure | Name | Data |
|---|---|---|---|
| 33 | 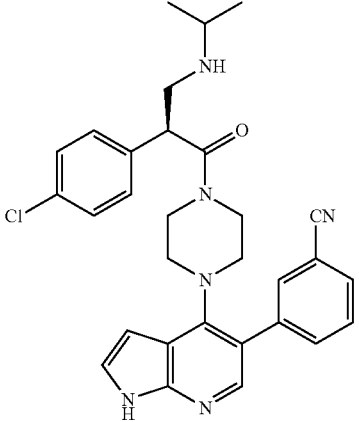 [SMILES: CC(C)NC[C@@H](C(=O)N1CCN(c2c(-c3cccc(C#N)c3)cnc3[nH]ccc23)CC1)c1ccc(Cl)cc1] | (S)-3-(4-(4-(2-(4-chlorophenyl)-3-(isopropylamino)-propanoyl)-piperazin-1-yl)-1H-pyrrolo[2,3-b]pyridin-5-yl)benzonitrile dihydrochloride | Yield 54%; $^1$H NMR (400 MHz, DMSO-$d_6$) δ 12.38 (s, 1H), 8.88 (s, 1H), 8.35 (s, 1H), 8.03 (s, 1H), 7.99 (s, 1H), 7.87-7.82 (m, 2H), 7.65 (t, 1H), 7.50-7.44 (m, 3H), 7.35-7.30 (m, 2H), 6.73 (s, 1H), 4.54 (m, 1H), 3.70-3.20 (m, 10H), 3.00-2.90 (m, 1H), 2.70-2.62 (m, 1H), 1.22 (dq, 6H); m/z (APCI pos) 527.0 (60%) [M]. |
| 34 | 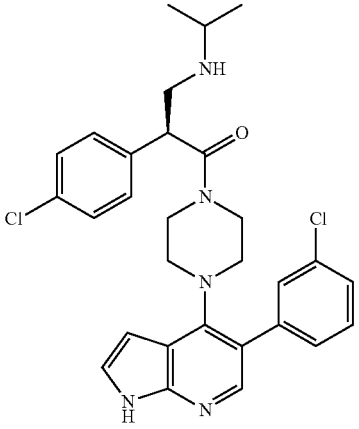 [SMILES: CC(C)NC[C@@H](C(=O)N1CCN(c2c(-c3cccc(Cl)c3)cnc3[nH]ccc23)CC1)c1ccc(Cl)cc1] | (S)-2-(4-chlorophenyl)-1-(4-(5-(3-chlorophenyl)-1H-pyrrolo[2,3-b]pyridin-4-yl)piperazin-1-yl)-3-(isopropylamino)-propan-1-one dihydrochloride | Yield 36%; m/z (APCI pos) 535.4 (30%) [M]. |
| 35 | 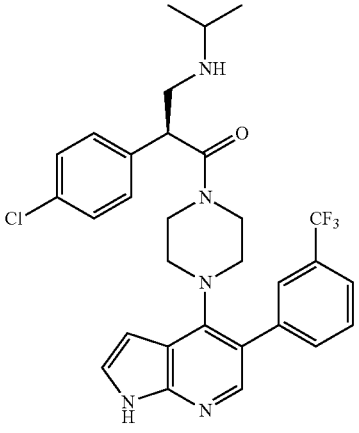 [SMILES: CC(C)NC[C@@H](C(=O)N1CCN(c2c(-c3cccc(C(F)(F)F)c3)cnc3[nH]ccc23)CC1)c1ccc(Cl)cc1] | (S)-2-(4-chlorophenyl)-3-(isopropylamino)-1-(4-(5-(3-(trifluoromethyl)phenyl)-1H-pyrrolo[2,3-b]pyridin-4-yl)piperazin-1-yl)propan-1-one dihydrochloride | Yield 55%; $^1$H NMR (400 MHz, DMSO-$d_6$) δ 12.42 (s, 1H), 8.95 (s, 1H), 8.40 (s, 1H), 8.06 (s, 1H), 7.90 (s, 1H), 7.84-7.78 (m, 1H), 7.76-7.68 (m, 2H), 7.50 (m, 1H), 7.46-7.42 (m, 2H), 7.33-7.28 (m, 2H), 6.77 (s, 1H), 4.54 (m, 1H), 3.60-3.10 (m, 10H), 3.00-2.92 (m, 1H), 2.73-2.66 (m, 1H), 1.22 (dq, 6H); m/z (APCI pos) 570.3 (20%) [M]. |

TABLE 1-continued

| Ex # | Structure | Name | Data |
|---|---|---|---|
| 36 | 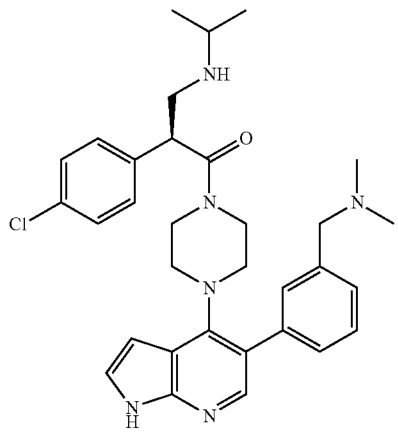 [SMILES: CC(C)NC[C@@H](C(=O)N1CCN(c2c(-c3cccc(CN(C)C)c3)cnc3[nH]ccc23)CC1)c1ccc(Cl)cc1] | (S)-2-(4-chlorophenyl)-1-(4-(5-(3-((dimethylamino)-methyl)phenyl)-1H-pyrrolo[2,3-b]pyridin-4-yl)piperazin-1-yl)-3-(isopropylamino)-propan-1-one trihydrochloride | Yield 47%; $^1$H NMR (400 MHz, DMSO-$d_6$) δ 12.42 (s, 1H), 10.88 (s, 1H), 9.08 (s, 1H), 8.48 (s, 1H), 8.06 (s, 1H), 7.73 (s, 1H), 7.58-7.43 (m, 5H), 7.35-7.30 (m, 2H), 6.78 (s, 1H), 4.62 (m, 1H), 4.34 (m, 2H), 3.60-3.15 (m, 10H), 3.00-2.92 (m, 1H), 2.86-2.80 (m, 1H), 2.74-2.68 (m, 6H), 1.23 (dq, 6H); m/z (APCI pos) 559.5 (100%) [M]. |
| 37 | 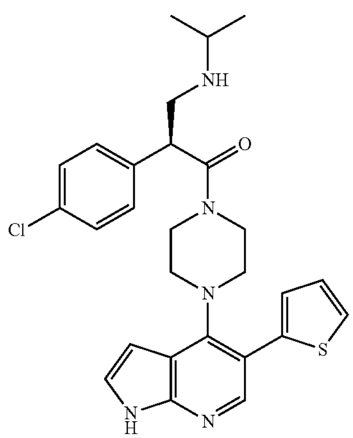 | (S)-2-(4-chlorophenyl)-3-(isopropylamino)-1-(4-(5-(thiophen-2-yl)-1H-pyrrolo[2,3-b]pyridin-4-yl)piperazin-1-yl)propan-1-one dihydrochloride | Yield 90%; $^1$H NMR (400 MHz, DMSO-$d_6$) δ 12.39 (s, 1H), 9.03 (s, 1H), 8.50 (s, 1H), 8.00 (d, 1H), 7.50-7.46 (m, 2H), 7.41-7.36 (m, 3H), 6.85 (s, 1H), 6.68-6.64 (m, 1H), 4.66 (m, 1H), 4.00-3.78 (m, 5H), 3.62-3.28 (m, 6H), 3.05-2.98 (m, 1H), 1.25 (dq, 6H); m/z (APCI pos) 426.2 (100%) [M + H-thiophene]. |
| 38 | 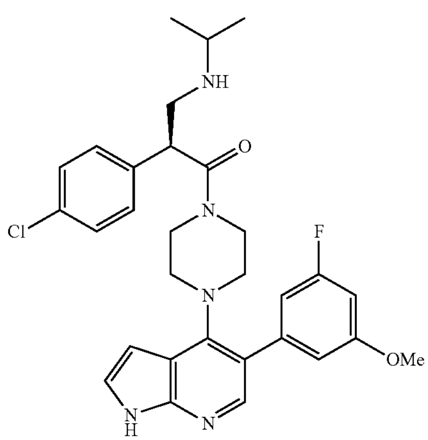 [SMILES: COc1cc(F)cc(-c2cnc3[nH]ccc3c2N2CCN(C(=O)[C@H](CNC(C)C)c3ccc(Cl)cc3)CC2)c1] | (S)-2-(4-chlorophenyl)-1-(4-(5-(3-fluoro-5-methoxyphenyl)-1H-pyrrolo[2,3-b]pyridin-4-yl)piperazin-1-yl)-3-(isopropylamino)-propan-1-one dihydrochloride | Yield 81%; $^1$H NMR (400 MHz, DMSO-$d_6$) δ 12.34 (s, 1H), 8.83 (s, 1H), 8.33 (s, 1H), 8.00 (d, 1H), 7.48-7.44 (m, 3H), 7.36-7.32 (m, 2H), 6.95-6.82 (m, 2H), 6.74 (s, 1H), 4.54 (m, 1H), 3.80 (d, 3H), 3.70-3.20 (m, 10H), 2.97 (s, 1H), 2.75 (s, 1H), 1.23 (dq, 6H); m/z (APCI pos) 550.5 (100%) [M]. |

TABLE 1-continued

| Ex # | Structure | Name | Data |
|---|---|---|---|
| 39 | 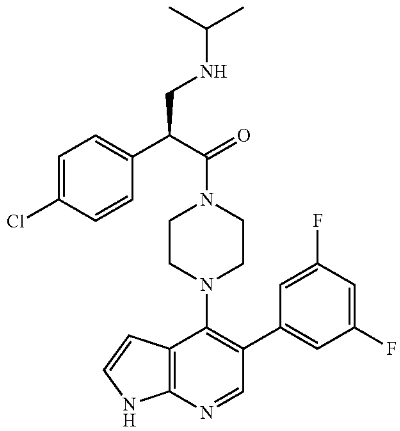 [SMILES: CC(C)NC[C@@H](C(=O)N1CCN(c2c(-c3cc(F)cc(F)c3)cnc3[nH]ccc23)CC1)c1ccc(Cl)cc1] | (S)-2-(4-chlorophenyl)-1-(4-(5-(3,5-difluorophenyl)-1H-pyrrolo[2,3-b]pyridin-4-yl)piperazin-1-yl)-3-(isopropylamino)-propan-1-one dihydrochloride | Yield 76%; $^1$H NMR (400 MHz, DMSO-d$_6$) δ 12.24 (s, 1H), 8.76 (s, 1H), 8.30 (s, 1H), 8.01 (d, 1H), 7.48-7.44 (m, 2H), 7.36-7.32 (m, 2H), 7.28-7.21 (m, 3H), 6.70 (s, 1H), 4.52 (m, 1H), 3.70-3.20 (m, 10H), 2.97 (s, 1H), 2.67 (s, 1H), 1.23 (dq, 6H); m/z (APCI pos) 538.3 (100%) [M]. |
| 40 | 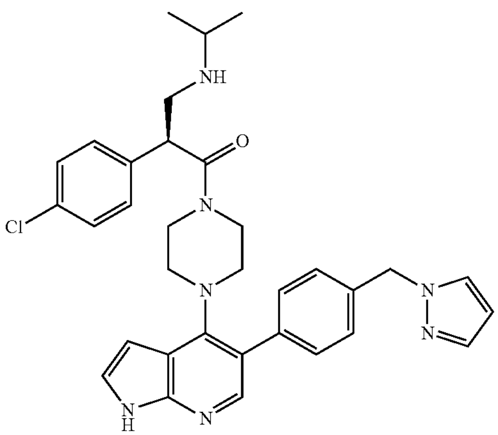 [SMILES: CC(C)NC[C@@H](C(=O)N1CCN(c2c(-c3ccc(Cn4cccn4)cc3)cnc3[nH]ccc23)CC1)c1ccc(Cl)cc1] | (S)-1-(4-(5-(4-((1H-pyrazol-1-yl)methyl)phenyl)-1H-pyrrolo[2,3-b]pyridin-4-yl)piperazin-1-yl)-2-(4-chlorophenyl)-3-(isopropylamino)-propan-1-one trihydrochloride | Yield 47%; $^1$H NMR (400 MHz, DMSO-d$_6$) δ 12.30 (s, 1H), 8.87 (s, 1H), 8.38 (s, 1H), 8.18 (s, 1H), 8.04 (s, 1H), 7.78 (s, 1H), 7.51-7.45 (m, 2H), 7.39-7.30 (m, 3H), 7.26-7.23 (m, 1H), 6.71 (s, 1H), 5.38 (s, 2H), 4.58 (m, 1H), 3.60-3.20 (m, 10H), 3.01 (s, 1H), 2.91 (s, 1H), 1.24 (dq, 6H); m/z (APCI pos) 582.3 (100%) [M]. |
| 41 | 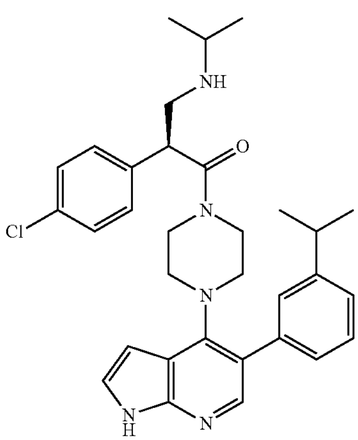 [SMILES: CC(C)NC[C@@H](C(=O)N1CCN(c2c(-c3cccc(C(C)C)c3)cnc3[nH]ccc23)CC1)c1ccc(Cl)cc1] | (S)-2-(4-chlorophenyl)-3-(isopropylamino)-1-(4-(5-(3-isopropylphenyl)-1H-pyrrolo[2,3-b]pyridin-4-yl)piperazin-1-yl)propan-1-one | Yield 21%; m/z (APCI pos) 545 (100%) [M + H]. |

Example 42

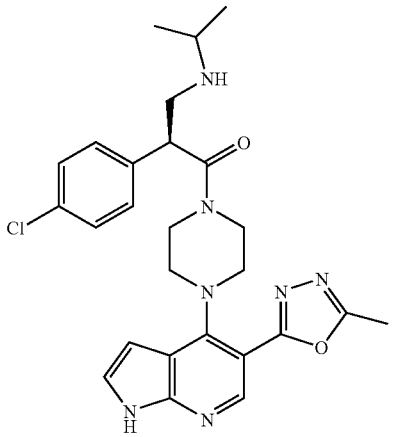 [SMILES: Cc1nnc(-c2cnc3[nH]ccc3c2N2CCN(C(=O)[C@H](CNC(C)C)c3ccc(Cl)cc3)CC2)o1]

(S)-2-(4-chlorophenyl)-3-(isopropylamino)-1-(4-(5-(5-methyl-1,3,4-oxadiazol-2-yl)-1H-pyrrolo[2,3-b]pyridin-4-yl)piperazin-1-yl)propan-1-one Ethyl 2-ethoxyquinoline-1(2H)-carboxylate (226 mg, 0.916 mmol) was added to acetic acid (50.0 mg, 0.832 mmol) in THF/ACN (5 mL), and the reaction was stirred at room temperature for 1 hour. tert-Butyl 4-(5-(hydrazinecarbonyl)-1H-pyrrolo[2,3-b]pyridin-4-yl)piperazine-1-carboxylate (300 mg, 0.832 mmol, Example 18) was added, and the reaction was heated to 70° C. for 1 hour. The reaction was then concentrated to dryness. The resulting residue was crystallized from DCM to yield tert-butyl 4-(5-(2-acetylhydrazinecarbonyl)-1H-pyrrolo[2,3-b]pyridin-4-yl)piperazine-1-carboxylate (241 mg, 71.9% yield) as a solid.

tert-Butyl 4-(5-(2-acetyllhydrazinecarbonyl)-1H-pyrrolo[2,3-b]pyridin-4-yl)piperazine-1-carboxylate (70 mg, 0.16 mmol) in POCl$_3$ (1 mL) was heated to 90° C. for 1 hour. The reaction was concentrated to dryness to yield 2-methyl-5-(4-(piperazin-1-yl)-1H-pyrrolo[2,3-b]pyridin-5-yl)-1,3,4-oxadiazole (58 mg, 125% yield) as an oil, which was used in the next step.

(S)-3-(tert-Butoxycarbonyl(isopropyl)amino)-2-(4-chlorophenyl)propanoic acid (180 mg, 0.52 mmol, see Example H), N1-((ethylimino)methylene)-N3,N3-dimethylpropane-1,3-diamine hydrochloride (134 mg, 0.70 mmol), HOBt-H$_2$O (108 mg, 0.70 mmol) and triethylamine (106 mg, 1 mmol) were added to 2-methyl-5-(4-(piperazin-1-yl)-1H-pyrrolo[2,3-b]pyridin-5-yl)-1,3,4-oxadiazole (100 mg, 0.36 mmol) in DCM (10 mL). The reaction was stirred at room temperature for 18 hours. After dilution with DCM, the mixture was washed with 1N HCl, 10% K$_2$CO$_3$ and brine. The organic phase was dried over MgSO$_4$ and purified by chromatography (SP4, 12+M, water/ACN 90/10→10/90, 20CV) to yield (S)-tert-butyl 2-(4-chlorophenyl)-3-(4-(5-(5-methyl-1,3,4-oxadiazol-2-yl)-1H-pyrrolo[2,3-b]pyridin-4-yl)piperazin-1-yl)-3-oxopropyl(isopropyl)carbamate (60 mg) as a solid.

(S)-tert-Butyl 2-(4-chlorophenyl)-3-(4-(5-(5-methyl-1,3,4-oxadiazol-2-yl)-1H-pyrrolo[2,3-b]pyridin-4-yl)piperazin-1-yl)-3-oxopropyl(isopropyl)carbamate (50 mg, 0.082 mmol) in TFA (3 mL) was stirred for 30 minutes and then concentrated to dryness. The resulting residue was dissolved in minimal DCM (0.2 mL) and added to 2N HCl in ether. The resulting solid was filtered and dried under nitrogen to yield (S)-2-(4-chlorophenyl)-3-(isopropylamino)-1-(4-(5-(5-methyl-1,3,4-oxadiazol-2-yl)-1H-pyrrolo[2,3-b]pyridin-4-yl)piperazin-1-yl)propan-1-one (21 mg, 50% yield) hydrochloride as a solid. $^1$H NMR (400 MHz, DMSO-d$_6$) δ 12.10 (s, 1H), 8.84 (s, 1H), 8.35 (s, 2H), 7.52-7.48 (m, 2H), 7.46-4.42 (m, 1H), 7.40-7.36 (m, 2H), 6.64 (s, 1H), 4.58 (m, 1H), 3.70-3.20 (m, 10H), 3.01 (s, 1H), 2.78 (s, 1H), 2.54 (s, 3H), 1.24 (dq, 6H); MS ESI (+) m/z 508 detected.

Example 43

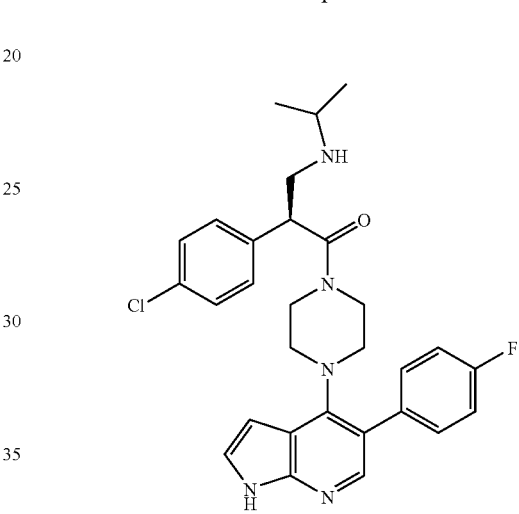

(S)-2-(4-chlorophenol)-1-(4-(5-(4-fluorophenyl)-1H-pyrrolo[2,3-b]pyri din-4-yl)piperazin-1-yl)-3-(isopropylamino)propan-1-one 4-Fluorophenylboronic acid (44.0 mg, 0.315 mmol), PS-palladium tetrakis (119 mg, 0.0131 mmol) and 2N sodium carbonate (262 µL, 0.525 mmol) were added to tert-butyl 4-(5-bromo-1H-pyrrolo[2,3-b]pyridin-4-yl)piperazine-1-carboxylate (100 mg, 0.262 mmol, see Example 1) in dioxane (1 mL, degassed with Ar). The reaction was heated to 150° C. for 1 hour under microwave irradiation. The reaction was then cooled down and filtered. The filtrate was diluted with DCM and dried with MgSO$_4$. After concentration, the residue was purified by chromatography (SP4, 25+M, water/ACN 90/10→10/90, 20CV) to yield tert-butyl 4-(5-(4-fluorophenyl)-1H-pyrrolo[2,3-b]pyridin-4-yl)piperazine-1-carboxylate (69 mg, 66.4% yield) as a solid.

tert-Butyl 4-(5-(4-fluorophenyl)-1H-pyrrolo[2,3-b]pyridin-4-yl)piperazine-1-carboxylate (60 mg, 0.15 mmol) was stirred in TFA (2 mL) for 1 hour. The solution was then concentrated to an oil and used in the next step.

(S)-3-(tert-Butoxycarbonyl(isopropyl)amino)-2-(4-chlorophenyl)propanoic acid (87 mg, 0.25 mmol, see Example H), N1-((ethylimino)methylene)-N3,N3-dimethylpropane-1,3-diamine hydrochloride (65 mg, 0.34 mmol), HOBt-H$_2$O (52 mg, 0.34 mmol) and triethylamine (51 mg, 0.51 mmol) were added to 5-(4-fluorophenyl)-4-(piperazin-1-yl)-1H-pyrrolo[2,3-b]pyridine (50 mg, 0.17 mmol) in DCM (10 mL). The reaction was stirred for 18 hours. The reaction was then diluted with DCM (50 mL) and washed with 1N HCl, 10% K$_2$CO$_3$ and brine. After drying with MgSO$_4$ and concentration, the resulting residue was purified by chromatography (SP4, 12+M, water/ACN 80/20→0/100, 20CV) to yield (S)-tert-butyl 2-(4-chlorophenyl)-3-(4-(5-(4-fluorophenyl)-1H-pyrrolo[2,3-b]pyridin-4-yl)piperazin-1-yl)-3-oxopropyl(isopropyl)carbamate (42 mg, 40% yield) as a solid.

(S)-tert-Butyl 2-(4-chlorophenyl)-3-(4-(5-(4-fluorophenyl)-1H-pyrrolo[2,3-b]pyridin-4-yl)piperazin-1-yl)-3-oxopropyl(isopropyl)carbamate (30 mg, 0.048 mmol) in TFA (3 mL) was stirred for 30 minutes and then concentrated to dryness. The resulting residue was dissolved in minimal DCM (0.2 mL) and added to 2N HCl in ether. The resulting solid was filtered and dried under nitrogen to yield (S)-2-(4-chlorophenyl)-1-(4-(5-(4-fluorophenyl)-1H-pyrrolo[2,3-b]pyridin-4-yl)piperazin-1-yl)-3-(isopropylamino)propan-1-one (23 mg, 91% yield) dihydrochloride. MS ESI (+) m/z 520 detected.

Example 44

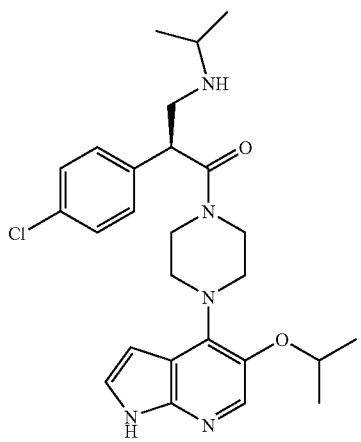 [SMILES: CC(C)NC[C@@H](C(=O)N1CCN(c2c(OC(C)C)cnc3[nH]ccc23)CC1)c1ccc(Cl)cc1]

(S)-2-(4-chlorophenyl)-1-(4-(5-isopropoxy-1H-pyrrolo[2,3-b]pyridin-4-yl)piperazin-1-yl)-3-(isopropylamino)propan-1-one sec-Butyl lithium (8.06 mL, 11.3 mmol, 1.4 M in cyclohexane) was added dropwise to 4-fluoro-1-(triisopropylsilyl)-1H-pyrrolo[2,3-b]pyridine (1.5 g, 5.13 mmol, prepared as described in L'Heureux, et al., Org. Lett., 5(26) p. 5023 (2003)) in THF (100 mL) at −78° C. The reaction was stirred for 30 minutes. (1R)-(−)-(10-camphorsulfonyl)oxaziridine (2.94 g, 12.8 mmol) in THF (10 mL) was added rapidly, and the reaction was stirred at −78° C. for 30 minutes. A solution of saturated ammonium chloride (50 mL) was added, and the reaction mixture was allowed to reach room temperature. After one hour, the aqueous phase was extracted with AcOEt, dried over MgSO$_4$ and concentrated to a solid, which was triturated in ether. The solid (most of the camphor side product) was filtered off, and the filtrate concentrated and purified by chromatography (25M, toluene/AcOEt 95/5) to yield a paste. The paste was triturated with hexanes, and the filtrate was concentrated to dryness to yield 4-fluoro-1-(triisopropylsilyl)-1H-pyrrolo[2,3-b]pyridin-5-ol (820 mg, 51.8% yield) as an oil, which solidified upon standing.

2-Bromopropane (120 mg, 0.973 mmol) and potassium carbonate (448 mg, 3.24 mmol) were added to 4-fluoro-1-(triisopropylsilyl)-1H-pyrrolo[2,3-b]pyridin-5-ol (200 mg, 0.648 mmol) in DMF (3 mL). The reaction was heated to 80° C. in a sealed tube for 18 hours and then cooled down. The reaction mixture was concentrated to dryness. The mixture was then suspended in DCM and filtered. The filtrate was concentrated and purified by chromatography (SP4, 12+M, water/ACN 80/20→10/90, 20CV) to yield 4-fluoro-5-isopropoxy-1-(triisopropylsilyl)-1H-pyrrolo[2,3-b]pyridine (65 mg, 42%) as a solid.

Piperazine (222 mg, 2.6 mmol) was added to 4-fluoro-5-isopropoxy-1H-pyrrolo[2,3-b]pyridine (50 mg, 0.26 mmol) in NMP (1 mL), and the reaction was heated to 200° C. for 1 hour under microwave irradiation. The reaction was concentrated to dryness under high vacuum and then purified by chromatography (SP4, 12+M, water/ACN 100/0→40/60, 20CV) to yield 5-isopropoxy-4-(piperazin-1-yl)-1H-pyrrolo[2,3-b]pyridine (33 mg, 49% yield) as an oil.

(S)-3-(tert-Butoxycarbonyl(isopropyl)amino)-2-(4-chlorophenyl)propanoic acid (59 mg, 0.17 mmol, see Example H), N1-((ethylimino)methylene)-N3,N3-dimethylpropane-1,3-diamine hydrochloride (44 mg, 0.23 mmol), HOBt-H$_2$O (35 mg, 0.23 mmol) and triethylamine (12 mg, 0.12 mmol) were added to 5-isopropoxy-4-(piperazin-1-yl)-1H-pyrrolo[2,3-b]pyridine (30 mg, 0.12 mmol) in DCM (10 mL). The reaction was stirred at room temperature for 18 hours. The reaction was then diluted with DCM (50 mL) and washed with 1N HCL, 10% K$_2$CO$_3$ and brine. After drying over MgSO$_4$, the residue was concentrated to dryness and purified by chromatography (SP4, 12+M, water/ACN 90/10→0/100, 20 CV) to yield (S)-tert-butyl 2-(4-chlorophenyl)-3-(4-(5-isopropoxy-1H-pyrrolo[2,3-b]pyri din-4-yl)piperazin-1-yl)-3-oxopropyl(isopropyl)carbamate (42 mg, 62% yield) as a solid.

(S)-tert-Butyl 2-(4-chlorophenyl)-3-(4-(5-isopropoxy-1H-pyrrolo[2,3-b]pyridin-4-yl)piperazin-1-yl)-3-oxopropyl(isopropyl)carbamate (30 mg, 0.051 mmol) in TFA (3 mL) was stirred for 30 minutes and then concentrated to dryness. The resulting residue was dissolved in minimal DCM (0.2 mL) and added to 2N HCl in ether. The resulting solid was filtered and dried under nitrogen to yield (S)-2-(4-chlorophenyl)-1-(4-(5-isopropoxy-1H-pyrrolo[2,3-b]pyridin-4-yl)piperazin-1-yl)-3-(isopropylamino)propan-1-one (15 mg, 60% yield) hydrochloride as a solid. $^1$H NMR (400 MHz, DMSO-d6) δ 12.30 (s, 1H), 9.23 (s, 1H), 8.56 (s, 1H), 7.99 (s, 1H), 7.51-7.47 (m, 2H), 7.44-7.39 (m, 3H), 6.69 (s, 1H), 4.76 (m, 1H), 4.43 (m, 1H), 3.85-3.50 (m, 7H), 3.47-3.40 (m, 1H), 3.35-3.27 (m, 1H), 3.23-3.15 (m, 1H), 3.05-2.98 (m, 1H), 1.28-1.20 (m, 12H); m/z (ESI pos) 484.4 (100%) [M].

Following the same procedure with the appropriate alkyl halide, the following compounds were prepared:

TABLE 2

| Ex # | Structure | Name | Data |
|---|---|---|---|
| 45 | 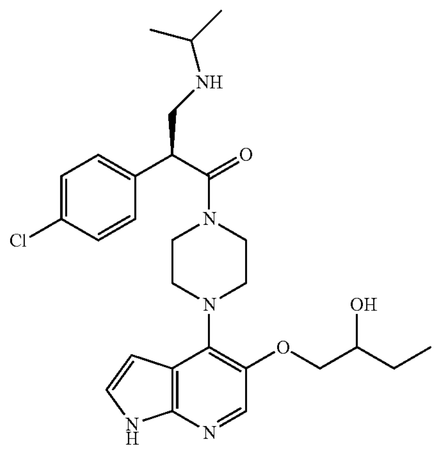 [SMILES: CCC(O)COc1cnc2[nH]ccc2c1N1CCN(C(=O)[C@H](CNC(C)C)c2ccc(Cl)cc2)CC1] | (2S)-2-(4-chlorophenyl)-1-(4-(5-(2-hydroxybutoxy)-1H-pyrrolo[2,3-b]pyridin-4-yl)piperazin-1-yl)-3-(isopropylamino)-propan-1-one dihydrochloride | Yield 86%; $^1$H NMR (400 MHz, DMSO-$d_6$) δ 12.19 (s, 1H), 9.02 (s, 1H), 8.45 (s, 1H), 7.99 (s, 1H), 7.51-7.46 (m, 2H), 7.42-7.37 (m, 3H), 6.67 (s, 1H), 4.69 (m, 1H), 3.94-3.20 (m, 13H), 3.02 (s, 1H), 1.40 (m, 1H), 1.25 (dq, 6H), 0.92 (t, 3H); m/z (APCI pos) 514.4 (20%) [M]. |
| 46 | 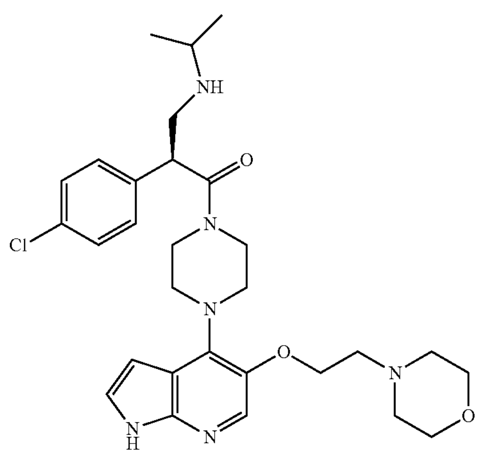 [SMILES: CC(C)NC[C@@H](C(=O)N1CCN(c2c(OCCN3CCOCC3)cnc3[nH]ccc23)CC1)c1ccc(Cl)cc1] | (S)-2-(4-chlorophenyl)-3-(isopropylamino)-1-(4-(5-(2-morpholinoethoxy)-1H-pyrrolo[2,3-b]pyridin-4-yl)piperazin-1-yl)propan-1-one trihydrochloride | Yield 84%; $^1$H NMR (400 MHz, DMSO-$d_6$) δ 12.33 (s, 1H), 11.69 m, 1H), 9.28 (s, 1H), 8.64 (s, 1H), 8.22 (s, 1H), 7.52-7.48 (m, 2H), 7.44-7.40 (m, 3H), 6.70 (s, 1H), 4.80 (m, 1H), 4.44 (m, 2H), 4.00-3.62 (m, 9H), 3.60-3.20 (m, 11H), 3.02 (s, 1H), 1.26 (dq, 6H); m/z (APCI pos) 555.4 (100%) [M]. |
| 47 | 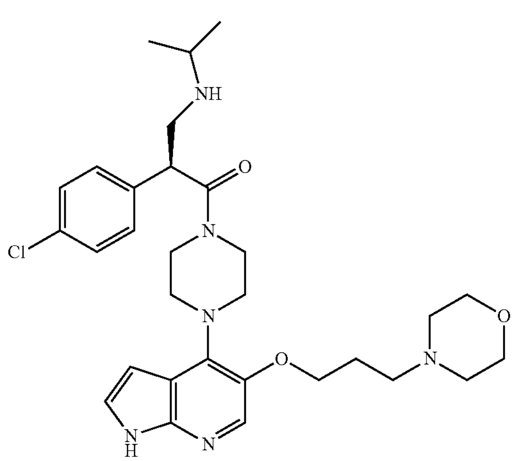 [SMILES: CC(C)NC[C@@H](C(=O)N1CCN(c2c(OCCCN3CCOCC3)cnc3[nH]ccc23)CC1)c1ccc(Cl)cc1] | (S)-2-(4-chlorophenyl)-3-(isopropylamino)-1-(4-(5-(3-morpholinopropoxy)-1H-pyrrolo[2,3-b]pyridin-4-yl)piperazin-1-yl)propan-1-one trihydrochloride | Yield 28%; $^1$H NMR (400 MHz, DMSO-$d_6$) □ 12.28 (s, 1H), 11.50 (s, 1H), 9.22 (s, 1H), 8.62 (s, 1H), 8.05 (s, 1H), 7.52-7.40 (m, 5H), 6.69 (s, 1H), 4.82-4.77 (m, 1H), 4.10 (dd, 2H), 4.01-3.00 (m, 21H), 2.28-2.20 (m, 2H), 1.26 (m, 6H); m/z (APCI pos) (100%) 569.2 [M]. |

Example 48

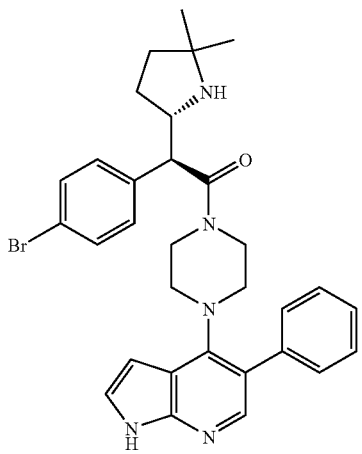 [SMILES: CC1(C)CC[C@@H]([C@@H](C(=O)N2CCN(c3c(-c4ccccc4)cnc4[nH]ccc34)CC2)c2ccc(Br)cc2)N1]

(S)-2-(4-bromophenyl)-2-((S)-5,5-dimethylpyrrolidin-2-yl)-1-(4-(5-phenyl-1H-pyrrolo[2,3-b]pyridin-4-yl)piperazin-1-yl)ethanone 5-Phenyl-4-(piperazin-1-yl)-1H-pyrrolo[2,3-b]pyridine dihydrochloride (0.0159 g, 0.0454 mmol, see Example 19), (S)-2-(4-bromophenyl)-2-((S)-1-(tert-butoxycarbonyl)-5,5-dimethylpyrrolidin-2-yl)acetic acid (0.017 g, 0.0412 mmol, see Example C) and TBTU (0.0159 g, 0.0495 mmol) in DCM (1 mL) were added to DIEA (0.0287 mL, 0.165 mmol) and stirred at room temperature for 1 hour. The mixture was directly loaded to column and purified by chromatography (1:1 hexane:ethyl acetate) to give (S)-tert-butyl 5-((S)-1-(4-bromophenyl)-2-oxo-2-(4-(5-phenyl-1H-pyrrolo[2,3-b]pyridin-4-yl)piperazin-1-yl)ethyl)-2,2-dimethylpyrrolidine-1-carboxylate as a solid. The solid was dissolved in DCM (1 mL), and TFA (0.2 mL) was added. The mixture was stirred at room temperature for 1 hour. The solvent was removed. The residue was dissolved in DCM (0.5 mL) and 2M HCl in ether (1 mL) was added. The resulting solid was collected by filtration to give (S)-2-(4-bromophenyl)-2-((S)-5,5-dimethylpyrrolidin-2-yl)-1-(4-(5-phenyl-1H-pyrrolo[2,3-b]pyridin-4-yl)piperazin-1-yl)ethanone dihydrochloride (0.025 g, 95%). MS APCI (+) m/z 574 detected.

Example 49

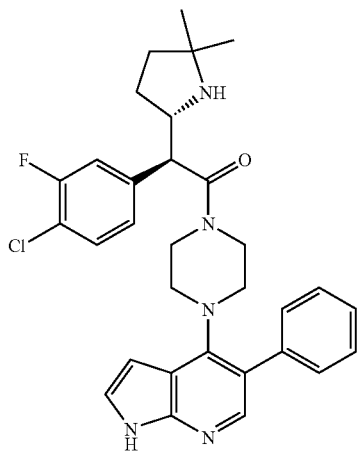 [SMILES: CC1(C)CC[C@@H]([C@@H](C(=O)N2CCN(c3c(-c4ccccc4)cnc4[nH]ccc34)CC2)c2ccc(Cl)c(F)c2)N1]

(S)-2-(4-chloro-3-fluorophenyl)-2-((S)-5,5-dimethylpyrrolidin-2-yl)-1-(4-(5-phenyl-1H-pyrrolo[2,3-b]pyridin-4-yl)piperazin-1-yl)ethanone 5-Phenyl-4-(piperazin-1-yl)-1H-pyrrolo[2,3-b]pyridine dihydrochloride (0.0200 g, 0.0570 mmol, see Example 19), (S)-2-((S)-1-(tert-butoxycarbonyl)-5,5-dimethylpyrrolidin-2-yl)-2-(4-chloro-3-fluorophenyl)acetic acid (0.020 g, 0.0518 mmol, see Example D) and TBTU (0.0200 g, 0.0622 mmol) in DCM (1 mL) were added to DIEA (0.0361 mL, 0.207 mmol) and stirred at room temperature for 1 hour. The mixture was directly loaded to column and purified by chromatography (1:1 hexane:ethyl acetate) to give (S)-tert-butyl 5-((S)-1-(4-chloro-3-fluorophenyl)-2-oxo-2-(4-(5-phenyl-1H-pyrrolo[2,3-b]pyridin-4-yl)piperazin-1-yl)ethyl)-2,2-dimethylpyrrolidine-1-carboxylate as a solid. The solid was dissolved in DCM (1 mL) and TFA (0.2 mL) was added. The mixture was stirred at room temperature for 1 hour. The solvent was removed. The resulting residue was dissolved in DCM (0.5 mL), and 2M HCl in ether (1 mL) was added. The resulting solid was collected by filtration to give (S)-2-(4-chloro-3-fluorophenyl)-2-((S)-5,5-dimethylpyrrolidin-2-yl)-1-(4-(5-phenyl-1H-pyrrolo[2,3-b]pyridin-4-yl)piperazin-1-yl)ethanone dihydrochloride (0.009 g, 28%). MS APCI (+) m/z 546 detected.

Example 50

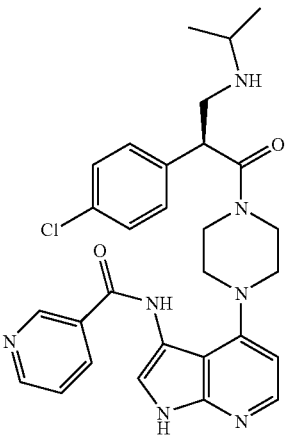 [SMILES: CC(C)NC[C@@H](C(=O)N1CCN(c2ccnc3[nH]cc(NC(=O)c4cccnc4)c23)CC1)c1ccc(Cl)cc1]

(S)—N-(4-(4-(2-(4-chlorophenyl)-3-(isopropylamino)propanoyl)piperazin-1-yl)-1H-pyrrolo[2,3-b]pyridin-3-yl)nicotinamide Crude 4-(4-benzylpiperazin-1-yl)-1H-pyrrolo[2,3-b]pyridin-3-amine (0.200 g, 0.651 mmol, see Example 25), nicotinic acid (0.0961 g, 0.781 mmol) and triethylamine (0.453 mL, 3.25 mmol) were placed in DMF (3 mL) at room temperature. Triethylamine (0.453 mL, 3.25 mmol) was then added, and the reaction was stirred for 1 hour at room temperature. The reaction was then diluted with MeOH (5 mL), and 3M LiOH (0.5 mL) was added and stirred for 10 minutes. The reaction was then poured into saturated Na₂CO₃ and extracted into DCM. The organic fractions were combined, dried, filtered and concentrated to give a crude residue that was purified by column chromatography (500:20-500:30 DCM:MeOH) to give N-(4-(4-benzylpiperazin-1-yl)-1H-pyrrolo[2,3-b]pyridin-3-yl)nicotinamide (0.160 g, 59.6% yield).

N-(4-(4-Benzylpiperazin-1-yl)-1H-pyrrolo[2,3-b]pyridin-3-yl)nicotinamide (0.080 g, 0.19 mmol) was placed in MeOH (2 mL). Pd/C (0.0206 g, 0.0194 mmol) was then added, followed by the addition of 4 drops of concentrated HCl. The reaction was then placed under a balloon of $H_2$ and stirred overnight. The reaction was filtered, washed with MeOH and concentrated to give the crude product N-(4-(piperazin-1-yl)-1H-pyrrolo[2,3-b]pyridin-3-yl)nicotinamide (0.050 g, 79.9% yield) which was used without further purification.

N-(4-(piperazin-1-yl)-1H-pyrrolo[2,3-b]pyridin-3-yl)nicotinamide (0.030 g, 0.0931 mmol) and (S)-3-(tert-butoxycarbonyl(isopropyl)amino)-2-(4-chlorophenyl)propanoic acid (0.0334 g, 0.0977 mmol, see Example H) were placed in DCM (2 mL) at room temperature. HOBT-$H_2O$ (0.020 g, 0.13 mmol), EDCI (0.023 g, 0.12 mmol), and DIEA (d 0.742; 0.0810 mL, 0.465 mmol) were then added. The reaction was stirred at room temperature for 3 hours. The reaction was then poured into saturated $Na_2CO_3$ and extracted into DCM. The organic fractions were combined, dried, filtered and concentrated to give a crude residue that was purified by column chromatography (500:10-500:30 DCM:MeOH) to give (S)-tert-butyl 2-(4-chlorophenyl)-3-(4-4(3-(nicotinamido)-1H-pyrrolo[2,3-b]pyridin-4-yl)piperazin-1-yl)-3-oxopropyl(isopropyl)carbamate (0.010 g, 16.6% yield).

(S)-tert-Butyl 2-(4-chlorophenyl)-3-(4-4(3-(nicotinamido)-1H-pyrrolo[2,3-b]pyridin-4-yl)piperazin-1-yl)-3-oxopropyl(isopropyl)carbamate (0.010 g, 0.015 mmol) was placed in DCM (3 mL) at room temperature. TFA (0.3 mL) was then added, and the reaction was stirred at room temperature for 1 hour. The reaction was then concentrated to dryness, and dissolved in minimal DCM. The DCM solution was then added dropwise to a stirring solution of 1M HCl in ether. The resulting solid was collected, washed with ether, and dried to give (S)—N-(4-(4-(2-(4-chlorophenyl)-3-(isopropylamino)propanoyl)piperazin-1-yl)-1H-pyrrolo[2,3-b]pyridin-3-yl)nicotinamide (0.007 g, 73% yield) as the dihydrochloride salt. MS APCI (+) m/z 547 detected.

Example 51

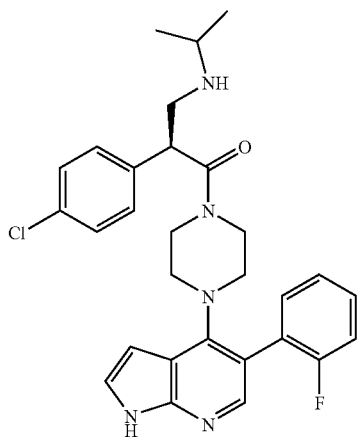 [SMILES: CC(C)NC[C@@H](C(=O)N1CCN(c2c(-c3ccccc3F)cnc3[nH]ccc23)CC1)c1ccc(Cl)cc1]

(S)-2-(4-chlorophenyl)-1-(4-(5-(2-fluorophenyl)-1H-pyrrolo[2,3-b]pyridin-4-yl)piperazin-1-yl)-3-(isopropylamino)propan-1-one s-BuLi (53.7 mL, 75.2 mmol, 1.4M in cyclohexane) was added to a solution of 4-fluoro-1-(triisopropylsilyl)-1H-pyrrolo[2,3-b]pyridine (10.0 g, 34.2 mmol, prepared as described in L'Heureux, et al. Org. Lett., 5(26), p. 5023 (2003)) in THF (250 mL) at −78° C., and the reaction was stirred at −78° C. for 30 minutes. A solution of $CBr_4$ (28.3 g, 85.5 mmol) in THF (40 mL) was added next, and the reaction was stirred at this temperature for 1 hour. A saturated ammonium chloride solution (80 mL) was then added, and the reaction was extracted with hexane (200 mL), washed with brine, dried over sodium sulfate, filtered and concentrated. The crude product was then purified by column chromatography (hexane) to give 5-bromo-4-fluoro-1-(triisopropylsilyl)-1H-pyrrolo[2,3-b]pyridine (7.8 g, 61.4% yield).

5-Bromo-4-fluoro-1-(triisopropylsilyl)-1H-pyrrolo[2,3-b]pyridine (12.60 g, 33.9 mmol) was placed in THF (200 mL) at 0° C. TBAF (33.9 mL, 1M THF solution) was then added, and the reaction was then stirred for 1 hour at 0° C. The reaction was quenched with $NaHCO_3$ (aq.) and extracted into DCM. The organic fractions were combined, dried, filtered and concentrated to give a crude residue that was purified by column chromatography (500:5 DCM:MeOH) to give 5-bromo-4-fluoro-1H-pyrrolo[2,3-b]pyridine (6.8 g, 93.2% yield).

5-Bromo-4-fluoro-1H-pyrrolo[2,3-b]pyridine (5.3 g, 24.7 mmol) was placed in DMF (53 mL) at 0° C. NaH (1.18 g, 29.6 mmol) was then added and stirred for 20 minutes. Benzenesulfonyl chloride (3.47 mL, 27.1 mmol) was then added next, and the reaction was stirred at 0° C. for 30 minutes. Water was then added, and the resulting solid was filtered and dried. The crude solid was then triturated in 1:1 hexane:EtOAc to give 5-bromo-4-fluoro-1-(phenylsulfonyl)-1H-pyrrolo[2,3-b]pyridine (5.2 g, 59.4% yield).

5-Bromo-4-fluoro-1-(phenylsulfonyl)-1H-pyrrolo[2,3-b]pyridine (0.200 g, 0.563 mmol, prepared as described in Scheme 1) and 2-fluorophenylboronic acid (0.0867 g, 0.619 mmol) were placed in degassed 2:1 toluene:EtOH (3 mL). $Pd(PPh_3)_4$ (0.0325 g, 0.0282 mmol) was then added, followed by the addition of $K_2CO_3$ (aq., 1.17 mL, 0.845 mmol). The reaction was then heated to 80° C. for 18 hours. The reaction was then cooled to room temperature, poured into water, and extracted into DCM. The organic fractions were combined, dried, filtered and concentrated to give a crude residue that was purified by column chromatography (1:1 hexane:DCM-4:1 hexane:DCM) to give 4-fluoro-5-(2-fluorophenyl)-1-(phenylsulfonyl)-1H-pyrrolo[2,3-b]pyridine (0.203 g, 97.3% yield).

4-Fluoro-5-(2-fluorophenyl)-1-(phenylsulfonyl)-1H-pyrrolo[2,3-b]pyridine (0.200 g, 0.540 mmol) and tert-butyl piperazine-1-carboxylate (0.121 g, 0.648 mmol) were placed in NMP (2 mL). The reaction was then placed in the microwave and heated to 160° C. for 1 hour. The reaction was then cooled, poured into water and extracted with ether. The combined organic fractions were dried, filtered, and concentrated to give a crude oil that was purified by column chromatography (3:1 hexane:EtOAc) to give tert-butyl 4-(5-(2-fluorophenyl)-1-(phenylsulfonyl)-1H-pyrrolo[2,3-b]pyridin-4-yl)piperazine-1-carboxylate (0.102 g, 35.2% yield).

tert-Butyl 4-(5-(2-fluorophenyl)-1-(phenylsulfonyl)-1H-pyrrolo[2,3-b]pyridin-4-yl)piperazine-1-carboxylate (0.100 g, 0.186 mmol) was placed in 1:1 THF:MeOH (6 mL). LiOH (0.621 mL, 1.86 mmol) was then added, and the reaction was stirred at 50° C. for 1 hour. The reaction was then poured into water and extracted into DCM. The organic fractions were combined, dried, filtered and concentrated to give the crude product tert-butyl 4-(5-(2-fluorophenyl)-1H-pyrrolo[2,3-b]pyridin-4-yl)piperazine-1-carboxylate (0.066 g, 89.3% yield) that was used without further purification.

tert-Butyl 4-(5-(2-fluorophenyl)-1H-pyrrolo[2,3-b]pyridin-4-yl)piperazine-1-carboxylate (0.045 g, 0.11 mmol) was placed in DCM (3 mL) at room temperature. TFA (0.3 mL) was then added, and the reaction was stirred at room temperature for 1 hour and concentrated to dryness. The resulting residue was then dissolved in minimal DCM and added to a stirring solution of 1M HCl in ether. The resulting solid was filtered, washed with ether and dried to give 5-(2-fluorophenyl)-4-(piperazin-1-yl)-1H-pyrrolo[2,3-b]pyridine (0.034 g, 81% yield).

5-(2-Fluorophenyl)-4-(piperazin-1-yl)-1H-pyrrolo[2,3-b]pyridine (0.034 g, 0.0921 mmol), (S)-3-(tert-butoxycarbonyl(isopropyl)amino)-2-(4-chlorophenyl)propanoic acid (0.0330 g, 0.0967 mmol, see Example H), HOBT-$H_2O$ (0.0197 g, 0.129 mmol), and EDCI (0.0229 g, 0.120 mmol) were placed in DCM (5 mL) at room temperature. DIEA (d 0.742; 0.0802 mL, 0.460 mmol) was then added, and the reaction was stirred at room temperature for 5 hours. The reaction was then poured into saturated $Na_2CO_3$ and extracted into DCM. The organic fractions were combined, dried, filtered and concentrated to give a crude residue that was purified by column chromatography (500:10 DCM:MeOH) to give tert-butyl (2S)-2-(4-chlorophenyl)-3-(4-(5-(2-fluorophenyl)-1H-pyrrolo[2,3-b]pyridin-4-yl)piperazin-1-yl)-3-oxopropyl(isopropyl)carbamate (0.040 g, 70.0% yield). MS APCI (+) m/z 520 detected.

Example 52

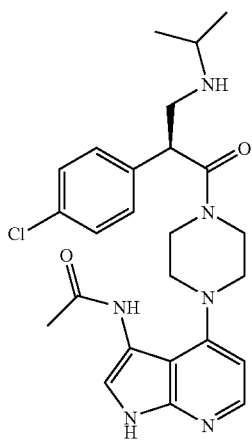 [SMILES: CC(=O)Nc1c[nH]c2nccc(N3CCN(C(=O)[C@H](CNC(C)C)c4ccc(Cl)cc4)CC3)c12]

(S)—N-(4-(4-(2-(4-chlorophenyl)-3-(isopropylamino)propanoyl)piperazin-1-yl)-1H-pyrrolo[2,3-b]pyridin-3-yl)acetamide 4-(4-Benzylpiperazin-1-yl)-1H-pyrrolo[2,3-b]pyridin-3-amine (0.35 g, 1.14 mmol, see Example 25) was placed in DCM (2 mL) and pyridine (1 mL). Acetic anhydride (0.129 mL, 1.37 mmol) was then added, and the reaction was stirred at room temperature for 1 hour. The reaction was then diluted with MeOH (5 mL), and 3M LiOH (0.5 mL) was added. The reaction was stirred for 10 minutes and then poured into saturated $Na_2CO_3$ and extracted into DCM. The organic fractions were combined, dried, filtered and concentrated to give a crude residue that was purified by column chromatography (500:8-500:20 DCM:MeOH) to give N-(4-(4-benzylpiperazin-1-yl)-1H-pyrrolo[2,3-b]pyridin-3-yl)acetamide (0.35 g, 88.0% yield).

N-(4-(4-Benzylpiperazin-1-yl)-1H-pyrrolo[2,3-b]pyridin-3-yl)acetamide (0.150 g, 0.429 mmol) was placed in MeOH (3 mL). Pd/C (0.0914 g, 0.0429 mmol) was then added, followed by the addition of 3 drops of concentrated HCl. The reaction was then placed under a $H_2$ balloon for 3 hours. The reaction was then filtered, but the product was insoluble. The solids were slurried with 1:1 MeOH:THF (5×) and filtered. The filtrate was then concentrated to give the crude product N-(4-(piperazin-1-yl)-1H-pyrrolo[2,3-b]pyridin-3-yl)acetamide (0.110 g, 77.1% yield), which was used without further purification.

N-(4-(piperazin-1-yl)-1H-pyrrolo[2,3-b]pyridin-3-yl)acetamide (0.050 g, 0.151 mmol), (S)-3-(tert-butoxycarbonyl(isopropyl)amino)-2-(4-chlorophenyl)propanoic acid (0.0540 g, 0.158 mmol, see Example H), HOBT-$H_2O$ (0.0323 g, 0.211 mmol), and EDCI (0.0375 g, 0.196 mmol) were placed in DCM (5 mL). DIEA (d 0.742; 0.131 mL, 0.752 mmol) was then added, and the reaction was stirred for 5 hours. The reaction was then poured into saturated $Na_2CO_3$ and extracted into DCM. The organic fractions were combined, dried, filtered and concentrated to give a crude residue that was purified by column chromatography (500:13-500:18 DCM:MeOH) to give (S)-tert-butyl 3-(4-(3-acetamido-1H-pyrrolo[2, 3-1])pyridin-4-yl)piperazin-1-yl)-2-(4-chlorophenyl)-3-oxopropyl(isopropyl)carbamate (0.043 g, 48% yield).

(S)-tert-Butyl 3-(4-(3-acetamido-1H-pyrrolo[2,3-b]pyridin-4-yl)piperazin-1-yl)-2-(4-chlorophenyl)-3-oxopropyl(isopropyl)carbamate (0.043 g, 0.074 mmol) was placed in DCM (5 mL) at room temperature. TFA (0.5 mL) was then added, and the reaction was stirred at room temperature for 1 hour. The reaction was then concentrated to dryness. The crude residue was then dissolved in minimal DCM and added dropwise to a stirring solution of 1M HCl in ether. The resulting solid was filtered, washed with ether and dried to give (S)—N-(4-(4-(2-(4-chlorophenyl)-3-(isopropylamino)propanoyl)piperazin-1-yl)-1H-pyrrolo[2, 3-1)]pyridin-3-yl)acetamide (0.035 g, 85% yield) as the dihydrochloride salt. MS APCI (+) m/z 484 detected.

Example 53

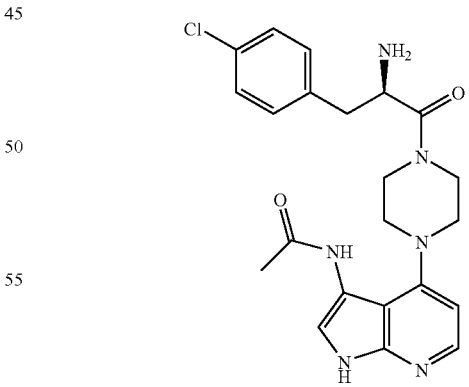

(R)—N-(4-(4-(2-amino-3-(4-chlorophenyl)propanoyl)piperazin-1-yl)-1H-pyrrolo[2,3-b]pyridin-3-yl)acetamide Crude N-(4-(piperazin-1-yl)-1H-pyrrolo[2,3-b]pyridin-3-yl)acetamide (0.050 g, 0.15 mmol, see Example 52), (R)-2-

(tert-butoxycarbonylamino)-3-(4-chlorophenyl)propanoic acid (0.0496 g, 0.166 mmol), HOBT-H$_2$O (0.0323 g, 0.211 mmol), and EDCI (0.0375 g, 0.196 mmol) were placed in DCM (5 mL). DIEA (d 0.742; 0.131 mL, 0.752 mmol) was then added, and the reaction was stirred for 5 hours. The reaction was then poured into saturated Na$_2$CO$_3$ and extracted into DCM. The organic fractions were combined, dried, filtered and concentrated to give a crude residue that was purified by column chromatography (500:13-500:18 DCM:MeOH) to give (R)-tert-butyl 1-(4-(3-acetamido-1H-pyrrolo[2,3-b]pyridin-4-yl)piperazin-1-yl)-3-(4-chlorophenyl)-1-oxopropan-2-ylcarbamate (0.047 g, 57.7% yield).

(R)-tert-Butyl 1-(4-(3-acetamido-1H-pyrrolo[2,3-b]pyridin-4-yl)piperazin-1-yl)-3-(4-chlorophenyl)-1-oxopropan-2-ylcarbamate (0.047 g, 0.087 mmol) was placed in DCM (5 mL) at room temperature. TFA (0.5 mL) was then added, and the reaction was stirred at room temperature for 1 hour. The reaction was then concentrated to dryness. The crude residue was then dissolved in minimal DCM and added dropwise to a stirring solution of 1M HCl in ether. The resulting solid was filtered, washed with ether and dried to give (R)—N-(4-(4-(2-amino-3-(4-chlorophenyl)propanoyl)piperazin-1-yl)-1H-pyrrolo[2,3-b]pyridin-3-yl)acetamide (0.04 g, 90% yield) as the dihydrochloride salt. MS APCI (+) m/z 441 detected.

Example 54

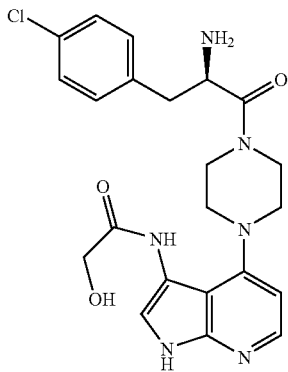 [SMILES: N[C@H](Cc1ccc(Cl)cc1)C(=O)N1CCN(c2ccnc3[nH]cc(NC(=O)CO)c23)CC1]

(R)—N-(4-(4-(2-amino-3-(4-chlorophenyl)propanoyl)piperazin-1-yl)-1H-pyrrolo[2,3-b]pyridin-3-yl)-2-hydroxyacetamide 4-(4-Benzylpiperazin-1-yl)-1H-pyrrolo[2,3-b]pyridin-3-amine (0.30 g, 0.976 mmol, see Example 25), 2-(benzyloxy)acetic acid (0.195 g, 1.17 mmol) and bis(2-oxo-3-oxazolidinyl)phosphonic chloride ("BOP—Cl"; 0.298 g, 1.17 mmol) were placed in DMF (3 mL) at room temperature. Triethylamine (0.680 mL, 4.88 mmol) was then added, and the reaction was stirred for 1 hour at room temperature. The reaction was then diluted with MeOH (5 mL), and 3M LiOH (0.5 mL) was added and stirred for 10 minutes. The reaction was then poured into saturated Na$_2$CO$_3$ and extracted into DCM. The organic fractions were combined, dried, filtered and concentrated to give a crude residue that was purified by column chromatography (500:10-500:20 DCM:MeOH) to give 2-(benzyloxy)-N-(4-(4-benzylpiperazin-1-yl)-1H-pyrrolo[2,3-b]pyridin-3-yl)acetamide (0.22 g, 49.4% yield).

2-(Benzyloxy)-N-(4-(4-benzylpiperazin-1-yl)-1H-pyrrolo[2,3-b]pyridin-3-yl)acetamide (0.100 g, 0.219 mmol) was placed in MeOH (2 mL). Pd/C (0.0467 g, 0.0220 mmol) was then added, followed by the addition of 3 drops of concentrated HCl. The reaction was next placed under an H$_2$ filled balloon for 3 hours. Additional Pd/C (0.0467 g, 0.0219 mmol) was then added, and the reaction was placed under an H$_2$ filled balloon for an additional 3 hours to drive the reaction to completion. DIEA was added to achieve solubility. The reaction was then filtered, washed with MeOH, and concentrated to give the crude product 2-hydroxy-N-(4-(piperazin-1-yl)-1H-pyrrolo[2,3-b]pyridin-3-yl)acetamide (0.060 g, 99.2% yield).

2-Hydroxy-N-(4-(piperazin-1-yl)-1H-pyrrolo[2,3-b]pyridin-3-yl)acetamide (0.060 g, 0.22 mmol), (R)-2-(tert-butoxycarbonylamino)-3-(4-chlorophenyl)propanoic acid (0.0719 g, 0.240 mmol), HOBT-H$_2$O (0.0467 g, 0.305 mmol) and EDCI (0.05-(3 g, 0.283 mmol) were placed in DCM (5 mL) at room temperature. DIEA (d 0.742; 0.190 mL, 1.09 mmol) was then added, and the reaction was stirred for 5 hours. The reaction was then poured into saturated Na$_2$CO$_3$ and extracted into DCM. The reaction was dried, filtered, concentrated, and purified (500:10 to 500:30 DCM:MeOH) to give (R)-tert-butyl 3-(4-chlorophenyl)-1-(4-(3-(2-hydroxyacetamido)-1H-pyrrolo[2,3-b]pyridin-4-yl)piperazin-1-yl)-1-oxopropan-2-yl carbamate (0.040 g, 32.9% yield).

(R)-tert-Butyl 3-(4-chlorophenyl)-1-(4-(3-(2-hydroxyacetamido)-1H-pyrrolo[2,3-b]pyridin-4-yl)piperazin-1-yl)-1-oxopropan-2-ylcarbamate (0.040 g, 0.072 mmol) was placed in DCM (3 mL) at room temperature. TFA (0.5 mL) was then added, and the reaction was stirred at room temperature for 1 hour. The reaction was then concentrated to dryness, and the resulting residue was dissolved in minimal DCM. The solution was added dropwise to a stirring solution of 1M HCl in ether. The resulting solid was filtered, washed with ether, and dried to give (R)—N-(4-(4-(2-amino-3-(4-chlorophenyl)propanoyl)piperazin-1-yl)-1H-pyrrolo[2,3-b]pyridin-3-yl)-2-hydroxyacetamide (0.030 g, 79% yield) as the dihydrochloride salt. MS APCI (+) m/z 457 detected.

Example 55

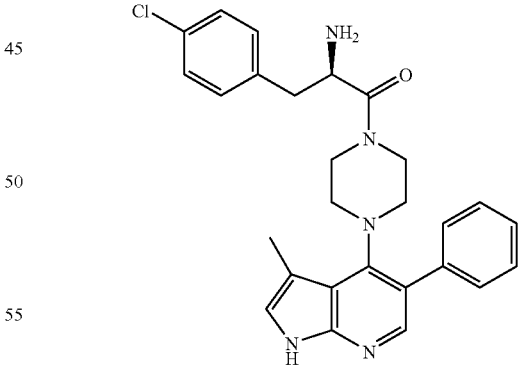

(R)-2-amino-3-(4-chlorophenyl)-4-(4-(3-methyl-5-phenyl-1H-pyrrolo[2,3-b]pyridin-4-yl)piperazin-1-yl)propan-1-one 3-Methyl-5-phenyl-4-(piperazin-1-yl)-1H-pyrrolo[2,3-b]pyridine (0.050 g, 0.14 mmol, see Example 15), (R)-2-(tert-butoxycarbonylamino)-3-(4-chlorophenyl)propanoic acid (0.0451 g, 0.151 mmol), HOBT-H$_2$O (0.0293 g, 0.192 mmol)

and EDCI (0.0341 g, 0.178 mmol) were placed in DCM (5 mL) at room temperature. DIEA (d 0.742; 0.119 mL, 0.684 mmol) was then added, and the reaction was stirred for 5 hours. The reaction was then poured into saturated $Na_2CO_3$ and extracted into DCM. The reaction was then dried, filtered, concentrated, and purified (500:5 DCM:MeOH) to give (R)-tert-butyl 3-(4-chlorophenyl)-1-(4-(3-methyl-5-phenyl-1H-pyrrolo[2,3-b]pyridin-4-yl)piperazin-1-yl)-1-oxopropan-2-ylcarbamate (0.030 g, 38.1% yield).

(R)-tert-Butyl 3-(4-chlorophenyl)-1-(4-(3-methyl-5-phenyl-1H-pyrrolo[2,3-b]pyridin-4-yl)piperazin-1-yl)-1-oxopropan-2-ylcarbamate (0.029 g, 0.051 mmol) was placed in DCM (3 mL) at room temperature. TFA (0.5 mL) was then added, and the reaction was stirred at room temperature for 1 hour. The reaction was then concentrated to dryness, and the resulting residue was dissolved in minimal DCM. The solution was added dropwise to a stirring solution of 1M HCl in ether. The resulting solid was filtered, washed with ether, and dried to give (R)-2-amino-3-(4-chlorophenyl)-1-(4-(3-methyl-5-phenyl-1H-pyrrolo[2,3-b]pyridin-4-yl)piperazin-1-yl)propan-1-one (0.020 g, 72% yield) as the dihydrochloride salt. MS APCI (+) m/z 475 detected.

Example 56

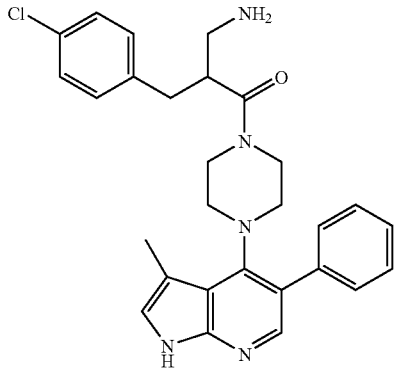 [SMILES: Cc1c[nH]c2ncc(-c3ccccc3)c(N3CCN(C(=O)C(CN)Cc4ccc(Cl)cc4)CC3)c12]

3-amino-2-(4-chlorobenzyl)-4-(4-(3-methyl-5-phenyl-1H-pyrrolo[2,3-b]pyridin-4-yl)piperazin-1-yl)propan-1-one 3-Methyl-5-phenyl-4-(piperazin-1-yl)-1H-pyrrolo[2,3-b]pyridine (0.125 g, 0.428 mmol, see Example 15), 3-(tert-butoxycarbonylamino)-2-(4-chlorobenzyl)propanoic acid (0.148 g, 0.470 mmol, see Example E), HOBT-$H_2O$ (0.0917 g, 0.599 mmol), EDCI (0.107 g, 0.556 mmol), and DIEA (d 0.742; 0.372 mL, 2.14 mmol) were placed in DCM (5 mL). The reaction was stirred at room temperature for 3 hours and then quenched with saturated $Na_2CO_3$. The mixture was then extracted with DCM. The organic fractions were dried, filtered, and concentrated to give a crude oil that was purified by column chromatography (500:6) to give tert-butyl 2-(4-chlorobenzyl)-3-(4-4(3-methyl-5-phenyl-1H-pyrrolo[2,3-b]pyridin-4-yl)piperazin-1-yl)-3-oxopropylcarbamate (0.115 g, 45.7% yield).

tert-Butyl 2-(4-chlorobenzyl)-3-(4-(3-methyl-5-phenyl-1H-pyrrolo[2,3-b]pyridin-4-yl)piperazin-1-yl)-3-oxopropylcarbamate (0.115 g, 0.196 mmol) was placed in DCM (3 mL) at room temperature. TFA (0.5 mL) was then added, and the reaction was stirred at room temperature for 1 hour. The reaction was then concentrated to dryness, and the resulting residue was dissolved in minimal DCM. The solution was added dropwise to a stirring solution of 1M HCl in ether. The resulting solid was filtered, washed with ether, and dried to give 3-amino-2-(4-chlorobenzyl)-4-(4-(3-methyl-5-phenyl-1H-pyrrolo[2,3-b]pyridin-4-yl)piperazin-1-yl)propan-1-one (0.092 g, 83.9% yield) as the dihydrochloride salt. MS APCI (+) m/z 489 detected.

Example 57

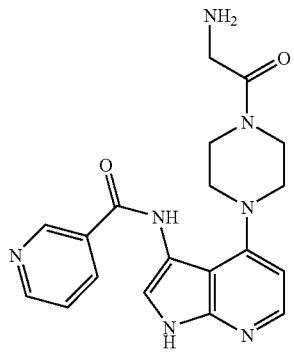 [SMILES: NCC(=O)N1CCN(c2ccnc3[nH]cc(NC(=O)c4cccnc4)c23)CC1]

N-(4-(4-(2-aminoacetyl)piperazin-1-yl)-1H-pyrrolo[2,3-b]pyridin-3-yl)nicotinamide Crude N-(4-(piperazin-1-yl)-1H-pyrrolo[2,3-b]pyridin-3-yl)nicotinamide (0.025 g, 0.058 mmol, see Example 50), 2-(tert-butoxycarbonylamino)acetic acid (0.0111 g, 0.0637 mmol), HOBT-$H_2O$ (0.0124 g, 0.0811 mmol) and EDCI (0.0144 g, 0.075 mmol) were placed in DCM (3 mL). DIEA (d 0.742; 0.0504 mL, 0.290 mmol) was then added. The reaction was stirred for 2 hours and quenched with saturated $Na_2CO_3$. The mixture was then extracted with DCM. The organic fractions were dried, filtered, and concentrated to give a crude oil that was purified by column chromatography (500:20-500:30) to give tert-butyl 2-(4-(3-(nicotinamido)-1H-pyrrolo[2,3-b]pyridin-4-yl)piperazin-1-yl)-2-oxoethylcarbamate (0.013 g, 46.8% yield).

tert-Butyl 2-(4-(3-(nicotinamido)-1H-pyrrolo[2, 3-1)]pyridin-4-yl)piperazin-1-yl)-2-oxoethylcarbamate (0.013 g, 0.027 mmol) was placed in DCM (3 mL) at room temperature. TFA (0.5 mL) was then added, and the reaction was stirred at room temperature for 1 hour. The reaction was then concentrated to dryness. The resulting residue was dissolved in minimal DCM and then added dropwise to a stirring solution of 1M HCl in ether. The resulting solid was filtered, washed with ether, and dried to give N-(4-(4-(2-aminoacetyl)piperazin-1-yl)-1H-pyrrolo[2,3-b]pyridin-3-yl)nicotinamide (0.012 g, 91% yield) as the trihydrochloride salt. MS APCI (+) m/z 380 detected.

Example 58

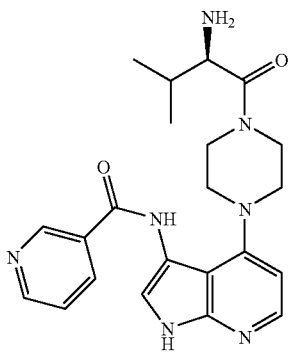 [SMILES: CC(C)[C@@H](N)C(=O)N1CCN(c2ccnc3[nH]cc(NC(=O)c4cccnc4)c23)CC1]

(R)—N-(4-(4-(2-amino-3-methylbutanoyl)piperazin-1-yl)-1H-pyrrolo[2,3-b]pyridin-3-yl)nicotinamide N-(4-(piperazin-1-yl)-1H-pyrrolo[2,3-b]pyridin-3-yl)nicotinamide (0.025 g, 0.058 mmol, see Example 50), (R)-2-(tert-butoxycarbonylamino)-3-methylbutanoic acid (0.0138 g, 0.0637 mmol), HOBT-H$_2$O (0.0124 g, 0.0811 mmol) and EDCI (0.0144 g, 0.0752 mmol) were placed in DCM (3 mL). DIEA (d 0.742; 0.0504 mL, 0.290 mmol) was then added, and the reaction was stirred for 2 hours. The reaction was quenched with saturated Na$_2$CO$_3$. The mixture was then extracted with DCM. The organic fractions were dried, filtered, and concentrated to give a crude oil that was purified by column chromatography (500:20-500:28) to give (R)-tert-butyl 3-methyl-1-(4-(3-(nicotinamido)-1H-pyrrolo[2,3-b]pyridin-4-yl)piperazin-1-yl)-1-oxobutan-2-ylcarbamate (0.009 g, 29.7% yield).

(R)-tert-Butyl 3-methyl-1-(4-(3-(nicotinamido)-1H-pyrrolo[2,3-b]pyridin-4-yl)piperazin-1-yl)-1-oxobutan-2-ylcarbamate (0.014 g, 0.027 mmol) was placed in DCM (3 mL) at room temperature. TFA (0.5 mL) was then added, and the reaction was stirred at room temperature for 1 hour. The reaction was then concentrated to dryness. The resulting residue was dissolved in minimal DCM and then added dropwise to a stirring solution of 1M HCl in ether. The resulting solid was filtered, washed with ether, and dried to give (R)—N-(4-(4-(2-amino-3-methylbutanoyl)piperazin-1-yl)-1H-pyrrolo[2,3-b]pyridin-3-yl)nicotinamide (0.009 g, 63% yield) as the trihydrochloride salt. MS APCI (+) m/z 422 detected.

Example 59

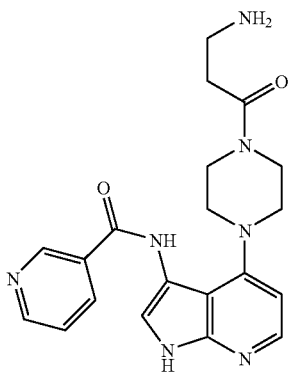 [SMILES: NCCC(=O)N1CCN(c2ccnc3[nH]cc(NC(=O)c4cccnc4)c23)CC1]

N-(4-(4-(3-aminopropanoyl)piperazin-1-yl)-1H-pyrrolo[2,3-b]pyridin-3-yl)nicotinamide N-(4-(piperazin-1-yl)-1H-pyrrolo[2,3-b]pyridin-3-yl)nicotinamide (0.025 g, 0.058 mmol, see Example 50), 3-(tert-butoxycarbonylamino)propanoic acid (0.0121 g, 0.0637 mmol), HOBT-H$_2$O (0.0124 g, 0.0811 mmol), and EDCI (0.0144 g, 0.0753 mmol) were placed in DCM (3 mL). DIEA (d 0.742; 0.0504 mL, 0.290 mmol) was then added. The reaction was stirred for 2 hours and quenched with saturated Na$_2$CO$_3$. The mixture was then extracted with DCM. The organic fractions were dried, filtered, and concentrated to give a crude oil that was purified by column chromatography (500:20-500:40) to give tert-butyl 3-(4-(3-(nicotinamido)-1H-pyrrolo[2,3-b]pyridin-4-yl)piperazin-1-yl)-3-oxopropylcarbamate (0.014 g, 48.9% yield).

tert-Butyl 3-(4-(3-(nicotinamido)-1H-pyrrolo[2, 3-1)]pyridin-4-yl)piperazin-1-yl)-3-oxopropylcarbamate (0.009 g, 0.02 mmol) was placed in DCM (3 mL) at room temperature. TFA (0.5 mL) was then added, and the reaction was stirred at room temperature for 1 hour. The reaction was then concentrated to dryness. The resulting residue was dissolved in minimal DCM and then added dropwise to a stirring solution of 1M HCl in ether. The resulting solid was filtered, washed with ether, and dried to give N-(4-(4-(3-aminopropanoyl)piperazin-1-yl)-1H-pyrrolo[2,3-b]pyridin-3-yl)nicotinamide (0.005 g, 55% yield) as the trihydrochloride salt. MS APCI (+) m/z 394 detected.

Example 60

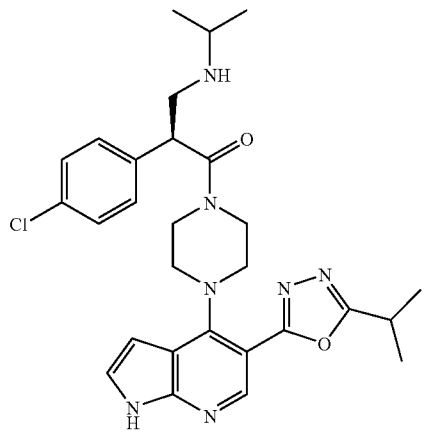 [SMILES: CC(C)NC[C@@H](C(=O)N1CCN(c2c(-c3nnc(C(C)C)o3)cnc3[nH]ccc23)CC1)c1ccc(Cl)cc1]

(S)-2-(4-chlorophenyl)-3-(isopropylamino)-1-(4-(5-(5-isopropyl-1,3,4-oxadiazol-2-yl)-1H-pyrrolo[2,3-b]pyridin-4-yl)piperazin-1-yl)propan-1-one Following the procedure described in Example 42 using isobutyric acid, (S)-2-(4-chlorophenyl)-1-(4-(5-(5-isopropyl-1,3,4-oxadiazol-2-yl)-1H-pyrrolo[2,3-b]pyridin-4-yl)piperazin-1-yl)-3-(isopropylamino)propan-1-one was isolated as a solid: $^1$H NMR (400 MHz, DMSO-d$_6$) δ 12.05 (s, 1H), 8.62 (s, 1H), 8.34 (s, 1H), 8.26 (s, 1H), 7.52-7.48 (m, 2H), 7.44-4.42 (m, 1H), 7.39-7.36 (m, 2H), 6.60 (s, 1H), 4.51 (m, 1H), 3.65-3.20 (m, 10H), 3.02 (s, 1H), 2.76-2.66 (m, 2H), 1.30 (d, 6H), 1.23 (dq, 6H); m/z (APCI pos) 536.3 (100%) [M].

Example 61

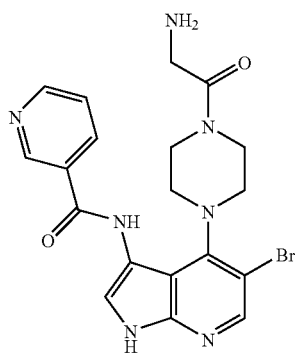 [SMILES: NCC(=O)N1CCN(c2c(Br)cnc3[nH]cc(NC(=O)c4cccnc4)c23)CC1]

N-(4-(4-(2-amino acetyl)piperazin-1-yl)-5-bromo-1H-pyrrolo[2,3-b]pyridin-3-yl)nicotinamide 5-Bromo-4-fluoro-1H-pyrrolo[2,3-b]pyridine (0.100 g, 0.465 mmol, see Example 51) was added slowly to fuming HNO₃ (5 mL) at 0° C. and stirred for 10 minutes. Ice was then added, followed by the addition of water. The resulting solid product was then filtered, and washed with water and dried to give 5-bromo-4-fluoro-3-nitro-1H-pyrrolo[2,3-b]pyridine (0.105 g, 86.8% yield).

5-bromo-4-fluoro-3-nitro-1H-pyrrolo[2,3-b]pyridine (2.0 g, 7.7 mmol) was placed in 6M HCl (30 mL) at room temperature. SnCl₂ (7.29 g, 38.5 mmol) was then added, and the reaction was stirred for 30 minutes at room temperature. The reaction was then cooled to 0° C. and a saturated aqueous solution of Na₂CO₃ was added to raise the pH to 8. The reaction was then extracted with DCM (with minimal MeOH to aid solubility). The combined organic fractions were dried, filtered, and concentrated to give the crude product 5-bromo-4-fluoro-1H-pyrrolo[2,3-b]pyridin-3-amine (0.50 g, 28.2% yield), which was used without purification.

5-Bromo-4-fluoro-1H-pyrrolo[2,3-b]pyridin-3-amine (0.044 g, 0.19 mmol), nicotinic acid (0.0283 g, 0.230 mmol), and BOP-Cl (0.0584 g, 0.230 mmol) were placed in DMF (3 mL) at room temperature. Triethylamine (0.133 mL, 0.956 mmol) was then added, and the reaction was stirred for 1 hour at room temperature. The reaction was then diluted with 3M LiOH (aq., 0.5 mL) and stirred for 10 minutes. The reaction was then poured into saturated Na₂CO₃, extracted into DCM, and the organic fractions were combined, dried, filtered and concentrated to give a crude residue. The crude residue was triturated with 1:2 MeOH/DCM to give N-(5-bromo-4-fluoro-1H-pyrrolo[2,3-b]pyridin-3-yl)nicotinamide (0.035 g, 54.6% yield) as a solid.

N-(5-Bromo-4-fluoro-1H-pyrrolo[2,3-b]pyridin-3-yl)nicotinamide (0.100 g, 0.298 mmol) and piperazine (0.257 g, 2.98 mmol) were placed in NMP (1.5 mL) and heated to 100° C. in a microwave for 1 hour. The reaction was then heated to 70° C. for 1 hour with rotary evaporation to remove excess piperazine. The reaction was then diluted with water and extracted with DCM (with minimal MeOH to aid solubility). The organic fractions were combined, dried, filtered and concentrated. The resulting crude NMP solution of N-(5-bromo-4-(piperazin-1-yl)-1H-pyrrolo[2,3-b]pyridin-3-yl)nicotinamide was used without further purification.

The above NMP solution of N-(5-bromo-4-(piperazin-1-yl)-1H-pyrrolo[2,3-b]pyridin-3-yl)nicotinamide (0.200 g, 0.498 mmol), 2-(tert-butoxycarbonylamino)acetic acid (0.114 g, 0.648 mmol), HOBT-H₂O (0.107 g, 0.698 mmol), and EDCI (0.124 g, 0.648 mmol) were placed in DCM (3 mL). DIEA (d 0.742; 0.434 mL, 2.49 mmol) was then added, and the reaction was stirred at room temperature for 4 hours. The reaction was then quenched with saturated Na₂CO₃ and extracted into DCM. The organic fractions were combined, dried, filtered, and concentrated to give the crude residue. Purification by column chromatography (500:15 to 500:25 DCM:MeOH) gave tert-butyl 2-(4-(5-bromo-3-(nicotinamido)-1H-pyrrolo[2,3-b]pyridin-4-yl)piperazin-1-yl)-2-oxoethylcarbamate (0.112 g, 40.2% yield).

tert-Butyl 2-(4-(5-bromo-3-(nicotinamido)-1H-pyrrolo[2,3-b]pyridin-4-yl)piperazin-1-yl)-2-oxoethylcarbamate (0.020 g, 0.036 mmol) was placed in DCM (3 mL). TFA (0.5 mL) was then added, and the reaction was stirred at room temperature for 1 hour. The reaction was then concentrated to dryness. The resulting residue was dissolved in minimal DCM and added to a stirring solution of 1M HCl in ether. The resulting solid product was filtered, washed with ether and dried to give N-(4-(4-(2-aminoacetyl)piperazin-1-yl)-5-bromo-1H-pyrrolo[2,3-b]pyridin-3-yl)nicotinamide (0.015 g, 74% yield) as the trihydrochloride salt. MS APCI (+) m/z 459 detected.

Example 62

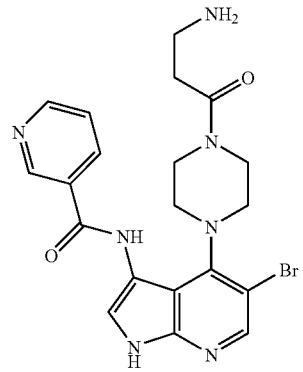 [SMILES: NCCC(=O)N1CCN(c2c(Br)cnc3[nH]cc(NC(=O)c4cccnc4)c23)CC1]

N-(4-(4-(3-aminopropanoyl)piperazin-1-yl)-5-bromo-1H-pyrrolo[2,3-b]pyridin-3-yl)nicotinamide Crude N-(5-bromo-4-(piperazin-1-yl)-1H-pyrrolo[2,3-b]pyridin-3-yl)nicotinamide (0.200 g, 0.498 mmol, see Example 61), 3-(tert-butoxycarbonylamino)propanoic acid (0.189 g, 0.997 mmol), HOBT-H₂O (0.107 g, 0.698 mmol) and EDCI (0.124 g, 0.648 mmol) were placed in DCM (5 mL) at room temperature. DIEA (d 0.742; 0.434 mL, 2.49 mmol) was then added, and the reaction was allowed to stir for 5 hours. The reaction was then poured into saturated Na₂CO₃ and extracted into DCM. The organic fractions were combined, dried, filtered, and concentrated to give the crude residue. Purification by column chromatography (500:15 to 500:25 D CM: MeOH) gave tert-butyl 3-(4-(5-bromo-3-(nicotinamido)-1H-pyrrolo[2,3-b]pyridin-4-yl)piperazin-1-yl)-3-oxopropylcarbamate (0.060 g, 21.0% yield).

tert-Butyl 3-(4-(5-bromo-3-(nicotinamido)-1H-pyrrolo[2,3-b]pyridin-4-yl)piperazin-1-yl)-3-oxopropylcarbamate (0.020 g, 0.035 mmol) was placed in DCM (3 mL) at room temperature. TFA (0.5 mL) was then added and the reaction was stirred at room temperature for 1 hour. The reaction was then concentrated to dryness, dissolved in minimal DCM, and added to a stirring solution of 1M HCl in ether. The resulting solid product was filtered, washed with ether and dried to give the product N-(4-(4-(3-aminopropanoyl)piperazin-1-yl)-5-bromo-1H-pyrrolo[2,3-b]pyri din-3-yl)nicotinamide (0.015 g, 74% yield) as the trihydrochloride salt. MS APCI (+) m/z 473 detected.

Example 63

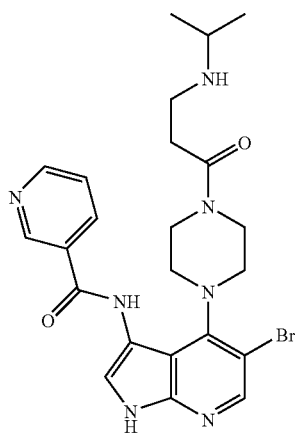 [SMILES: CC(C)NCCC(=O)N1CCN(c2c(Br)cnc3[nH]cc(NC(=O)c4cccnc4)c23)CC1]

N-(5-bromo-4-(4-(3-(isopropylamino)propanoyl)
piperazin-1-yl)-1H-pyrrolo[2,3-b]pyridin-3-yl)nicoti-
namide N-(4-(4-(3-aminopropanoyl)piperazin-1-yl)-5-bromo-1H-pyrrolo[2,3-b]pyridin-3-yl)nicotinamide (0.060 g, 0.103 mmol, see Example 62) and acetone (0.0599 g, 1.03 mmol) were placed in 1:1 DCE:DMF (5 mL). DIEA (d 0.742; 0.0898 mL, 0.516 mmol) was then added, followed by the addition of NaBH(OAc)₃ (0.0437 g, 0.206 mmol). The reaction was then stirred for 30 minutes, and poured into Na₂CO₃ and extracted into DCM (3×30 mL). The organic fractions were combined, dried, filtered and concentrated. The resulting residue was purified by reverse phase HPLC to give a pure product. The product was then dissolved in minimal DCM and added to a stirring solution of 1M HCl in ether (10 mL). The resulting solid was collected to give N-(5-bromo-4-(4-(3-(isopropylamino)propanoyl)piperazin-1-yl)-1H-pyrrolo[2,3-b]pyridin-3-yl)nicotinamide (0.030 g, 46.6% yield) as the trihydrochloride salt. MS APCI (+) m/z 515 detected.

Example 64

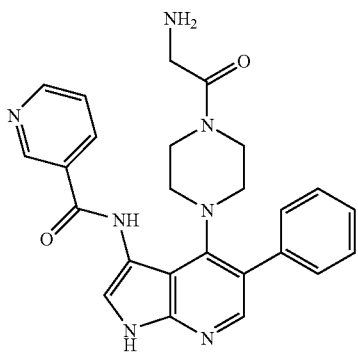 [SMILES: NCC(=O)N1CCN(c2c(-c3ccccc3)cnc3[nH]cc(NC(=O)c4cccnc4)c23)CC1]

N-(4-(4-(2-aminoacetyl)piperazin-1-yl)-5-phenyl-
1H-pyrrolo[2,3-b]pyridin-3-yl)nicotinamide tert-Butyl 2-(4-(5-bromo-3-(nicotinamido)-1H-pyrrolo[2,3-b]pyridin-4-yl)piperazin-1-yl)-2-oxoethylcarbamate (0.090 g, 0.16 mmol) and phenylboronic acid (0.039 g, 0.32 mmol) were placed in dioxane (1.5 mL) and degassed for 30 minutes. A 20% Na₂CO₃ (0.5 mL) solution was then added, followed by the addition of PS-Pd(PPh₃)₄ (0.081 g, 0.0081 mmol). The reaction was then heated in a microwave at 150° C. for 1 hour. The reaction was next diluted with DCM and filtered to remove the catalyst The reaction was then purified by prep HPLC to give a mixture of tert-butyl 2-(4-(3-(nicotinamido)-5-phenyl-1H-pyrrolo[2,3-b]pyridin-4-yl)piperazin-1-yl)-2-oxoethylcarbamate (0.013 g, 15% yield) and N-(5-phenyl-4-(piperazin-1-yl)-1H-pyrrolo[2,3-b]pyridin-3-yl)nicotinamide (0.020 g, 31% yield).

tert-Butyl 2-(4-(3-(nicotinamido)-5-phenyl-1H-pyrrolo[2,3-b]pyridin-4-yl)piperazin-1-yl)-2-oxoethylcarbamate (0.013 g, 0.023 mmol) was placed in DCM (3 mL) at room temperature. TFA (0.5 mL) was then added, and the reaction was stirred at room temperature for 1 hour. The reaction was then concentrated to dryness. The resulting residue was dissolved in minimal DCM and added to a stirring solution of 1M HCl in ether. The resulting solid product was filtered, washed with ether and dried to give N-(4-(4-(2-amino acetyl)piperazin-1-yl)-5-phenyl-1H-pyrrolo[2,3-b]pyridin-3-yl)nicotinamide (0.004 g, 38% yield) as the trihydrochloride salt. MS APCI (+) m/z 456 detected.

Example 65

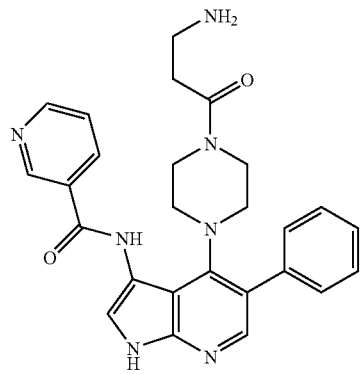 [SMILES: NCCC(=O)N1CCN(c2c(-c3ccccc3)cnc3[nH]cc(NC(=O)c4cccnc4)c23)CC1]

N-(4-(4-(3-aminopropanoyl)piperazin-1-yl)-5-phe-
nyl-1H-pyrrolo[2,3-b]pyridin-3-yl)nicotinamide N-(5-Phenyl-4-(piperazin-1-yl)-1H-pyrrolo[2,3-b]pyridin-3-yl)nicotinamide (0.050 g, 0.125 mmol, see Example 64), 3-(tert-butoxycarbonylamino)propanoic acid (0.0475 g, 0.251 mmol), HOBT-H₂O (0.0269 g, 0.176 mmol), and EDCI (0.0313 g, 0.163 mmol) were placed in DCM (5 mL) at room temperature. DIEA (d 0.742; 0.109 mL, 0.627 mmol) was then added, and the reaction was stirred for 5 hours. The reaction was then poured into Na₂CO₃ and extracted into DCM. The organic fractions were dried, filtered, and concentrated to give the crude product that was purified by column chromatography (500:20 DCM:MeOH) to give tert-butyl 3-(4-(3-(nicotinamido)-5-phenyl-1H-pyrrolo[2,3-b]pyridin-4-yl)piperazin-1-yl)-3-oxopropylcarbamate (0.065 g, 90.9% yield).

tert-Butyl 3-(4-(3-(nicotinamido)-5-phenyl-1H-pyrrolo[2,3-b]pyridin-4-yl)piperazin-1-yl)-3-oxopropylcarbamate (0.020 g, 0.035 mmol) was placed in DCM (3 mL) at room temperature. TFA (0.5 mL) was then added, and the reaction was stirred at room temperature for 1 hour. The reaction was then concentrated to dryness, dissolved in minimal DCM, and added to a stirring solution of 1M HCl in ether. The resulting solid product was filtered, washed with ether and dried to give the product N-(4-(4-(3-aminopropanoyl)piperazin-1-yl)-5-phenyl-1H-pyrrolo[2,3-b]pyridin-3-yl)nicotinamide (0.008 g, 39% yield) as the trihydrochloride salt. MS APCI (+) m/z 470 detected.

Example 66

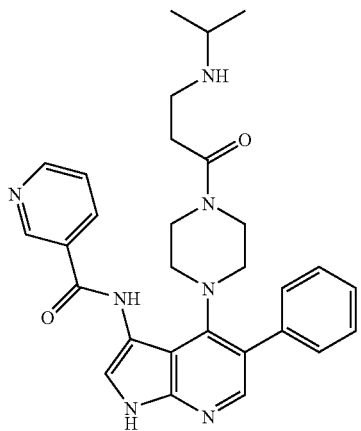 [SMILES: CC(C)NCCC(=O)N1CCN(c2c(-c3ccccc3)cnc3[nH]cc(NC(=O)c4cccnc4)c23)CC1]

N-(4-(4-(3-(isopropylamino)propanoyl)piperazin-1-yl)-5-phenyl-1H-pyrrolo[2,3-b]pyridin-3-yl)nicotinamide N-(4-(4-(3-Aminopropanoyl)piperazin-1-yl)-5-phenyl-1H-pyrrolo[2,3-b]pyridin-3-yl)nicotinamide (0.015 g, 0.026 mmol, see Example 65) and acetone (0.0150 g, 0.259 mmol) were placed in 1:1 DCE:DMF (2 mL). DIEA (d 0.742; 0.0226 mL, 0.130 mmol) was then added, followed by the addition of NaBH(OAc)$_3$ (0.0110 g, 0.0518 mmol). The reaction was then stirred for 30 minutes, and poured into Na$_2$CO$_3$ and extracted into DCM. The organic fractions were combined, dried, filtered and concentrated. The residue was purified by reverse phase HPLC to give the product. The product was then dissolved in minimal DCM and MeOH and added to a stirring solution of 1M HCl in ether. The resulting solid was collected to give N-(4-(4-(3-(isopropylamino)propanoyl)piperazin-1-yl)-5-phenyl-1H-pyrrolo[2,3-b]pyridin-3-yl)nicotinamide (0.001 g, 6.2% yield) as the trihydrochloride salt. MS APCI (+) m/z 512 detected.

Examples 67-74 shown in Table 3 can also be made according to the above described methods.

TABLE 3

| Ex # | Structure | Name | NMR/LCMS |
|---|---|---|---|
| 67 | 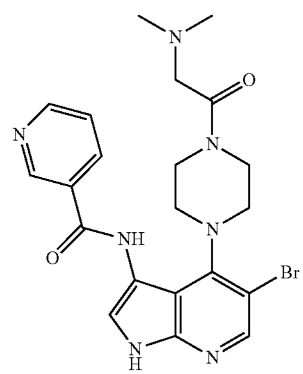 [SMILES: CN(C)CC(=O)N1CCN(c2c(Br)cnc3[nH]cc(NC(=O)c4cccnc4)c23)CC1] | N-(5-bromo-4-(4-(2-(dimethylamino)acetyl)piperazin-1-yl)-1H-pyrrolo[2,3-b]pyridin-3-yl)-nicotinamide hydrochloride | LCMS (APCI+) m/z 486 (M + H)+ |
| 68 | 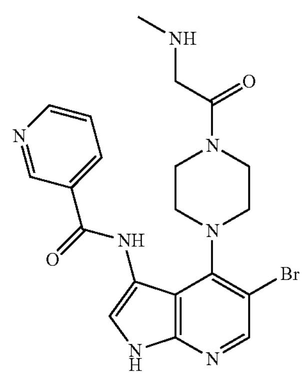 [SMILES: CNCC(=O)N1CCN(c2c(Br)cnc3[nH]cc(NC(=O)c4cccnc4)c23)CC1] | N-(5-bromo-4-(4-(2-(methylamino)acetyl)piperazin-1-yl)-1H-pyrrolo[2,3-b]pyridin-3-yl)-nicotinamide hydrochloride | LCMS (APCI+) m/z 472 (M + H)+ |

TABLE 3-continued

| Ex # | Structure | Name | NMR/LCMS |
|---|---|---|---|
| 69 | 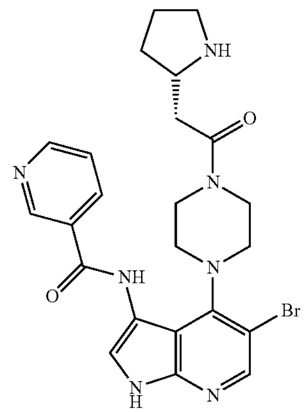 | (S)-N-(5-bromo-4-(4-(2-(pyrrolidin-2-yl)acetyl)piperazin-1-yl)-1H-pyrrolo[2,3-b]pyridin-3-yl)-nicotinamide hydrochloride | LCMS (APCI+) m/z 512 (M + H)+ |
| 70 | 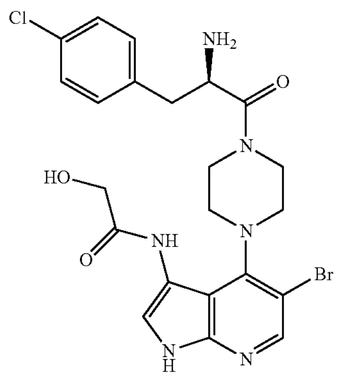 [SMILES: N[C@H](Cc1ccc(Cl)cc1)C(=O)N1CCN(c2c(Br)cnc3[nH]cc(NC(=O)CO)c23)CC1] | (R)-N-(4-(4-(2-amino-3-(4-chlorophenyl)propanoyl)piperazin-1-yl)-5-bromo-1H-pyrrolo[2,3-b]pyridin-3-yl)-2-hydroxyacetamide hydrochloride | LCMS (APCI+) m/z 535 (M + H)+ |
| 71 | 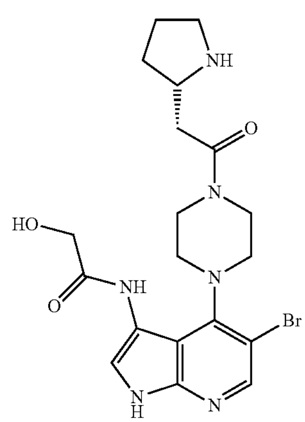 | (S)-N-(5-bromo-4-(4-(2-(pyrrolidin-2-yl)acetyl)piperazin-1-yl)-1H-pyrrolo[2,3-b]pyridin-3-yl)-2-hydroxyacetamide hydrochloride | LCMS (APCI+) m/z 565 (M + H)+ |

TABLE 3-continued

| Ex # | Structure | Name | NMR/LCMS |
|---|---|---|---|
| 72 | 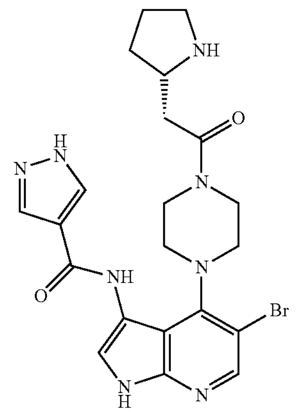 | (S)-N-(5-bromo-4-(4-(2-(pyrrolidin-2-yl)acetyl)piperazin-1-yl)-1H-pyrrolo[2,3-b]pyridin-3-yl)-1H-pyrazole-4-carboxamide hydrochloride | LCMS (APCI+) m/z 501 (M + H)+ |
| 73 | 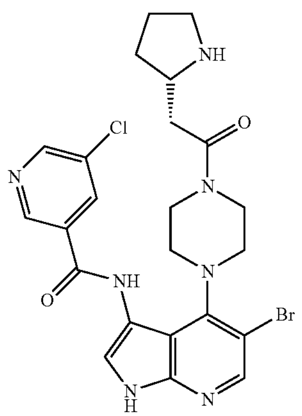 | (S)-N-(5-bromo-4-(4-(2-(pyrrolidin-2-yl)acetyl)piperazin-1-yl)-1H-pyrrolo[2,3-b]pyridin-3-yl)-5-chloronicotinamide hydrochloride | LCMS (APCI+) m/z 546 (M + H)+ |
| 74 | 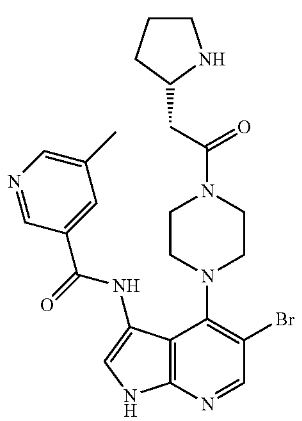 | (S)-N-(5-bromo-4-(4-(2-(pyrrolidin-2-yl)acetyl)piperazin-1-yl)-1H-pyrrolo[2,3-b]pyridin-3-yl)-5-methylnicotinamide hydrochloride | LCMS (APCI+) m/z 526 (M + H)+ |

While the invention has been described in conjunction with the enumerated embodiments, it will be understood that they are not intended to limit the invention to those embodiments. On the contrary, the invention is intended to cover all alternatives, modifications and equivalents, which may be included within the scope of the present invention as defined by the claims. Thus, the foregoing description is considered as illustrative only of the principles of the invention.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

The invention claimed is:

1. A compound of Formula I:

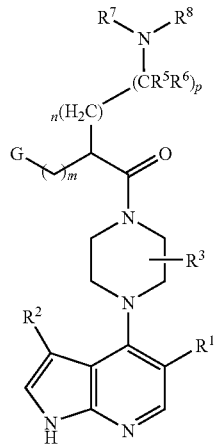

or a stereoisomer or pharmaceutically acceptable salts thereof, wherein:

G is cyclohexyl or phenyl optionally substituted by 1-3 independent $R^4$ groups, or when m is 0, G may additionally be absent or $C_1$-$C_4$ alkyl;

$R^1$ is —C(=O)$OR^a$, —$OR^e$, $C_3$-$C_6$ cycloalkyl, 5 or 6 membered heteroaryl, phenyl or —O-phenyl, wherein the heteroaryl, phenyl or —O-phenyl may be optionally substituted with one or two $R^b$ groups;

$R^2$ is hydrogen, $CH_3$, or —NHC(=O)$R^f$, $R^3$ is hydrogen or $C_1$-$C_3$ alkyl;

each $R^4$ is independently halogen, $CF_3$, $OCF_3$ or CN;

$R^5$ and $R^6$ are independently hydrogen or $CH_3$;

$R^7$ and $R^8$ are independently hydrogen or $C_1$-$C_6$ alkyl;

$R^a$ is $C_1$-$C_4$ alkyl;

each $R^b$ group is independently halogen, CN, $OCH_3$ or $C_1$-$C_4$ alkyl optionally substituted with halogen, OH, oxo, 5 or 6 membered heteroaryl or $NR^gR^h$;

$R^e$ is $C_1$-$C_4$ alkyl substituted with OH or 5 or 6 membered heterocycle;

$R^f$ is $C_1$-$C_4$ alkyl optionally substituted with OH, a 5 or 6 membered heterocycle optionally substituted with one or two groups selected from the group consisting of oxo, halogen, CN, $CF_3$ and $C_1$-$C_3$ alkyl, or a 5 or 6 membered heteroaryl optionally substituted with one or two groups selected from the group consisting of halogen, CN, $CF_3$ and $C_1$-$C_3$ alkyl;

$R^g$ and $R^h$ are independently hydrogen or $C_1$-$C_4$ alkyl;

m, n and p are independently 0 or 1;

or $R^5$ is hydrogen, $R^6$ and $R^7$ together with the atoms to which they are attached form an optionally substituted 5-6 membered heterocyclic ring having one ring nitrogen atom, and $R^8$ is selected from the group consisting of hydrogen and $C_1$-$C_4$ alkyl optionally substituted with OH or O($C_1$-$C_3$ alkyl) such that the compound of Formula I has the structure of Formula II:

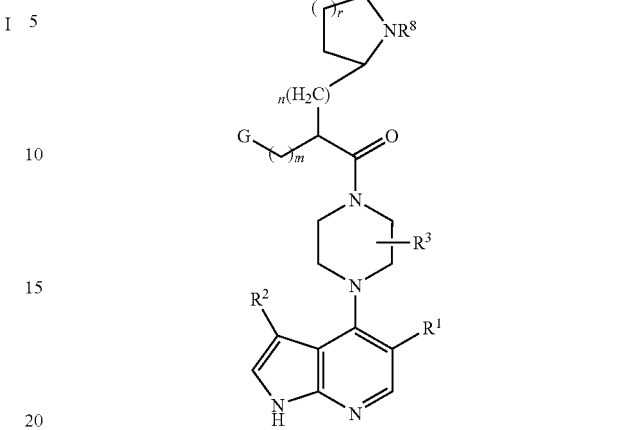

wherein $R^c$ and $R^d$ are independently hydrogen or $C_1$-$C_4$ alkyl; and r is 1 or 2.

2. A compound of claim 1, wherein $R^1$ is C(=O)$OR^a$.
3. A compound of claim 2, $R^1$ is wherein C(=O)$OCH_3$.
4. A compound of claim 1, wherein $R^1$ is —$OR^e$.
5. A compound of claim 4, wherein $R^1$ is —$OCH_2CH(OH)CH_2CH_3$, —$OCH_2CH_2$-morpholin-4-yl or —$OCH_2CH_2CH_2$-morpholin-4-yl.
6. A compound of claim 1, wherein $R^1$ is a 5 or 6 membered heteroaryl optionally substituted with one or two $R^b$ groups.
7. A compound of claim 6, wherein the 5 or 6 membered heteroaryl is pyrazolyl, 1-oxa-3,4-diazolyl, thiophenyl or pyridinyl.
8. A compound of claim 6, wherein $R^1$ is 1-methyl-1H-pyrazol-yl, 2-isopropyl-1-oxa-3,4-diazol-5-yl, 2-methyl-1-oxa-3,4-diazol-5-yl, pyridin-3-yl or thiophen-2-yl.
9. A compound of claim 1, wherein $R^1$ is phenyl optionally substituted with one or two $R^b$ groups.
10. A compound of claim 9, wherein $R^1$ is phenyl, 2-fluorophenyl, 3-fluorophenyl, 3-chlorophenyl, 4-fluorophenyl, 3-cyanophenyl, 3-methoxyphenyl, 4-methoxyphenyl, 3-isopropylphenyl, 3-trifluoromethylphenyl, 3-hydroxymethylphenyl, 4-hydroxymethylphenyl, 4-((1H-pyrazol-1-yl)methyl)phenyl, 3-($CH_2N(CH_3)_2$)phenyl, 4-(C(=O)NH$CH_3$)phenyl, 3-($CH_2C$(=O)$NH_2$)phenyl, 3-(C(=O)$NH_2$)phenyl, 4-(C(=O)$NH_2$)phenyl, 3,4-dimethoxyphenyl, 3,5-difluorophenyl or 3-fluoro-5-methoxyphenyl.
11. A compound of claim 1, wherein $R^2$ is hydrogen.
12. A compound of claim 1, wherein $R^2$ is $CH_3$.
13. A compound of claim 1, wherein $R^2$ is —NHC(=O)$R^f$.
14. A compound of claim 13, wherein $R^2$ is —NHC(=O)$CH_3$, —NHC(=O)$CH_2CH_2CH_3$, —NHC(=O)$CH_2OH$ or N-nicotinamide.
15. A compound of claim 13, wherein $R^2$ is —NHC(=O)$CH_3$, —NHC(=O)$CH_2CH_2CH_3$, —NHC(=O)$CH_2OH$, N-nicotinamide, N-1H-pyrazole-4-carboxamide, N-5-chloronicotinamide and N-5-methylnicotinamide.
16. A compound of claim 1, wherein $R^7$ is hydrogen.
17. A compound of claim 1, wherein $R^7$ is $C_1$-$C_6$ alkyl.
18. A compound of claim 16, wherein $R^7$ is isopropyl.
19. A compound of claim 1, wherein $R^8$ is hydrogen.
20. A compound of claim 1, wherein $R^8$ is methyl.
21. A compound of claim 1, wherein p is 1.
22. A compound of claim 1, wherein $R^5$ is hydrogen.
23. A compound of claim 1, wherein $R^5$ is $CH_3$.
24. A compound of claim 1, wherein $R^6$ is hydrogen.
25. A compound of claim 1, wherein $R^6$ is methyl.

26. A compound of claim 1, wherein p is 0.
27. A compound of claim 1, wherein $R^3$ is hydrogen.
28. A compound of claim 1, wherein n is 0.
29. A compound of claim 1, wherein n is 1.
30. A compound of claim 1, wherein G is cyclohexyl.
31. A compound of claim 1, wherein G is phenyl optionally substituted by one to three $R^4$ groups.
32. A compound of claim 31, wherein G is 4-fluorophenyl, 4-chlorophenyl, 4-bromophenyl, 3-fluoro-4-chlorophenyl or 3-chloro-4-fluorophenyl.
33. A compound of claim 1, wherein m is 0.
34. A compound of claim 1, wherein m is 1.
35. A compound of claim 1, wherein m is 0 and G is $G^1$, having the structure of Formula V:

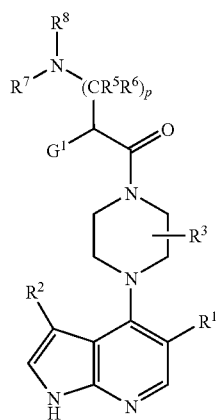

V wherein $G^1$ is absent or $C_1$-$C_4$ alkyl.
36. A compound of claim 35, wherein $G^1$ is absent.
37. A compound of claim 35, wherein $G^1$ is $C_1$-$C_4$ alkyl.
38. A compound of claim 35, wherein $G^1$ is isopropyl.
39. A compound of claim 1, wherein $R^5$ is hydrogen, $R^6$ and $R^7$ together with the atoms to which they are attached form an optionally substituted 5-6 membered heterocyclic ring having one ring nitrogen atom, and $R^8$ is hydrogen or $C_1$-$C_4$ alkyl optionally substituted with OH or $O(C_1$-$C_3$ alkyl) such that the compound of Formula I has the structure of Formula II:

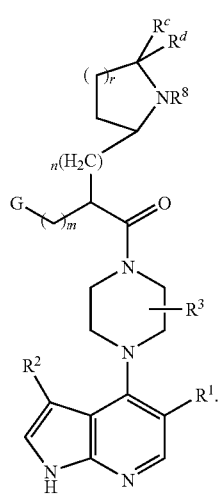

II

40. A compound of claim 39, wherein r is 1.
41. A compound of claim 39, wherein r is 2.
42. A compound of claim 39, wherein $R^c$ is hydrogen.
43. A compound of claim 39, wherein $R^c$ is methyl.
44. A compound of claim 39, wherein $R^d$ is hydrogen.
45. A compound of claim 39, wherein $R^d$ is methyl.
46. A compound of claim 39, wherein $R^8$ is hydrogen.
47. A compound of claim 39, wherein $R^8$ is methyl.
48. A compound of Formula I as defined in claim 1 and having the structure:

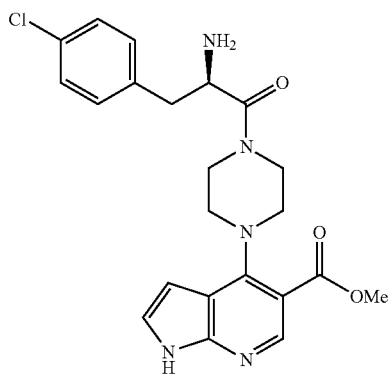

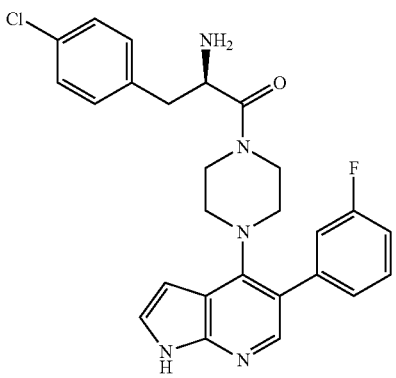

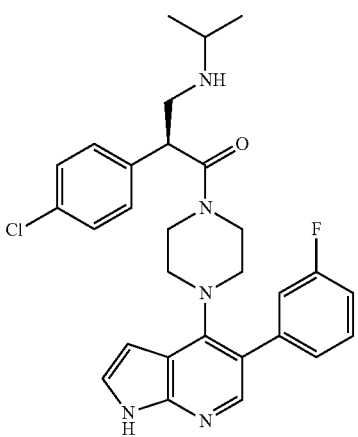

125
-continued
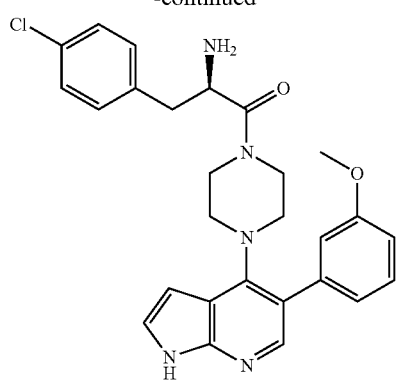
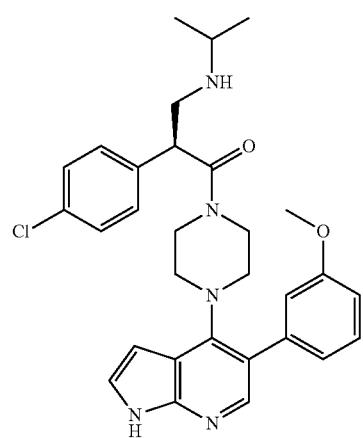
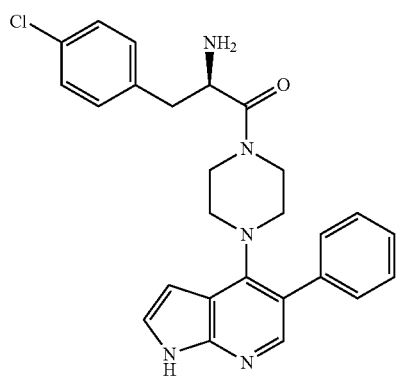
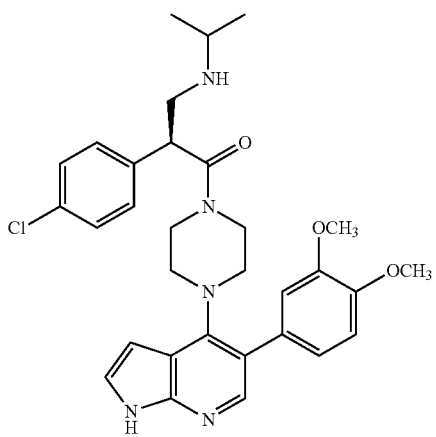
126
-continued
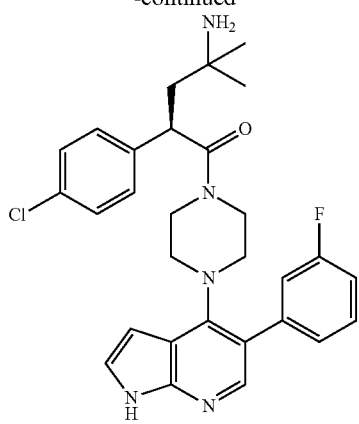
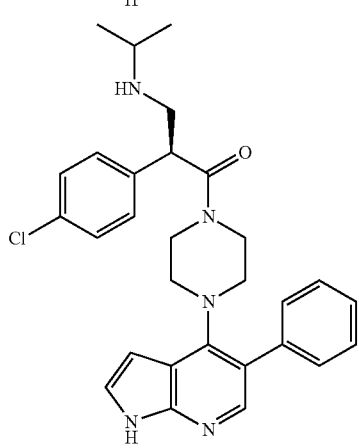
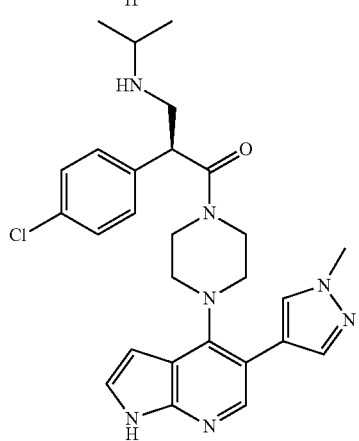
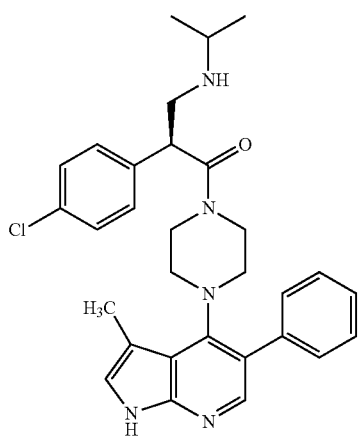

127
-continued
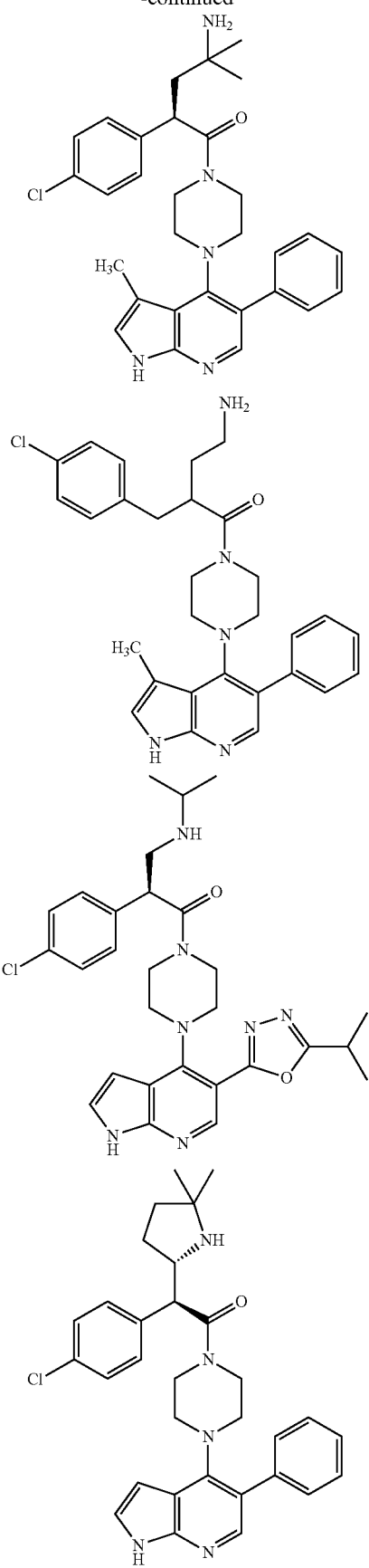
128
-continued
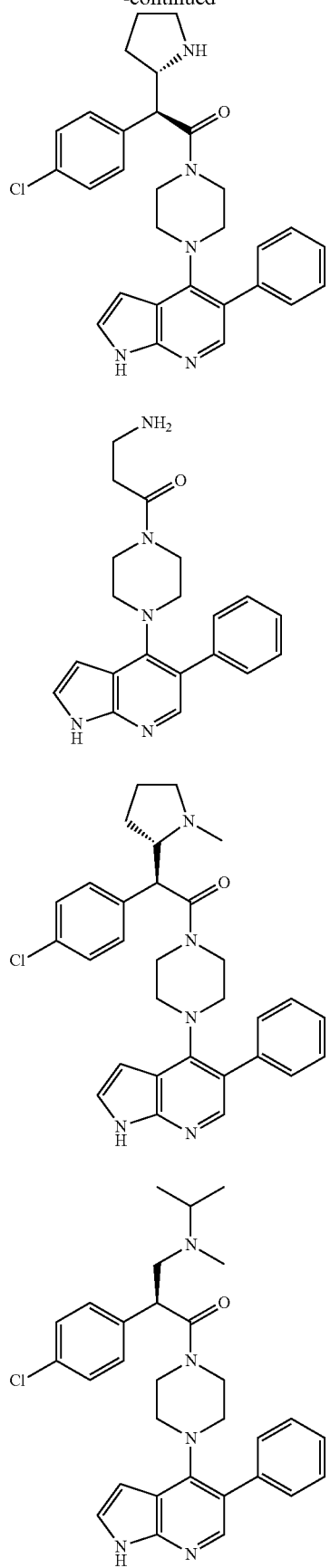

129
-continued
130
-continued
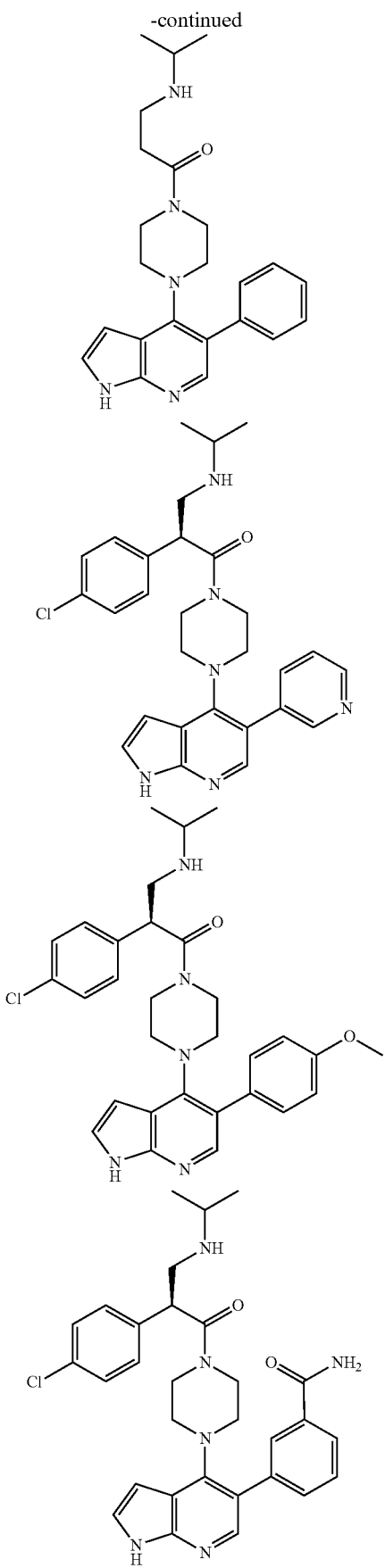
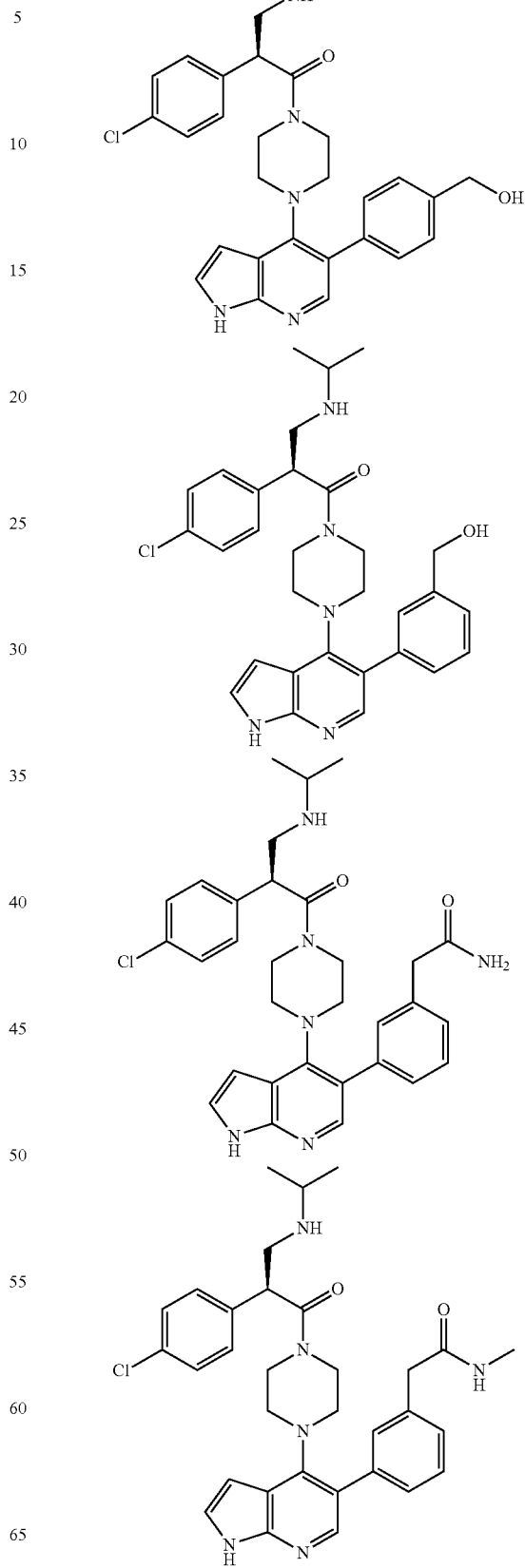

131
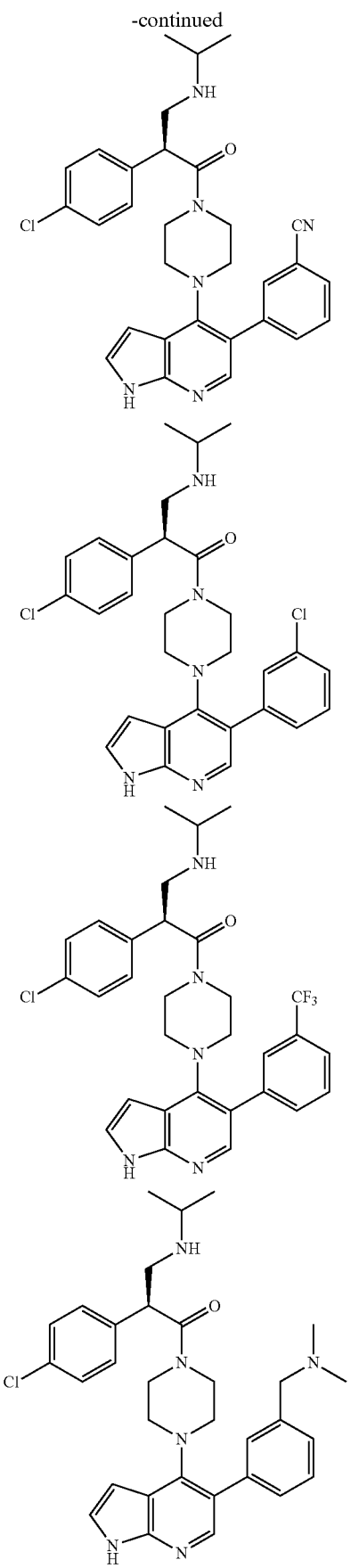
132
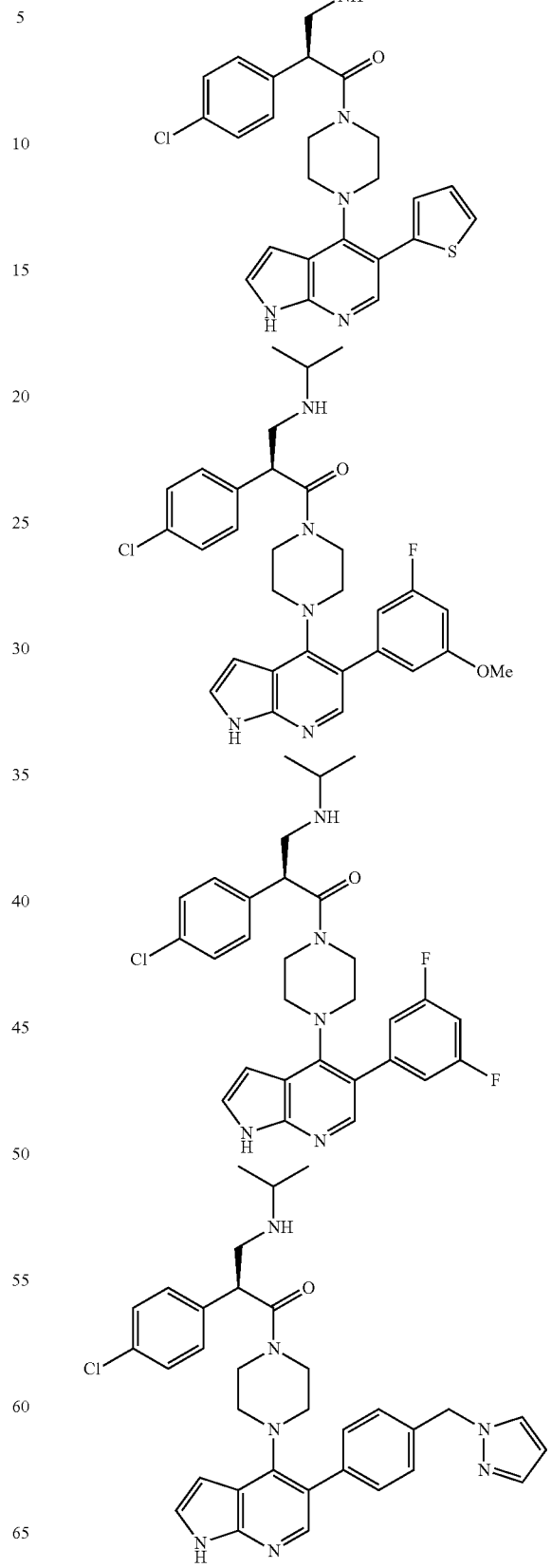

133
-continued
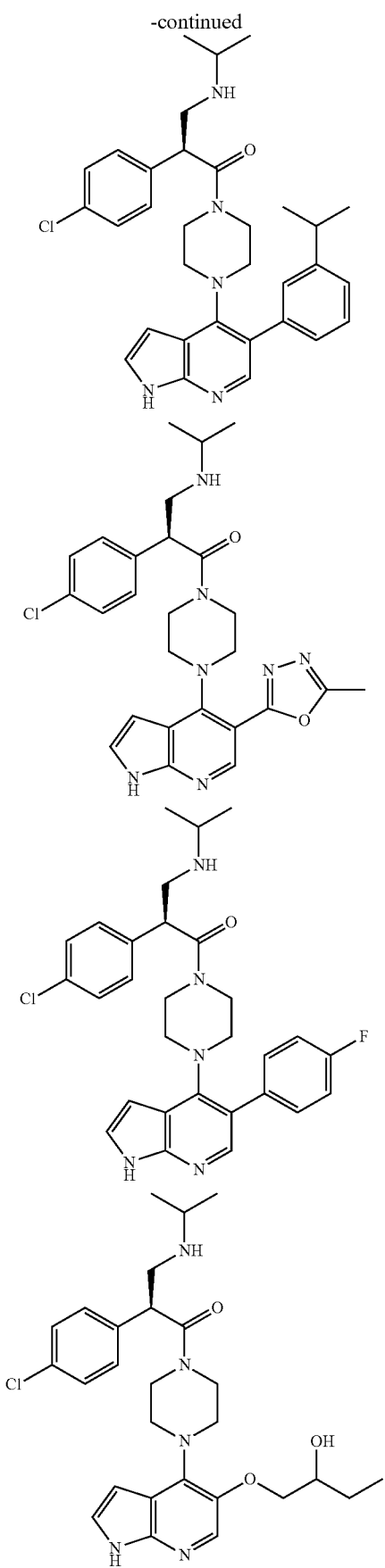
134
-continued
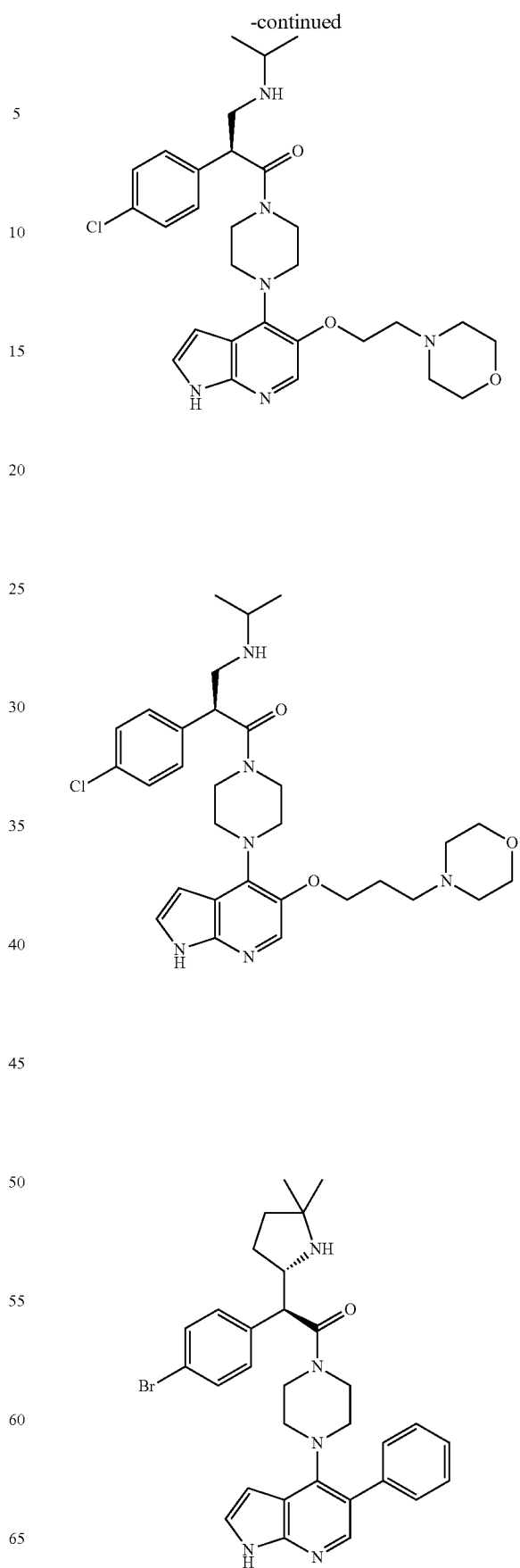

135
-continued
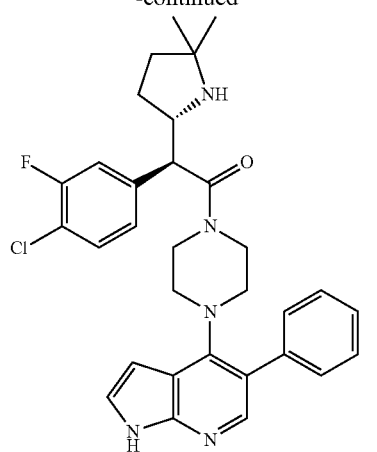
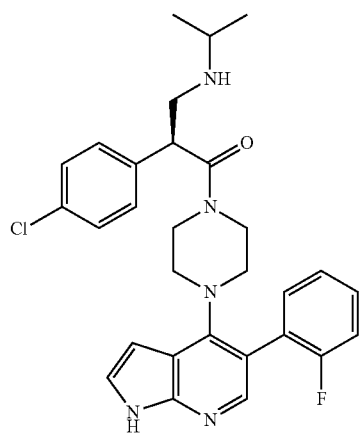
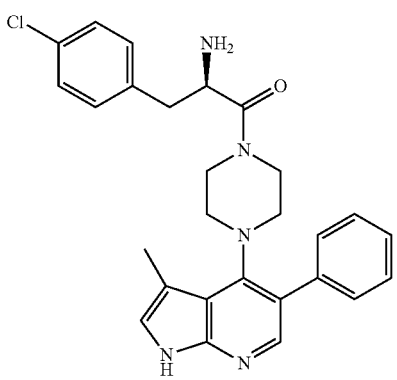
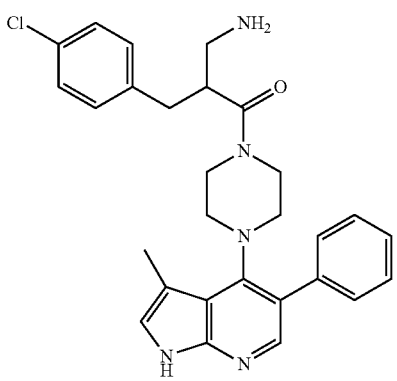
136
-continued
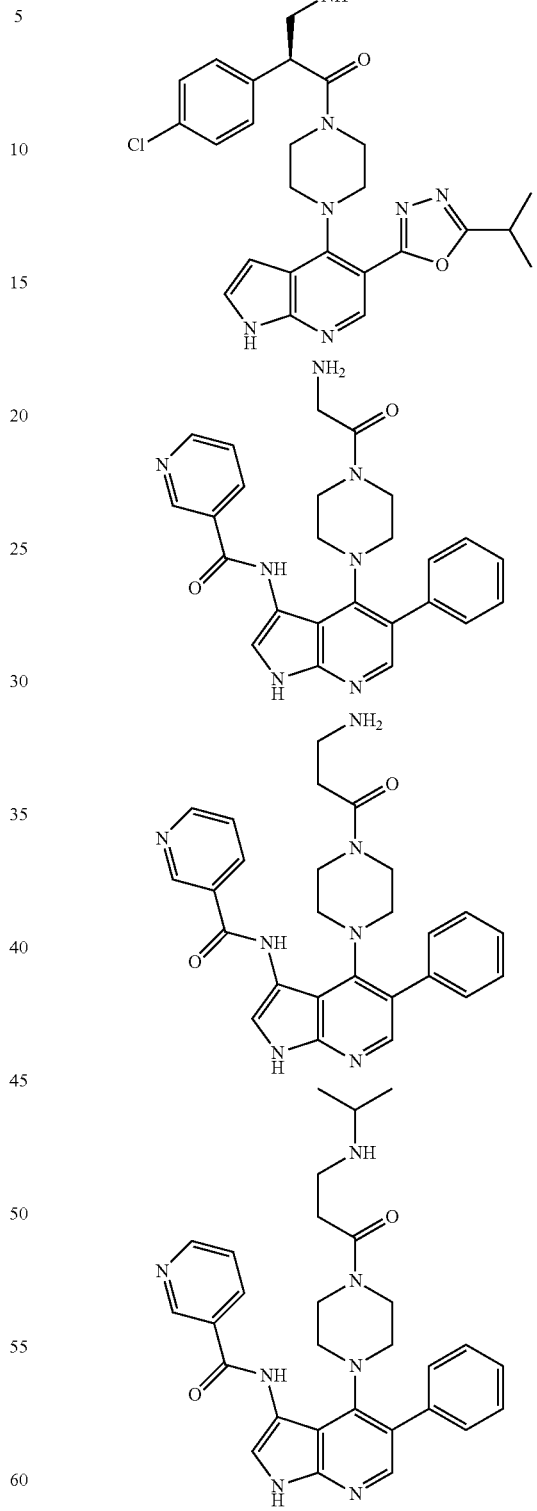
or a pharmaceutically acceptable salt thereof.
49. A pharmaceutical composition, comprising a compound of claim 1, and a pharmaceutically acceptable carrier or excipient.

50. A compound of claim 1 having the structure of Formula IIa:

IIa

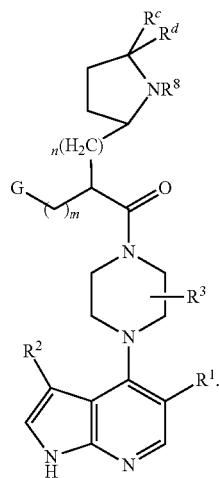

51. A compound of claim 50, wherein $R^c$ and $R^d$ are both hydrogen.

52. A compound of claim 50, wherein $R^c$ and $R^d$ are both methyl.

53. A compound of claim 50, wherein $R^8$ is H.

54. A compound of claim 1 having the structure of Formula IIa1:

IIa1

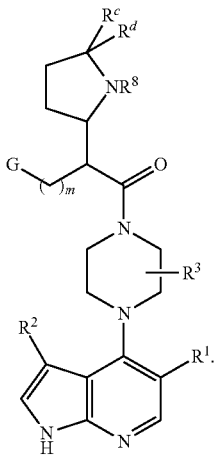

55. A compound of claim 1 having the structure of Formula IIb:

IIb

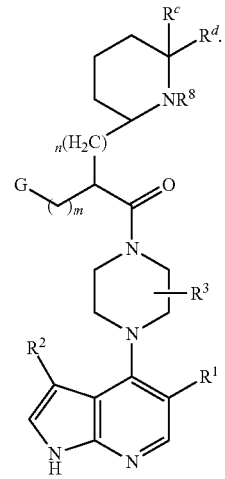

56. A compound of claim 1 having the structure of Formula IIb1:

IIb1

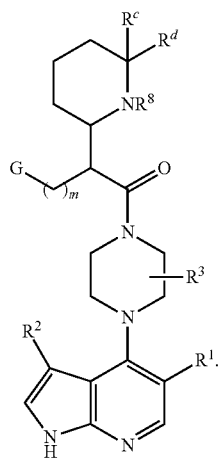

57. A compound of claim 1 having the structure of Formula III:

III

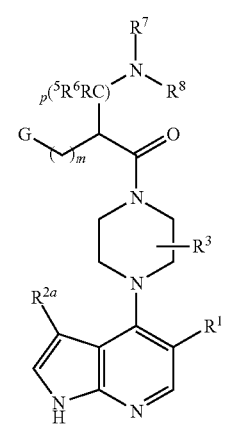

wherein $R^{2a}$ is H or methyl.

58. A compound of claim 1 having the structure of Formula VI:
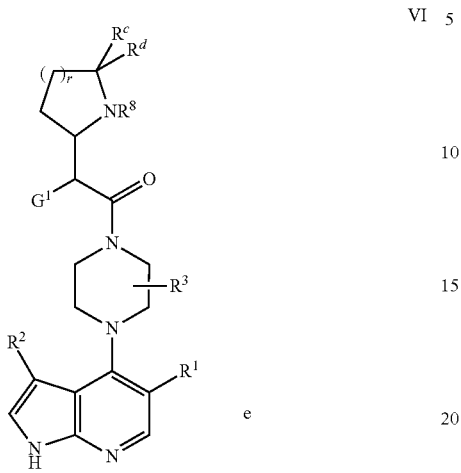
wherein $G^1$ is absent or $C_1$-$C_4$ alkyl.
59. A compound of claim 58, wherein $G^1$ is absent.
60. A compound of claim 58, wherein $G^1$ is $C_1$-$C_4$ alkyl.
61. A compound of claim 58, wherein r is 1.
62. A compound of claim 58, wherein r is 2.
63. A compound of claim 58, wherein $R^8$ is hydrogen or $C_1$-$C_4$ alkyl optionally substituted with OH or O($C_1$-$C_3$ alkyl).
* * * * *